United States Patent [19]

Fujii et al.

[11] Patent Number: 5,162,305

[45] Date of Patent: Nov. 10, 1992

[54] POLYPEPTIDE DERIVATIVES

[75] Inventors: Setsuro Fujii, Kyoto; Yoshihito Yamamoto; Fumio Shimizu, both of Otsu; Masatoshi Inai, Tokushima; Mitsuru Hirohashi, Otsu, all of Japan

[73] Assignees: Otsuka Pharmaceutical Co., Ltd.; Otsuka Pharmaceutical Factory, Inc., Japan

[21] Appl. No.: 314,018

[22] Filed: Feb. 23, 1989

[30] Foreign Application Priority Data

| Feb. 29, 1988 | [JP] | Japan | 63-47322 |
| Apr. 27, 1988 | [JP] | Japan | 63-106452 |
| Jul. 28, 1988 | [JP] | Japan | 63-190159 |
| Sep. 30, 1988 | [JP] | Japan | 63-248473 |
| Dec. 15, 1988 | [JP] | Japan | 63-317932 |

[51] Int. Cl.$^5$ ............................................. A61K 37/02
[52] U.S. Cl. ................................... 514/12; 530/324; 530/307
[58] Field of Search .................. 530/324, 307; 514/12

[56] References Cited

U.S. PATENT DOCUMENTS

| 4,086,221 | 4/1978 | Sakakibara et al. | 530/307 |
| 4,277,393 | 7/1981 | Sakakibara et al. | 530/307 |
| 4,639,511 | 1/1987 | Orlowski et al. | |
| 4,663,309 | 5/1987 | Kaiser et al. | 530/307 |
| 4,703,106 | 10/1987 | Hirone et al. | 530/307 |
| 4,743,677 | 5/1988 | Noda et al. | 530/307 |

FOREIGN PATENT DOCUMENTS 51-128993 11/1976 Japan .
61-112099 5/1986 Japan .

OTHER PUBLICATIONS

Findlay, D. M., et al., "Biological Activities and Receptor Interactions of des-Leu-16 Salmon and des-Phe-16 Human Calcitonin," Endocrinology, vol. 112, No. 4, pp. 1288-1291, 1989.
Current Therapeutic Research 45:502-515 (1989).
Morikawa et al., Experientia 32:1104-1106 (1976).

*Primary Examiner*—Merrell C. Cashion, Jr.
*Assistant Examiner*—B. Celsa
*Attorney, Agent, or Firm*—Finnegan, Henderson, Farabow, Garrett & Dunner

[57] ABSTRACT

Novel synthetic polypeptide derivatives, i.e., novel calcitonin derivatives, having improved basic physiological activities of the corresponding natural calcitonins, i.e., the activity for lowering the blood level of calcium, the activity as an analgesic, as well as the activity for inhibiting the secretion of the gastric juice. Thus these synthetic calcitonins are effective as agents for curing hypercalcemia, analgetic agents, anti-ulcerative agents and the like.

23 Claims, No Drawings

POLYPEPTIDE DERIVATIVES

FIELD OF THE INVENTION

The present invention relates to polypeptide derivatives. More particularly, the invention relates to novel polypeptide derivatives, acid-addition salts thereof and complexes thereof, having the activity for lowering the blood level of calcium, the activity as an analgesic, and the activity for inhibiting secretion of the gastric juice.

PRIOR ART

Calcitonins have widely been known chemically as polypeptide derivatives, which have the activity for lowering the blood level of calcium. The calcitonins may be obtained by extracting from the thyroid glands of human being and other mammals, birds, and the branchiogenic organs of fishes and amphibious animals. Various types of calcitonins occur in nature, and they have different constitutive amino acids depend on the difference of species as the sources. These calcitonins, being obtained from various natural sources, are polypeptides and each of which consist of 32 constitutive amino acids, and such polypeptides have common chemical structures in that the first and the seventh amino acids are both L-cysteine and the mercapto groups in said L-cysteine form disulfide bonding, furthermore, it is common in that the terminal carboxyl group exists in each of said polypeptides forms as a prolinamide.

However, the disulfide bonding occurring in each of these natural calcitonins is presumably quite unstable in a solution, therefore, when such calcitonins are used as agents for curing various symptoms being caused by an extraordinary high blood level of calcium such as hypercalcemia, and for curing Paget's disease, osteoporosis and the like, then there may possibly be happened lowering of the physiological activities of calcitonins and appearing of the antigenecity caused by the by-produced substances formed therefrom.

In recent years, there have been reported a number of synthetic calcitonins having the chemical structures similar to those of the above-mentioned natural calcitonins. Among these synthetic calcitonins, there are involved polypeptides having the amino acid sequence based on that in the natural chicken calcitonins and eel calcitonins, in which the above-mentioned disulfide bonding is replaced with a lower alkylene bonding by deactivating the first cysteine in the amino acid sequence, and at the same time by replacing the seventh cysteine in the amino acid sequence with an α-amino acid having the specific lower alkylene group, and the carboxyl group of the side-chain in said α-amino acid is subjected to ring-closure with the amino group of the second alanine or serine in the amino acid sequence so as to form the above-mentioned alkylene bonding. [Cf. Japanese Patent Kokai (Laid-open) No. 51-128993 (1976) and Japanese Patent Kokai (Laid-open) No. 61-112099 (1986)]However, there have been reported in that the above-mentioned disulfide bonding exists in these natural calcitonins is essential for the manifestation of their physiological activities, so that the stability of said synthetic polypeptides having no such disulfide bonding may be improved in some extent as compared with the stability of the corresponding natural type calcitonins, but such synthetic polypeptides have the tendency for lowering their physiological activities as compared with the fundamental physiological activities shown by the corresponding natural type calcitonins.

SUMMARY OF THE INVENTION

An object of the present invention is to provide novel synthetic polypeptides, i.e., novel calcitonin derivatives which do not have the above-mentioned disulfide bonding so as to avoid the unstability thereof, furthermore by improving the fundamental physiological activities of the corresponding natural calcitonins, i.e., the activity for lowering the blood level of calcium, the activity as analgesic, as well as the activity for inhibiting the secretion of the gastric juice, so that these synthetic calcitonins are quite effective as agents for curing hypercalcemia, analgetic agents, anti-ulcerative agents and the like.

Another object of the present invention is to provide process for preparing said synthetic polypeptides.

Further object of the present invention is to provide a pharmaceutical composition containing, as the active ingredient, the synthetic polypeptide derivative represented by the general formula (1) mentioned below.

The present inventors have made an extensive study to achieve the above-mentioned objectives of the present invention, and as the result that they have successfully synthesized the novel polypeptide derivatives having the specific chemical structural formula represented by the general formula (1), and further they have found that such novel polypeptide derivatives possess excellent properties to meet the requirements as medicines as mentioned in the above described objects, so that the present invention has been completed.

DETAILED EXPLANATION OF THE INVENTION

The present invention relates to polypeptide derivatives, acid-addition salts thereof and complexes thereof represented by the general formula (1),

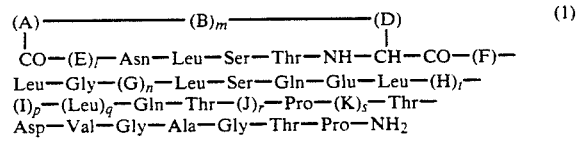

wherein (A) is a lower alkylene group or a phenylene group; (B) is a group of —NHCO—, a group of —S— or an oxyphenylene group; (D) is a lower alkylene group; (E) is a serine residue, a γ-aminobutyric acid residue or a β-alanine residue; (F) is a valine residue, a glycine residue or an isoleucine residue; (G) is a lysine residue, a glycine residue or an alanine residue; (H) is a histidine residue, an asparagine residue, a glycine residue, an aspartic acid residue, a glutamine residue, a leucine residue, a phenylalanine residue, an alanine residue or tyrosine residue; (I) is a lysine residue, a glycine residue or an asparagine residue; (J) is a tyrosine residue, a D-tyrosine residue or a leucine residue; (K) is an arginine residue, a glutamine residue, a glycine residue or an asparagine residue, respectively; each of l, m, n, t, p, q, r and s is 0 or 1; provided that, when l is 0, then A should not be of a methylene group; and when m is 0, then A should be of a phenylene group; further the amino group in the side-chain of the lysine (Lys) residue may be acylated, and the carboxyl groups in the side-chain of aspartic acid (Asp) residue and in the side-chain of the glutamic acid (Glu) residue may be esterified.

In the general formula (1), each of the amino acids is indicated in numerical order as follows:

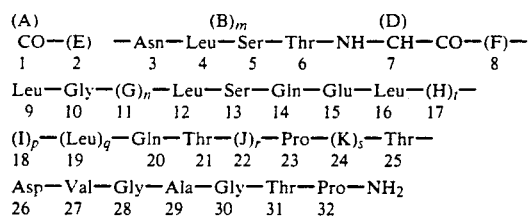

In the present specification, amino acids, peptides, protecting groups, active groups and the like are illustrated by their abbreviations and their symbols which are indicated under provisions of IUPAC (International Union of Pure and Applied Chemistry) and of IBU (International Union of Biochemistry) or by symbols being used commonly in the art. In connection with describing the optical isomers of amino acids, generally L-form (levo-form) of the isomers will be mentioned unless otherwise specifically noticed. Examples of such abbreviations and symbols are shown as follows:

alkoxy group and a halogen atom, on the phenyl ring, may be exemplified.

As to the lower alkanoyl group, a straight chain or branched chain alkanoyl group having 1 to 6 carbon atoms, such as formyl, acetyl, propionyl, butyryl, isobutyryl, pentanoyl and hexanoyl groups may be exemplified.

As to the benzoyl group having 1 to 3 substituents selected from the group consisting of a lower alkyl group, a lower alkoxy group and a halogen atom, on the phenyl ring, a benzoyl group having 1 to 3 substituents selected from the group consisting of a straight chain or branched chain alkyl group having 1 to 6 carbon atoms, a straight chain or branched chain alkoxy group having 1 to 6 carbon atoms, and a halogen atom, on the phenyl ring, such as in addition to benzoyl group, 2-chlorobenzoyl, 3-chlorobenzoyl, 4-chlorobenzoyl, 2-fluorobenzoyl, 3-fluorobenzoyl, 4-fluor 2-bromobenzoyl, 3-bromobenzoyl, 4-bromobenzoyl, 4-iodobenzoyl, 2,4-dichlorobenzoyl, 2,6-dichlorobenzoyl, 3,4-dichlorobenzoyl, 2,4,6-trichlorobenzoyl, 4-methoxybenzoyl, 3-ethoxybenzoyl, 2-propoxybenzoyl, 4-tert-butoxybenzoyl, 3-pentyloxybenzoyl, 2-hexyloxybenzoyl, 2,4-

| | | |
|---|---|---|
| Ala: alanine | β-Ala: β-alanine | Arg: arginine |
| Asp: aspartic acid | Asn: asparagine | Cys: cysteine |
| Gln: glutamine | Glu: glutamic acid | Gly: glycine |
| His: histidine | Ile: isoleucine | Leu: leucine |
| Lys: lysine | Pro: proline | Thr: threonine |
| Ser: serine | Val: valine | Tyr: tyrosine |
| Phe: phenylalanine | Bz: benzoyl group | Bzl: benzyl group |
| Bu$^t$: tert-butyl group | Boc: tert-butoxycarbonyl group | |
| OBzl: benzyloxy group | ONp: p-nitrophenyloxy group | |
| OEt: ethyloxy group | Z: benzyloxycarbonyl group | |
| Cl-Bz: 4-chlorobenzoyl group | | |
| Cl$_2$Bzl: 2.6-dichlorobenzyl group | | |
| OSu: N-oxysuccinimido group | | |
| HOSu: N-hydroxysucciniimide | | |
| Cl-Z: o-chlorobenzyloxycarbonyl group | | |
| Tos: p-toluenesulfonyl group | | |
| OcHex: cyclohexyloxy group | | |
| DCC: N,N'-dicyclohexylcarbodiimide | | |
| DMF: dimethylformamide | TFA: trifluoroacetic acid | |
| THF: tetrahydrofuran | HOBT: 1-hydroxybenzotriazole | |
| WSC: N-ethyl-N'-dimethylaminopropyl-carbodiimide | | |
| HONB: N-hydroxy-5-norbornene-2,3-carboximide | | |
| Acp: ε-aminocaproic acid | Abu: γ-aminobutyric acid | |
| DCHA: dicyclohexylamine | Cmc: S-carboxymethylcystein | |
| Cpc: S-(3-carboxypropyl)cysteine | | |
| Cec: S-(2-carboxyethyl)cysteine | | |
| 4-CPA: L-2-amino-3-(4-carboxyphenyl)propionic acid | | |

In addition to the above, in the present specification, each of these groups being defined by the symbols of (A), (B) and (D) in the general formula (1) and other groups are exemplified specifically as follows:

As to the lower alkylene group, a straight chain or branched chain alkylene group having 1 to 6 carbon atoms, such as methylene, ethylene, trimethylene, 1-methylethylene, tetramethylene, 2-trimethylene, pentamethylene and hexamethylene groups may be exemplified.

As to the phenylene group, any one of o-phenylene, m-phenylene and p-phenylene groups may be exemplified.

As to the oxyphenylene group, any one of oxy-o-phenylene, oxy-m-phenylene and oxy-p-phenylene groups may be exemplified.

As to the acyl group for acylating the amino group in the side chain of lysine (Lys), a lower alkanoyl group or a benzoyl group having 1 to 3 substituents selected from the group consisting of a lower alkyl group, a lower dimethoxybenzoyl, 2,4,6-trimethoxybenzoyl, 4-methylbenzoyl, 3-ethylbenzoyl, 2-propyl 4-tert-butylbenzoyl, 3-pentylbenzoyl, 2-hexylbenzoyl, 3,4-dimethylbenzoyl, 2,6-dimethylbenzoyl and 2,4,6-tr benzoyl may be exemplified.

As to the ester residue for esterifying the carboxyl groups of the side chains in aspartic acid (Asp) and glutamic acid (Glu), an alkyl group having 1 to 6 carbon atoms such as methyl, ethyl, propyl, isopropyl, butyl, isobutyl, tert-butyl, pentyl and hexyl groups may be exemplified.

As to preferable examples represented by the formula

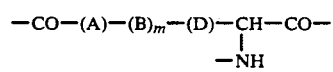

shown in the above-mentioned general formula 1), there may be exemplified the following groups:

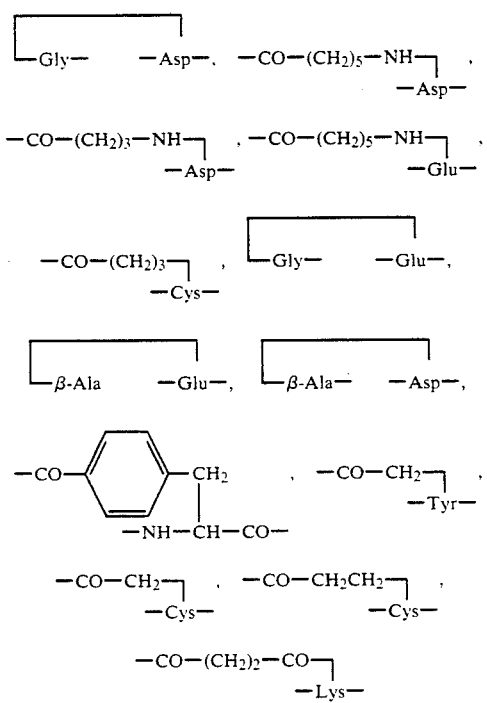

and the like.

Furthermore, the polypeptide derivatives represented by the above-mentioned general formula (1) according to the present invention will be explained in detail by classifying the following groups of the general formulas (1-a$^1$), (1-a$^2$), (1-a$^3$), (1-b$^2$) and (1-c) which are preferable derivatives.

General formula (1-a$^1$):

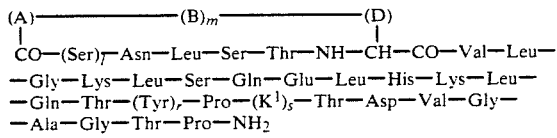

wherein
(A) is a lower alkylene group or a phenylene group;
(B) is a group of —NHCO—, a group of —S— or an oxyphenylene group;
(D) is·a lower alkylene group;
(K$^1$) is a glutamine residue (Gln), a glycine residue (Gly), or an asparagine residue (Asn); respectively;
and l, m, r and s are each 0 or 1, respectively; provided that, when l is 0, then A should not be a methylene group; and when m is 0, then A is a phenylene group; further the amino group in the side-chain of lysine residue (Lys) may be acylated.

General formula (1-a$^2$):

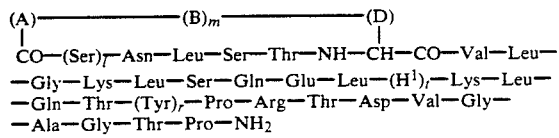

wherein
(A) is a lower alkylene group or a phenylene group;
(B) is a group of —NHCO—, a group of —S— or an oxyphenylene group;
(D) is a lower alkylene group;
(H$^1$) is an asparagine residue (Asn), a glycine residue (Gly), an aspartic acid residue (Asp), a glutamine residue (Gln), a leucine residue (Leu), a phenylalanine residue (Phe), or an alanine residue (Ala); respectively,
and , l, r and t are each 0 or 1;, provided that, when l is 0, then A should not be a methylene group; and when m is 0, then A is a phenylene group; further, the amino group in the side-chain of lysine residue (Lys) may be acylated.

General formula (1-a$^3$):

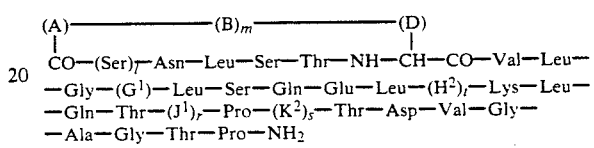

wherein
(A) is a lower alkylene group or a phenylene group;
(B) is a group of —NHCO—, or a group of —S— or an oxyphenylene group;
(D) is a lower alkylene group;
(G$^1$) is a lysine residue (Lys)or an alanine residue (Ala);
(H$^2$) is an asparagine residue (Asn), a glycine residue (Gly), a glutamine residue (Gln), a tyrosine residue (Tyr), a leucine residue (Leu), or an aspartic acid residue (Asp);
(J$^1$) is a tyrosine residue (Tyr) or a leucine residue (Leu);
(K$^2$) is a glutamine residue (Gln) or an asparagine residue (Asn); respectively,
and l, m, r, s and t are each 0 or 1, respectively; provided that, when l, is 0, then A should not be a methylene group; and when m is 0, then A is a phenylene group; further, the amino group in the side-chain of lysine residue (Lys) may be acylated.

General formula (1-b$^1$):

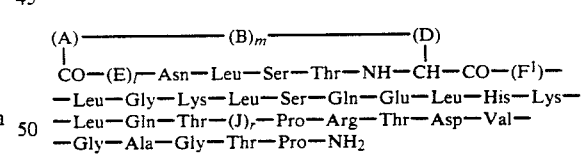

wherein
(A) is a lower alkylene group or a phenylene group;
(B) is a group of —NHCO—, a group of —S— or an oxyphenylene group;
(D) is a lower alkylene group;
(E) is a serine residue (Ser), a γ-aminobutyric acid residue (Abu), or a β-alanine residue (β-Ala);
(F$^1$) is a valine residue (Val), or a glycine residue (Gly);
(J) is a tyrosine residue (Tyr), a D-tyrosine residue (D-Tyr), or a leucine residue (Leu), respectively; and l, m and r are each 0 or 1, respectively; provided that, when l is 0, then A should not be a methylene group; and when m is 0, then A is a phenylene group; further the amino group in the side-chain of lysine residue (Lys) may be acylated.

General formula (1-b$^2$):

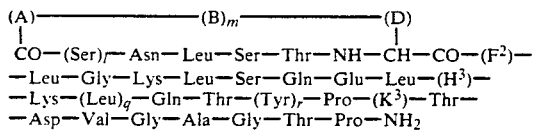

```
CO—(Ser)ᵣ—Asn—Leu—Ser—Thr—NH—CH—CO—(F²)—
—Leu—Gly—Lys—Leu—Ser—Gln—Glu—Leu—(H³)—
—Lys—(Leu)_q—Gln—Thr—(Tyr)ᵣ—Pro—(K³)—Thr—
—Asp—Val—Gly—Ala—Gly—Thr—Pro—NH₂
``` wherein
(A) is a lower alkylene group or a phenylene group;
(B) is a group of —NHCO—, a group of —S— or an oxyphenylene group;
(D) is a lower alkylene group;
(F²) is a valine residue (Val) or an isoleucine residue (Ile);
(H³) is a histidine residue (His) or an asparagine residue (Asn);
(K³) is an arginine residue (Arg) or a glutamine residue (Gln), respectively;
and l, m, q and r are each 0 or 1, respectively; provided that, when l is 0, then A should not be a methylene group; and when m is o, then A is a phenylene group; further, the amino group in the side-chain of lysine residue (Lys) may be acylated; and the carboxyl groups in the side-chains of aspartic acid residue (Asp) and glutamic acid residue (Glu) may be esterified.

General formula (1-c):

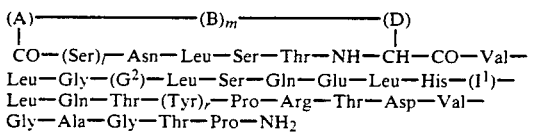

```
CO—(Ser)ᵣ—Asn—Leu—Ser—Thr—NH—CH—CO—Val—
Leu—Gly—(G²)—Leu—Ser—Gln—Glu—Leu—His—(I¹)—
Leu—Gln—Thr—(Tyr)ᵣ—Pro—Arg—Thr—Asp—Val—
Gly—Ala—Gly—Thr—Pro—NH₂
``` wherein
(A) is a lower alkylene group or a phenylene group;
(B) is a group of —NHCO—, a group of —S— or an oxyphenylene group;
(D) is a lower alkylene group;
(G²) is a lysine residue (Lys) or a glycine residue (Gly);
(I¹) is a lysine residue (Lys) or a glycine residue (Gly), respectively;
and l, m and r are each 0 or 1; provided that, when l is 0, then A should not be a methylene group; and when m is 0, then A is a phenylene group; further the amino group in the side-chain of lysine residue (Lys) may be acylated, provided that the case of both (G²) and (I¹) are lysine residue (Lys) at the same time is excluded.

The polypeptide derivatives represented by the general formula (1) and the above-mentioned general formulas (1-a¹), (1-a²), (1-a³), (1-b¹), (1-b²) and (1-c) according to the present invention possess excellent activities for lowering the blood level of calcium, activities as analgesic, activities for inhibiting the secretion of the gastric juice and other pharmacological activities over those shown by natural calcitonins on the basis of the specific chemical structures in each of these general formulas, in addition to the above, the stabilities of these polypeptide derivatives are considerably improved even though under conditions of storing in the state of solutions, the above-mentioned various pharmacological activities are not decreased. Therefore, the polypeptide derivatives according to the present invention are quite effective as agents for curing various symptoms being caused by an extraordinary high blood level of calcium, for example bone Paget's disease, osteoporosis and the like, and analgetics as well as anti-ulcerative agents. In addition to the above, the polypeptide derivatives according to the present invention have excellent long acting property and absorbability, as well as they have features of less side-effects of antigenicity, blood-sugar increasing activity, losing the body weight action, inhibitory effects in intestinal movements, and decreasing food-intake effect and the like, also they have low toxicity, thus in view of these features, the polypeptide derivatives according to the present invention are quite suitable compounds as the above-mentioned drugs.

Next, processes for preparing the polypeptide derivatives according to the present invention are explained in detail as follows.

The polypeptide derivatives represented by the above-mentioned general formula (1) according to the present invention can be prepared basically by conventional methods for synthesizing polypeptides, for example, by a so-called "stepwise method", thus by condensing amino acids with the terminal amino acid stepwise according to the above-mentioned chemical structure in the amino acid sequence so as to prolong the amido bondings (peptide bondings) in sequence, or by, first dividing the above-mentioned chemical structures of polypeptides into several fragments, then each of these divided fragments are synthesized and then by condensing the fragments. Thus, at first, a polypeptide chain corresponding to the above-mentioned chemical structure is prepared, then the free functional groups in the specific N-terminal amino acid being formed during the preparation of said polypeptide is combined with the side-chain functional group of the seventh amino acid or related compound thereof so as to make the desired polypepetide derivative by the ring-closure.

Among the related compounds of the seventh amino acid, some of them include novel compounds, and these related compounds can be prepared from a suitable protected amino acid and a halogenated compound corresponding thereto as the starting materials, by the methods as mentioned below. Thus, the hydroxyl group of Z-Tyr—OCH₃ or the mercapto group of HCl.H-Cys—OCH₃ is reacted with a halogenated lower alkyl carboxylic acid of which the carboxyl group is protected, in the presence of a basic compound in a suitable solvent. As to the basic compound used in this reaction, triethylamine; a metal hydride such as sodium hydride, potassium hydride, lithium hydride or the like; an inorganic basic compound such as potassium carbonate, sodium carbonate, potassium hydrogen carbonate, sodium hydroxide, potassium hydroxide or the like can be used; and as to the solvent, a halogenated hydrocarbon such as dichloromethane, carbon tetrachloride, chloroform, tetrachloroethane or the like; an ether such as dioxane, THF (tetrahydrofuran), dimethoxy ethane or the like; a ketone such as acetone, methyl ethyl ketone or the like; acetonitrile, ethyl acetate, DMF (dimethylformamide), dimethylacetamide, dimethyl sulfoxide or the like can be used. Each of these solvents is used preferably as in the form of anhydrous state. As to the carboxyl group protecting group in the halogenated lower alkyl carboxylic acid of which the carboxyl group is protected, to be reacted with the above-mentioned amino acid may be any group capable of forming a common ester, and as to the ester to be formed from such group, an alkyl ester (methyl, ethyl, propyl, butyl, tert-butyl or the like) or Bzl ester can be typically exemplified. As to the ratio of amounts of the starting materials used in the above reaction, there is not any specific restriction, and generally an equimolar quantity to 5 times the molar quantity, preferably an equimolar quantity to 1.5 times the molar quantity of the above-mentioned carboxylic acid may be used to the amino acid. The above reaction may be carried out generally at about 0° to 100° C., preferably at about room temperature to 60° C., and the reaction is completed generally in about 30 minutes to 120 hours.

As to methods to be employed for synthesizing the peptides as mentioned above, there are concretely described, for example, in "The Peptides" Vol. 1, (1979), pp. 66-100, Chapter 2, by Johan H. Jones, The Formation of Peptide Bonds, (Edided by Erhard Gross and Johannes Meienhofer, published from Academic Press, Inc., New York, N. Y., U. S. A.); and in "PEPTIDO-GOHSEI-NO-KISO-TO-JIKKEN" (Fundamentals and Experiments in the Synthesis of Peptides), by Izumiya, et al., published from Maruzen Publishing Co., Ltd., Tokyo, Japan. For example, azide method, acid chloride method, acid anhydride method, mixed acid anhydride method, DCC (N, N'-dicyclohexylcarbodiimide) method, activated ester methods (such as p-nitrophenyl ester method, N-hydroxysuccinimide method, cyanomethyl ester method, etc.), Woodward-K reagent method, carboxyl diimidazol method, oxidation-reduction method, DCC/additive (such as HONB, HOBT and HOSu) method and the like can be exemplified. In carrying out the above-mentioned methods, either solid phase synthesis method or liquid phase synthesis method can be employed. In the case, when the solid phase synthesis method is carried out, at the first step, a C-terminal amino acid (an amino acid in which the terminal amino group is protected) is coupled to an insoluble carrier through the carboxyl group thereof. As to the insoluble carrier, there is not any specific restriction thereto, and it can be selected from any material having a coupling ability to a reactive carboxyl group, for example, a halogenomethyl resin or the like, phenol resin, tert-alkyloxycarbonylhydrazide resin, benzhydrylamine resin, and the like can be used. Next, after the removal of amino-protecting group, then in accordance with the amino acid sequence represented by the above-mentioned general formula (1), each one of the amino group protected-amino acid is coupled sequentially with another amino group protected-amino acid by condensing the reactive amino group with the reactive carboxyl group through condensation reactions (peptide bonding formation reaction and acid-amide bonding formation reaction, hereinafter referred to simply as "condensation"), so as to proceed the synthesis of the polypeptide by means of a stepwise method and to extend the chain length thereof suitably within the 32nd to 8th positions in the whole amino acid sequence, then the thus obtained polypeptide is coupled to another polypeptide which is corresponding to the remaining portion of the polypeptide of the present invention, which is synthesized separately by a method such as a liquid phase synthesis method, and thus prepared polypeptide is obtained by removing the insoluble carrier to yield the desired corresponding polypeptide. The desired ring-formation reaction of polypeptide according to the present invention is carried out by an acid amide formation reaction method similar to that employed in the above-mentioned condensation reaction.

In carrying out of the above-mentioned various methods, each one of amino acids, for example Arg, Tyr, Glu, Thr, Asp, Lys, His, Ser and the like, having the side-chain functional group may preferably be protected by means of protecting their side-chain functional groups by using conventional protecting groups, then said protecting groups can be removed after the completion of the above-mentioned reactions. The functional groups relating to the above-mentioned reactions are usually activated. Each of these reactions is known in the art and the reagents being used therein may be selected suitably from known reagents.

For example, as to groups for protecting the amino group, there may be exemplified benzyloxycarbonyl, tert-butoxycarbonyl, tert-amyloxycarbonyl, isobornyloxycarbonyl, p-methoxybenzyloxycarbonyl, 2-chlorobenzyloxycarbonyl, adamantyloxycarbonyl, trifluoroacetyl, phthalyl, formyl, o-nitrophenylsulfenyl, diphenylphosphinothioyl and 9-fluorenylmethoxycarbonyl groups and the like.

As to groups for protecting the carboxyl group, any groups capable of forming, for example, alkyl esters (chain- or cyclic-alkyl esters, such as methyl, ethyl, propyl, butyl, tert-butyl and cyclohexyl esters, and the like), Bzl ester, p-nitrobenzyl ester, p-methoxybenzyl ester, p-chlorobenzyl ester, benzhydryl ester, benzyloxycarbonylhydrazide, tert-butyloxycarbonylhydrazide and tritylhydrazide and the like can be exemplified.

As to groups for protecting the guanidino group of Arg, there may be exemplified p-toluenesulfonyl, nitro, benzyloxycarbonyl and amyloxycarbonyl groups and the like.

The hydroxyl groups of Ser and Thr can be protected by means of esterification or etherification method, but they may not necessarily be protected. As to groups suitable for esterifying the hydroxyl groups, there may be exemplified lower alkanoyl groups such as acetyl group and the like, aroyl groups such as benzoyl group and the like, and groups derived from carbonic acid such as benzyloxycarbonyl, ethyloxycarbonyl groups and the like. Further, as to groups suitable for etherifying the hydroxyl groups, there may be exemplified benzyl, tetrahydropyranyl, tert-butyl groups and the like.

As to groups for protecting the hydroxyl group of Tyr, there may exemplified Bzl, 2,6-dichlorobenzyl, benzyloxycarbonyl, acetyl, and p-toluenesulfonyl groups and the like.

As to groups for protecting the side-chain amino group of Lys, there may be exemplified acyl groups, for example lower alkanoyl groups, substituted benzoyl groups which may have 1 to 3 substituents selected from the group consisting of a lower alkyl group, a lower alkoxy group and a halogen atoms, on the phenyl ring, and further benzyloxycarbonyl, 2-chlorobenzyloxycarbonyl, 2,6-dichlorobenzyloxycarbonyl, Boc and p-toluenesulfonyl groups and the like.

As to groups for protecting the imino group of His, there may be exemplified p-toluenesulfonyl and Bzl groups and the like.

The protection of the carboxyl groups of Asp and Glu may be carried out by esterifying with an alcohol for example benzyl alcohol, methanol, ethanol, tert-butyl alcohol, and cyclohexyl alcohol and the like.

As to the activated carboxyl groups, there may be exemplified the corresponding acid chloride, acid anhydride or mixed acid anhydride, azide, activated ester (esters of pentachlorophenol, p-nitrophenol, N-hydroxysuccinimide, 1-hydroxybenzotriazole and N-hydroxy-5-norbornene-2,3-dicarboxyimide and the like).

In the above-mentioned method, the condensation of the reactive amino group with the reactive carboxyl group can be carried out in the presence of a basic compound, in a suitable solvent. As to the suitable basic compound, an organic basic compound such as triethylamine, trimethylamine, N,N-diisopropylethylamine, pyridine, dimethylaniline, N-methylmorpholine, 1,5-diazabicyclo[4,3,0]-5-nonene [DBN], 1,5-diazabicyclo[5,4,0]-5-undecene [DBU], 1,4-diazabicyclo[2,2,2]octane [DABCO]and the like; an compound such as potassium carbonate, sodium carbonate, potassium hydrogen carbonate, sodium hydrogen carbonate and the like can be used. As to the solvent, any solvent which is known as a suitable solvent for this type of condensation reaction, for example anhydrous or water-containing DMF, dimethyl sulfoxide (DMSO), pyridine, chloroform, dioxane, dichloromethane, THF, ethyl acetate, N-methylpyrrolidone and hexamethylphosphoric triamide (HMPA) and the like and mixed solvents thereof can be used. As to the ratio of amounts of the starting materials used in this reaction, there is not any specific restriction thereto, and generally, an equimolar to 5 times the molar quantity, preferably an equimolar to 1.5 times the molar quantity of one starting material to another starting materials may be used. The reaction temperature may be within usual temperature range being employed in this type of condensation reaction, and generally it is selected suitably from the range of about −40° C. to about 60° C., preferably, from about −20° C. to about 40° C. The reaction may generally be carried out within about several minutes to 120 hours.

Among the above-mentioned condensation reactions, mixed acid anhydride method is carried out in a suitable solvent, in the presence of a basic compound, by using an alkyl halocarboxylic acid for example methyl chloroformate, methyl bromoformate, ethyl chloroformate, ethyl bromoformate, isobutyl chloroformate and the like. As to the basic compound, an organic basic compound such as triethylamine, trimethylamine, N, N'-diisopropylethylamine, pyridine, dimethylaniline, N-methylmorpholine, DBN, DBU and DABCO and the like, an inorganic basic compound such as potassium carbonate, sodium carbonate, potassium hydrogen carbonate, and sodium hydrogen carbonate can be used. Further, as to the solvent, any solvent which may be used for such mixed acid anhydride method, for example a halogenated hydrocarbon such as methylene chloride, chloroform, dichloroethane and the like, an aromatic hydrocarbon such as benzene, toluene, xylene and the like, an ether such as diethyl ether, THF, dimethoxyethane and the like, an ester such as methyl acetate, ethyl acetate and the like, an aprotic polar solvent such as DMF, DMSO, HMPA and the like may be used. The reaction is carried out, generally under conditions of about −20° to 100° C., preferably at about −20° to 50° C., and is completed, generally within several minutes to about 10 hour, preferably in about several minutes to about 2 hours.

In explaining the above-mentioned azide method in detail, this method of reaction is carried out, at first, by activating the carboxyl group of amino acid with an alcohol such as methyl alcohol, ethyl alcohol, benzyl alcohol or the like, then thus obtained activated carboxyl group is reacted with hydrazine hydrate in a suitable solvent to obtain the desired azide compound. As to the solvent, dioxane, DMF, DMSO, HMPA, an alcohol or a mixed solvent thereof can be used. The amount of hydrazine hydrate is generally about 5 to 20 times the molar quantity, preferably 5 to 10 times the molar quantity thereof to the activated carboxyl group. The reaction is generally carried out at temperature below 50° C., preferably at −20° to 30° C., so as to obtain a compound (hydrazine derivative) in which the carboxyl group portion is substituted with hydrazine. Further, a compound in which the carboxyl group portion is substituted with azide can be prepared by reacting the above-mentioned hydrazine derivative with a nitrous acid compound in the presence of an acid in a suitable solvent. As to acid used in this reaction, hydrochloric acid can be used typically, and as to the nitrous acid compound, sodium nitrite, isoamyl nitrite, nitrosyl chloride or the like can be used. Said nitrous acid compound may be used in an amount generally about an equimolar to 2 times the molar quantity, preferably about an equimolar to 1.5 times the molar quantity to the hydrazine compound. The reaction is generally carried out at about −20° to 0° C., preferably at about −20° to −10° C., and is completed in about several minutes to 30 minutes.

The above-mentioned various condensation reactions may be carried out in the presence of a suitable condensing agent, for example a carbodiimide reagent such as DCC, WSC, WSC.HCl or the like; N,N'-carbonyldiimidazole, tetraethylpyrophosphine or the like. Said condensing agent is used in an amount of an equimolar to about 4 times the molar quantity to the starting material. The above-mentioned reaction by using said condensing agent is carried out in a suitable solvent for example a halogenated hydrocarbon such as dichloromethane, chloroform, carbon tetrachloride, tetrachloroethane or the like; an ether such as dioxane, THF, dimethoxyethane or the like, a ketone such as acetone, methyl ethyl ketone or the like; acetonitrile, ethyl acetate, DMF, dimethylacetamide, DMSO or the like, preferably an anhydrous solvent thereof, and at reaction temperature of about, generally −10° to 60° C.; preferably about 0° C. to room temperature, and in about several ten minutes to 120 hours.

In the above-mentioned various reaction steps and in the final reaction step, when the protecting group is removed necessarily, said removal reactions can be carried out by method similar to those employed in usual reactions for removal of protecting groups. As to the method for removal of the protecting groups, hydrogenation by using a catalyst such as palladium-carbon, palladium black or the like; reducing method by using sodium metal as the reducing agent in a liquid ammonia; removal reaction under a basic condition by using piperidine or the like; and acidolysis by using a strong acid such as trifluoroacetic acid, hydrochloric acid, hydrogen fluoride, methanesulfonic acid, hydrobromic acid or the like can be exemplified.

In carrying out of the hydrogenation by using the above-mentioned catalyst, the reaction can be conducted under conditions of 1 atmospheric hydrogen pressure, at about 0° to 40° C., and the amount of the catalyst may be used generally within the range of about 100 mg to 1 g, and the reaction can be completed in about 1 hour to several days. The above-mentioned acidolysis can be carried out in the presence of a solvent, and generally at about −40° to 60° C., preferably at about −20° to 20° C., for about several minutes to several hours. The amount of the acid used in the acidolysis may be generally a large excess quantity to the starting material. In the carrying out of the acidolysis, when the only protecting group of the amino group is removed, trifluoroacetic acid or hydrochloric acid is preferably used as the acid. Furthermore, in carrying out of the reduction by use of sodium metal in an aqueous ammonia, the reduction is carried out by using sodium metal in an amount that the reaction mixture keeps permanent blue in color for about 30 seconds to 10 minutes, and generally at about −40° to −70° C.

In the present invention, chain structural polypeptide derivatives are prepared by the above-mentioned condensation reactions, as well as follows by said preparation step for obtaining such polypeptides, or on the way of said step, it is important to employ the specific cyclization reaction process step in accordance with similar condensation reaction, thus ring closing reaction of the free functional group of N-terminal amino acid formed in the preparation step of the above-mentioned polypeptides, with the side-chain functional group of the 7th amino acid or its related compound.

As to one of the preferably examples of preparation of the polypeptides according to the present invention is that, for example as illustrated in Example 1 below-mentioned, at the first a protected polypeptide

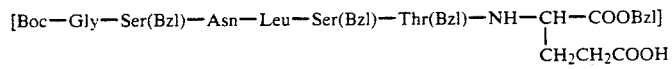

which is corresponding to 1st to 7th amino acid sequence counted from the N-terminal is prepared, then this product is converted into an activated ester by adding TFA—ONp in dried pyridine, next, it is subjected to removal of Boc group by using TFA, then thus obtained protected peptide

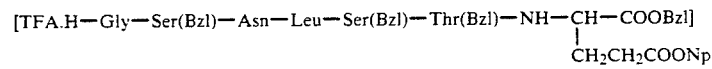

is dissolved in DMF, and the solution thus obtained is added dropwise into a large amount of dried pyridine 50° C., with vigorous stirring condition for taking several hours, further the mixture is stirred for additional several hours to obtain the desired cyclized protected peptide, next a peptide of the 8th to 10th position in the amino acid sequence is condensed by means of fragment condensation to obtain the protected decapeptide.

On the other hand, a protected peptide of the 11th to 32nd amino acid in the amino acid sequence is synthesized by the stepwise method or a fragment condensation method, then this is coupled to the previously prepared protected decapeptide, and then is subjected to removal reaction of the protecting group.

The thus obtained polypeptides prepared by various methods as mentioned above can be separated and purified by methods usually employed in separation of peptides, for example, solvent extraction method, distribution method, column chromatography method and the like. The desired polypeptide derivatives represented by the general formula (1) according to the present invention can be thus obtained.

The polypeptide derivatives thus obtained according to the present invention are generally in the form of free bases or salts thereof, and also have iological activities similar to those shown by the corresponding original natural polypeptides, and thus they are useful as various pharmaceutical preparations. Thus, they are converted into pharmaceutical acceptable acid-addition salts or complexes thereof by means of conventional methods. The examples of said acids for preparing the above-mentioned acid-addition salts include inorganic acids such as hydrochloric acid, hydrobromic acid, sulfuric acid, phosphoric acid and the like; organic acids such as formic acid, acetic acid, propionic acid, glycolic acid, lactic acid, pyruvic acid, oxalic acid, succinic acid, malic acid, tartaric acid, citric acid, benzoic acid, salicylic acid, a lower alkanesulfonic acid, benzenesulfonic acid, toluenesulfonic acid and the like. The above-mentioned complexes can be prepared by adding a certain types of inorganic or organic substance which gives long-acting property to the polypeptides. The examples of such inorganic substances to be used for the formation of such complexes include inorganic compounds which are derived from metals such as calcium, magnesium, cobalt, zinc and the like, particularly, phosphates, pyrophosphates, polyphosphates of these metals which are salts thereof having slight solubility, and hydroxide thereof; and other inorganic compounds such as polyphosphates of alkali metals. Further, the examples of said organic materials include non-antigenic gelatin, CMC (carboxymethyl cellulose), phosphoric acid esters or sulfonic acid esters of alginic acid, dextran, polyalcohol phytic acid, polyglutamic acid, protamine and the like.

In using the polypeptide derivatives of the present invention as pharmaceutical preparations, they can be used in the form of pharmaceutical compositions together with usual pharmaceutically acceptable carriers, including diluents or excipients such as fillers, binders, wetting agents, disintegrators, surface active agents, lubricants and the like. As to the form of pharmaceutical compositions, any type of forms may be selected from a wide range thereof depend on the purpose of curing, and the examples of pharmaceutical compositions including tablets, pills, powders, liquids, suspensions, emulsions, granules, capsules, suppositories, injection preparations (including solutions, suspensions, and the like), and ointments. For the purpose of to shape in the form of tablets, carriers which are widely used in this field can be used, for example excipients such as lactose, sucrose, sodium chloride, glucose, urea, starch, calcium carbonate, kaolin, crystalline cellulose, silicic acid, and the like; binding agents such as water, ethanol, propanol, simple syrup, glucose solution, starch solution, gelatin solution, carboxymethyl cellulose, shelac, methyl cellulose, potassium phosphate, polyvinylpyrrolidone, and the like; disintegrators such as dried starch, sodium alginate, agar-agar powder, laminalia powder, sodium hydrogen carbonate, calcium carbonate, esters of polyoxyethylenesorbitan fatty acids, sodium laurylsulfate, monoglycerides of stearic acid, starch, lactose and the like; disintegration inhibitors such as sucrose, stearin, coconut butter, hydrogenated oil and the like; absorption accelerators such as quarternary ammonium bases, sodium laurylsulfate and the like; wetting agents such as glycerin, starch and the like; absorbing agents such as starch, lactose, kaolin, bentonite, colloidal silicic acid and the like; and lubricants such as purified talc, stearic acid salts, boric acid powder, polyethylene glycol and the like. In case of preparing the tablets, they can be further coated with usual coating materials to make them as sugar coated tablets, gelatin film coated tablets, tablets coated with enteric coatings, tablets coated with films or double layered tablets and multi-layered tablets.

For the purpose of to shape in the form of pills, carriers which are known and widely used in this field can also be used, for example, excipients such as glucose, lactose, starch, coconut butter, hydrogenated vegetable oils, oils, kaolin, talc and the like; binding agents such as powdered gum arabic, powdered tragacanth gum, gelatin, ethanol and the like; and desintegrators such as laminalia, agar-agar and the like are included.

For the purpose of to shape in the form of suppositories, carriers which are known and widely used in this field can also be used, for example, polyethylene glycols, coconut butter, higher alcohols, esters of higher alcohols, gelatin, semi-synthesized glycerides and the like are included.

For the purpose of to shape in the form of capsule preparations, the polypeptide derivatives of the present invention can be mixed with the above-mentioned carriers, and the obtained mixture is filled in solid gelatin capsules or in soft capsules to prepare capsule preparations.

For the purpose of to shape in the form of injection preparations, solutions, emulsions or suspensions of the polypeptide derivatives of the present invention are sterilized and are preferably isotonic to blood, and in making them in these forms, diluents for example water, ethyl alcohol, polyethylene glycols, propylene glycol, ethoxylated isostearyl alcohol, polyoxylated isostearyl alcohol, and polyoxyethylenesorbitan fatty acid esters, and the like can be used. In these cases, adequate amounts of sodium chloride, glucose or glycerin can be added to the desired preparations for the purpose of to have them isotonic to the blood, furthermore, usual dissolving agents, buffers, analgesic agents, and the like may be added. In addition to the above, coloring agents, preservatives, perfumes, seasoning agents, sweetening agents as well as other medicines can also be added into the desired injection preparations.

For the purpose of to shape in the form of pastes, creams and gels, diluents which are known and widely used in this field can also be used, for example, white petrolatum, paraffin, glycerin, cellulose derivatives, polyethylene glycols, silicones, bentonite and the like are included.

The amount of the polypeptide derivatives of the present invention to be contained in these pharmaceutical compositions are not specifically restricted, and it can be selected suitably from wide range, and usually 1 µg to 1 mg thereof may be contained in the compositions.

Methods for administering the above-mentioned pharmaceutical compositions are not specifically restricted, and they can be selected depend on each of their composition forms, the age of the patient, distinction of sex and other conditions, degree of the symptoms and the like. For example, tablets, pills, liquids, suspensions, emulsions, granules and capsules are administered orally; injection preparations are administered intravenously singly or are mixed with injection transfusions such as glucose solutions and amino acids solutions, and if necessary the injection preparations are administered singly intramuscularly, intracutaneously, subcutaneously or intraperitoneally. The suppositories are administered into rectum.

The dosage of the above-mentioned pharmaceutical compositions of the present invention are suitably selected depend on the usages, the age of the patient, distinction of sex and other conditions, degree of the symptoms, and usually they are administered so as to give about 20 ng to 20µg/kg of the body weight/day of the polypeptide derivatives of the present invention, and such pharmaceutical compositions can be administered dividedly in 1 to 4 times a day.

The polypeptide derivatives of the present invention are indeed effective as the active ingredient when the pharmaceutical composition containing thereof is administered singly, addition to the above, there can be expected increasing of the absorption ratio and pharmacological effects when said pharmaceutical composition is administered in the form of being mixed with usual protein absorption accelerating agents, or is administered together with the above-mentioned protein absorption accelerating agents at the same time. As to these protein absorption accelerating, agent, the examples including, preferably, trypsin inhibitors [Life Science, Vol. 31, 2837;(1982); Biochemical Pharmacology, Vol. 36, 1035, (1987)]; IGAKU-NO-AYUMI (Progress of the Medicine), Vol. 138, 59, (1986)-; chymotrypsins inhibitors [Japanese Patent Kokai (Laid-open) No. 58-225080 (1983), The Journal of Biochemistry, Vol. 95, 319,(1984); Biochemistry, Vol. 2, 252, (1963); Journal of the American Chemical Society, Vol. 93, 2351, (1971); Journal of Pharmacy and Pharmacology, Vol. 32, 182, (1980); and The Journal of Antibiotics, Vol. 23, 425, (1970)].

EFFECTS OF THE INVENTION

According to the present invention, calcitonin derivatives (polypeptide derivatives) which possess excellent activity for lowering the blood level of calcium, the activity as analgesic, and the activity for inhibiting secretion of the gastric juice, and they are stable even in the state of solutions.

Particularly, the polypeptide derivatives according to the present invention have properties, i.e., (1) high solubility in water, (2) good absorbability (3) good long-acting property, (4) good stability, (5) strong pharmacological activities, and (6) low toxicity, thus they possess excellent properties as pharmaceutical applications.

Next, in order to explain the present invention in more detail, examples for producing raw material compounds from which polypeptide derivatives of the present invention are produced, are mentioned as Reference Examples, and then examples for producing polypeptide derivatives of the present invention are mentioned as Examples.

Further, examples for producing the polypeptide derivatives of the present invention are mentioned as Reference Preparation Examples. Furthermore, Pharmacological Test Examples for the polypeptide derivatives of the present invention are mentioned.

In each example, the amino acid analysis was conducted by adding 6 N hydrochloric acid (phenol added thereto) to a test compound, hydrolyzing the test compound at 110° C. for 24 hours or 48 hours, subjecting the reaction mixture to vacuum drying and subjecting the residue to analysis by amino acid analyzer.

REFERENCE EXAMPLE 1

Preparation of Boc-Thr(Bzl)-Glu—OBzl

To a solution of 2.83 g of H-Glu—OBzl dissolved in 40 ml of acetonitrile were added 3.3 ml of triethylamine and 5.00 g of Boc-Thr(Bzl)—OSu, with ice-cooling. The mixture was stirred overnight at room temperature. The reaction mixture was concentrated under reduced pressure. The residue was dissolved in 50 ml of ethyl acetate and the resulting solution was washed with 30 ml of water twice. The ethyl acetate layer was dried with anhydrous magnesium sulfate. The solvent was removed by distillation to dry the ethyl acetate layer, whereby 5.50 g (yield: 87.2%) of the above objective compound was obtained in a powder form.

REFERENCE EXAMPLE 2

Preparation of Boc-Ser(Bzl)-Thr(Bzl)-Glu—OBzl.H$_2$O 5.50 g of Boc-Thr(Bzl)-Glu—OBzl was dissolved in 15 ml of TFA with ice-cooling. The mixture was stirred for 30 minutes at room temperature. The reaction mixture was concentrated under reduced pressure. The residue was subjected to vacuum drying over sodium hydroxide.

The resulting product was dissolved in 50 ml of acetonitrile and then neutralized with triethylamine with ice-cooling. Thereto was added 4.20 g of Boc-Ser(Bzl)—OSu and the mixture was stirred overnight at room temperature. The reaction mixture was concentrated under reduced pressure. The residue was dissolved in 50 ml of ethyl acetate. The ethyl acetate layer was washed with 20 ml of 1 N hydrochloric acid twice and then with 20 ml of water twice. The ethyl acetate layer was then concentrated under reduced pressure. The residue was washed with n-hexane to obtain 6.90 g (yield: 91.6%) of the above objective compound in a powder form.

Elemental analysis (C$_{38}$H$_{47}$N$_3$O$_{10}$.H$_2$O):
Calculated (%): C 63.06, H 6.82, N 5.81.
Found (%): C 63.33, H 6.60, N 5.80.
Amino acid analysis:
Thr: 0.98 (1)
Ser: 0.93 (1)
Glu: 1.09 (1).

REFERENCE EXAMPLE 3

Preparation of Boc-Asn-Leu—OEt 5.00 g of H-Leu—OEt.HCl, 5.95 g of Boc-Asn—OH and 4.11 g of HOBT.H$_2$O were suspended in 100 ml of THF. Thereto was added 4.70 ml of WSC with ice-cooling. The mixture was stirred for 7 hours at room temperature. To the reaction mixture were added 100 ml of ethyl acetate and 200 ml of water to effect extraction. The ethyl acetate layer was washed with 50 ml of a saturated aqueous sodium bicarbonate solution three times, 50 ml of a saturated aqueous sodium chloride solution once, 50 ml of 1 N hydrochloric acid three times and 50 ml of a saturated aqueous sodium chloride solution once in this order, dried with anhydrous magnesium sulfate and concentrated under reduced pressure. The residue was solidified with isopropyl ether to obtain 7.00 g (yield: 72.9%) of the above objective compound having a melting point of 155°–157° C.

REFERENCE EXAMPLE 4

Preparation of Boc-Ser(Bzl)-Asn-Leu—OEt 6.90 g of Boc-Asn-Leu—OEt was dissolved in 25 ml of TFA with ice-cooling. The mixture was stirred for 30 minutes at room temperature. The reaction mixture was concentrated under reduced pressure. The residue was mixed with isopropyl ether and n-hexane. The resulting precipitate was separated by decantation and dried under reduced pressure over sodium hydroxide.

The resulting product was dissolved in 50 ml of THF. Thereto were added 5.18 ml of triethylamine and 7.30 g of Boc-Ser(Bzl)—OSu with ice-cooling. The mixture was stirred for 5 hours at room temperature. The reaction mixture was mixed with 100 ml of ethyl acetate and 50 ml of water to effect extraction. The ethyl acetate layer was washed with 50 ml of water three times and then concentrated under reduced pressure. The residue was mixed with isopropyl ether and the resulting precipitate was collected by filtration and dried to obtain 8.20 g (yield: 80.6%) of the above objective compound having a melting point of 149°–151° C.

REFERENCE EXAMPLE 5

Preparation of Boc-Gly-Ser(Bzl)-Asn-Leu—OEt 3.00 g of Boc-Ser(Bzl)-Asn-Leu—OEt was dissolved in 10 ml of TFA with ice-cooling. The mixture was stirred for 30 minutes at room temperature. The reaction mixture was concentrated under reduced pressure. The residue was mixed with isopropyl ether, and the resulting precipitate was collected by filtration and dried under reduced pressure over sodium hydroxide.

The resulting product was dissolved in 50 ml of THF and then neutralized with triethylamine with ice-cooling. Thereto was added 1.50 g of Boc-Gly—OSu. The mixture was stirred overnight at room temperature. The reaction mixture was concentrated under reduced pressure. The residue was dissolved in 50 ml of ethyl acetate. The solution was washed with 20 ml of 1 N hydrochloric acid twice and 20 ml of a saturated aqueous sodium chloride solution twice, dried with anhydrous magnesium sulfate and concentrated under reduced pressure. The residue was washed with isopropyl ether to obtain 2.90 g (87.7%) of the above objective compound having a melting point of 165°–167° C.

REFERENCE EXAMPLE 6

Preparation of Boc-Gly-Ser(Bzl)-Asn-Leu—NHNH$_2$ 2.80 g of Boc-Gly-Ser(Bzl)-Asn-Leu—OEt was dissolved in 30 ml of methanol. Thereto was added 2.25 ml of NH$_2$NH$_2$.H$_2$O. The mixture was allowed to stand for 2 days at room temperature. The resulting precipitate was collected by filtration and washed with methanol to obtain 2.16 g (yield: 79.0%) of the above objective compound having a melting point of 221°–224° C.

REFERENCE EXAMPLE 7

Preparation of
Boc-Gly-Ser(Bzl)-Asn-Leu-Ser(Bzl)-Thr(Bzl)-Glu—OBzl 0.86 g of Boc-Ser(Bzl)-Thr(Bzl)-Glu—OBzl.H$_2$O was dissolved in 5 ml of TFA with ice-cooling. The solution was stirred for 30 minutes at room temperature. The reaction mixture was concentrated under reduced pressure. The residue was dried under reduced pressure over sodium hydroxide.

To a solution of 0.78 g of Boc-Gly-Ser(Bzl)-Asn-Leu—N₂H₃ dissolved in 10 ml of DMF were added, with stirring at −15° C., 0.73 ml of 4 N hydrochloric acid/dioxane and 0.18 ml of isoamyl nitrite in this order to form an azide. Then, triethylamine was added to effect neutralization.

The above product obtained by TFA treatment was dissolved in 10 ml of DMF and neutralized with triethylamine with ice-cooling. Thereto was added the above azide compound, and the mixture was allowed to stand overnight at 4° C. The reaction mixture was concentrated under reduced pressure. The residue was mixed with water to solidify. The resulting precipitate was collected by filtration and recrystallized from methanol to obtain 1.10 g (yield: 79.4%) of the above objective compound having a melting point of 194°–196° C.

REFERENCE EXAMPLE 8

Preparation of ⌐Gly—Ser(Bzl)—Asn—Leu—Ser(Bzl)—
⌐
Thr(Bzl)—Glu—OBzl.½H₂O 1.00 g of Boc-Gly-Ser(Bzl)-Asn-Leu-Ser(Bzl)-Thr(Bzl)-Glu—OBzl was dissolved in 10 ml of dry pyridine. Thereto was added 1.00 g of TFA—ONp and the mixture was allowed to stand for 8 hours at 40° C. The reaction mixture was concentrated under reduced pressure. The residue was solidified with isopropyl ether. The resulting precipitate was collected by filtration, washed with isopropyl ether and dried. The product was dissolved in 8 ml of TFA with ice-cooling. The solution was stirred for 30 minutes at room temperature. The reaction mixture was concentrated under reduced pressure, and the residue was dried under reduced pressure over sodium hydroxide.

The above TFA-treated product was dissolved in 15 ml of DMF. The solution was dropped into 700 ml of dry pyridine in 30 minutes with stirring at room temperature. The mixture was stirred for 5 hours at 50° C. The reaction mixture was concentrated under reduced pressure. The residue was mixed with 50 ml of ethyl acetate. The mixture was washed with 30 ml of 1 N hydrochloric acid three times and 30 ml of a saturated aqueous sodium chloride solution three times, dried with anhydrous magnesium sulfate and concentrated under reduced pressure to remove ethyl acetate. The residue was mixed with methanol-ethyl acetate, and the insolubles were removed by filtration and the filtrate was concentrated. The residue was mixed with isopropyl ether, and the resulting precipitate was collected by filtration and washed with isopropyl ether and a small amount of ethyl acetate to obtain 0.46 g (yield: 50.7%) of the above objective compound having a melting point of 203°–207° C.

REFERENCE EXAMPLE 9

Preparation of ⌐Gly—Ser(Bzl)—Asn—Leu—Ser(Bzl)—
⌐
Thr(Bzl)—Glu—N₂H₃

3.30 g of

⌐Gly—Ser(Bzl)—Asn—Leu—Ser(Bzl)—
⌐
Thr(Bzl)—Glu—OBzl.½H₂O was dissolved in 100 ml of methanol. Thereto was added 2.00 ml NH₂NH₂.H₂O. The mixture was allowed to stand for 2 days at room temperature. The reaction mixture was concentrated under reduced pressure. The residue was washed with isopropyl ether and the insolubles were collected by filtration. The insolubles were then suspended in a methanol-ethyl acetate mixture. The suspension was concentrated under reduced pressure. The resulting insolubles were filtered and dried to obtain 1.98 g (yield: 65.2%) of the above objective compound having a melting point of 230°–233° C.

REFERENCE EXAMPLE 10

Preparation of Boc-Leu-Gly—OEt 9.10 ml of WSC was gradually added to 100 ml of a solution of 12.47 g of Boc-Leu—OH.H₂O, 6.98 g of HCl.H-Gly—OEt and 6.76 g of HOBT dissolved in dichloromethane, with ice-cooling. The mixture was stirred for 42 hours at room temperature. The reaction mixture was mixed with 100 ml of 1 N hydrochloric acid, and the resulting precipitate was removed by filtration. The filtrate was washed with 100 ml of 1 N hydrochloric acid, two 100-ml portions of a saturated aqueous sodium bicarbonate solution and 100 ml of a saturated aqueous sodium chloride solution in this order, dried with anhydrous magnesium sulfate and concentrated under reduced pressure. To the residue was added petroleum ether to crystallize the residue. The resulting crystal was recrystallized from ethyl acetate-petroleum ether to obtain 8.68 g (yield: 56.6%) of the above objective compound having a melting point of 79.5°–82.5° C.

REFERENCE EXAMPLE 11

Preparation of Boc-Val-Leu-Gly—OEt 7.66 g of Boc-Leu-Gly—OEt was dissolved in 30 ml of TFA with ice-cooling. The solution was stirred for 30 minutes at room temperature. The reaction mixture was concentrated under reduced pressure. The residue was washed with petroleum ether and dried under reduced pressure over sodium hydroxide. The resulting product was dissolved in 60 ml of DMF and adjusted to a pH 6 with triethylamine with ice-cooling. Thereto were added 5.43 g of Boc-Val—OH, 3.38 g of HOBT and 4.79 ml of WSC, and the mixture was stirred for 20 hours at room temperature. 200 ml of water was added to the reaction mixture. The resulting mixture was extracted with two 70-ml portions of ethyl acetate. The two organic layers were combined, washed with 1 N hydrochloric acid, a saturated aqueous sodium bicarbonate solution and a saturated aqueous sodium chloride solution each two times and then dried with anhydrous magnesium sulfate. The resulting solution was concentrated under reduced pressure to remove ethyl acetate. The residue was mixed with petroleum ether to crystallize the residue. The crystal obtained was recrystallized from diethyl ether-petroleum ether twice to obtain 8.03 g (yield: 79.2%) of the above objective compound having a melting point of 69°–73.5° C.

REFERENCE EXAMPLE 12

Preparation of Boc-Val-Leu-Gly—OH 7.3 g of Boc-Val-Leu-Gly—OEt was dissolved in 50 ml of ethanol. Thereto was added 20 ml of 1 N aqueous sodium hydroxide solution with ice-cooling, and the mixture was stirred for 1 hour. The reaction mixture was adjusted to pH 7 with 1 N hydrochloric acid and concentrated under reduced pressure. The residue was washed with diethyl ether. The aqueous layer was adjusted to pH 2 with 1 N hydrochloric acid with ice-cooling and extracted with three 60-ml portions of ethyl acetate. The organic layers were combined, washed with a saturated aqueous sodium chloride solution and dried with anhydrous magnesium sulfate. The resulting solution was concentrated under reduced pressure to remove ethyl acetate. The residue was mixed with petroleum ether to crystallize the residue, whereby 5.33 g (yield: 78.4%) of the objective compound was obtained.

Melting point: 99°–118° C.

Amino acid analysis:

Val: 0.95 (1)
Leu: 0.95 (1)
Gly: 1.10 (1).

REFERENCE EXAMPLE 13

Preparation of

Preparation of ⌐Gly—Ser(Bzl)—Asn—Leu—

Ser(Bzl)—Thr(Bzl)—Glu—Val—Leu—Gly—OH 2.20 g of Boc-Val-Leu-Gly—OH was dissolved in 10 ml of TFA with ice-cooling. The solution was stirred for 30 minutes at room temperature. The reaction mixture was concentrated under reduced pressure. The residue was dried under reduced pressure over sodium hydroxide.

1.00 ml of 4 N hydrochloric acid/dioxane and 0.40 ml of isoamyl nitrite were added in this order to a solution of 1.90 g of ⌐Gly—Ser(Bzl)—Asn—Leu—Ser(Bzl)—

Thr(Bzl) — Glu—N$_2$H$_3$ dissolved in 20 ml of DMF, with stirring at −15° C., to form an azide. Then, triethylamine was added to effect neutralization.

The above TFA-treated product was dissolved in 40 ml of DMF and then neutralized with triethylamine with ice-cooling. Thereto was added the above azide compound. The mixture was stirred overnight with ice-cooling. The reaction mixture was concentrated under reduced pressure. The residue was mixed with 0.5 N hydrochloric acid. The resulting precipitate was collected by filtration and washed with water and hot methanol in this order to obtain 1.78 g (yield: 74.2%) of the above objective compound having a melting point of 244°–250° C.

REFERENCE EXAMPLE 14

Preparation of L-2-amino-3-(4-carboxyphenyl)propionic acid.1/2H$_2$O 11.0 g of DL-2-acetamino-3-(4-carboxyphenyl)propionic acid was suspended in 20 ml of water. Thereto was slowly added 2 N aqueous sodium hydroxide solution to adjust the suspension to pH 7.5. Separately, 0.50 g of cobalt acetate tetrahydrate and 3.0 g of acylase (a product of Tokyo Kasei, 10,000 U/g) were dissolved in 30 ml of water. The resulting insolubles were removed by filtration to obtain a solution. This solution was added to the above suspension, and the mixture was stirred overnight at 37° C. During this period, the pH of the mixture was adjusted to 7–8 by addition of 6 N hydrochloric acid. The resulting insolubles were collected by filtration and dissolved in 2 N aqueous sodium hydroxide solution. The solution was adjusted to pH 3 with 6 N hydrochloric acid. The resulting precipitate was collected by filtration and washed with methanol to obtain 3.47 g (yield: 36.3%) of the above objective compound having a melting point of 290°–294° C. (decomposed).

REFERENCE EXAMPLE 15

Preparation of L-2-benzyloxycarbonylamino-3-(4-carboxyphenyl)propionic acid [Z-4-CPA]

1.90 g of L-2-amino-3-(4-carboxyphenyl)propionic acid.1/2H$_2$O [4-CPA.½H$_2$O]was dissolved in 5 ml of 2 N aqueous sodium hydroxide solution with ice-cooling. Thereinto was gradually dropped 1.70 g of benzyloxycarbonyl chloride. After the completion of the dropping, the mixture was stirred for 2 hours. During this period, the pH of the reaction mixture was controlled at about 8 by addition of 2 N aqueous sodium hydroxide solution. After the completion of the reaction, excessive benzyloxycarbonyl chloride was extracted with ether. The aqueous layer was adjusted to a pH of about 3 with 6 N hydrochloric acid, with ice-cooling and stirring. The resulting precipitate was collected by filtration and dried to obtain 2.25 g (yield: 75.3%) of the above objective compound having a melting point of 207°–209° C.

REFERENCE EXAMPLE 16

Preparation of methyl L-2-benzyloxycarbonylamino-3-(4-carboxyphenyl)propionate [Z-4-CPA—OCH3]

3.56 g of L-2-benzyloxycarbonylamino-3-(4-carboxyphenyl)propionic acid [Z-4-CPA]was dissolved in 40 ml of methanol. Thereinto was dropped 1.10 ml of thionyl chloride with stirring under ice-cooling. The mixture was stirred for 3 hours at room temperature. The reaction mixture was concentrated under reduced pressure. The residue was solidified with n-hexane. The solvent was removed by decantation. The residue was washed with isopropyl ether to obtain 3.40 g (yield: 91.8%) of the above objective compound having a melting point of 77°–81° C.

REFERENCE EXAMPLE 17

Preparation of methyl L-2-amino-3-(4-carboxyphenyl)propionate acetate [4-CPA—OCH$_3$.AcOH]

3.40 g of methyl L-2-benzyloxycarbonylamino-3-(4-carbonylphenyl)propionate was dissolved in 30 ml of acetic acid. To this solution was added 100 mg of 5% palladium-carbon. The mixture was subjected to catalytic reduction in a hydrogen stream with stirring at room temperature. The catalyst was removed by filtration using Celite. The filtrate was concentrated with water under reduced pressure. The residue was mixed with ethanol, and the resulting precipitate was collected by filtration to obtain 2.60 g (yield: 96.5%) of the above objective compound.

Melting point: turned yellow at 162° C. and turned brown and decomposed at about 200° C.

Elemental analysis ($C_{11}H_{13}NO_4.CH_3COOH$) Calculated (%): C 55.12, H 6.05, N 4.94. Observed (%): C 55.21, H 6.56, N 5.05.

NMR spectrum (DMSO-$d_6$) δ:
7.84 (2H, d, J=8Hz, $C_{3',5'}$-H)
7.29 (2H, d, J=8Hz, $C_{2',6'}$-H)
5.40 and 5.19 (4H, bs respectively, $NH_2$, COOHx2)
3.72-3.58 (4H, m, $CH(NH_2)COOCH_3$)
2.94-2.85 (2H, m, $CH_2$)
1.91 (3H, s, $CH_3COOH$).

REFERENCE EXAMPLE 18

Preparation of Boc-Thr(Bzl)-4-CPA—$OCH_3$ 1.50 g of 4-CPA—$OCH_3$.AcOH was dissolved in 50 ml of acetonitrile. To this solution being ice-cooled were added 2.00 ml of triethylamine and 2.30 g of Boc-Thr(Bzl)—OSu, and the mixture was stirred overnight at room temperature. The reaction mixture was concentrated under reduced pressure. The residue was dissolved in 50 ml of ethyl acetate. The solution was washed with three 30-ml portions of 1 N hydrochloric acid and three 30-ml portions of water in this order. The solution was then concentrated under reduced pressure to remove ethyl acetate. The residue was solidified with isopropyl ether, and the resulting precipitate was collected by filtration to obtain 2.29 g (yield: 84.0%) of the above objective compound.

Melting point: 120° C. (glass-like appearance).

Elemental analysis ($C_{27}H_{34}N_2O_8$): Calculated (%): C 63.02, H 6.66, N 5.44. Found (%): C 62.70, H 6.97, N 5.54.

REFERENCE EXAMPLE 19

Preparation of
Boc-Ser(Bzl)-Thr(Bzl)-4-CPA—$OCH_3.1/2H_2O$ 2.20 g of Boc-Thr(Bzl)-4-CPA—$OCH_3$ was dissolved in 10 ml of TFA with ice-cooling. The mixture was stirred for 30 minutes at room temperature. The reaction mixture was concentrated under reduced pressure. The residue was dried over sodium hydroxide under reduced pressure. The product was dissolved in 20 ml of THF. The solution was neutralized with triethylamine with ice-cooling. Thereto was added 1.90 g of Boc-Ser(Bzl)—OSu, and the mixture was stirred overnight at room temperature. The reaction mixture was concentrated under reduced pressure. The residue was dissolved in 50 ml of ethyl acetate. The solution was washed with three 30-ml portions of 1 N hydrochloric acid and three 30-ml portions of water in this order. The solution was then concentrated under reduced pressure to remove ethyl acetate. The residue was mixed with isopropyl ether, and the resulting precipitate was collected by filtration to obtain 2.81 g (yield: 93.8%) of the above objective compound having a melting point of 103°-108° C.

REFERENCE EXAMPLE 20

Preparation of Boc-Ser(Bzl)-Asn-Leu—$N_2H_3$ 5.10 g of Boc-Ser(Bzl)-Asn-Leu—OEt was dissolved in methanol. Thereto was added 5.00 ml of $NH_2NH_2.H_2O$. The mixture was allowed to stand overnight at room temperature. The resulting precipitate was collected by filtration and washed with isopropyl ether to obtain 3.93 g (yield: 79.1%) of the above objective compound having a melting point of 205°-208° C.

REFERENCE EXAMPLE 21

Preparation of Boc-Ser(Bzl)-Asn-Leu-Ser(Bzl)-Thr(Bzl)-4-CPA—$OCH_3.\frac{1}{2}H_2O$ 2.70 g of Boc-Ser(Bzl)-Thr(Bzl)-4-CPA—$OCH_3.\frac{1}{2}$ $H_2O$ was dissolved in 7 ml of TFA with ice-cooling The solution was stirred for 30 minutes at room temperature. The reaction mixture was concentrated under reduced pressure. The residue was dried over sodium hydroxide under reduced pressure.

Separately, 2.40 g of Boc-Ser(Bzl)-Asn-Leu—$N_2H_3$ was dissolved in 40 ml of DMF. To the solution being stirred at −15° C. were added 2.24 ml of 4 N hydrochloric acid/dioxane and 0.60 ml of isoamyl nitrite in this order to form an azide. 1.90 ml of triethylamine was added to effect neutralization.

The above TFA-treated product was dissolved in 10 ml of DMF. Thereto was added triethylamine with ice-cooling, to effect neutralization. Thereto was added the above azide compound, and the mixture was allowed to stand overnight at 4° C. The reaction mixture was concentrated under reduced pressure. The residue was mixed with water, and the resulting precipitate was collected by filtration and recrystallized from methanol to obtain 3.24 g (yield: 76.1%) of the above objective compound having a melting point of 203°-206° C.

REFERENCE EXAMPLE 22

Preparation of
⌐Ser(Bzl)—Asn—Leu—Ser(Bzl)—
⌐Thr(Bzl)-4-CPA—$OCH_3$ 1.50 g of Boc-Ser(Bzl)-Asn-Leu-Ser(Bzl)-Thr(Bzl)-4.CPA—$OCH_3$. $\frac{1}{2}H_2O$ was dissolved in 15 ml of dry pyridine. Thereto was added 1.61 g of TFA—ONp. The mixture was allowed to stand for 3 hours at 40° C. The reaction mixture was concentrated under reduced pressure. The residue was solidified with isopropyl ether. The product was dissolved in 10 ml of TFA with ice-cooling. The solution was stirred for 30 minutes at room temperature. The reaction mixture was concentrated under reduced pressure. The residue was treated with ethyl acetate, and the resulting precipitate was collected by filtration and dried over sodium hydroxide under reduced pressure. This TFA-treated product was dissolved in 20 ml of DMF. The solution was dropped into 1 liter of dry pyridine in one hour with ice-cooling at room temperature. The mixture was stirred for 8 hours at 50° C. The reaction mixture was concentrated under reduced pressure. The residue was dissolved in 60 ml of ethyl acetate. The solution was washed with three 30-ml portions of 1 N hydrochloric acid and two 30-ml portions of water in this order. The solution was then concentrated under reduced pressure. The residue was treated with isopropyl ether, and the resulting precipitate was collected by filtration and washed with a methanol-ethyl acetate mixture. This washings were combined with the above isopropyl ether washings, and the mixture was concentrated under reduced pressure. The residue was dissolved in ethyl acetate. The insolubles were removed by filtration. The filtrate was concentrated under reduced pressure. The residue was mixed with isopropyl ether, and the resulting precipitate was collected by filtration to obtain 0.72 g (yield: 53.8%) of the above objective compound having a melting point of 110°–116° C.

REFERENCE EXAMPLE 23

Preparation of ⌐Ser(Bzl)—Asn—Leu—Ser(Bzl)—
 Thr(Bzl)-4-CPA—N₂H₃.H₂O 0.70 g of

⌐Ser(Bzl)—Asn—Leu—Ser(Bzl)—Thr(Bzl)—
 4-CPA—OCH₃ was dissolved in 5 ml of methanol. Thereto was added 1.00 ml of NH₂NH₂.H₂O. The mixture was allowed to stand for 2 days at room temperature. The reaction mixture was concentrated under reduced pressure. The residue was mixed with isopropyl ether. The resulting insolubles were collected by filtration, dissolved in a methanol-ethyl acetate mixture and concentrated under reduced pressure. The residue was mixed with isopropyl ether. The resulting precipitate was collected by filtration and dried to obtain 0.70 g (yield: 98.2%) of the above objective compound having a melting point of 130°–138° C.

REFERENCE EXAMPLE 24

Preparation of ⌐Ser(Bzl)—Asn—Leu—Ser(Bzl)—
 Thr(Bzl)-4-CPA—Val—Leu—Gly—OH 0.78 g of Boc-Val-Leu-Gly—OH was dissolved in 5 ml of TFA with ice-cooling. The solution was stirred for 30 minutes at room temperature. The reaction mixture was concentrated under reduced pressure. The residue was dried over sodium hydroxide under reduced pressure.

0.68 g of

⌐Ser(Bzl)—Asn—Leu—Ser(Bzl)—Thr(Bzl)—
 4-CPA—N₂H₃.H₂O was dissolved in 10 ml of DMF. To solution being stirred at −15° C were added 0.40 ml of 4 N hydrochloric acid/dioxane and 0.15 ml of isoamyl nitrite in this order to form an azide. Triethylamine was added thereto to effect neutralization.

The above TFA treated product was dissolved in 30 ml of DMF. The solution was neutralized with triethylamine with ice-cooling. Thereto was added the above azide compound. The mixture was stirred overnight with ice-cooling. 0.5N hydrochloric acid was added to the residue, and the resulting precipitate was collected by filtration and washed with water. The precipitate was then dissolved in a methanolethyl acetate mixture. The solution was concentrated under reduced pressure and the resulting precipitate was collected by filtration to obtain 0.58 g (yield: 68.9%) of the above objective compound having a melting point of 162°–170° C.

REFERENCE EXAMPLE 25

Preparation of Boc-Thr(Bzl)-Asp—OEt 2.3 g of H-Asp—OEt and 5.8 g of Boc-Thr(Bzl)—OSu were suspended in 20 ml of THF and 20 ml of DMF. Thereto was added 2 ml of triethylamine with ice-cooling. The mixture was stirred for 1 hour. The mixture was reacted for 36 hours at room temperature while controlling the pH of the mixture at about 7. The reaction mixture was concentrated under reduced pressure. The residue was made acidic by addition of 1N hydrochloric acid. The mixture was extracted with three 80-ml portions of ethyl acetate. The organic layers were combined, washed with water and a saturated aqueous sodium chloride solution in this order, dried with anhydrous magnesium sulfate and concentrated under reduced pressure. The residue was crystallized and recrystallized from diethyl ether-petroleum ether in each case to obtain 5.59 g (yield: 86.6%) of the above objective compound having a melting point of 93°–95° C.

REFERENCE EXAMPLE 26

Preparation of Boc-Ser(Bzl)-Thr(Bzl)-Asp—OEt 4.52 g of Boc-Thr(Bzl)-Asp—OEt was dissolved in 20 ml of TFA with ice-cooling. The solution was stirred for 30 minutes at room temperature. The reaction mixture was concentrated under reduced pressure. The residue was dried over sodium hydroxide under reduced pressure. The product was dissolved in 20 ml of THF and the solution was adjusted to pH 7 with triethylamine with ice-cooling.

Thereto was added 3.29 g of Boc-Ser(Bzl)—OSu and the mixture was stirred for 20 hours. The reaction mixture was concentrated under reduced pressure. The residue was dissolved in 150 ml of ethyl acetate. The solution was washed with two 50-ml portions of 1N hydrochloric acid, two 50-ml portions of a saturated aqueous sodium bicarbonate solution and two 50-ml portions of a saturated aqueous sodium chloride solution in this order, dried with anhydrous magnesium sulfate and concentrated under reduced pressure. The residue was crystallized with diethyl ether-pertoleum ether and recrystallized from ethyl acetate-pertoleum ether to obtain 3.61 g (yield: 57.3%) of the above objective compound having a melting point of 90°–92° C.

REFERENCE EXAMPLE 27

Preparation of Boc-β-Ala-Ser(Bzl)-Asn-Leu—OEt 4.41 g of Boc-Ser(Bzl)-Asn-Leu—OEt was dissolved in 20 ml of TFA with ice-cooling. The solution was stirred for 30 minutes at room temperature. The reaction mixture was concentrated under reduced pressure. The residue was mixed with diethyl ether. The resulting precipitate was collected by filtration and dried over sodium hydroxide under reduced pressure.

The above product was dissolved in a mixture of 100 ml of THF and 20 ml of DMF. The solution was adjusted to a pH of about 7 with triethylamine with ice-cooling. Thereto was added 2.75 g of Boc-β-Ala—OSu and the mixture was stirred overnight at room temperature. The reaction mixture was concentrated under reduced pressure. The residue was mixed with 200 ml of water. The resulting precipitate was collected by filtration and recrystallized from ethanol twice to obtain 3.41 g (yield: 68.6%) of the above objective compound having a melting point of 190°–192° C.

REFERENCE EXAMPLE 28

Preparation of Boc-8-Ala-Ser(Bzl)-Asn-Leu—$N_2H_3$ 3 g of Boc-8-Ala-Ser(Bzl)-Asn-Leu—OEt was dissolved in 20 ml of methanol. Thereto was added 2.4 ml of $NH_2NH_2 \cdot H_2O$ and the mixture was stirred overnight. The resulting precipitate was dissolved in 20 ml of DMF. The solution was stirred overnight. The reaction mixture was concentrated under reduced pressure. The residue was mixed with 15 ml of water. The resulting precipitate was collected by filtration and recrystallized from ethanol twice to obtain 1.72 g (yield: 58.7%) of the above objective compound having a melting point of 241°–245° C.

REFERENCE EXAMPLE 29

Preparation of Boc-8-Ala-Ser(Bzl)-Asn-Leu-Ser(Bzl)-Thr(Bzl)-Asp—OEt 6.6 g of Boc-Ser(Bzl)-Thr(Bzl)-Asp—OEt was dissolved in 30 ml of TFA with ice-cooling. The solution was stirred for 30 minutes at room temperature. The reaction mixture was concentrated under reduced pressure. The residue was mixed with petroleum ether, and the resulting precipitate was dried over sodium hydroxide under reduced pressure.

Separately, 7.0 g of Boc-β-Ala-Ser(Bzl)-Asn-Leu—$N_2H_3$ was dissolved in 30 ml of DMF. To the solution being stirred at −15° to −20° C. were added 7.2 ml of 4N hydrochloric acid/dioxane and 2 ml of isoamyl nitrite in this order to form an azide. Triethylamine was added to effect neutralization.

The above TFA-treated product was dissolved in 20 ml of DMF. The solution was neutralized with triethylamine with ice-cooling. Thereto was added the above azide compound. The mixture was stirred for 20 hours at 4° C. while maintaining its pH at 7–8. The reaction mixture was concentrated under reduced pressure. The residue was mixed with 30 ml of 0.5N hydrochloric acid. The resulting precipitate was collected by filtration and recrystallized from methanol twice to obtain 10.46 g (yield: 90.4%) of the above objective compound having a melting point of 236°–245° C. (decomposed).

REFERENCE EXAMPLE 30

Preparation of ┌─β-Ala—Ser(Bzl)—Asn—Leu—Ser(Bzl)—
            └────────┐
Thr(Bzl)—Asp—OEt 4.3 g of Boc-β-Ala-Ser(Bzl)-Asn-Leu-Ser(Bzl)-Thr(Bzl)-Asp—OEt was dissolved in 45 ml of dry pyridine. Thereto was added 3.66 g of TFA—ONp. The mixture was allowed to stand for 4 hours at 40° C. The reaction mixture was concentrated under reduced pressure. The residue was mixed with diethyl ether. The resulting precipitate was collected by filtration and dried over sodium hydroxide under reduced pressure.

The above TFA-treated product was dissolved in 50 ml of DMF. The solution was dropped into 800 ml of dry pyridine of 50° C. in 6 hours, with stirring. After the completion of the dropping, the mixture was stirred overnight at room temperature. The reaction mixture was concentrated under reduced pressure. The residue was mixed with 100 ml of water, and the resulting precipitate was collected by filtration and dissolved in ethanol with heating. The solution was allowed to cool. The resulting precipitate was removed by filtration. The filtrate was mixed with ethyl acetate. The resulting precipitate was collected by filtration to obtain 1.9 g (yield: 49.5%) of the above objective compound having a melting point of 230°–233° C.

REFERENCE EXAMPLE 31

Preparation of ┌─β-Ala—Ser(Bzl)—Asn—Leu—
            └────────┐
Ser(Bzl)—Thr(Bzl)—Asp—$N_2H_3 \cdot H_2O$ 1.89 g of ┌─β-Ala—Ser(Bzl)—Asn—Leu—Ser(Bzl)—
└────────┐
Thr(Bzl)—Asp—OEt was dissolved in a mixture of 50 ml of methanol and 15 ml of DMF. Thereto was added 1.7 ml of $NH_2NH_2 \cdot H_2O$. The mixture was stirred overnight at room temperature. The reaction mixture was mixed with 200 ml of water. The resulting precipitate was collected by filtration and dried thoroughly. The precipitate was then suspended in methanolethyl acetate. The suspension was concentrated under reduced pressure. The resulting precipitate was collected by filtration to obtain 620 mg (yield: 34.4%) of the above objective compound having a melting point of 235°–238° C.

REFERENCE EXAMPLE 32

Preparation of ┌─β-Ala—Ser(Bzl)—Asn—Leu—Ser(Bzl)—
            └────────┐
Thr(Bzl)—Asp—Val—Leu—Gly—OH 440 mg of Boc-Val-Leu-Gly—OH was dissolved in 5 ml of TFA with ice-cooling. The solution was stirred for 30 minutes at room temperature. The reaction mixture was concentrated under reduced pressure. The residue was mixed with diethyl ether. The resulting precipitate was collected by filtration and dried over sodium hydroxide under reduced pressure.

550 mg of

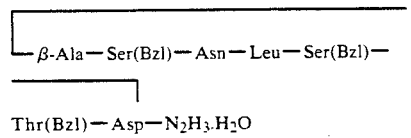

was dissolved in 20 ml of DMF. To the solution were added 0.43 ml of 4N hydrochloric acid/dioxane and 0.11 ml of isoamyl nitrite in this order with stirring at −15° to −20° C., to form an azide. Triethylamine was added thereto to effect neutralization.

The above TFA-treated product was dissolved in 10 ml of DMF. The solution was neutralized with triethylamine with ice-cooling. Thereto was added the above azide compound. The mixture was stirred for 4 hours at 4° C. while maintaining its pH at 7–8. The reaction mixture was concentrated under reduced pressure. The residue was mixed with 30 ml of 0.5N hydrochloric acid. The resulting precipitate was collected by filtration and washed with ethanol and ethyl acetate in this order to obtain 580 mg (yield: 83.8%) of the above objective compound.

Melting point: 228°–248° C. (decomposed).
Amino acid analysis:
Asp 2.07 (2)
β-Ala 0.85 (1)
Thr 1.06 (1)
Ser 2.02 (2)
Gly 1.07 (1)
Val 0.92 (1)
Leu 2.00 (2).

REFERENCE EXAMPLE 33

Preparation of Z-Lys(COCH$_2$CH$_2$COOH)—OCH$_3$ 5.00 g of Z-Lys(Boc)—OCH$_3$ was dissolved in 15 ml of TFA. The solution was stirred for 30 minutes at room temperature. The reaction mixture was concentrated under reduced pressure. The residue was mixed with petroleum ether. The resulting oily matter was separated by decantation and dried over sodium hydroxide under reduced pressure.

The above product was dissolved in 40 ml of pyridine with ice-cooling. Thereto was added 3.08 g of succinic anhydride. The mixture was stirred for 18 hours at room temperature. The reaction mixture was concentrated under reduced pressure. The residue was extracted with 100 ml of ethyl acetate. The ethyl acetate layer was washed with 1N hydrochloric acid and then with a saturated aqueous sodium chloride solution three times, dried with anhydrous sodium sulfate and concentrated under reduced pressure. The residue was dissolved in chloroform. The solution was poured into a silica gel column. Elution was conducted using 200 ml of chloroform and 400 ml of 3% methanol-chloroform in this order to purify the above residue. Thus, 3.63 g (yield: 71.9%) of the above objective compound was obtained in a form of an oily matter.

NMR (CDCl$_3$) δ:
7.27–7.33 (6H, m, CH$_2$C$_6$H$_5$, OCONH or CONH)
6.34–6.07 (1H, bs, OCONH or CONH)
5.10 (2H, s, CH$_2$C$_6$H$_5$)
4.41–4.15 (1H, m, NHCHCO)
3.71 (3H, s, OCH$_3$)
3.25–3.13 (2H, m, NHCH$_2$-)
2.76–2.34 (4H, m, COCH$_2$CH$_2$CO)
1.89–1.15 (6H, m, NHCH$_2$(CH$_2$)$_3$).

REFERENCE EXAMPLE 34

Preparation of Boc-Thr(Bzl)-Lys-(COCH$_2$CH$_2$COOH)—OCH$_3$ 3.60 g of Z-Lys(COCH$_2$CH$_2$COOH)—OCH$_3$ was dissolved in 30 ml of methanol. Thereto were added 100 mg of 5% palladium-carbon and 9.13 ml of 1N hydrochloric acid. The mixture was subjected to catalytic reduction in a hydrogen stream. The catalyst was removed by filtration. The filtrate was concentrated under reduced pressure. The residue was dried over sodium hydroxide under reduced pressure. The product was dissolved in a mixture of 30 ml of THF and 5 ml of water. The solution was adjusted to pH 6–7 with triethylamine with ice-cooling. Thereto was added 4.08 g of Boc-Thr(Bzl)—OSu. The mixture was adjusted to pH 7–8 with N-methylmorpholine and then stirred for 1 hour under ice-cooling and for 18 hours at room temperature. The reaction mixture was concentrated under reduced pressure. The residue was extracted with 50 ml of ethyl acetate. The ethyl acetate layer was washed with 1N hydrochloric acid and a saturated aqueous sodium chloride solution three times in this order, dried with anhydrous sodium sulfate and concentrated under reduced pressure. The residue was dissolved in chloroform and poured into a silica gel. Elution was conducted using 200 ml of chloroform and 500 ml of 2% methanol/chloroform in this order to collect fractions containing the above objective compound. They were combined and concentrated under reduced pressure. The residue was mixed with diethyl ether to solidify it to obtain 960 mg (yield: 19.1%) of the above objective compound having a melting point of 60°–63° C.

REFERENCE EXAMPLE 35

Preparation of Boc-Ser(Bzl)-Thr(Bzl)-Lys(COCH$_2$CH$_2$COOH)—OCH$_3$.1/2H$_2$O 900 mg of Boc-Thr(Bzl)-Lys(COCH$_2$CH$_2$COOH)—OCH$_3$ was dissolved in 2 ml of TFA. The solution was stirred for 30 minutes at room temperature. The reaction mixture was concentrated under reduced pressure. The residue was dried over sodium hydroxide under reduced pressure.

The above product was mixed with 30 ml of THF. The mixture was adjusted to pH 6–7 with triethylamine with ice-cooling. Thereto was added 768 mg of Boc-Ser(Bzl)—OSu. The mixture was adjusted to pH 7–8 with N-methylmorpholine and then stirred for 1 hour under ice-cooling and for 40 hours at room temperature. The reaction mixture was concentrated under reduced pressure. The residue was extracted with 30 ml of ethyl acetate. The ethyl acetate layer was washed with 1N hydrochloric acid, a saturated aqueous sodium chloride solution, a saturated aqueous sodium bicarbonate solution twice and water three times in this order and then concentrated under reduced pressure. The residue was mixed with ethanol and the mixture was concentrated. The residue was solidified with diethyl ether and reprecipitated from methanol-diethyl ether to obtain 810 mg (yield: 67.4%) of the above objective compound having a melting point of 81°–83° C.

REFERENCE EXAMPLE 36

Preparation of Boc-Ser(Bzl)-Asn-Leu-Ser(Bzl)-Thr(Bzl)-Lys(-COCH₂CH₂COOH)—OCH₃

700 mg of Boc-Ser(Bzl)-Thr(Bzl)-Lys(COCH₂CH₂COOH)—OCH₃.H₂O was dissolved in 4 ml of TFA. The solution was stirred for 30 minutes at room temperature. The reaction mixture was concentrated under reduced pressure. The residue was mixed with diethyl ether. The precipitated oily matter was separated by decantation and dried over sodium hydroxide under reduced pressure.

Separately, 570 mg of Boc-Ser(Bzl)-Asn-Leu—N₂H₃ was dissolved in 15 ml of DMF. Thereto were added 0.96 ml of 4N hydrochloric acid/dioxane and 0.13 ml of isoamyl nitrite in this order with stirring at −15° to −20° C., to form an azide. Triethylamine was added thereto to effect neutralization.

The above TFA-treated product was dissolved in 10 ml of DMF. The solution was adjusted to pH 6-7 with triethylamine with ice-cooling. Thereto was added the above azide compound. The mixture was adjusted to pH 7-8 with N-methylmorpholine and stirred for 20 hours at 4° C.

The reaction mixture was concentrated under reduced pressure. The residue was mixed with 50 ml of water. The resulting precipitate was collected by filtration, water-washed and reprecipitated from methanol-diethyl ether twice to obtain 650 mg (yield: 60.4%) of the above objective compound having a melting point of 186°–190° C.

REFERENCE EXAMPLE 37

Preparation of
```
CH₂—CH₂————————————
 |
 CO—Ser(Bzl)—Asn—Leu—Ser(Bzl)—
————————CO
         |
 Thr(Bzl)—Lys—OCH₃
```

3.08 g of Boc-Ser(Bzl)-Asn-Leu-Ser(Bzl)-Thr(Bzl)-Lys(COCH₂CH₂COOH)—OCH₃ was dissolved in 50 ml of dry pyridine. Thereto was added 2.56 g of TFA—ONp. The mixture was allowed to stand for 3 hours at 40° C. The reaction mixture was concentrated under reduced pressure. The residue was mixed with diethyl ether. The resulting precipitate was collected and dried under reduced pressure. The product was dissolved in 10 ml of TFA. The solution was stirred for 40 minutes at room temperature. The reaction mixture was concentrated under reduced pressure. The residue was dried over sodium hydroxide under reduced pressure.

The above TFA-treated product was dissolved in 30 ml of DMF. The solution was dropped into 1,000 ml of dry pyridine in 3 hours with stirring at 55° C. The mixture was stirred for 5 hours at 55° C. and for 16 hours at room temperature. The reaction mixture was concentrated under reduced pressure. The residue was mixed with 300 ml of water. The resulting precipitate was collected by filtration and reprecipitated from methanol-ethyl acetate twice to obtain 1.53 g (yield: 55.5%) of the above objective compound having a melting point of 195°–200° C.

REFERENCE EXAMPLE 38

Preparation of
```
CH₂—CH₂————————————
 |
 CO—Ser(Bzl)—Asn—Leu—Ser(Bzl)—
————————CO
         |
 Thr(Bzl)—Lys—N₂H₃
```

1.43 g of
```
CH₂—CH₂————————————
 |
 CO—Ser(Bzl)—Asn—Leu—Ser(Bzl)—Thr(Bzl)—
 —CO
  |
 Lys—OCH₃
``` was dissolved in a mixture of 30 ml of methanol and 10 ml of DMF. Thereto was added 0.69 ml of NH₂NH₂.H₂O. The mixture was stirred for 24 hours at room temperature. The reaction mixture was concentrated under reduced pressure. The residue was mixed with 50 ml of water. The resulting precipitate was collected by filtration and washed with water and methanol-ethyl acetate in this order to obtain 1.30 g (yield: 90.8%) of the above objective compound having a melting point of 239°–242° C.

REFERENCE EXAMPLE 39

Preparation of
```
CH₂—CH₂————————————
 |
 CO—Ser(Bzl)—Asn—Leu—Ser(Bzl)—
————————CO
         |
 Thr(Bzl)—Lys—Val—Leu—Gly—OH
```

915 mg of Boc-Val-Leu-Gly—OH was dissolved in 4 ml of TFA with ice-cooling. The solution was stirred for 30 minutes at room temperature. The reaction mixture was concentrated under reduced pressure. The residue was mixed with diethyl ether. The resulting precipitate was collected by filtration and dried under reduced pressure.

1.20 g of
```
CH₂—CH₂————————————
 |
 CO—Ser(Bzl)—Asn—Leu—Ser(Bzl)—
————————CO
         |
 Thr(Bzl)—Lys—N₂H₃
``` was dissolved in 10 ml of DMF. To the solution were added 1.18 ml of 4N hydrochloric acid/dioxane and 0.16 ml of isoamyl nitrite in this order with stirring at −15° to −20° C., to form an azide. Triethylamine was added thereto to effect neutralization.

The above TFA-treated product was dissolved in 5 ml of DMF. The solution was adjusted to pH 6-7 with triethylamine with ice-cooling. Thereto was added the above azide compound. The mixture was adjusted to pH 7-8N-methylmorpholine and stirred for 40 hours at 4° C. The reaction mixture was concentrated under reduced pressure. The residue was mixed with 1N hydrochloric acid. The resulting precipitate was collected by filtration and washed with water and hot methanol to obtain 910 mg (yield: 60.8%) of the above objective compound having a melting point of 260°–268° C. (decomposed).

REFERENCE EXAMPLE 40

Preparation of Boc-Ser(Bzl)-Asn-Leu-Ser(Bzl)-Thr(Bzl)-Asp—OEt 3.15 g of Boc-Ser(Bzl)-Thr(Bzl)-Asp—OEt and 3.22 g of Boc-Ser(Bzl)-Asn-Leu—N₂H₃ were subjected to the same procedure as in REFERENCE EXAMPLE 36 to obtain 3.69 g (yield: 71.4%) of the above objective compound having a melting point of 182°–186° C.

REFERENCE EXAMPLE 41

Preparation of Boc Gly-Ser(Bzl)-Asn-Leu-Ser(Bzl)-Thr(Bzl)-Asp—OEt

Using 3.54 g of Boc-Ser(Bzl)-Asn-Leu-Ser(Bzl)-Thr(Bzl)-Asp—OEt and 1.03 g of Boc-Gly—OSu, the same procedure as in REFERENCE EXAMPLE 35 was repeated to obtain 3.10 g (yield: 83.1%) of the above objective compound having a melting point of 198°–205° C.

REFERENCE EXAMPLE 42

Preparation of ⌐Gly—Ser(Bzl)—Asn—Leu—Ser(Bzl)—
Thr(Bzl)—Asp—OEt

Using 3.00 g of Boc-Gly-Ser(Bzl)-Asn-Leu-Ser(Bzl)-Thr(Bzl)-Asp—OEt, the same procedure as in Reference Example 37 was repeated to obtain 1.64 g (yield: 61.3%) of the above objective compound having a melting point of 207°–211° C:

REFERENCE EXAMPLE 43

Preparation of ⌐Gly—Ser(Bzl)—Asn—Leu—Ser(Bzl)—
Thr(Bzl)—Asp—N₂H₃

Using 1.50 g of

⌐Gly—Ser(Bzl)—Asn—Leu—Ser(Bzl)—
Thr(Bzl)—Asp—OEt, the same procedure as in Reference Example 38 was repeated to obtain 700 mg (yield: 47.4%) of the above objective compound having a melting point of 215°–218° C.

REFERENCE EXAMPLE 44

Preparation of ⌐Gly—Ser(Bzl)—Asn—Leu—Ser(Bzl)—
Thr(Bzl)—Asp—Val—Leu—Gly—OH

Using 650 mg of

⌐Gly—Ser(Bzl)—Asn—Leu—Ser(Bzl)—
Thr(Bzl)—Asp—N₂H₃ and 525 mg of Boc-Val-Leu-Gly—OH, the same procedure as in REFERENCE EXAMPLE 39 was repeated to obtain 140 mg (yield: 17.0%) of the above objective compound having a melting point of 249°–251° C. (decomposed).

REFERENCE EXAMPLE 45

Preparation of Boc-Acp-Asn-Leu—OEt

Using 4.00 g of Boc-Asn-Leu—OEt and 3.40 g of Boc-Acp—OSu, the same procedure as in Reference Example 35 was repeated to obtain 4.98 g (yield: 95.5%) of the above objective compound having a melting point of 145°–146° C.

REFERENCE EXAMPLE 46

Preparation of Boc-Acp-Asn-Leu—N₂H₃

Using 4.90 g of Boc-Acp-Asn-Leu—OEt, the same procedure as in REFERENCE EXAMPLE 6 was repeated to obtain 4.26 g (yield: 86.2%) of the above objective compound having a melting point of 200°–202° C.

REFERENCE EXAMPLE 47

Preparation of Boc-Acp-Asn-Leu-Ser(Bzl)-Thr(Bzl)-Asp—OEt

Using 2.66 g of Boc-Ser(Bzl)-Thr(Bzl)-Asp—OEt and 2.20 of Boc-Acp-Asn-Leu—N₂H₃, the same procedure as in Reference Example 36 was repeated to obtain 3.22 g (yield: 78.5%) of the above objective compound having a melting point of 200°–203° C.

REFERENCE EXAMPLE 48

Preparation of ⌐Acp—Asn—Leu—Ser(Bzl)—Thr(Bzl)—
Asp—OEt

Using 3.00 g of Boc-Acp-Asn-Leu-Ser(Bzl)-Thr(Bzl)-Asp—OEt, the same procedure as in Reference Example 37 was repeated to obtain 700 mg (Yield: 26.6%) of the above objective compound having a melting point of 228°–231° C.

REFERENCE EXAMPLE 49

Preparation of ⌐Acp—Asn—Leu—Ser(Bzl)—Thr(Bzl)—
Asp—N₂H₃

Using 650 mg of

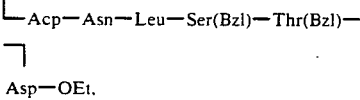

the same procedure as in Reference Example 38 was repeated to obtain 400 mg (yield: 62.6%) of the above objective compound having a melting point of 212°–218° C.

REFERENCE EXAMPLE 50

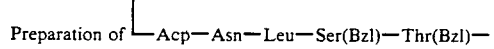

Using 350 mg of

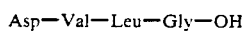

and 324 mg of Boc-Val-Leu-Gly—OH, the same procedure as in Reference Example 39 was repeated to obtain 320 mg (yield: 70.0%) of the above objective compound having a melting point of 235°–240° C. (decomposed).

REFERENCE EXAMPLE 51

Preparation of Boc-Abu-Ser(Bzl)-Asn-Leu—OEt

Using 4.40 g of Boc-Ser(Bzl)-Asn-Leu—OEt and 2.50 g of Boc-Abu—OSu, the same procedure as in Reference Example 35 was repeated to obtain 4.27 g (yield: 84.0%) of the above objective compound having a melting point of 175°–177° C.

REFERENCE EXAMPLE 52

Preparation of Boc-Abu-Ser(Bzl)-Asn-Leu—$N_2H_3$

Using 4.00 g of Boc-Abu-Ser(Bzl)-Asn-Leu—OEt, the same procedure as in REFERENCE EXAMPLE 6 was repeated to obtain 2.84 g (yield: 76.1%) of the above objective compound having a melting point of 224°–227° C.

REFERENCE EXAMPLE 53

Preparation of
Boc-Abu-Ser(Bzl)-Asn-Leu-Ser(Bzl)-Thr(Bzl)-Asp—OEt

Using 2.30 g of Boc-Ser(Bzl)-Thr(Bzl)-Asp—OEt and 2.50 g of Boc-Abu-Ser(Bzl)-Asn-Leu—$N_2H_3$, the same procedure as in Reference Example 36 was repeated to obtain 2.26 g (yield: 55.3%) of the above objective compound.
Melting point: 201°–216° C.
Amino acid analysis:
Asp: 197 (2)
Thr: 1.00 (1)
Ser: 1.89 (2)
Abu: 1.13 (1)
Leu: 1.01 (1)

REFERENCE EXAMPLE 54

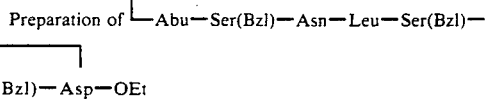

Using 2.00 g of Boc-Abu-Ser(Bzl)-Asn-Leu-Ser(Bzl)-Thr(Bzl)-Asp—OEt, the same procedure as in Reference Example 37 was repeated to obtain 1.91 g (yield: 106.6%) of the above objective compound having a melting point of 208°–225° C.

REFERENCE EXAMPLE 55

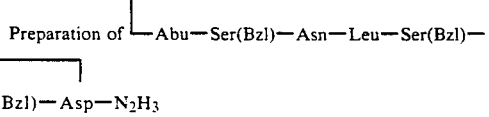

Using 1.73 g of

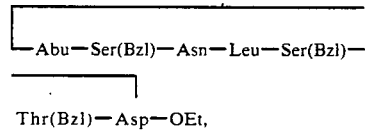

the same procedure as in Reference Example 38 was repeated to obtain 730 mg (yield: 42.7%) of the above objective compound having a melting point of 201°–208° c.

REFERENCE EXAMPLE 56

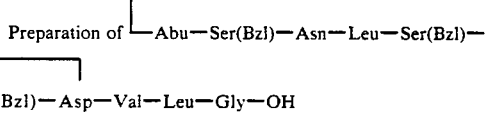

Using 610 mg of

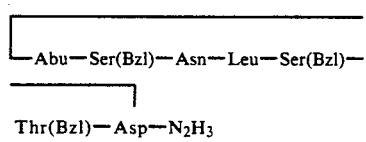

and 526 mg of Boc-Val-Leu-Gly—OH, the same procedure as in REFERENCE EXAMPLE 39 was repeated to obtain 440 mg (yield: 57.3%) of the above objective compound.
Melting point: 225°–240° C. (decomposed).
Amino acid analysis:

| Asp: 1.93 (2) | Val: 0.93 (1) |
| Thr: 1.08 (1) | Leu: 2.01 (2) |
| Ser: 2.05 (2) | Abu: 0.98 (1) |
| Gly: 1.01 (1) | |

REFERENCE EXAMPLE 57

Preparation of HCl.H-Cpc(OBu')—OCH$_3$ 7.42 g of HCl.H-Cys—OCH$_3$ and 11.58 g of BrCH$_2$-(CH$_2$)$_2$COOBu' were dissolved in 30 ml of DMF. Thereto was added 12.1 ml of triethylamine with ice-cooling. The mixture was stirred for 2 days at room temperature. The reaction mixture was poured into 100 ml of ice water. The mixture was extracted with three 50-ml portions of ethyl acetate. The organic layers were combined and washed with 50 ml of water and 50 ml of a saturated aqueous sodium chloride solution (twice) in this order. The resulting liquid was dried with anhydrous magnesium sulfate and then concentrated under reduced pressure. The residue was mixed with 20 ml of 4N hydrochloric acid/dioxane with ice-cooling. The mixture was concentrated under reduced pressure. The residue was crystallized from diethyl ether and recrystallized from ethyl acetate-diethyl ether to obtain 9.30 g (yield: 68.5%) of the above objective compound having a melting point of 90°–93° C.

REFERENCE EXAMPLE 58

Preparation of Boc-Thr(Bzl)-Cpc(OBu')—OCH$_3$

Using 1.30 g of HCl.H-Cpc(OBu')—OCH$_3$, 1.85 g of Boc-Thr(Bzl)—OSu and 550 mg of HOBT, the same procedure as in Reference Example 25 was repeated to obtain 1.92 g (yield: 81.5%) of the above objective compound having a melting point of 53°–55° C.

REFERENCE EXAMPLE 59

Preparation of Boc-Ser(Bzl)-Thr(Bzl)-Cpc—OCH$_3$

Using 1.85 g of Boc-Thr(Bzl)-Cpc(OBu')—OCH$_3$ and 1.30 g of Boc-Ser(Bzl)—OSu, the same procedure as in Reference Example 35 was repeated to obtain 1.46 g (yield: 60.2%) of the above objective compound having an oily appearance.

REFERENCE EXAMPLE 60

Preparation of Boc-Ser(Bzl)-Asn-Leu-Ser(Bzl)-Thr(Bzl)-Cpc—OCH$_3$

Using 1.46 g of Boc-Ser(Bzl)-Thr(Bzl)-Cpc—OCH$_3$ and 1.36 g of Boc-Ser(Bzl)-Asn-Leu—N$_2$H$_3$, the same procedure as in Reference Example 36 was repeated to obtain 1.66 g (yield: 73.6%) of the above objective compound having a melting point of 183°–186° C.

REFERENCE EXAMPLE 61

Preparation of ⌐Ser(Bzl)—Asn—Leu—Ser(Bzl)—
          └Thr(Bzl)—Cpc—OCH$_3$

Using 950 mg of Boc-Ser(Bzl)-Asn-Leu-Ser(Bzl)-Thr(Bzl)-Cpc—OCH$_3$, the same procedure as in Reference Example 37 was repeated to obtain 450 mg (yield: 55.9%) of the above objective compound having a melting point of 158°–161° C.

REFERENCE EXAMPLE 62

Preparation of ⌐Ser(Bzl)—Asn—Leu—Ser(Bzl)—
          └Thr(Bzl)—Cpc—N$_2$H$_3$

Using 430 mg of

⌐Ser(Bzl)—Asn—Leu—Ser(Bzl)—
└Thr(Bzl)—Cpc—OCH$_3$.

the same procedure as in Reference Example 38 was repeated to obtain 424 mg (yield: 98.5%) of the above objective compound having a melting point of 208°–213° C.

REFERENCE EXAMPLE 63

Preparation of ⌐Ser(Bzl)—Asn—Leu—Ser(Bzl)—
          └Thr(Bzl)—Cpc—Val—Leu—Gly—OH Using 380 mg of ⌐Ser(Bzl)—Asn—Leu—Ser(Bzl)—
└Thr(Bzl)—Cpc—N$_2$H$_3$ and 301 mg of Boc-Val-Leu-Gly—OH, the same procedure as in Reference Example 39 was repeated to obtain 371 mg (yield: 77.5%) of the above objective compound.

Melting point: 246°–256° C.
Amino acid analysis:

| | |
|---|---|
| Asp: 1.03 (1) | Val: 0.96 (1) |
| Thr: 1.01 (1) | Leu: 2.07 (2) |
| Ser: 1.92 (2) | Cpc: 1.00 (1) |
| Gly: 1.00 (1) | |

REFERENCE EXAMPLE 64

Preparation of Boc-Asn-Leu—N$_2$H$_3$

Using 3.00 g of Boc-Asn-Leu—OEt, the same procedure as in REFERENCE EXAMPLE 6 was repeated to obtain 2.45 g (yield: 81.7%) of the above objective compound having a melting point of 219°–221° C.

REFERENCE EXAMPLE 65

Preparation of Boc-Asn-Leu-Ser(Bzl)-Thr(Bzl)-Lys(COCH$_2$CH$_2$COOH)—OCH$_3$

Using 3.60 g of Boc-Ser(Bzl)-Thr(Bzl)-Lys(COCH$_2$CH$_2$COOH)—OCH$_3$ and 2.21 g of Boc-Asn- Leu—N₂H₃, the same procedure as in Reference Example 36 was repeated to obtain 3.37 g (yield: 71.4%) of the above objective compound having a melting point of 206°-209° C.

REFERENCE EXAMPLE 66

Preparation of
```
    ┌─COCH₂CH₂CO—Asn—Leu—Ser(Bzl)—
    │
    └─Thr(Bzl)—Lys—OCH₃
```

Using 3.27 g of Boc-Asn-Leu-Ser(Bzl)-Thr(Bzl)-Lys(COCH₂CH₂COOH)—OCH₃, the same procedure as in Reference Example 37 was repeated to obtain 1.00 g (yield: 34.9%) of the above objective compound having a melting point of 115°-117° C.

REFERENCE EXAMPLE 67

Preparation of
```
    ┌─COCH₂CH₂CO—Asn—Leu—Ser(Bzl)—
    │
    └─Thr(Bzl)—Lys—N₂H₃
```

Using 850 mg of -COCH₂CH₂Co-Asn-Leu-Ser(Bzl)-Thr(Bzl)-Lys—OCH₃, the same procedure as in Reference Example 38 was repeated to obtain 630 mg (yield: 73.8%) of the above objective compound.
Melting point: 170°-183° C.
Amino acid analysis:

| | |
|---|---|
| Asp: 1.01 (1) | Leu: 1.07 (1) |
| Thr: 0.99 (1) | Lys: 0.85 (1) |
| Ser: 0.93 (1) | |

REFERENCE EXAMPLE 68

Preparation of
```
    ┌─COCH₂CH₂CO—Asn—Leu—Ser(Bzl)—
    │
    └─Thr(Bzl)—Lys—Val—Leu—Gly—OH
```

Using 580 mg of
```
    ┌─COCH₂CH₂CO—Asn—Leu—Ser(Bzl)—
    │
    └─Thr(Bzl)—Lys—N₂H₃
```
and 535 mg of Boc-Val-Leu-Gly—OH, the same procedure as in Reference Example 39 was repeated to obtain 540 mg (yield: 71.7%) of the above objective compound having a melting point of 245°-249° C. (decomposed).

REFERENCE EXAMPLE 69

Preparation of Boc-Lys(Bzl)-Leu-Ser(Bzl)—OH 950 mg of Boc-Lys(Bz)—OH and 328 mg of HOSu were dissolved in 15 ml of THF. Thereto was added 587 mg of DCC with ice-cooling. The mixture was stirred at 4° C. The insolubles were removed by filtration. The filtrate was concentrated under reduced pressure.

Separately, 1.11 g of Boc-Leu-Ser(Bzl)—OH was dissolved in 5 ml of TFA. The solution was allowed to stand for 30 minutes at room temperature. The reaction mixture was concentrated under reduced pressure. The residue was dried over sodium hydroxide under reduced pressure.

The above TFA-treated product was dissolved in 15 ml of THF. The solution was neutralized with triethylamine with ice-cooling. Thereto was added 2 ml of water to dissolve the resulting precipitate. Thereto was added the above synthesized Boc-Lys(Bz)—OSu. The mixture was adjusted to pH 8 with N-methylmorpholine and then stirred for 40 hours at room temperature.

The reaction mixture was concentrated under reduced pressure. The residue was extracted with 50 ml of ethyl acetate. The ethyl acetate layer was washed with water and a saturated aqueous sodium chloride solution (twice) in this order, dried with anhydrous sodium sulfate and concentrated under reduced pressure. The residue was mixed with diethyl ether to solidify it and reprecipitated from methanol-diethyl ether to obtain 760 mg (yield: 43.8%) of the above objective compound having a melting point of 108°-111° C.

REFERENCE EXAMPLE 70

Preparation of
Boc-Lys(Bz)-Leu-Ser(Bzl)-Gln-Glu(OBzl)-Leu-His-Lys(Cl-Z)-Leu-Gln-Thr(Bzl)-Tyr(Bzl)-Pro-Arg(Tos)
Thr(Bzl)-Asp(OBzl)-Val-Gly-Ala-Gly-Thr(Bzl)-Pro—NH₂

2.09 g of Boc-Gln-Glu-(OBzl)-Leu-His-Lys(cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ [reference is made to Japanese Patent Application Kokai (Laid—Open) No. 112099/1986] was dissolved in 10 ml of TFA with ice-cooling. The solution was stirred for 30 minutes at room temperature. The reaction mixture was concentrated under reduced pressure. The residue was mixed with diethyl ether. The resulting precipitate was collected by filtration and dried over sodium hydroxide under reduced pressure.

The above product was dissolved in 15 ml of DMF. The solution was neutralized with triethylamine with ice-cooling. Thereto were added 650 mg of Boc-Lys(Bz)-Leu-Ser(Bzl)—OH, 138 mg of HOBT and 0.186 ml of WSC. The mixture was neutralized with 4N hydrochloric acid/dioxane and then stirred for 40 hours at room temperature.

The reaction mixture was concentrated under reduced pressure. The residue was mixed with 50 ml of water. The resulting precipitate was collected by filtration, dried and reprecipitated from methanoldiethyl ether to obtain 1.97 g (yield: 80.6%) of the above objective compound.

Melting point: 184°-204° C.
Amino acid analysis:

| | |
|---|---|
| Asp: 1.07 (1) | Leu: 2.88 (3) |
| Thr: 3.02 (3) | Tyr: 0.57 (1) |
| Ser: 0.82 (1) | Lys: 1.91 (2) |
| Glu: 3.01 (3) | His: 0.92 (1) |
| Gly: 2.15 (2) | Arg: 0.96 (1) |
| Ala: 1.06 (1) | Pro: 2.16 (2) |
| Val: 1.06 (1) | |

REFERENCE EXAMPLE 71

Preparation of Boc-Thr(Bzl)-Glu—OCH$_3$ 9.45 g of Z-Glu—OCH$_3$.DCHA was suspended in 200 ml of ethyl acetate. To the suspension was added 6N hydrochloric acid gradually with stirring under ice-cooling, to make the suspension acidic. The resulting insolubles were removed by filtration. The ethyl acetate layer was washed with water, dried with anhydrous magnesium sulfate and concentrated under reduced pressure. The resulting oily residue was dissolved in 15 ml of 25% hydrogen bromideacetic acid, and the solution was allowed to stand for 1 hour at room temperature. The reaction mixture was mixed with isopropyl ether. The precipitated oily matter was separated and dried under reduced pressure.

Using the above product and 7.30 g of Boc-Thr(Bzl)—OSu, the same procedure as in Reference Example was repeated to obtain 6.20 g (yield: 76.3%) of the above objective compound in an oily form.

REFERENCE EXAMPLE 72

Preparation of Boc-Ser(Bzl)-Thr(Bzl)-Glu—OCH$_3$

Using 6.20 g of Boc-Thr(Bzl)-Glu—OCH$_3$ and 5.38 g of Boc-Ser(Bzl)—OSu, the same procedure as in Reference Example 35 was repeated to obtain 8.00 g (yield: 92.7%) of the above objective compound having a melting point of 120°-123° C.

REFERENCE EXAMPLE 73

Preparation of
Boc-β-Ala-Ser(Bzl)-Asn-Leu-Ser(Bzl)-Thr(Bzl)-Glu—OCH$_3$

Using 1.10 g of Boc-Ser(Bzl)-Thr(Bzl)-Glu—OCH$_3$ and 1.07 g of Boc-⊖-Ala-Ser(Bzl)-Asn-Leu—N$_2$H$_3$, the same procedure as in Reference Example 36 was repeated to obtain 1.23 g (yield: 63.7%) of the above objective compound having a melting point of 208°-214° C.

REFERENCE EXAMPLE 74

Preparation of ⌐β—Ala—Ser(Bzl)—Asn—Leu—Ser(Bzl)—
Thr(Bzl)—Glu—OCH$_3$

Using 1.20 g of Boc-β-Ala-Ser(Bzl)-Asn-Leu-Ser(Bzl)-Thr(Bzl)-Glu—OCH$_3$, Ser(Bzl)-Thr(Bzl)-Glu—OCH$_3$, the same procedure as in Reference Example 37 was repeated to obtain 0.73 g (yield: 68.1%) of the above objective compound having a melting point of 200°-204° C.

REFERENCE EXAMPLE 75

Preparation of ⌐β—Ala—Ser(Bzl)—Asn—Leu—
Ser(Bzl)—Thr(Bzl)—Glu—N$_2$H$_3$

Using 0.90 g of

⌐β—Ala—Ser(Bzl)—Asn—Leu—
Ser(Bzl)—Thr(Bzl)—Glu—OCH$_3$, the same procedure as in Reference Example 38 was repeated to obtain 0.90 g (yield: 100%) of the above objective compound having a melting point of 218°-221° C.

REFERENCE EXAMPLE 76

Preparation of ⌐β—Ala—Ser(Bzl)—Asn—Leu—
Ser(Bzl)—Thr(Bzl)—Glu—Val—Leu—Gly—OH

Using 0.90 g of β-Ala-Ser(Bzl)-Asn-Leu-Ser(Bzl)-Thr(Bzl)-Glu—N$_2$H$_3$ and 1.30 g of Boc-Val-Leu-Gly—OH, the same procedure as in Reference Example 39 was repeated to obtain 0.64 g (yield: 56.6%) of the above objective compound having a melting point of 247°-253° C.

REFERENCE EXAMPLE 77

Preparation of
Boc-Acp-Asn-Leu-Ser(Bzl)-Thr(Bzl)-Glu—OCH$_3$

Using 2.50 g of Boc-Ser(Bzl)-Thr(Bzl)-Glu—OCH$_3$ and 1.80 g of Boc-Acp-Asn-Leu—N$_2$H$_3$, the same procedure as in Reference Example 36 was repeated to obtain 3.34 g (yield: 86.7%) of the above objective compound having a melting point of 178°-181° C.

REFERENCE EXAMPLE 78

Preparation of ⌐Acp—Asn—Leu—Ser(Bzl)—Thr(Bzl)—
⌐
Glu—OCH₃

Using 3.30 g of Boc-Acp-Asn-Leu-Ser(Bzl)-Thr(Bzl)-Glu—OCH₃, the same procedure as in Reference Example 37 was repeated to obtain 33 g (yield: 45.9%) of the above objective compound having a melting point of 234°–237° C.

REFERENCE EXAMPLE 79

Preparation of ⌐Acp—Asn—Leu—Ser(Bzl)—Thr(Bzl)—
⌐
Glu—N₂H₃

Using 1.30 g of

⌐Acp—Asn—Leu—Ser(Bzl)—Thr(Bzl)—
⌐
Glu—OCH₃.

the same procedure as in REFERENCE EXAMPLE 38 was repeated to obtain 0.96 g (yield: 73.8%) of the above objective compound having a melting point of 216°–219° C.

REFERENCE EXAMPLE 80

Preparation of ⌐Acp—Asn—Leu—Ser(Bzl)—Thr(Bzl)—
⌐
Glu—Val—Leu—Gly—OH

Using 0.93 g of

⌐Acp—Asn—Leu—Ser(Bzl)—Thr(Bzl)—
⌐
Glu—N₂H₃ and 0.42 g of Boc-Val-Leu-Gly—OH, the same procedure as in REFERENCE EXAMPLE 39 was repeated to obtain 0.55 g (yield: 45.5%) of the above objective compound having a melting point of 248°–253° C.

REFERENCE EXAMPLE 81

Preparation of Boc-Lys(Bz)-Leu—OEt

Using 2.30 g of Boc-Lys(Bz)—OH and 1.35 g of HCl.H-Leu—OEt, the same procedure as in Reference Example 3 was repeated to obtain 2.96 g (yield: 91.8%) of the above objective compound having a melting point of 50°–54° C.

REFERENCE EXAMPLE 82

Preparation of Boc-Lys(Bz)-Leu—OH

Using 2.86 g of Boc-Lys(Bz)-Leu—OEt, the same procedure as in Reference Example 12 was repeated to obtain 2.21 g (yield: 81.9%) of the above objective compound in a powder form.

REFERENCE EXAMPLE 83

Preparation of Boc-Lys(Bz)-Leu-Gln-Thr(Bzl)-Tyr(Bzl)-Pro-Arg(Tos)-Thr(Bzl)-Asp(Obzl)-Val-Gly-Ala-Gly-Thr(Bzl)-Pro—NH₂

Using 2.50 g of Boc-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ [reference is made to Japanese Patent Application Kokai (Laid—Open) No. 112099/1986] and 841 mg of Boc-Lys(Bz)-Leu—OH, the same procedure as in Reference Example 70 was repeated to obtain 2.78 g (yield: 95.3%) of the above objective compound having a melting point of 166°–171° C.

REFERENCE EXAMPLE 84

Preparation of Boc-Leu-His-Lys(Bz)-Leu-Gln-Thr(Bzl)-Tyr-(Bzl)-Pro-Arg(Tos)-Thr(Bzl)-Asp(OBzl)-Val-Gly-Ala-Gly-Thr(Bzl)-Pro—NH₂

Using Boc-Lys(Bz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ (2.58 g), Boc-Leu-His—OH (591 mg) and, in place of HOBT, HOSu, the same procedure as in Reference Example 70 was repeated to obtain 2.62 g (yield: 92.0%) of the above objective compound having a melting point of 165°–172° C.

REFERENCE EXAMPLE 85

Preparation of Boc-Glu(OBzl)-Leu-His-Lys(Bz)-Leu-Gln-Thr-(Bzl)-Tyr(Bzl)-Pro-Arg(Tos)-Thr(Bzl)-Asp-(OBzl)-Val-Gly-Ala-Gly-Thr(Bzl)-Pro—NH₂

2.30 g of Boc-Leu-His-Lys(Bz)-Leu-Gln-Thr(Bzl)-Tyr(Bzl)-Pro-Arg(Tos)-Thr(Bzl)-Asp(OBzl)-Val-Gly-

Ala-Gly-Thr(Bzl)-Pro—NH₂ was dissolved in 10 ml of TFA. The solution was allowed to stand for 30 minutes at room temperature. The reaction mixture was concentrated under reduced pressure. The residue was mixed with diethyl ether, and the resulting precipitate was collected by filtration and dried over sodium hydroxide under reduced pressure.

The above product was dissolved in 20 ml of DMF. The solution was neutralized with triethylamine with ice-cooling. Thereto were added 563 mg of Boc-Glu(OBzl)—OSu and 175 mg of HOBT. The mixture was stirred for 42 hours at room temperature while maintaining its pH at 8 with N-methylmorpholine.

The reaction mixture was mixed with 80 ml of water. The resulting precipitate was collected by filtration, dried and washed with hot ethyl acetate to obtain 1.87 g (yield: 75.1%) of the above objective compound having a melting point of 167°–170° C.

REFERENCE EXAMPLE 86

Preparation of
Boc-Gln-Glu(OBzl)-Leu-His-Lys(Bz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂

Using Boc-Glu(OBzl)-Leu-His-Lys(Bz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ (1.77 g) and Boc-Gln—ONp (338 mg), the same procedure as in Reference Example 85 was repeated to obtain 1.68 g (yield: 90.9%) of the above objective compound having a melting point of 170°–174° C.

REFERENCE EXAMPLE 87

Preparation of
Boc-Lys(Z)-Leu-Ser(Bzl)-Gln-Glu(OBzl)-Leu-His-Lys(Bzl)-Leu-Gln-Thr-(Bzl)-Tyr(Bzl)-Pro-Arg(Tos)-Thr(Bzl)-Asp(OBzl)-Val-Gly-Ala-Gly-Thr(Bzl)-Pro—NH₂

Using Boc-Gln-Glu(OBzl)-Leu-His-Lys(Bz)-Leu-Gln-Thr(Bzl)-Tyr(Bzl)-Pro-Arg(Tos)-Thr(Bzl)-Asp-(OBzl)-Val-Gly-Ala-Gly-Thr(Bzl)-Pro—NH₂ (500 mg) and Boc-Lys(Z)-Leu-Ser(Bzl)—OH (167 mg), the same procedure as in Reference Example 70 was repeated to obtain 560 mg (yield: 94.7%) of the above objective compound having a melting point of 209°–214° C.

REFERENCE EXAMPLE 88

Preparation of
Boc-Lys(Bz)-Leu-Ser(Bzl)-Gln-Glu(OBzl)-Leu-His-Lys(Bz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂

Using Boc-Gln-Glu(OBzl)-Leu-His-Lys(Bz)-Leu-Gln-Thr(Bzl)-Tyr(Bzl)-Pro-Arg(Tos)-Thr(Bzl)-Asp-(OBzl)-Val-Gly-Ala-Gly-Thr(Bzl)-Pro—NH₂ (500 mg) and Boc-Lys(Bz)-Leu-Ser(Bzl)—OH (160 mg), the same procedure as in Reference Example 70 was repeated to obtain 580 mg (yield: 98.9%) of the above objective compound having a melting point of 206°–210° C.

REFERENCE EXAMPLE 89

Preparation of Z-Tyr(CH₂COOBzl)—OCH₃

5.70 g of Z-Tyr—OCH₃ was dissolved in DMF to obtain 25 ml of a solution. Thereto was added 692 mg of 60% sodium hydride with ice-cooling. The mixture was stirred for 30 minutes. Then, 3.96 g of benzyl bromoacetate was added and the mixture was stirred for 1 hour at 50° C.

The reaction mixture was concentrated under reduced pressure. The residue was extracted with 100 ml of ethyl acetate. The ethyl acetate layer was washed with water and a saturated aqueous sodium chloride solution twice in this order, dried with anhydrous sodium sulfate and concentrated under reduced pressure. The residue was poured into a silica gel column. Elution was conducted using petroleum ether/chloroform (1:4) to obtain 6.00 g (yield: 72.6%) of the above objective compound.

Appearance: oily.

NMR (CDCl₃) δ:

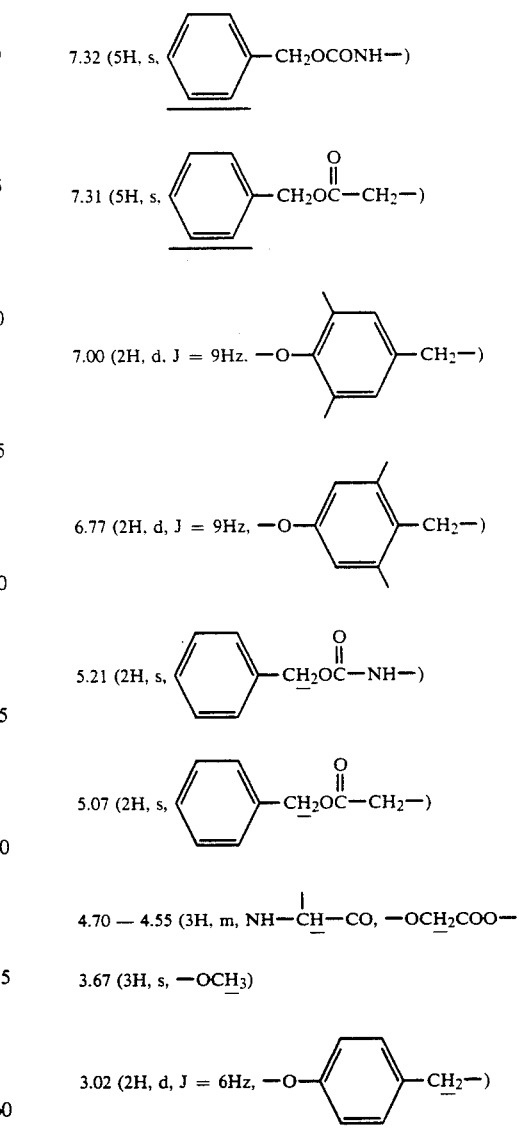

REFERENCE EXAMPLE 90

Preparation of
Boc-Thr(Bzl)-Tyr(CH₂—COOH)—OCH₃

5.80 g of Z-Tyr(CH₂COOBzl)—OCH₃ was dissolved in THF to obtain 50 ml of a solution. Thereto were added 12 ml of 1N hydrochloric acid and 300 mg of 10% palladium-carbon. The mixture was subjected to catalytic reduction in a hydrogen stream. After the completion of the reaction, the 10% palladium carbon was removed by filtration using Celite, and the filtrate was concentrated to dryness under reduced pressure.

Using the above product and 4.92 g of Boc-Thr(Bzl)—OSu, the same procedure as in Reference Example 25 was repeated to obtain 5.00 g (yield: 75.7%) of the above objective compound having a melting point of 101°-106° C.

REFERENCE EXAMPLE 91

Preparation of Boc-Ser(Bzl)-Thr(Bzl)-Tyr(CH$_2$COOH)—OCH$_3$

Using 4.90 g of Boc-Thr(Bzl)-Tyr(CH$_2$COOH)—OCH$_3$ and 4.23 g of Bos-Ser(Bzl)—OSu, the same procedure as in Reference Example 35 was repeated to obtain 4.51 g (yield: 69.5%) of the above objective compound in an oily form.

REFERENCE EXAMPLE 92

Preparation of Boc-Ser(Bzl)-Asn-Leu-Ser(Bzl)-Thr(Bzl)-Tyr(CH$_2$COOH)—OCH$_3$

Using 2.50 g of Boc-Ser(Bzl)-Thr(Bzl)-Tyr(CH$_2$COOH)—OCH$_3$ and 2.23 g of Boc-Ser(Bzl)-Asn-Leu—N$_2$H$_3$, the same procedure as in Reference Example 36 was repeated to obtain 2.49 g (63.8%) of the above objective compound having a melting point of 186°-190° C.

REFERENCE EXAMPLE 93

Preparation of ⎣—CH$_2$CO—Ser(Bzl)—Asn—Leu—

⎤

Ser(Bzl)—Thr(Bzl)—Tyr—N$_2$H$_3$

Using 2.43 g of Boc-Ser(Bzl)-Asn-Leu-Ser(Bzl)-Thr(Bzl)-Tyr(CH$_2$COOH)—OCH$_3$, the same procedures as in Reference Example 37 and 38 were repeated in this order to obtain 950 mg (yield: 43.8%) of the above objective compound having a melting point of 202°-208° C.

REFERENCE EXAMPLE 94

Preparation of ⎣—CH$_2$CO—Ser(Bzl)—Asn—Leu—

⎤

Ser(Bzl)—Thr(Bzl)—Tyr—Val—Leu—Gly—OH

Using 450 mg of

⎣—CH$_2$CO—Ser(Bzl)—Asn—Leu—

⎤

Ser(Bzl)—Thr(Bzl)—Tyr—N$_2$H$_3$ and 349 mg of Boc-Val-Leu-Gly—OH, the same procedure as in Reference Example 39 was repeated to obtain 430 mg (yield: 75.6%) of the above objective compound having a melting point of 229°-232° C. (decomposed).

REFERENCE EXAMPLE 95

Preparation of Boc-Asp(OcHex)-Val-Gly-Ala-Gly-Thr(Bzl)-Pro—NH$_2$

Using 10.35 g of Boc-Val-Gly-Ala-Gly-Thr(Bzl)-Pro—NH$_2$ [reference is made to Japanese Patent Application Kokai (Laid—Open) No. 112099/1986] and 5.36 g of Boc-Asp-(OcHex)—OH, the same procedure as in Reference Example 70 was repeated to obtain 11.05 g (yield: 83.0%) of the above objective compound having a melting point of 228°-230° C.

REFERENCE EXAMPLE 96

Preparation of Boc-Thr(Bzl) Asp(OcHex)-Val-Gly-Ala-Gly-Thr(Bzl)-Pro—NH$_2$

Using 10.00 g of Boc-Asp(OcHex)-Val-Gly-Ala-Gly-Thr(Bzl)-Pro—NH$_2$ and 5.50 g of Boc-Thr(Bzl)—OSu, the same procedure as in Reference Example 85 was repeated to obtain 10.29 g (yield: 84.5%) of the above objective compound having a melting point of 168°-171° C.

REFERENCE EXAMPLE 97

Preparation of Boc-Arg(Tos)-Thr(Bzl)-Asp(OcHex)-Val-Gly-Ala-Gly-Thr(Bzl)-Pro—NH$_2$ Using 10.00 g of Boc-Thr(Bzl)-Asp(OcHex)-Val-Ala-Gly-Thr(Bzl)-Pro—NH$_2$ and 5.79 g of Boc-Arg(Tos)—OH.CH$_3$COOHC$_2$H$_5$.1/5H$_2$O, the same procedure as in Reference Example 70 was repeated to obtain 11.55 g (yield: 89.7%) of the above objective compound having a melting point of 221°-226° C.

REFERENCE EXAMPLE 98

Preparation of Boc-Thr(Bzl)-Pro—OBzl

Using 8.66 g of Boc-Thr(Bzl)—OH and 7.42 g of HCl.H-Pro—OBzl, the same procedure as in Reference Example 3 was repeated to obtain 13.25 g (yield: 95.3%) of the above objective compound in an oily form.

REFERENCE EXAMPLE 99

Preparation of Boc-Thr(Bzl)-Pro—OH

Using 13.25 g of Boc-Thr(Bzl)-Pro—OBzl, the same procedure as in Reference Example 12 was repeated to obtain 9.72 g (yield: 89.6%) of the above objective compound in a powder form.

REFERENCE EXAMPLE 100

Preparation of Boc-Thr(Bzl)-Pro-Arg(Tos)-Thr(Bzl)-Asp(OcHex)-Val-Gly-Ala-Gly-Thr(Bzl)-Pro—NH$_2$ Using 2.00 g of Boc-Arg(Tos)-Thr(Bzl)-Asp(OcHex)-Val-Gly-Ala-Gly-Thr(Bzl)-Pro—NH$_2$ and 878 mg of Boc-Thr(Bzl)-Pro—OH, the same procedure as in Reference Example 70 was repeated to obtain 2.00 g (yield: 82.8%) of the above objective compound having a melting point of 199°-201° C.

REFERENCE EXAMPLE 101

Preparation of
Boc-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Thr(Bzl)-Pro-Arg(Tos)-Thr(Bzl)-Asp(OcHex)-Val-Gly-Ala-Gly-Thr(Bzl)-Pro—NH$_2$ (1.95 g) and Boc-Gln—ONp (639 mg), the same procedure as in Reference Example 85 was repeated to obtain 2.02 g (yield: 96.5%) of the above objective compound having a melting point of 185°–189° C.

REFERENCE EXAMPLE 102

Preparation of
Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using 1.97 g of Boc-Gln-Thr(Bzl)-Pro-Arg(Tos)-Thr(Bzl)-Asp(OcHex)-Val-Gly-Ala-Gly-Thr(Bzl)-Pro—NH$_2$ and 863 mg of Boc-Lys(Cl-Z)-Leu—OH, the same procedure as in REFERENCE EXAMPLE 70 was repeated to obtain 2.31 g (yield: 95.7%) of the above objective compound having a melting point of 177°–182° C.

REFERENCE EXAMPLE 103

Preparation of
Boc-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (2.26 g), Boc-His(Tos)—OH (626 mg) and, in place of HOBT, HOSu, the same procedure as in Reference Example 70 was repeated to obtain 2.55 g (yield: 99.7%) of the above objective compound having a melting point of 168°–175° C.

REFERENCE EXAMPLE 104

Preparation of
Boc-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(bzl)-Pro—NH$_2$ Using Boc-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (2.50 g) and Boc-Leu—OSu (493 mg), the same procedure as in REFERENCE EXAMPLE 85 was repeated to obtain 2.31 g (yield: 88.2%) of the above objective compound having a melting point of 176°–178° C.

REFERENCE EXAMPLE 105

Preparation of
Boc-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (2.26 g) and Boc-Glu(OcHex)—OH (424 mg), the same procedure as in Reference Example 70 was repeated to obtain 2.33 g (yield: 95.7%) of the above objective compound having a melting point of 174°–177° C.

REFERENCE EXAMPLE 106

Preparation of Boc-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (2.28 g) and Boc-Gln—ONp (446 mg), the same procedure as in Reference Example 85 was repeated to obtain 2.19 g (yield: 91.4%) of the above objective compound having a melting point of 178°–180° C.

REFERENCE EXAMPLE 107

Preparation of
Boc-Lys(Z)-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (1.14 g) and Boc-Lys(Z)-Leu-Ser(Bzl)—OH (393 mg), the same procedure as in Reference Example 70 was repeated to obtain 1.30 g (yield: 95.0%) of the above objective compound having a melting point of 189°–193° C.

REFERENCE EXAMPLE 108

Preparation of HCl.H-Cys(CH$_2$COOBu$^t$)—OCH$_3$ 1.67 g of HCl.H-Cys—OCH$_3$ was dissolved in DMF to obtain 30 ml of a solution. To the solution were added 3.80 g of BrCH$_2$COOBu$^t$ and 2.73 ml of triethylamine. The mixture was stirred for 20 hours at room temperature. The reaction mixture was concentrated under reduced pressure. The residue was extracted with 50 ml of ethyl acetate. The ethyl acetate layer was washed with a saturated aqueous sodium bicarbonate solution and a saturated aqueous sodium chloride solution, dried with anhydrous sodium sulfate and concentrated under reduced pressure. The resulting oily residue was dissolved in diethyl ether. Thereto was added 3.86 ml of 4N hydrochloric acid/dioxane with ice-cooling. The resulting precipitate was collected by filtration to obtain 1.44 g (yield: 51.8%) of the above objective compound having a melting point of 146°–147° C.

REFERENCE EXAMPLE 109

Preparation of
Boc-Thr(Bzl)-Cys(CH$_2$COOBu$^t$)—OCH$_3$

Using 1.30 g of HCl.H-Cys(CH$_2$COOBu$^t$)—OCH$_3$ and 1.41 g of Boc-Thr(Bzl)—OH, the same procedure as in Reference Example 3 was repeated to obtain 2.36 g (yield: 95.9%) of the above objective compound in an oily form.

REFERENCE EXAMPLE 110

Preparation of Boc-Ser(Bzl)-Thr(Bzl)-Cmc—OCH$_3$

Using 2.36 g of Boc-Thr(Bzl)-Cys(CH$_2$COOBu$^t$)—OCH$_3$ and 1.88 g of Boc-Ser(Bzl)—OSu, the same procedure as in Reference Example 35 was repeated to obtain 1.48 g (yield: 51.2%) of the above objective compound.

Appearance: oily.
Amino acid analysis:
Thr: 0.94 (1)

Ser: 1.16 (1)
Cmc: 0.90 (1).

REFERENCE EXAMPLE 111

Preparation of
Boc-Ser(Bzl)-Asn-Leu-Ser(Bzl)-Thr(Bzl)-Cmc—OCH$_3$

Using 1.30 g of Boc-Ser(Bzl)-Thr(Bzl)-Cmc—OCH$_3$ and 1.26 g of Boc-Ser(Bzl)-Asn-Leu—N$_2$H$_3$, the same procedure as in Reference Example 36 was repeated to obtain 1.20 g (yield: 57.7%) of the above objective compound having a melting point of 194°–196° C.

REFERENCE EXAMPLE 112

Preparation of ⌐Ser(Bzl)—Asn—Leu—Ser(Bzl)—
Thr(Bzl)—Cmc—OCH$_3$

Using 1.10 g of Boc-Ser(Bzl)-Asn-Leu-Ser(Bzl)-Thr(Bzl)-Cmc—OCH$_3$, the same procedure as in Reference Example 37 was repeated to obtain 400 mg (yield: 41.0%) of the above objective compound having a melting point of 116°–118° C.

REFERENCE EXAMPLE 113

Preparation of ⌐Ser(Bzl)—Asn—Leu—Ser(Bzl)—
Thr(Bzl)—Cmc—N$_2$H$_3$

Using 0.37 g of

⌐Ser(Bzl)—Asn—Leu—Ser(Bzl)—
Thr(Bzl)—Cmc—OCH$_3$, the same procedure as in Reference Example 38 was repeated to obtain 269 mg (yield: 72.7%) of the above objective compound having a melting point of 115°–117° C.

REFERENCE EXAMPLE 114

Preparation of ⌐Ser(Bzl)—Asn—Leu—Ser(Bzl)—
Thr(Bzl)—Cmc—Val—Leu—Gly—OH

Using

⌐Ser(Bzl)—Asn—Leu—Ser(Bzl)—Thr(Bzl)—
Cmc—N$_2$H$_3$ (240 mg) and Boc-Val-Leu-Gly—OH (196 mg), the same procedure as in Reference Example 39 was re-peated to obtain 171 mg (yield: 56.2%) of the above objective compound having a melting point of 241°–243° C. (decomposed).

REFERENCE EXAMPLE 115

Preparation of Boc-D-Tyr(cl$_2$-Bzl)-Pro—OBzl

Using 3.00 g of Boc-D-Tyr(Cl$_2$-Bzl)—OH and 1.73 g of HCl.H-Pro—OBzl, the same procedure as in Reference Example 3 was repeated to obtain 4.10 g (yield: 95.9%) of the above objective compound in a powder form.

REFERENCE EXAMPLE 116

Preparation of
Box-Thr(Bzl)-D-Tyr(Cl$_2$-Bzl)-Pro—OBzl

Using 4.00 g of Box-D-Tyr(cl$_2$-Bzl)-Pro—OBzl and 1.97 g of Boc-Thr(Bzl)—OH, the same procedure as in Reference Example 70 was repeated to obtain 4.10 g (yield: 78.6%) of the above objective compound in a powder form.

REFERENCE EXAMPLE 117

Preparation of Boc-Thr(Bzl)-D-Tyr(Cl$_2$-Bzl)-Pro—OH

Using 4.00 g of Boc-Thr(Bzl)-D-Tyr(Cl$_2$-Bzl)-Pro—OBzl, the same procedure as in Reference Example 12 was repeated to obtain 1.80 g (yield: 50.5%) of the above objective compound.

Appearance: Powder.
Amino acid analysis:
Thr: 0.91 (1)
Tyr: 1.04 (1)
Pro: 1.04 (1).

REFERENCE EXAMPLE 118

Preparation of
Boc-Thr(Bzl)-D-Tyr(Cl$_2$-Bzl)-Pro-Arg(Tos)-Thr(Bzl)-Asp(OcHex)-Val-Gly-Ala-Gly-Thr(Bzl)-Pro—NH$_2$ Using 1.50 g of Boc-Arg(Tos)-Thr(Bzl)-Asp(O-cHex)-Val-Gly-Ala-Gly-Thr(Bzl)-Pro—NH$_2$ and 1.18 g of Boc-Thr(Bzl)-D-Tyr(Cl$_2$-Bzl)-Pro—OH, the same procedure as in Reference Example 70 was repeated to obtain 1.55 g (yield: 71.8%) of the above objective compound having a melting point of 182°–184° C.

REFERENCE EXAMPLE 119

Preparation of
Boc-Gln-Thr(Bzl)-D-Tyr(Cl$_2$-Bzl)-Pro-Arg(Tos)-Thr(Bzl)-Asp(OcHex)-Val-Gly-Ala-Gly-Thr(Bzl)-Pro—NH$_2$ Using Boc-Thr(Bzl)-D-Tyr(Cl$_2$-Bzl)-Pro-Arg(Tos)-Thr(Bzl)-Asp(OcHex)-Val-Gly-Ala-Gly-Thr-(Bzl)-Pro—NH$_2$ (1.50 g) and Boc-Gln—ONp (413 mg), the same procedure as in REFERENCE EXAMPLE 85 was repeated to obtain 1.48 g (yield: 92.8%) of the above objective compound having a melting point of 168°–174° C.

REFERENCE EXAMPLE 120

Preparation of
Boc-Lys(Cl-Z)-Leu-Gln-Thr(Bzl)-D-Tyr(Cl$_2$-Bzl))-Pro-Arg(Tos)-Thr(Bzl)-Asp(OcHex)-Val-Gly-Ala-Gly-Thr(Bzl)-Pro—NH$_2$ Using Boc-Gln-Thr(Bzl)-D-Tyr(Cl$_2$-Bzl)-Pro-Arg(Tos)-Thr(Bzl)-Asp(OcHex)-Val-Gly-Ala-Cly- Thr(Bzl)-Pro—NH₂ (1.43 g) and Boc-Lys(Cl-Z)-Leu—OH (531 mg), the same procedure as in Reference Example 70 was repeated to obtain 1.42 g (yield: 83.5%) of the above objective compound.

Melting point: 165°-180° C.
Amino acid analysis:

| | |
|---|---|
| Asp: 1.04 (1) | Leu: 0.93 (1) |
| Thr: 2.88 (3) | Tyr: 0.97 (1) |
| Glu: 0.93 (1) | Lys: 0.94 (1) |
| Gly: 2.08 (2) | Arg: 1.03 (1) |
| Ala: 1.07 (1) | Pro: 2.06 (2) |
| Val: 1.06 (1) | |

REFERENCE EXAMPLE 121

Preparation of Boc-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂

Using Boc-Lys(Cl-Z)-Leu-Gln-Thr(Bzl)-D-Tyr(Cl₂-Bzl)-Pro-Arg(Tos)-Thr(Bzl) Asp(OcHex)-Val-Gly-Ala-Gly-Thr(Bzl)-Pro—NH₂ (1.37 g), Boc-His(Tos)—OH (332 mg) and, in place of HOBT, HOSu, the same procedure as in Reference Example 70 was repeated to obtain 1.36 g (yield: 89.0%) of the above objective compound having a melting point of 195°-197° C.

REFERENCE EXAMPLE 122

Preparation of Boc-Leu-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂

Using Boc-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂ (1.31 g) and Boc-Leu—OSu (227 mg), the same procedure as in Reference Example 85 was repeated to obtain 1.25 g (yield: 92.4%) of the above objective compound having a melting point of 174°-176° C.

REFERENCE EXAMPLE 123

Preparation of Boc-Glu(OcHex)-Leu-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂

Using Boc-Leu-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂ (1.20 g) and Boc-Glu(OcHex)—OH (202 mg), the same procedure as in Reference Example 70 was repeated to obtain 1.20 g (yield: 92.9%) of the above objective compound having a melting point of 200°-204° C.

REFERENCE EXAMPLE 124

Preparation of Boc-Gln-Glu(OcHex)-Leu-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂

Using Boc-Glu(OcHex)-Leu-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂ (1.15 g) and Boc-Gln—ONp (199 mg), the same procedure as in Reference Example 85 was repeated to obtain 1.16 g (yield: 98.2%) of the above objective compound having a melting point of 215°-217° C.

REFERENCE EXAMPLE 125

Preparation of Boc-Lys(Z)-Leu-Ser(Bzl)-Gln-Glu(OcHex)-Leu-His(-Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂

Using Boc-Gln-Glu(OcHex)-Leu-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂ (500 mg) and Boc-Lys(Z)-Leu-Ser(Bzl)—OH (153 mg), the same procedure as in Reference Example 70 was repeated to obtain 550 mg (yield: 94.4%) of the above objective compound having a melting point of 214°-220° C.

REFERENCE EXAMPLE 126

Preparation of Boc-Leu-Pro—OBzl

Using 4.98 g of Boc-Leu—OH.H₂O and 4.82 g of HCl.H-Pro—OBzl, the same procedure as in Reference Example 3 was repeated to obtain 7.65 g (yield: 91.4%) of the above objective compound having an oily appearance.

REFERENCE EXAMPLE 127

Preparation of Boc-Thr(Bzl)-Leu-Pro—OBzl

Using 7.60 g of Boc-Leu-Pro—OBzl and 5.61 g of Boc-Thr(Bzl)—OH, the same procedure as in Reference Example 70 was repeated to obtain 8.96 g (yield: 81.0%) of the above objective compound having an oily appearance.

REFERENCE EXAMPLE 128

Preparation of Boc-Thr(Bzl)-Leu-Pro—OH

Using 5.00 g of Boc-Thr(Bzl)-Leu-Pro—OBzl, the same procedure as in Reference Example 12 was repeated to obtain 2.93 g (yield: 68.8%) of the above objective compound having a melting point of 61°-70° C.

REFERENCE EXAMPLE 129

Preparation of Boc-Thr(Bzl)-Leu-Pro-Arg(Tos)-Thr(Bzl)-Asp(OcHex)-Val-Gly-Ala-Gly-Thr(Bzl)-Pro—NH₂

Using Boc-Arg(Tos)-Thr(Bzl)-Asp(OcHex)-Val-Gly-Ala-Gly-Thr(Bzl)-Pro—NH₂ (1.50 g) and Boc-Thr(Bzl)-Leu-Pro—OH (0.67 g), the same procedure as in Reference Example 70 was repeated to obtain 1.64 g (yield: 84.9%) of the above objective compound having a melting point of 197°-199° C.

REFERENCE EXAMPLE 130

Preparation of Boc-Gln-Thr(Bzl)-Leu-Pro-Arg(Tos) Thr(Bzl)-Asp(OcHex)-Val-Gly-Ala-Gly-Thr(Bzl)-Pro—NH₂

Using Boc-Thr(Bzl)-Leu-Pro-Arg(Tos)-Thr(Bzl)-Asp(OcHex)-Val-Gly-Ala-Gly-Thr(Bzl)-Pro—NH2 (1.59 g) and Boc-Gln—ONp (0.36 g), the same procedure as in Reference Example 85 was repeated to obtain 1.47 g (yield: 86.5%) of the above objective compound having a melting point of 188°-190° C.

REFERENCE EXAMPLE 131

Preparation of
Boc-Lys(Cl-Z)-Leu-Gln-Thr(Bzl)-Leu-Pro-Arg(Tos)-
Thr(Bzl)-Asp(OcHex)-Val-Gly-Ala-Gly-Thr(Bzl)-
Pro—NH₂

Using Boc-Gln-Thr(Bzl)-Leu-Pro-Arg(Tos)-
Thr(Bzl)-Asp(OcHex)-Val-Gly-Ala-Gly-Thr(Bzl)-
Pro—NH₂ (1.42 g) and Boc-Lys(Cl-Z)-Leu—OH (0.43 g), the same procedure as in Reference Example 70 was repeated to obtain 1.20 g (yield: 67.0%) of the above objective compound having a melting point of 174°-176° C.

REFERENCE EXAMPLE 132

Preparation of
Boc-Leu-His-Lys(Cl-Z)-Leu-Gln-Thr(Bzl)-Leu-Pro-
Arg(Tos)-Thr(Bzl)-Asp(OcHex)-Val-Gly-Ala-Gly-
Thr(Bzl)-Pro—NH₂

Using Boc-Lys(Cl-Z)-Leu-Gln-Thr(Bzl)-Leu-Pro-
Arg(Tos)-Thr(Bzl)-Asp(OcHex)-Val-Gly-Ala-Gly-
Thr(Bzl)-Pro—NH₂ (1.15 g), Boc-Leu-His—OH (191 mg) and, in place of HOBT, HOSu, the same procedure as in Reference Example 70 was repeated to obtain 1.18 g (yield: 93.6%) of the objective compound having a melting point of 182°-183° C.

REFERENCE EXAMPLE 133

Preparation of
Boc-Glu(OBzl)-Leu-His-Lys(Cl-Z)-Leu-Gln-Thr(Bzl)-
Leu-Pro-Arg(Tos)-Thr(Bzl)-Asp(OcHex)-Val-Gly-
Ala-Gly-Thr(Bzl)-Pro—NH₂

Using Boc-Leu-His-Lys(Cl-Z)-Leu-Gln-Thr(Bzl)-
Leu-Pro-Arg(Tos)-Thr(Bzl)-Asp(OcHex)-Val-Gly-
Ala-Gly-Thr(Bzl)-Pro—NH₂ (1.13 g) and Boc-
Glu(OBzl)—OSu (274 mg), the same procedure as in Reference Example 85 was repeated to obtain 0.89 g (yield: 73.0%) of the above objective compound having a melting point of 177°-179° C.

REFERENCE EXAMPLE 134

Preparation of
Boc-Gln-Glu(OBzl)-Leu-His-Lys(Cl-Z)-Leu-Gln-
Thr(Bzl)-Leu-Pro-Arg(Tos)-Thr(Bzl)-Asp(OcHex)-
Val-Gly-Ala-Gly-Thr(Bzl)-Pro—NH₂

Using Boc-Glu(OBzl)-Leu-His-Lys(Cl-Z)-Leu-Gln-
Thr(Bzl)-Leu-Pro-Arg(Tos)-Thr(Bzl)-Asp(OcHex)-
Val-Gly-Ala-Gly-Thr(Bzl)-Pro—NH₂ (0.84 g) and Boc-Gln—ONp (130 mg), the same procedure as in Reference Example 85 was repeated to obtain 620 mg (yield: 71.3%) of the above objective compound having a melting point of 209°-210° C.

REFERENCE EXAMPLE 135

Preparation of
Boc-Lys(Z)-Leu-Ser(Bzl)-Gln-Glu(OBzl)-Leu-His-
Lys(Cl-Z)-Leu-Gln-Thr(Bzl)-Leu-Pro-Arg(Tos)-
Thr(Bzl)-Asp(OcHex)-Val-Gly-Ala-Gly-Thr(Bzl)-
Pro—NH₂

Using Boc-Gln-Glu(OBzl)-Leu-His-Lys(Cl-Z)-Leu-
Gln-Thr(Bzl)-Leu-Pro-Arg(Tos)-Thr(Bzl)-Asp(O-
cHex)-Val-Gly-Ala-Gly-Thr(Bzl)-Pro—NH₂ (570 mg) and Boc-Lys(Z)-Leu-Ser(Bzl)—OH (151 mg), the same procedure as in Reference Example 70 was repeated to obtain 600 mg (yield: 89.6%) of the above objective compound having a melting point of 225°-231° C.

REFERENCE EXAMPLE 136

Preparation of Boc-Lys(COCH₃)-Leu-Ser(Bzl)—OH

Using 1.12 g of Boc-Leu-Ser(Bzl)—OH and 1.02 g of Boc-Lys(COCH₃)—OSu, the same procedure as in Reference Example 35 was repeated to obtain 0.91 g (yield: 62.8%) of the above objective compound having a melting point of 88°-90° C.

REFERENCE EXAMPLE 137

Preparation of
Boc-Lys(COCH₃)-Leu-Ser(Bzl)-Gln-Glu(OBzl)-Leu-
His-Lys(Cl-Z)-Leu-Gln-Thr(Bzl)-Tyr(Bzl)-Pro-
Arg(Tos)-Thr(Bzl)-Asp(OBzl)-Val-Gly-Ala-Gly-
Thr(Bzl)-Pro—NH₂

Using Boc-Gln-Glu(OBzl)-Leu-His-Lys(Cl-Z)-Leu-
Gln-Thr(Bzl)-Tyr(Bzl)-Pro-Arg(Tos)-Thr(Bzl)-
Asp(OBzl)-Val-Gly-Ala-Gly-Thr(Bzl)-Pro—NH₂ (509 mg) and Boc-Lys(COCH₃)-Leu-Ser(Bzl)—OH (141 mg), the same procedure as in Reference Example 70 was repeated to obtain 368 mg (yield: 63.9%) of the above objective Melting point: 192°-214° C.

Amino acid analysis:

| | |
|---|---|
| Asp: 1.06 (1) | Leu: 3.07 (3) |
| Thr: 3.00 (3) | Tyr: 0.59 (1) |
| Ser: 0.85 (1) | Lys: 2.19 (2) |
| Glu: 2.88 (3) | His: 0.88 (1) |
| Gly: 1.97 (2) | Arg: 0.97 (1) |
| Ala: 1.02 (1) | Pro: 2.10 (2) |
| Val: 1.02 (1) | |

REFERENCE EXAMPLE 138

Preparation of Boc-Lys(Cl-Bz)-Leu-Ser(Bzl)—OH

Using 1.44 g of Boc-Leu-Ser(Bzl)—OH and 1.62 g of Boc-Lys(Cl-Bz)-OSu, the same procedure as in Reference Example 35 was repeated to obtain 1.72 g (yield: 79.6%) of the above objective compound having a melting point of 103°-106° C.

REFERENCE EXAMPLE 139

Preparation of
Boc-Lys(Cl-Bz)-Leu-Ser(Bzl)-Gln-Glu(OBzl)-Leu-His-
Lys(Cl-Z)-Leu-Gln-Thr(Bzl)-Tyr(Bzl)-Pro-Arg(Tos)-
Thr(Bzl)-Asp(OBzl)-Val-Gly-Ala-Gly-Thr(Bzl)-
Pro—NH₂

Using Boc-Gln-Glu(OBzl)-Leu-His-Lys(Cl-Z)-Leu-
Gln-Thr(Bzl)-Tyr(Bzl)-Pro-Arg(Tos)-Thr(Bzl)-
Asp(OBzl)-Val-Gly-Ala-Gly-Thr(Bzl)-Pro—NH₂ (510 mg) and Boc-Lys(Cl-Bz)-Leu-Ser(Bzl)—OH (165 mg), the same procedure as in Reference Example 70 was repeated to obtain 345 mg (yield: 58.3%) of the above objective compound having a melting point of 196°-205° C.

REFERENCE EXAMPLE 140

Preparation of HCl·H-Cec(OBuᵗ)—OCH₃

8.58 g of HCl·H-Cys—OCH₃ and 11.7 g of BrCH₂CH₂COOBuᵗ were dissolved in 30 ml of DMF. Thereto was added 14.7 ml of triethylamine with ice-cooling. The mixture was stirred for 48 hours at room temperature. The reaction mixture was mixed with 100 ml of ice water. The mixture was extracted with ethyl acetate (50 ml×3). The ethyl acetate layers were combined, washed with water (50 ml) and a saturated aqueous sodium chloride solution (50 ml×2), dried with anhydrous magnesium sulfate and concentrated under reduced pressure. The residue was mixed with 20 ml of 4N hydrochloric acid/dioxane with ice-cooling. The mixture was concentrated under reduced pressure. The residue was crystallized from diethyl ether and recrystallized from ethyl acetate and diethyl ether to obtain 11.4 g (yield: 76.0%) of the above objective compound having a melting point of 65°–67° C.

REFERENCE EXAMPLE 141

Preparation of Boc-Thr(Bzl)-Cec(OBu$^t$)—OCH$_3$

Using 7.22 g of Boc-Thr(Bzl)—OH and 7.70 g of HCl·H-Cec(OBu$^t$)—OCH$_3$, the same procedure as in Reference Example 3 was repeated to obtain 9.31 g (yield: 71.9%) of the above objective compound in an oily form.

REFERENCE EXAMPLE 142

Preparation of Boc-Ser(Bzl)-Thr(Bzl)-Cec—OCH$_3$

Using 9.05 g of Boc-Thr(Bzl)-Cec(OBu$^t$)—OCH$_3$ and 6.28 g of Boc-Ser(Bzl)-OSu, the same procedure as in Reference Example 35 was repeated to obtain 10.2 g (yield: 92.5%) of the above objective compound in an oily form.

REFERENCE EXAMPLE 143

Preparation of Boc-Abu-Asn-Leu-OEt

Using 6.50 g of Boc-Asn-Leu-OEt and 5.48 g of Boc-Abu-OSu, the same procedure as in Reference Example 35 was repeated to obtain 7.20 g (yield: 90.2%) of the above objective compound having a melting point of 152°–155° C.

REFERENCE EXAMPLE 144

Preparation of Boc-Abu-Asn-Leu-N$_2$H$_3$

Using 6.23 g of Boc-Abu-Asn-Leu-OEt, the same procedure as in Reference Example 6 was repeated to obtain 4.47 g (yield: 74.0%) of the above objective compound having a melting point of 205°–208° C.

REFERENCE EXAMPLE 145

Preparation of Boc-Abu-Asn-Leu-Ser(Bzl)-Thr(Bzl)-Cec—OCH$_3$

Using 2.63 g of Boc-Ser(Bzl)-Thr(Bzl)-Cec-OCH$_3$ and 2.00 g of Boc-Abu-Asn-Leu-N$_2$H$_3$, the same procedure as in Reference Example 36 was repeated to obtain 2.75 g (yield: 67.9%) of the above objective compound having a melting point of 194°–198° C.

REFERENCE EXAMPLE 146

Preparation of ⌐Abu—Asn—Leu—Ser(Bzl)—Thr(Bzl)—

⌐Cec—OCH$_3$

Using 2.50 g of Boc-Abu-Asn-Leu-Ser(Bzl)-Thr(Bzl)-Cec—OCH$_3$, the same procedure as in Reference Example 37 was repeated to obtain 1.04 g (yield: 47.1%) of the above objective compound having a melting point of 222°–226° C.

REFERENCE EXAMPLE 147

Preparation of ⌐Abu—Asn—Leu—Ser(Bzl)—Thr(Bzl)—

⌐Cec—N$_2$H$_3$

Using 950 mg of,

⌐Abu—Asn—Leu—Ser(Bzl)—Thr(Bzl)—

⌐Cec—OCH$_3$, the same procedure as in Reference Example 38 was repeated to obtain 641 mg (yield: 66.8%) of the above objective compound.

Melting point: 205°–220° C.
Amino acid analysis:

| Asp: 1.02 (1) | Leu: 1.06 (1) |
|---|---|
| Thr: 1.00 (1) | Abu: 1.21 (1) |
| Ser: 0.94 (1) | Cec: 0.98 (1) |

REFERENCE EXAMPLE 148

Preparation of ⌐Abu—Asn—Leu—Ser(Bzl)—Thr(Bzl)—

⌐Cec—Val—Leu—Gly—OH

Using 508 mg of Boc-Val-Leu-Gly—OH and 550 mg of

⌐Abu—Asn—Leu—Ser(Bzl)—Thr(Bzl)—Cec—N$_2$H$_3$, the same procedure as in Reference Example 39 was repeated to obtain 504 mg (yield: 70.2%) of the above objective compound having a melting point of 242°–249° C. (decomposed).

REFERENCE EXAMPLE 149

Preparation of Boc-β-Ala-Asn-Leu-OEt

Using 5.60 g of Boc-Asn-Leu-OEt and 5.60 g of Boc-β-Ala-OSu, the same procedure as in Reference Example 35 was repeated to obtain 4.71 g (yield: 70.6%) of the above objective compound having a melting point of 148°–153° C.

REFERENCE EXAMPLE 150

Preparation of Boc-β-Ala-Asn-Leu-N$_2$H$_3$

Using 4.60 g of Boc-β-Ala-Asn-Leu-OEt, the same procedure as in Reference Example 6 was repeated to obtain 2.05 g (yield: 46.0%) of the above objective compound having a melting point of 200°–202° C.

REFERENCE EXAMPLE 151

Preparation of Boc-β-Ala-Asn-Leu-Ser(Bzl)-Thr(Bzl)-Cec—OCH₃

Using 2.70 g of Boc-Ser(Bzl)-Thr(Bzl)-Cec-OCH₃ and 1.80 g of Boc-β-Ala-Asn-Leu-N₂H₃, the same procedure as in Reference Example 36 was repeated to obtain 2.40 g (yield: 60.9%) of the above objective compound having a melting point of 195°-199° C.

REFERENCE EXAMPLE 152

Preparation of 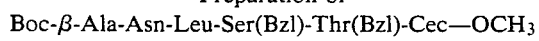
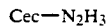

Using 2.20 g of Boc-β-Ala-Asn-Leu-Ser(Bzl)-Thr(Bzl)-Cec—OCH₃, the same procedure as in Reference Example 37 was repeated to obtain 792 mg (yield: 39.5%) of the above objective compound having a melting point of 231°-236° C.

REFERENCE EXAMPLE 153

Preparation of 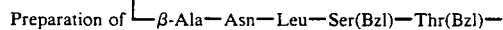
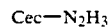

Using 750 mg of

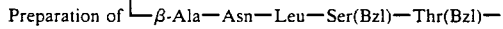
Cec—OCH₃.

the same procedure as in Reference Example 38 was repeated to obtain 428 mg (yield: 54.5%) of the above objective compound.

Melting point: above 221° C. (decomposed).
Amino acid analysis:

| | |
|---|---|
| Asp: 1.01 (1) | Leu: 1.05 (1) |
| Thr: 0.99 (1) | β-Ala: 1.03 (1) |
| Ser: 0.93 (1) | Cec: 1.00 (1) |

REFERENCE EXAMPLE 154

Preparation of 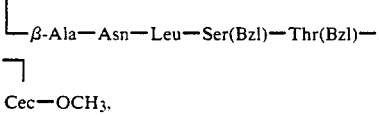

Using 362 mg of Boc-Val-Leu-Gly—OH and 400 mg of

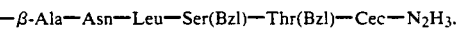

the same procedure as in Reference Example 39 was repeated to obtain 227 mg (yield: 42.9%) of the above objective compound.

Melting point: Above 285° C. (decomposed).
Amino acid analysis:

| | |
|---|---|
| Asp: 1.06 (1) | Val: 0.72 (1) |
| Thr: 1.04 (1) | Leu: 1.88 (2) |
| Ser: 0.98 (1) | β-Ala: 1.07 (1) |
| Gly: 0.82 (1) | Cec: 0.97 (1) |

REFERENCE EXAMPLE 155

Preparation of Boc-Leu-Gly—OH 2.63 g of H-Gly—OH and 3.50 g of sodium hydrogencarbonate were suspended in 50 ml of water. Thereto was added 50 ml of a dioxane solution containing 10.0 g of Boc-Leu-OSu, and the mixture was stirred for 30 minutes with ice-cooling and then for 15 hours at room temperature.

The reaction mixture was concentrated under reduced pressure. The residue was extracted with 70 ml of ethyl acetate. The ethyl acetate layer was washed with 1N hydrochloric acid and a saturated aqueous sodium chloride solution, dried with anhydrous magnesium sulfate and concentrated under reduced pressure. The residue was recrystallized from ethyl acetate-n-hexane to obtain 6.65 g (yield: 75.7%) of the above objective compound having a melting point of 115°-123° C.

REFERENCE EXAMPLE 156

Preparation of Boc-Gly-Leu-Gly—OH

Using 6.41 g of Boc-Leu-Gly—OH and 6.04 g of Boc-Gly-OSu, the same procedure as in Reference Example 35 was repeated to obtain 4.67 g (yield: 61.4%) of the above objective compound having a melting point of 67°-70° C.

REFERENCE EXAMPLE 157

Preparation of 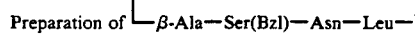

Using Boc-Gly-Leu-Gly—OH (355 mg) and

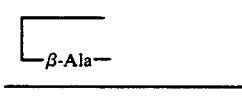
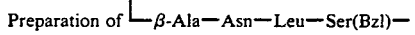

the same procedure as in Reference Example 39 was repeated to obtain 326 mg (yield: 53.5%) of the above objective compound.

Melting point: 200°-220° C. (decomposed).
Amino acid analysis:

| | |
|---|---|
| Asp: 2.07 (2) | Gly: 1.85 (2) |
| Thr: 1.04 (1) | Leu: 2.05 (2) |
| Ser: 1.97 (2) | β-Ala: 1.02 (1) |

REFERENCE EXAMPLE 158

Preparation of Boc-Gly-Leu-Ser(Bzl)—OH

Using 1.50 g of Boc-Leu-Ser(Bzl)—OH and 1.10 g of Boc-Gly-OSu, the same procedure as in Reference Example 35 was repeated to obtain 950 mg (yield: 55.6%) of the above objective compound having a melting point of 170°–172° C.

REFERENCE EXAMPLE 159

Preparation of
Boc-Gly-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂

Using 300 mg of Boc-Gln-Glu(OcHex)-Leu-His(-Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ and 70 mg of Boc-Gly-Leu-Ser(Bzl)—OH, the same procedure as in Reference Example 70 was repeated to obtain 320 mg (yield: 96.8%) of the above objective compound having a melting point of 190°–195° C.

REFERENCE EXAMPLE 160

Preparation of Boc-Gly-Leu—OH

Using 2.65 g of H-Leu—OH and 5.0 g of Boc-Gly-OSu, the same procedure as in Reference Example 155 was repeated to obtain 3.71 g (yield: 69.9%) of the above objective compound having a melting point of 135°–137° C.

REFERENCE EXAMPLE 161

Preparation of
Boc-Gly-Leu-Gln-Thr(Bzl)-Pro-Arg(Tos)-Thr(Bzl)-Asp(OcHex)-Val-Gly-Ala-Gly-Thr(Bzl)-Pro—NH₂

Using Boc-Gln-Thr(Bzl)-Pro-Arg(Tos)-Thr(Bzl)-Asp(OcHex)-Val-Gly-Ala-Gly-Thr(Bzl)-Pro—NH₂ (1.60 g) and Boc-Gly-Leu—OH (385 mg), the same procedure as in Reference Example 70 was repeated to obtain 1.67 g (yield: 95.0%) of the above objective compound having a melting point of 182°–185° C.

REFERENCE EXAMPLE 162

Preparation of
Boc-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂

Using Boc-Gly-Leu-Gln-Thr(Bzl)-Pro-Arg(Tos)-Thr(Bzl)-Asp(OcHex)-Val-Gly-Ala-Gly-Thr(Bzl)-Pro—NH (1.62 g), Boc-Leu-His—OH (453 mg) and, in place of HOBT, HOSu, the same procedure as in Reference Example 70 was repeated to obtain 1.79 g (yield: 98.1%) of the above objective compound having a melting point of 179°–183° C.

REFERENCE EXAMPLE 163

Preparation of
Boc-Glu(OcHex)-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂

Using Boc-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂ (1.74 g) and Boc-Glu(OcHex)—OH (384 mg), the same procedure as in Reference Example 70 was repeated to obtain 1.73 g (yield: 91.1%) of the above objective compound having a melting point of 178°–182° C.

REFERENCE EXAMPLE 164

Preparation of
Boc-Gln-Glu(OcHex)-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂

Using Boc-Glu(OcHex)-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂ (1.68 g) and Boc-Gln-ONp (380 mg), the same procedure as in Reference Example 85 was repeated to obtain 1.74 g (yield: 98.4%) of the above objective compound having a melting point of 177°–180° C.

REFERENCE EXAMPLE 165

Preparation of
Boc-Lys(Z)-Leu-Ser(Bzl)-Gln-Glu(OcHex)-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂

Using Boc-Gln-Glu(OcHex)-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂ (500 mg) and Boc-Lys(Z)-Leu-Ser(Bzl)—OH (201 mg), the same procedure as in Reference Example 70 was repeated to obtain 620 mg (yield: 99.5%) of the above objective compound having a melting point of 178°–182° C.

REFERENCE EXAMPLE 166

Preparation of Boc-Thr(Bzl)-Pro-Gly-OEt

Using 1.18 g of HCl·H-Gly-OEt and 3.44 g of Boc-Thr(Bzl)-Pro—OH, the same procedure as in Reference Example 3 was repeated to obtain 3.87 g (yield: 93.0%) of the above objective compound having an oily appearance.

REFERENCE EXAMPLE 167

Preparation of Boc-Thr(Bzl)-Pro-Gly—OH

Using 3.80 g of Boc-Thr(Bzl)-Pro-Gly-OEt, the same procedure as in Reference Example 12 was repeated to obtain 3.28 g (yield: 91.9%) of the above objective compound.

Melting point: 35°–45° C.

Amino acid analysis:
Thr: 0.99 (1)
Gly: 0.99 (1)
Pro: 1.02 (1).

REFERENCE EXAMPLE 168

Preparation of
Boc-Thr(Bzl)-Pro-Gly-Thr(Bzl)-Asp(OcHex)-Val-Gly-Ala-Gly-Thr(Bzl)-Pro—NH₂

Using Boc-Thr(Bzl)-Asp(OcHex)-Val-Gly-Ala-Gly-Thr(Bzl)-Pro—NH₂ (2.00 g) and Boc-Thr(Bzl)-Pro-Gly—OH (940 mg), the same procedure as in Reference Example 70 was repeated to obtain 2.12 g (yield: 80.6%) of the above objective compound having a melting point of 207°–210° C.

REFERENCE EXAMPLE 169

Preparation of
Boc-Gln-Thr(Bzl)-Pro-Gly-Thr(Bzl)-Asp(OcHex)-Val-Gly-Ala-Gly-Thr(Bzl)-Pro—NH₂

Using Boc-Thr(Bzl)-Pro-Gly-Thr(Bzl)-Asp(OcHex)-Val-Gly-Ala-Gly-Thr(Bzl)-Pro—NH₂ (2.07 g) and Boc-Gln-ONp (640 mg), the same procedure as in Reference Example 85 was repeated to obtain 1.87 g (yield: 83.1%) of the above objective compound having a melting point of 192°–194° C.

REFERENCE EXAMPLE 170

Preparation of
Boc-Lys(Cl-Z)-Leu-Gln-Thr(Bzl)-Pro-Gly-Thr(Bzl)-Asp(OcHex)-Val-Gly-Ala-Gly-Thr(Bzl)-Pro—NH₂

Using Boc-Gln-Thr(Bzl)-Pro-Gly-Thr(Bzl)-Pro-Gly-Thr(Bzl)-Asp(OcHex)-Val-Gly-Ala-Gly-Thr(Bzl)-Pro—NH₂ (800 mg) and Boc-Lys(Cl-Z)-Leu—OH (290 mg), the same procedure as in Reference Example 70 was repeated to obtain 870 mg (yield: 86.1%) of the above objective compound having a melting point of 178°–180° C.

REFERENCE EXAMPLE 171

Preparation of
Boc-Leu-His-Lys(Cl-Z)-Leu-Gln-Thr(Bzl)-Pro-Gly-Thr(Bzl)-Asp(OcHex)-Val-Gly-Ala-Gly-Thr(Bzl)-Pro—NH₂

Using Boc-Lys(Cl-Z)-Leu-Gln-Thr(Bzl)-Pro-Gly-Thr(Bzl)-Asp(OcHex)-Val-Gly-Ala-Gly-Thr(Bzl)-Pro-NH₂ (810 mg), Boc-Leu-His—OH (170 mg) and, in place of HOBT, HOSu, the same procedure as in Reference Example 70 was repeated to obtain 800 mg (yield: 87.6%) of the above objective compound having a melting point of 161°–170° C.

REFERENCE EXAMPLE 172

Preparation of
Boc-Glu(OBzl)-Leu-His-Lys(Cl-Z)-Leu-Gln-Thr(Bzl)-Pro-Gly-Thr(Bzl)-Asp(OcHex)-Val-Gly-Ala-Gly-Thr(Bzl)-Pro—NH₂

Using Boc-Leu-His-Lys(Cl-Z)-Leu-Gln-Thr(Bzl)-Pro-Gly-Thr(Bzl)-Asp(OcHex)-Val-Gly-Ala-Gly-Thr(Bzl)-Pro—NH₂ (750 mg) and Boc-Glu(OBzl)—OH (126 mg), the same procedure as in Reference Example 70 was repeated to obtain 580 mg (yield: 70.4%) of the above objective compound having a melting point of 198°–201° C.

REFERENCE EXAMPLE 173

Preparation of
Boc-Gln-Glu(OBzl)-Leu-His-Lys-Cl-Z)-Leu-Gln-Thr(Bzl)-Pro-Gly-Thr(Bzl)-Asp(OcHex)-Val-Gly-Ala-Gly-Thr(Bzl)-Pro—NH₂

Using Boc-Glu(OBzl)-Leu-His-Lys(Cl-Z)-Leu-Gln-Thr(Bzl)-Pro-Gly-Thr(Bzl)-Asp(OcHex)-Val-Gly-Ala-Gly-Thr(Bzl)-Pro—NH₂ (530 mg) and Boc-Gln-ONp (96 mg), the same procedure as in Reference Example 85 was repeated to obtain 470 mg (yield: 84.4%) of the above objective compound having a melting point of 218°–220° C.

REFERENCE EXAMPLE 174

Preparation of
Boc-Lys(Z)-Leu-Ser(Bzl)-Gln-Glu(OBzl)-Leu-His-Lys(Cl-Z)-Leu-Gln-Thr(Bzl)-Pro-Gly-Thr(Bzl)-Asp(OcHex)-Val-Gly-Ala-Gly-Thr(Bzl)-Pro-NH₂

Using Boc-Gln-Glu(OBzl)-Leu-His-Lys(Cl-Z)-Leu-Gln-Thr(Bzl)-Pro-Gly-Thr(Bzl)-Asp(OcHex)-Val-Gly-Ala-Gly-Thr(Bzl)-Pro—NH₂ (440 mg) and Boc-Lys(Z)-Leu-Ser(Bzl)—OH (138 mg), the same procedure as in Reference Example 70 was repeated to obtain 410 mg (yield: 76.6%) of the above objective compound having a melting point of 215°–220° C.

REFERENCE EXAMPLE 175

Preparation of Boc-Asn-Lys(Cl-Z)-Leu—OH

Using 2.00 g of Boc-Lys(Cl-Z)-Leu—OH and 1.48 g of Boc-Asn-ONp, the same procedure as in Reference Example 35 was repeated to obtain 1.76 g (yield: 72.3%) of the above objective compound having a melting point of 160°–163° C.

REFERENCE EXAMPLE 176

Preparation of
Boc-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂

Using Boc-Gln-Thr(Bzl)-Pro-Arg(Tos)-Thr(Bzl)-Asp(OcHex)-Val-Gly-Ala-Gly-Thr(Bzl)-Pro—NH₂ (1.00 g) and Boc-Asn-Lys(Cl-Z)-Leu—OH (427 mg), the same procedure as in Reference Example 70 was repeated to obtain 1.22 g (yield: 94.3%) of the above objective compound having a melting point of 168°–173° C.

REFERENCE EXAMPLE 117

Preparation of Boc-Glu(OcHex)-Leu-OBzl

Using 13.2 g of Boc-Glu(OcHex)—OH and 15.7 g of H-Leu-OBzl·Tos—OH, the same procedure as in Reference Example 3 was repeated to obtain 23.19 g (yield: 108.8%) of the above objective compound having an oily appearance.

REFERENCE EXAMPLE 178

Preparation of Boc-Gln-Glu(OcHex)-Leu-OBzl

Using 23.19 g of Boc-Glu(OcHex)-Leu-OBzl and 14.7 g of Boc-Gln-ONp, the same procedure as in Reference Example 35 was repeated to obtain 22.42 g (yield continued from Reference Example 177: 84.8%) of the above objective compound having a melting point of 128°–131° C.

REFERENCE EXAMPLE 179

Preparation of Boc-Gln-Glu(OcHex)-Leu—OH 21.0 g of Boc-Gln-Glu(OcHex)-Leu-OBzl was dissolved in 200 ml of THF and subjected to catalytic reduction in the presence of 2.00 g of 5% palladium-carbon. After the completion of the reaction, the catalyst was removed by filtration and the filtrate was concentrated under reduced pressure. The residue was mixed with diethyl ether-n-hexane to effect crystallization to obtain 17.86 g (yield: 98.5%) of the above objective compound having a melting point of 111°–114° C.

REFERENCE EXAMPLE 180

Preparation of Boc-Ser(Bzl)-Gln-Glu(OcHex)-Leu—OH

Using 12.0 g of Boc-Gln-Glu(OcHex)-Leu—OH and 10.2 g of Boc-Ser(Bzl)-OSu, the same procedure as in Reference Example 35 was repeated to obtain 6.97 g (yield: 44.3%) of the above objective compound having a melting point of 149°–153° C.

REFERENCE EXAMPLE 181

Preparation of Boc-Ser(Bzl)-Gln-Glu(OcHex)-Leu-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (800 mg) and Boc-Ser(Bzl)-Gln-Glu(OcHex)-Leu—OH (301 mg), the same procedure as in Reference Example 70 was repeated to obtain 965 mg (yield: 95.0%) of the above objective compound having a melting point of 236°–243° C (decomposed).

REFERENCE EXAMPLE 182

Preparation of Boc-Lys(Cl-Z)-Leu-Ser(Bzl)-Gln-Glu(OcHex)-Leu-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Ser(Bzl)-Gln-Glu(OcHex)-Leu-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (850 mg) and Boc-Lys(Cl-Z)-Leu—OH (197 mg), the same procedure as in Reference Example 70 was repeated to obtain 871 mg (yield: 90.0%) of the above objective compound.

Melting point: 230°–245° C.
Amino acid analysis:

| | | |
|---|---|---|
| Asp: 1.99 (2) | Gly: 1.97 (2) | Lys: 2.03 (2) |
| Thr: 2.90 (3) | Ala: 1.00 (1) | Arg: 0.96 (1) |
| Ser: 0.94 (1) | Val: 1.00 (1) | Pro: 2.02 (2) |
| Glu: 3.10 (3) | Leu: 3.10 (3) | |

REFERENCE EXAMPLE 183

Preparation of Boc-Gly-Lys(Cl-Z)-Leu—OH

Using 2.0 g of Boc-Lys(Cl-Z)-Leu—OH and 1.10 g of Boc-Gly-OSu, the same procedure as in Reference Example 35 was repeated to obtain 1.69 g (yield: 76.0%) of the above objective compound in a powder form.

REFERENCE EXAMPLE 184

Preparation of Boc-Gly-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Gln-Thr(Bzl)-Pro-Arg(Tos)-Thr(Bzl)-Asp(OcHex)-Val-Gly-Ala-Gly-Thr(Bzl)-Pro—NH$_2$ (1.00 g) and Boc-Gly-Lys(Cl-Z)-Leu—OH (390 mg), the same procedure as in Reference Example 70 was repeated to obtain 1.16 g (yield: 92.0%) of the above objective compound having a melting point of 174°–176° C.

REFERENCE EXAMPLE 185

Preparation of Boc-Ser(Bzl)-Gln-Glu(OcHex)-Leu-Gly-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Gly-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (1.00 g) and Boc-Ser(Bzl)-Gln-Glu(OcHex)-Leu—OH (396 mg), the same procedure as in Reference Example 70 was repeated to obtain 1.18 g (yield: 92.4%) of the above objective compound.

Melting point: 220°–245° C.
Amino acid analysis:

| | | |
|---|---|---|
| Asp: 1.03 (1) | Ala: 1.03 (1) | Pro: 2.09 (2) |
| Thr: 2.98 (3) | Val: 1.00 (1) | |
| Ser: 0.91 (1) | Leu: 2.00 (2) | |
| Glu: 3.00 (3) | Lys: 0.99 (1) | |
| Gly: 2.99 (3) | Arg: 0.99 (1) | |

REFERENCE EXAMPLE 186

Preparation of Boc-Lys(Cl-Z)-Leu-Ser(Bzl)-Gln-Glu(OcHex)-Leu-Gly-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Ser(Bzl)-Gln-Glu(OcHex)-Leu-Gly-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (1.00 g) and Boc-Lys(Cl-Z)-Leu—OH (237 mg), the same procedure as in Reference Example 70 was repeated to obtain 1.07 g (yield: 93.8%) of the above objective compound having a melting point of 224°–231° C.

REFERENCE EXAMPLE 187

Preparation of Boc-$\beta$-Ala-$\beta$-Ala—OH

Using 2.94 g of H-$\beta$-Ala—OH and 7.16 g of Boc-$\beta$-Ala-OSu, the same procedure as in Reference Example 155 was repeated to obtain 3.12 g (yield: 47.9%) of the above objective compound having a melting point of 116°–126° C.

REFERENCE EXAMPLE 188

Preparation of Boc-$\beta$-Ala-$\beta$-Ala-Asn-Leu-OEt

Using 3.60 g of Boc-Asn-Leu-OEt and 2.5 g of Boc-$\beta$-Ala-$\beta$-Ala—OH, the same procedure as in Reference Example 70 was repeated to obtain 3.08 g (yield: 62.0%) of the above objective compound having a melting point of 184°–187° C.

REFERENCE EXAMPLE 189

Preparation of Boc-β-Ala-β-Ala-Asn-Leu-N₂H₃

Using 2.70 g of Boc-β-Ala-β-Ala-Asn-Leu-OEt, the same procedure as in Reference Example 6 was repeated to obtain 2.31 g (yield: 87.9%) of the above objective compound having a melting point of 209°–213° C.

REFERENCE EXAMPLE 190

Preparation of Boc-β-Ala-β-Ala-Asn-Leu-Ser(Bzl)-Thr(Bzl)-Asp-OEt

Using 2.50 g of Boc-Ser(Bzl)-Thr(Bzl)-Asp-OEt and 2.20 g of Boc-β-Ala-β-Ala-Asn-Leu-N₂H₃, the same procedure as in Reference Example 36 was repeated to obtain 3.94 g (yield: 98.8%) of the above objective compound having a melting point of 198°–205° C.

REFERENCE EXAMPLE 191

Preparation of ⌐β-Ala-β-Ala—Asn—Leu—Ser(Bzl)—
Thr(Bzl)—Asp—OEt

Using 3.50 g of Boc-β-Ala-β-Ala-Asn-Leu-Ser(Bzl)-Thr(Bzl)-Asp-OEt, the same procedure as in Reference Example 37 was repeated to obtain 1.62 g (yield: 52.5%) of the above objective compound having a melting point of 200°–203° C.

REFERENCE EXAMPLE 192

Preparation of ⌐β-Ala-β-Ala—Asn—Leu—Ser(Bzl)—
Thr(Bzl)—Asp—N₂H₃

Using 1.50 g of

⌐β-Ala-β-Ala—Asn—Leu—Ser(Bzl)—
Thr(Bzl)—Asp—OEt, the same procedure as in Reference Example 38 was repeated to obtain 1.36 g (yield: 92.1%) of the above objective compound having a melting point of 220°–222° C.

REFERENCE EXAMPLE 193

Preparation of ⌐β-Ala-β-Ala—Asn—Leu—Ser(Bzl)—
Thr(Bzl)—Asp—Val—Leu—Gly—OH

Using 891 mg of Boc-Val-Leu-Gly—OH and 1.00 g of

⌐β-Ala-β-Ala—Asn—Leu—Ser(Bzl)—Thr(Bzl)—Asp—N₂H₃, the same procedure as in Reference Example 39 was repeated to obtain 352 mg (yield: 27.3%) of the above objective compound.

Melting point: Above 220° C. (decomposed).

Amino acid analysis:

| Asp: 1.97 (2) | Val: 1.01 (1) |
|---|---|
| Thr: 1.00 (1) | Leu: 2.07 (2) |
| Ser: 0.95 (1) | β-Ala: 1.94 (2) |
| Gly: 1.07 (1) | |

REFERENCE EXAMPLE 194

Preparation of Boc-Gln Thr(Bzl)-Asp(OBzl)-Val-Gly-Ala-Gly-Thr(Bzl)-Pro—NH₂

Using 3.51 g of Boc-Thr(Bzl)-Asp(OBzl)-Val-Gly-Ala-Gly-Thr(Bzl)-Pro—NH₂ and 1.66 g of Boc-Gln-ONp, the same procedure as in REFERENCE EXAMPLE 85 was repeated to obtain 3.41 g (yield: 87.9%) of the above objective compound having a melting point of 192°–195° C.

REFERENCE EXAMPLE 195

Preparation of Boc-Thr(Bzl)-Pro-Gln-Thr(Bzl)-Asp(OBzl)-Val-Gly-Ala-Gly-Thr(Bzl)-Pro—NH₂

Using 3.08 g of Boc-Gln-Thr(Bzl)-Asp(OBzl)-Val-Gly-Ala-Gly-Thr(Bzl)-Pro—NH₂ and 1.52 g of Boc-Thr(Bzl)-pro—OH, the same procedure as in Reference Example 70 was repeated to obtain 3.21 g (yield: 85.4%) of the above objective compound having a melting point of 190°–193° C.

REFERENCE EXAMPLE 196

Preparation of Boc-Gln-Thr(Bzl)-Pro-Gln-Thr(Bzl)-Asp(OBzl)-Val-Gly-Ala-Gly-Thr(Bzl)-Pro—NH₂

Using Boc-Thr(Bzl)-Pro-Gln-Thr(Bzl)-Asp(OBzl)-Val-Gly-Ala-Gly-Thr(Bzl)-Pro—NH₂ (3.15 g) and Boc-Gln-ONp (1.16 g), the same procedure as in Reference Example 85 was repeated to obtain 3.07 g (yield: 89.8%) of the above objective compound having a melting point of 173°–178° C.

REFERENCE EXAMPLE 197

Preparation of Boc-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH₂

Using Boc-Gln-Thr(Bzl)-Pro-Gln-Thr(Bzl)-Asp(OBzl)-Val-Gly-Ala-Gly-Thr(Bzl)-Pro—NH₂ (2.02 g) and Boc-Lys(Cl-Z)-Leu—OH (982 mg), the same procedure as in Reference Example 70 was repeated to obtain 2.41 g (yield: 95.3%) of the above objective compound having a melting point of 204°–209° C.

REFERENCE EXAMPLE 198

Preparation of
Boc-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH$_2$ Using Boc-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH$_2$ (2.36 g), Boc-Leu-His—OH (639 mg) and, in place of HOBT, HOSu, the same procedure as in Reference Example 70 was repeated to obtain 2.46 g (yield: 91.3%) of the above objective compound having a melting point of 209°–215° C (decomposed).

REFERENCE EXAMPLE 199

Preparation of
Boc-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH$_2$ Using Boc-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH$_2$ (1.82 g) and Boc-Glu(OcHex)-OSu (498 mg), the same procedure as in Reference Example 85 was repeated to obtain 1.87 g (yield: 95.9%) of the above objective compound having a melting point of 209°–217° C. (decomposed).

REFERENCE EXAMPLE 200

Preparation of
Boc-Gln-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH$_2$ Using Boc-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH$_2$ (1.87 g) and Boc-Gln-ONp (404 mg), the same procedure as in Reference Example 85 was repeated to obtain 1.77 g (yield: 90.3%) of the above objective compound.
Melting point: 200°–217° C.
Amino acid analysis:

| | |
|---|---|
| Asp: 1.03 (1) | Val: 1.01 (1) |
| Thr: 2.96 (3) | Leu: 2.06 (2) |
| Glu: 3.87 (4) | Lys: 1.03 (1) |
| Gly: 2.02 (2) | His: 0.94 (1) |
| Ala: 1.00 (1) | Pro: 2.08 (2) |

REFERENCE EXAMPLE 201

Preparation of Boc-Lys(Cl-Z)-Leu-Ser(Bzl)—OH

Using 4.61 g of Boc-Leu-Ser(Bzl)—OH and 5.61 g of Boc-Lys(Cl-Z)-OSu, the same procedure as in Reference Example 35 was repeated to obtain 4.92 g (yield: 64.0%) of The above objective compound having a melting point of 88°–92° C.

REFERENCE EXAMPLE 202

Preparation of
Boc-Lys(Cl-Z)-Leu-Ser(Bzl)-Gln-Glu(OcHex)-Leu-His-Lys(Cl-Z)-Leu-Gln-Thr Bzl)-Pro-Gln-Thr(Bzl)-Asp(OBzl)-Val-Gly-Ala-Gly-Thr(Bzl)-Pro—NH$_2$ Using Boc-Gln-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH$_2$ (501 mg) and Boc-Lys(Cl-Z)-Leu-Ser(Bzl)—OH (198 mg), the same procedure as in Reference Example 70 was repeated to obtain 554 mg (yield: 92.0%) of the above objective compound.
Melting point: 230°–241° C. (decomposed)
Amino acid analysis:

| | |
|---|---|
| Asp: 1.02 (1) | Val: 1.01 (1) |
| Thr: 2.93 (3) | Leu: 3.08 (3) |
| Ser: 0.78 (1) | Lys: 2.12 (2) |
| Glu: 3.86 (4) | His: 0.89 (1) |
| Gly: 2.01 (2) | Pro: 2.07 (2) |
| Ala: 1.01 (1) | |

REFERENCE EXAMPLE 203

Preparation of
Boc-Gln-Thr(Bzl)-Asp(OcHex)-Val-Gly-Ala-Gly-Thr(Bzl)-Pro—NH$_2$

Using Boc-Thr(Bzl)-Asp(OcHex)-Val-Gly-Ala-Gly-Thr(Bzl)-Pro—NH$_2$ (10.00 g) and Boc-Gln-ONp (4.01 g), the same procedure as in Reference Example 85 was repeated to obtain 10.12 g (yield: 92.1%) of the above objective compound having a melting point of 211°–221° C.

REFERENCE EXAMPLE 204

Preparation of
Boc-Thr(Bzl)-Pro-Gln-Thr(Bzl)-Asp(OcHex)-Val-Gly-Ala-Gly-Thr(Bzl)-Pro—NH$_2$ Using Boc-Gln-Thr(Bzl)-Pro-Gln-Thr(Bzl)-Asp(OcHex)-Val-Gly-Ala-Gly-Thr(Bzl)-Pro—NH$_2$ (10.00 g) and Boc-Thr(Bzl)-Pro—OH (4.38 g), the same procedure as in Reference Example 70 was repeated to obtain 11.14 g (yield: 89.9%) of the above objective compound having a melting point of 186°–195° C.

REFERENCE EXAMPLE 205

Preparation of
Boc-Gln-Thr(Bzl)-Pro-Gln-Thr(Bzl)-Asp(OcHex)-Val-Gly-Ala-Gly-Thr(Bzl)-Pro—NH$_2$ Using Boc-Thr(Bzl)-Pro-Gln-Thr(Bzl)-Asp(OcHex)-Val-Gly-Ala-Gly-Thr(Bzl)-Pro—NH$_2$ (11.00 g) and Boc-Gln-ONp (3.51 g), the same procedure as in Reference Example 85 was repeated to obtain 9.32 g (yield: 78.0%) of the above objective compound having a melting point of 193°–196° C.

REFERENCE EXAMPLE 206

Preparation of
Boc-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ Using Boc-Gln-Thr(Bzl)-Pro-Gln-Thr(Bzl)-Asp(OcHex)-Val-Gly-Ala-Gly-Thr(Bzl)-Pro—NH$_2$ (2.55 g) and Boc-Asn-Lys(Cl-Z)-Leu—OH (1.21 g), the same procedure as in Reference Example 70 was repeated to obtain 2.75 g (yield: 81.5%) of the above objective compound having a melting point of 207°–214° C.

REFERENCE EXAMPLE 207

Preparation of
Boc-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂

Using Boc-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (2.65 g) and Boc-Gln-Glu(OcHex)-Leu—OH 887 mg), the same procedure as in Reference Example 70 was repeated to obtain 3.09 g (yield: 96.6%) of the above objective compound.
Melting point: 224°–241° C. (decomposed).
Amino acid analysis:

| | |
|---|---|
| Asp: 1.99 (2) | Val: 1.00 (1) |
| Thr: 2.90 (3) | Leu: 2.04 (2) |
| Glu: 4.06 (4) | Lys: 1.03 (1) |
| Gly: 1.99 (2) | Pro: 1.98 (2) |
| Ala: 1.01 (1) | |

REFERENCE EXAMPLE 208

Preparation of
Boc-Lys(Z)-Leu-Ser(Bzl)-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro-NH₂

Using Boc-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (1.00 g) and Boc-Lys(Z)-Leu-Ser(Bzl)—OH (336 mg), the same procedure as in Reference Example 70 was repeated to obtain 1.08 g (yield: 88.0%) of the above objective compound.
Melting point: 235°–249° C. (decomposed).
Amino acid analysis:

| | |
|---|---|
| Asp: 2.01 (2) | Ala: 1.00 (1) |
| Thr: 2.93 (3) | Val: 1.01 (1) |
| Ser: 0.84 (1) | Leu: 3.01 (3) |
| Glu: 4.08 (4) | Lys: 2.03 (2) |
| Gly: 2.00 (2) | Pro: 1.92 (2) |

REFERENCE EXAMPLE 209

Preparation of
Boc-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂

Using Boc-Gln-Thr(Bzl)-Pro-Gln-Thr(Bzl)-Asp(OcHex)-Val-Gly-Ala-Gly-Thr(Bzl)-Pro—NH₂ (2.27 g) and Boc-Gly-Lys(Cl-Z)-Leu—OH (980 mg), the same procedure as in Reference Example 70 was repeated to obtain 1.84 g (yield: 62.9%) of the above objective compound having a melting point of 218°–222° C.

REFERENCE EXAMPLE 210

Preparation of
Boc-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂

Using Boc-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro-NH₂ (1.75 g) and Boc-Gln-Glu(OcHex)-Leu—OH (604 mg), the same procedure as in Reference Example 70 was repeated to obtain 2.03 g (yield: 95.4%) of the above objective compound having a melting point of 239°–246° C. (decomposed).

REFERENCE EXAMPLE 211

Preparation of
Boc-Lys(Z)-Leu-Ser(Bzl)-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂

Using Boc-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (800 mg) and Boc-Lys(Z)-Leu-Ser(Bzl)—OH (274 mg), the same procedure as in Reference Example 70 was repeated to obtain 804 mg (yield: 82.5%) of the above objective compound having a melting point of 235°–243° C. (decomposed).

REFERENCE EXAMPLE 212

Preparation of Boc-Ile-Leu-Gly-OEt

Using 2.00 g of Boc-Leu-Gly-OEt and 1.67 g of Boc-Ile—OH·½H₂O, the same procedure as in Reference Example 70 was repeated to obtain 1.99 g (yield: 73.3%) of the above objective compound having a melting point of 123°–124° C.

REFERENCE EXAMPLE 213

Preparation of Boc-Ile-Leu-Gly—OH

Using 1.89 g of Boc-Ile-Leu-Gly-OEt, the same procedure as in Reference Example 12 was repeated to obtain 1.53 g (yield: 86.6%) of the above objective compound.
Appearance: Powder.
Amino acid analysis:
Gly: 1.07 (1)
Ile: 0.96 (1)
Leu: 0.97 (1).

REFERENCE EXAMPLE 214

Preparation of ⌐—Gly—Ser(Bzl)—Asn—Leu—Ser(Bzl)—
Thr(Bzl)—Glu—Ile—Leu—Gly—OH

Using 600 mg of Boc-Ile-Leu-Gly—OH and 500 mg of

⌐—Gly—Ser(Bzl)—Asn—Leu—Ser(Bzl)—Thr(Bzl)—Glu—N₂H₃, the same procedure as in Reference Example 39 was repeated to obtain 580 mg (yield: 90.9%) of the above objective compound having a melting point of 243°–247° C.

REFERENCE EXAMPLE 215

Preparation of
Boc-Asp(OEt)-Val-Gly-Ala-Gly-Thr(Bzl)-Pro—NH₂

Using 2.95 g of Boc-Val-Gly-Ala-Gly-Thr(Bzl)-Pro—NH₂ and 2.30 g of Boc-Asp(OEt)-OSu, the same procedure as in Reference Example 85 was repeated to obtain 3.07 g (yield: 86.2%) of the above objective compound having a melting point of 103°–111° C.

REFERENCE EXAMPLE 216

Preparation of
Boc-Thr(Bzl)-Asp(OEt)-Val-Gly-Ala-Gly-Thr(Bzl)-Pro—NH₂

Using 3.01 g of Boc-Asp(OEt)-Val-Gly-Ala-Gly-Thr(Bzl)-Pro—NH₂ and 1.91 g of Boc-Thr(Bzl)-OSu, the same procedure as in Reference Example 85 was repeated to obtain 2.97 g (yield: 81.4%) of the above objective compound having a melting point of 188°–192° C.

REFERENCE EXAMPLE 217

Preparation of
Boc-Arg(Tos)-Thr(Bzl)-Asp(OEt)-Val-Gly-Ala-Gly-Thr(Bzl)-Pro—NH₂

Using Boc-Thr(Bzl)-Asp(OEt)-Val-Gly-Ala-Gly-Thr(Bzl)-Pro—NH₂ (2.92 g) and Boc-Arg(Tos)—OH (1.60 g), the same procedure as in Reference Example 70 was repeated to obtain 3.64 g (yield: 94.8%) of the above objective compound having a melting point of 187°–190° C.

REFERENCE EXAMPLE 218

Preparation of
Boc-Thr(Bzl)-Pro-Arg(Tos)-Thr(Bzl)-Asp(OEt)-Val-Gly-Ala-Gly-Thr(Bzl)-Pro—NH₂

Using Boc-Arg(Tos)-Thr(Bzl)-Asp(OEt)-Val-Gly-Ala-Gly-Thr(Bzl)-Pro—NH₂ (2.63 g) and Boc-Thr(Bzl)-Pro—OH (1.22 g), the same procedure as in Reference Example 70 was repeated to obtain 2.84 g (yield: 88.5%) of the above objective compound having a melting point of 185°–194° C.

REFERENCE EXAMPLE 219

Preparation of
Boc-Gln-Thr(Bzl)-Pro-Arg(Tos)-Thr(Bzl)-Asp(OEt)-Val-Gly-Ala-Gly-Thr(Bzl)-Pro—NH₂

Using Boc-Thr(Bzl)-Pro-Arg(Tos)-Thr(Bzl)-Asp(OEt)-Val-Gly-Ala-Gly-Thr(Bzl)-Pro—NH₂ (2.76 g) and Boc-Gln-ONp (937 mg), the same procedure as in Reference Example 85 was repeated to obtain 2.94 g (yield: 98.8%) of the above objective compound having a melting point of 175°–179° C.

REFERENCE EXAMPLE 220

Preparation of
Boc-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH₂

Using Boc-Gln-Thr(Bzl)-Pro-Arg(Tos)-Thr(Bzl)-Asp(OEt)-Val-Gly-Ala-Gly-Thr(Bzl)-Pro—NH₂ (2.88) and Boc-Lys(Cl-Z)-Leu—OH (1.33 g), the same procedure as in Reference Example 70 was repeated to obtain 3.43 g (yield: 96.9%) of the above objective compound having a melting point of 167°–171° C.

REFERENCE EXAMPLE 221

Preparation of
Boc-Leu-His-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH₂

Using Boc-Lys(Cl-Z)-Leu-Gln-Thr(Bzl -Pro-Arg(Tos)-Thr(Bzl)-Asp(OEt)-Val-Gly-Ala-Gly-Thr(Bzl)-Pro-NH₂ (2.33 g), Boc-Leu-His—OH (516 mg) and, in place of HOBT, HONB (250 mg), the same procedure as in Reference Example 70 was repeated to obtain 2.36 g (yield: 90.8%) of the above objective compound having a melting point of 161°–166° C.

REFERENCE EXAMPLE 222

Preparation of
Boc-Glu(OEt)-Leu-His-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH₂

Using Boc-Leu-His-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH₂ (2.28 g) and Boc-Glu(OEt)-OSu (528 mg), the same procedure as in Reference Example 85 was repeated to obtain 2.33 g (yield: 96.3%) of the above objective compound having a melting point of 164°–171° C.

REFERENCE EXAMPLE 223

Preparation of
Boc-Gln-Glu(OEt)-Leu-His-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH₂

Using Boc-Glu(OEt)-Leu-His-Lys(Cl-Z)-Leu-Thr(Bzl)-Pro-Arg(Tos)-Thr(Bzl)-Asp(OEt)-Val-Gly-Ala-Gly-Thr(Bzl)-Pro—NH₂ (2.20 g) and Boc-Gln-ONp (472 mg), the same procedure as in Reference Example 85 was repeated to obtain 2.10 g (yield: 90.9%) of the above objective compound.

Melting point: 157°–178° C.

Amino acid analysis:

| | |
|---|---|
| Asp: 1.03 (1) | Leu: 2.02 (2) |
| Thr: 2.93 (3) | Lys: 0.98 (1) |
| Glu: 2.42 (3) | His: 0.92 (1) |
| Gly: 2.03 (2) | Arg: 1.01 (1) |
| Ala: 1.02 (1) | Pro: 2.02 (2) |
| Val: 1.05 (1) | |

REFERENCE EXAMPLE 224

Preparation of
Boc-Lys(Cl-Z)-Leu-Ser(Bzl)-Gln-Glu(OEt)-Leu-His-Lys(Cl-Z)-Leu-Gln-Thr(Bzl)-Pro-Arg(Tos)-Thr(Bzl)-Asp(OEt)-Val-Vly-Ala-Gly-Thr(Bzl)-Pro—NH₂

Using Boc-Gln-Glu(OEt)-Leu-His-Lys(Cl-Z)-Leu-Gln-Thr(Bzl)-Pro-Arg-(Tos)-Thr(Bzl)-Asp(OEt)-Val-Gly-Ala-Gly-Thr(Bzl)-Pro—NH₂ (715 mg), Boc-Lys(Cl-Z)-Leu-Ser(Bzl)—OH (280 mg) and, in place of HOBT, HOSu (46 mg), the same procedure as in Reference Example 70 was repeated to obtain 763 mg (yield: 87.7%) of the above objective compound.

Melting point: 184°–201° C.

Amino acid analysis:

| | |
|---|---|
| Asp: 1.04 (1) | Val: 1.05 (1) |
| Thr: 3.04 (3) | Leu: 2.89 (3) |
| Ser: 0.73 (1) | Lys: 1.78 (2) |
| Glu: 2.53 (3) | His: 0.91 (1) |
| Gly: 2.14 (2) | Arg: 0.96 (1) |
| Ala: 1.05 (1) | Pro: 2.14 (2) |

REFERENCE EXAMPLE 225

Preparation of
Boc-Thr(Bzl)-Pro-Thr(Bzl)-Asp(OBzl)-Val-Gly-Ala-Gly-Thr(Bzl)-Pro—NH$_2$ Using Boc-Thr(Bzl)-Asp(OBzl)-Val-Gly-Ala-Gly-Thr(Bzl)-Pro—NH$_2$ (1.12 g) and Boc-Thr(Bzl)-Pro—OH (616 mg), the same procedure as in Reference Example 70 was repeated to obtain 1.30 g (yield: 93.9%) of the above objective compound having a melting point of 170°–178° C.

REFERENCE EXAMPLE 226

Preparation of
Boc-Gln-Thr(Bzl)-Pro-Thr(Bzl)-Asp(OBzl)-Val-Gly-Ala-Gly-Thr(Bzl)-Pro—NH$_2$ Using Boc-Thr(Bzl)-Pro-Thr(Bzl)-Asp(OBzl)-Val-Gly-Ala-Gly-Thr(Bzl)-Pro—NH$_2$ (1.25 g) and Boc-Gln-ONp (501 mg), the same procedure as in Reference Example 85 was repeated to obtain 1.27 g (yield: 93.5%) of the above objective compound having a melting point of 149°–152° C.

REFERENCE EXAMPLE 227

Preparation of
Boc-Lys(Cl-Z)-Leu-Gln-Thr(Bzl)-Pro-Thr(Bzl)-Asp(OBzl)-Val-Gly-Ala-Gly-Thr(Bzl)-Pro—NH$_2$ Using Boc-Gln-Thr(Bzl)-Pro-Thr(Bzl)-Asp(OBzl)-Val-Gly-Ala-Gly-Thr(Bzl)-Pro—NH$_2$ (1.24 g) and Boc-Lys(Cl-Z)-Leu—OH (653 mg), the same procedure as in Reference Example 70 was repeated to obtain 1.56 g (yield: 98.7%) of the above objective compound having a melting point of 144°–147° C.

REFERENCE EXAMPLE 228

Preparation of
Boc-His(Tos)-Lys(Cl-Z)-Leu-Gln-Thr(Bzl)-Pro-Thr(Bzl)-Asp(OBzl)-Val-Gly-Ala-Gly-Thr(Bzl)-Pro—NH$_2$ Using Boc-Lys(Cl-Z)-Leu-Gln-Thr(Bzl)-Pro-Thr(Bzl)-Asp(OBzl)-Val-Gly-Ala-Gly-Thr(Bzl)-Pro—NH$_2$ (1.52 g), Boc-His(Tos)—OH (482 mg) and, in place of HOBT, HONB (211 mg), the same procedure as in Reference Example 70 was repeated to obtain 1.58 g (yield: 91.3%) of the above objective compound having a melting point of 195°–199° C. (decomposed).

REFERENCE EXAMPLE 229

Preparation of
Boc-Gln-Glu(OcHex)-Leu-His(Tos)-Lys(Cl-Z)-Leu-Gln-Thr(Bzl)-Pro-Thr(Bzl)-Asp(OBzl)-Val-Gly-Ala-Gly-Thr(Bzl)-Pro—NH$_2$ Using Boc-His(Tos)-Lys(Cl-Z)-Leu-Gln-Thr(Bzl)-Pro-Thr(Bzl)-Asp(OBzl)-Val-Gly-Ala-Gly-Thr(Bzl)-Pro-NH$_2$ (1.25 g), Boc-Gln-Glu(OcHex)-Leu—OH (409 mg) and, in place of HOBT, HONB (132 mg), the same procedure as in Reference Example 70 was repeated to obtain 1.43 g (yield: 94.7%) of the above objective compound having a melting point of 202°–208° C. (decomposed).

REFERENCE EXAMPLE 230

Preparation of
Boc-Lys(Cl-Z)-Leu-Ser(Bzl)-Gln-Glu(OcHex)-Leu-His(Tos)-Lys(Cl-Z)-Leu-Gln-Thr(Bzl)-Pro-Thr(Bzl)-Asp(OBzl)-Val-Gly-Ala-Gly-Thr(Bzl)-Pro—NH$_2$ Using Boc-Gln-Glu(OcHex)-Leu-His(Tos)-Lys(Cl-Z)-Leu-Gln-Thr(Bzl)-Pro-Thr(Bzl)-Asp(OBzl)-Val-Gly-Ala-Gly-Thr(Bzl)-Pro—NH$_2$ (600 mg), Boc-Lys(Cl-Z)-Leu-Ser(Bzl)—OH (207 mg) and, in place of HOBT, HONB (53 mg), the same procedure as in Reference Example 70 was repeated to obtain 633 mg (yield: 86.4%) of the above objective compound.

Melting point: 207°–220° C.
Amino acid analysis:

| Asp: 1.00 (1) | Gly: 2.00 (2) | Lys: 2.02 (2) |
|---|---|---|
| Thr: 2.85 (3) | Ala: 0.98 (1) | His: 0.98 (1) |
| Ser: 0.90 (1) | Val: 0.96 (1) | Pro: 2.03 (2) |
| Glu: 3.07 (3) | Leu: 3.11 (3) | |

REFERENCE EXAMPLE 231

Preparation of
Boc-His(Tos)-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH$_2$ Using Boc-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH$_2$ (1.06 g), Boc-His(Tos)—OH (261 mg) and, in place of HOBT, HONB (114 mg), the same procedure as in Reference Example 70 was repeated to obtain 1.05 g (yield: 87.5%) of the above objective compound.

Melting point: 145°–167° C.
Amino acid analysis:

| Asp: 1.02 (1) | Ala: 1.01 (1) | His: 0.97 (1) |
|---|---|---|
| Thr: 2.95 (3) | Val: 1.00 (1) | Arg: 1.01 (1) |
| Glu: 1.01 (1) | Leu: 1.02 (1) | Pro: 2.02 (2) |
| Gly: 2.03 (2) | Lys: 0.98 (1) | |

REFERENCE EXAMPLE 232

Preparation of
Boc-Gln-Glu(OcHex)-Leu-His(Tos)-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH$_2$ Using Boc-His(Tos)-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH$_2$ (1.02 g), Boc-Gln-Glu(OcHex)-Leu—OH (317 mg) and, in place of HOBT, HONB (102 mg), the same procedure as in Reference Example 70 was repeated to obtain 1.12 g (yield: 94.1%) of the above objective compound.

Melting point: 193°–205° C. (decomposed)
Amino acid analysis:

| Asp: 1.02 (1) | Leu: 2.04 (2) |
|---|---|
| Thr: 2.92 (3) | Lys: 0.98 (1) |
| Glu: 3.05 (3) | His: 0.96 (1) |
| Gly: 2.01 (2) | Arg: 1.00 (1) |
| Ala: 0.99 (1) | Pro: 2.01 (2) |
| Val: 1.01 (1) | |

REFERENCE EXAMPLE 233

Preparation of
Boc-Lys(Cl-Z)-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH$_2$ Using Boc-Gln-Glu(OcHex)-Leu-His(Tos)-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH$_2$ (1.07 g), Boc-Lys(Cl-Z)-Leu-Ser(Bzl)—OH (390 mg) and, in place of HOBT, HONB (99 mg), the same procedure as in Reference Example 70 was repeated to obtain 1.16 g (yield: 90.3%) of the above objective compound.

Melting point: 190°–206° C. (decomposed)
Amino acid analysis:

| | |
|---|---|
| Asp: 1.03 (1) | Val: 1.00 (1) |
| Thr: 2.98 (3) | Leu: 3.00 (3) |
| Ser: 0.86 (1) | Lys: 2.01 (2) |
| Glu: 3.05 (3) | His: 0.97 (1) |
| Gly: 2.01 (2) | Arg: 0.95 (1) |
| Ala: 1.01 (1) | Pro: 1.99 (2) |

REFERENCE EXAMPLE 234

Preparation of Boc-Tyr(Cl$_2$-Bzl)-Pro-OBzl

Using 5.00 g of Boc-Tyr(Cl$_2$-Bzl)—OH and 2.89 g of H-Pro-OBzl·HCl, the same procedure as in Reference Example 3 was repeated to obtain 6.84 g (yield: 95.6%) of the above objective compound in an oily form.

REFERENCE EXAMPLE 235

Preparation of Boc-Thr(Bzl)-Tyr(Cl$_2$-Bzl)-Pro-OBzl

Using 6.84 g of Boc-Tyr(Cl$_2$-OBzl)-Pro-OBzl and 4.43 g of Boc-Thr(Bzl)-OSu, the same procedure as in Reference Example 85 was repeated to obtain 5.54 g (yield: 62.1%) of the above objective compound having a melting point of 119°–121° C.

REFERENCE EXAMPLE 236

Preparation of Boc-Thr(Bzl)-Tyr(Cl$_2$-Bzl)-Pro—OH

Using 5.34 g of Boc-Thr(Bzl)-Tyr(Cl$_2$-Bzl)-Pro-OBzl, the same procedure as in Reference Example 12 was repeated to obtain 2.03 g (yield: 42.7%) of the above objective compound.

Melting point: 72°–85° C.
Amino acid analysis:
Thr: 0.93 (1)
Tyr: 1.02 (1)
Pro: 1.05 (1).

REFERENCE EXAMPLE 247

Preparation of
Boc-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ Using Boc-Arg(Tos)-Thr(Bzl)-Asp(OBzl)-Val-Gly-Ala-Gly-Thr(Bzl)-Pro—NH$_2$ (1.32 g) and Boc-Thr(Bzl)-Tyr(Cl$_2$-Bzl)-Pro—OH (1.03 g), the same procedure as in Reference Example 70 was repeated to obtain 1.80 g (yield: 94.9%) of the above objective compound having a melting point of 186°–188° C.

REFERENCE EXAMPLE 238

Preparation of
Boc-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ Using Boc-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ (1.75 g) and Boc-Gln-ONp (480 mg), the same procedure as in Reference Example 85 was repeated to obtain 1.81 g (yield: 97.3%) of the above objective compound having a melting point of 173°–177° C.

REFERENCE EXAMPLE 239

Preparation of
Boc-Lys(Cl-Z)-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ Using Boc-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ (1.75 g) and Boc-Lys(Cl-Z)-OSu (629 mg), the same procedure as in Reference Example 85 was repeated to obtain 1.85 g (yield: 93.0%) of the above objective compound having a melting point of 170°–173° C.

REFERENCE EXAMPLE 240

Preparation of
Boc-His(Tos)-Lys(Cl-Z)-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ Using Boc-Lys(Cl-Z)-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ (1.83 g), Boc-His(Tos)—OH (394 mg) and, in place of HOBT, HONB (172 mg), the same procedure as in Reference Example 70 was repeated to obtain 1.89 g (yield: 93.6%) of the above objective compound having a melting point of 163°–169° C.

REFERENCE EXAMPLE 241

Preparation of
Boc-Gln-Glu(OcHex)-Leu-His(Tos)-Lys(Cl-Z)-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ Using Boc-His(Tos)-Lys(Cl-Z)-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ (1.04 g), Boc-Gln-Glu(OcHex)-Leu—OH (285 mg) and, in place of HOBT, HONB (91 mg), the same procedure as in Reference Example 70 was repeated to obtain 1.08 g (yield: 92.3%) of the above objective compound having a melting point of 175°–179° C.

REFERENCE EXAMPLE 242

Preparation of
Boc-Lys(Cl-Z)-Leu-Ser(Bzl)-Gln-Glu(OcHex)-Leu-His(Tos)-Lys(Cl-Z)-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ Using Boc-Gln-Glu(OcHex)-Leu-His(Tos)-Lys(Cl-Z)-Gln-Thr(Bzl)-Tyr(Cl$_2$-Bzl)-Pro-Arg(Tos)-Thr(Bzl)-Asp(OBzl)-Val-Gly-Ala-Gly-Thr(Bzl)-Pro—NH$_2$ (702 mg), Boc-Lys(Cl-Z)-Leu-Ser(Bzl)—OH (234 mg) and, in place of HOBT, HONB (59 mg), the same procedure as in Reference Example 70 was repeated to obtain 715 mg (yield: 86.4%) of the above objective compound.

Melting point: 182°–194° C. (decomposed).

Amino acid analysis:

| | |
|---|---|
| Asp: 1.06 (1) | Leu: 1.92 (2) |
| Thr: 3.03 (3) | Tyr: 0.92 (1) |
| Ser: 0.90 (1) | Lys: 1.94 (2) |
| Glu: 3.00 (3) | His: 0.94 (1) |
| Gly: 2.08 (2) | Arg: 0.97 (1) |
| Ala: 1.05 (1) | Pro: 2.15 (2) |
| Val: 1.03 (1) | |

REFERENCE EXAMPLE 243

Preparation of Boc-Ala-Leu-Ser(Bzl)—OH

Using 4.0 g of Boc-Leu-Ser(Bzl)—OH and 3.08 g of Boc-Ala-OSu, the same procedure as in Reference Example 35 was repeated to obtain 3.13 g (yield: 66.7%) of the above objective compound having a melting point of 144°–146° C.

REFERENCE EXAMPLE 244

Preparation of Boc-Ala-Leu-Ser(Bzl)-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro-NH₂

Using Boc-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (500 mg) and Boc-Ala-Leu-Ser(Bzl)—OH (138 mg), the same procedure as in Reference Example 70 was repeated to obtain 550 mg (yield: 96.7%) of the above objective compound.

Melting point: 245°–257° C. (decomposed).

Amino acid analysis:

| | |
|---|---|
| Asp: 2.02 (2) | Ala: 2.01 (2) |
| Thr: 2.91 (3) | Val: 0.99 (1) |
| Ser: 0.92 (1) | Leu: 3.07 (3) |
| Glu: 4.07 (4) | Lys: 1.05 (1) |
| Gly: 2.02 (2) | Pro: 1.95 (2) |

REFERENCE EXAMPLE 245

Preparation of Boc-Thr(Bzl)-Leu-Pro-Gln-Thr(Bzl)-Asp(OcHex)-Val-Gly-Ala-Gly-Thr(Bzl)-Pro—NH₂

Using Boc-Gln-Thr(Bzl)-Asp(OcHex)-Val-Gly-Ala-Gly-Thr(Bzl)-Pro—NH₂ (500 mg) and Boc-Thr(Bzl)-Leu-Pro—OH (303 mg), the same procedure as in Reference Example 70 was repeated to obtain 566 mg (yield: 85.0%) of the above objective compound having a melting point of 194°–197° C.

REFERENCE EXAMPLE 246

Preparation of Boc-Gln-Thr(Bzl)-Leu-Pro-Gln-Thr(Bzl)-Asp(OcHex)-Val-Gly-Ala-Gly-Thr(Bzl)-Pro—NH₂

Using Boc-Thr(Bzl)-Leu-Pro-Gln-Thr(Bzl)-Asp(OcHex)-Val-Gly-Ala-Gly-Thr(Bzl)-Pro—NH₂ (516 mg) and Boc-Gln-ONp (141 mg), the same procedure as in Reference Example 85 was repeated to obtain 434 mg (yield: 77.9%) of the above objective compound having a melting point of 183°–185° C.

REFERENCE EXAMPLE 247

Preparation of Boc-Asn-Lys(Cl-Z)-Leu-Gln-Thr(Bzl)-Leu-Pro-Gln-Thr(Bzl)-Asp(OcHex)-Val-Gly-Ala-Gly-Thr(Bzl)-Pro—NH₂

Using Boc-Gln-Thr(Bzl)-Leu-Pro-Gln-Thr(Bzl)-Asp(OcHex)-Val-Gly-Ala-Gly-Thr(Bzl)-Pro—NH₂ (400 mg) and Boc-Asn-Lys(Cl-Z)-Leu—OH (193 mg), the same procedure as in Reference Example 70 was repeated to obtain 480 mg (yield: 92.3%) of the above objective compound having a melting point of 163°–166° C.

REFERENCE EXAMPLE 248

Preparation of Boc-Ser Bzl -Gln-Glu(OcHex)-Leu-Asn-Lys(Cl-Z)-Leu-Gln-Thr(Bzl)-Leu-Pro-Gln-Thr(Bzl)-Asp(OcHex)-Val-Gly-Ala-Gly-Thr(Bzl)-Pro—NH₂

Using Boc-Asn-Lys(Cl-Z)-Leu-Gln-Thr(Bzl)-Leu-Pro-Gln-Thr-(Bzl)-Asp(OcHex)-Val-Gly-Ala-Gly-Thr(Bzl)-Pro—NH₂ (450 mg) and Boc-Ser(Bzl)-Gln-Glu(OcHex)-Leu—OH (189 mg), the same procedure as in Reference Example 70 was repeated to obtain 545 mg (yield: 94.7%) of the above objective compound.

Melting point: 230°–247° C. (decomposed).

Amino acid analysis:

| | |
|---|---|
| Asp: 2.02 (2) | Ala: 0.93 (1) |
| Thr: 2.81 (3) | Val: 0.92 (1) |
| Ser: 0.94 (1) | Leu: 3.18 (3) |
| Glu: 4.11 (4) | Lys: 1.08 (1) |
| Gly: 2.03 (2) | Pro: 1.97 (2) |

REFERENCE EXAMPLE 249

Preparation of Boc-Lys(Cl-Z)-Leu-Ser(Bzl)-Gln-Glu(OcHex)-Leu-Asn-Lys(Cl-Z)-Leu-Gln-Thr(Bzl)-Leu-Pro-Gln-Thr(Bzl)-Asp(OcHex)-Val-Gly-Ala-Gly-Thr(Bzl)-Pro—NH₂

Using Boc-Ser(Bzl)-Gln-Glu(OcHex)-Leu-Asn-Lys(Cl-Z)-Leu-Gln-Thr(Bzl)-Leu-Pro-Gln-Thr(Bzl)-Asp(OcHex)-Val-Gly-Ala-Gly-Thr(Bzl)-Pro—NH₂ (500 mg) and Boc-Lys(Cl-Z)-Leu—OH (119 mg), the same procedure as in Reference Example 70 was repeated to obtain 510 mg (yield: 89.3%) of the above objective compound.

Melting point: 225°–243° C. (decomposed).

Amino acid analysis:

| | |
|---|---|
| Asp: 2.03 (2) | Ala: 0.95 (1) |
| Thr: 2.80 (3) | Val: 0.93 (1) |
| Ser: 0.95 (1) | Leu: 4.13 (4) |
| Glu: 4.05 (4) | Lys: 2.06 (2) |
| Gly: 2.11 (2) | Pro: 2.00 (2) |

REFERENCE EXAMPLE 250

Preparation of Boc-Lys(COCH₃)-Leu-Ser(Bzl)-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂

Using Boc-Gln-Glu(OcHex)-Leu-Asn-Lys(Cl-Z)-Leu-Gln-Thr(Bzl)-Pro-Gln-Thr(Bzl)-Asp(OcHex)-Val- Gly-Ala-Gly-Thr(Bzl)-Pro—NH$_2$ (502 mg) and Boc-Lys(COCH$_3$)-Leu-Ser(Bzl)—OH (167 mg), the same procedure as in Reference Example 70 was repeated to obtain 530 mg (yield: 91.2%) of the above objective compound.

Melting point: 239°-249° C. (decomposed).
Amino acid analysis:

| | |
|---|---|
| Asp: 2.01 (2) | Ala: 0.99 (1) |
| Thr: 2.89 (3) | Val: 0.99 (1) |
| Ser: 0.88 (1) | Leu: 3.08 (3) |
| Glu: 4.06 (4) | Lys: 2.06 (2) |
| Gly: 1.99 (2) | Pro: 1.94 (2) |

REFERENCE EXAMPLE 251

Preparation of
Boc-Asn-Leu-Gln-Thr(Bzl)-Pro-Gln-Thr(Bzl)-Asp(OcHex)-Val-Gly-Ala-Gly-Thr(Bzl)-Pro—NH$_2$ Using Boc-Gln-Thr(Bzl)-Pro-Gln-Thr(Bzl)-Asp(OcHex)-Val-Gly-Ala-Gly-Thr(Bzl)-Pro—NH$_2$ (1.00 g) and Boc-Asn-Leu-N$_2$H$_3$ (240 mg), the same procedure as in Reference Example 36 was repeated to obtain 810 mg (yield: 71.1%) of the above objective compound having a melting point of 234°-236° C.

REFERENCE EXAMPLE 252

Preparation of
Boc-Asn-Asn-Leu-Gln-Thr(Bzl)-Pro-Gln-Thr(Bzl)-Asp(OcHex)-Val-Gly-Ala-Gly-Thr(Bzl)-Pro—NH$_2$ Using Boc-Asn-Leu-Gln-Thr(Bzl)-Pro-Gln-Thr(Bzl)-Asp(OcHex)-Val-Gly-Ala-Gly-Thr(Bzl)-Pro—NH$_2$ (930 mg) and Boc-Asn-ONp (190 mg), the same procedure as in Reference Example 85 was repeated to obtain 770 mg (yield: 78.1%) of the above objective compound of 239°-242° C.

REFERENCE EXAMPLE 253

Preparation of
Boc-Gln-Glu(OcHex)-Leu-Asn-Asn-Leu-Gln-Thr(Bzl)-Pro-Gln-Thr(Bzl)-Asp(OcHex)-Val-Gly-Ala-Gly-Thr(Bzl)-Pro—NH$_2$ Using Boc-Asn-Asn-Leu-Gln-Thr(Bzl)-Pro-Gln-Thr(Bzl)-Asp(OcHex)-Val-Gly-Ala-Gly-Thr(Bzl)-Pro—NH$_2$ (740 mg) and Boc-Gln-Glu(OcHex)-Leu—OH (240 mg), the same procedure as in Reference Example 70 was repeated to obtain 860 mg (yield: 94.5%) of the above objective compound having a melting point of 258°-265° C. (decomposed).

REFERENCE EXAMPLE 254

Preparation of
Boc-Ala-Leu-Ser(Bzl)-Gln-Glu(OcHex)-Leu-Asn-Asn-Leu-Gln-Thr(Bzl)-Pro-Gln-Thr(Bzl)-Asp(OcHex)-Val-Gly-Ala-Gly-Thr(Bzl)-Pro—NH$_2$ Using Boc-Gln-Glu(OcHex)-Leu-Asn-Asn-Leu-Gln-Thr(Bzl)-Pro-Gln-Thr(Bzl)-Asp(OcHex)-Val-Gly-Ala-Gly-Thr(Bzl)-Pro—NH$_2$ (400 mg) and Boc-Ala-Leu-Ser(Bzl)—OH (87 mg), the same procedure as in Reference Example 70 was repeated to obtain 370 mg (yield: 80.8%) of the above objective compound having a melting point of 273°-280° C. (decomposed).

REFERENCE EXAMPLE 255

Preparation of
Boc-Gly-Asn-Leu-Gln-Thr(Bzl)-Pro-Gln-Thr(Bzl)-Asp(OcHex)-Val-Gly-Ala-Gly-Thr(Bzl)-Pro—NH$_2$ Using Boc-Asn-Leu-Gln-Thr(Bzl)-Pro-Gln-Thr(Bzl)-Asp(OcHex)-Val-Gly-Ala-Gly-Thr(Bzl)-Pro—NH$_2$ (930 mg) and Boc-Gly-OSu (150 mg), the same procedure as in Reference Example 85 was repeated to obtain 750 mg (yield: 78.4%) of the above objective compound having a melting point of 241°-245° C.

REFERENCE EXAMPLE 256

Preparation of
Boc-Gln-Glu(OcHex)-Leu-Gly-Asn-Leu-Gln-Thr(Bzl)-Pro-Gln-Thr(Bzl)-Asp OcHex)-Val-Gly-Ala-Gly-Thr(Bzl)-Pro—NH$_2$ Using Boc-Gly-Asn-Leu-Gln-Thr(Bzl)-Pro-Gln-Thr(Bzl)-Asp(OcHex)-Val-Gly-Ala-Gly-Thr(Bzl)-Pro—NH$_2$ (700 mg) and Boc-Gln-Glu(OcHex)-Leu—OH (230 mg), the same procedure as in Reference Example 70 was repeated to obtain 730 mg (yield: 84.3%) of the above objective compound having a melting point of 242°-247° C.

REFERENCE EXAMPLE 257

Preparation of
Boc-Lys(Z)-Leu-Ser(Bzl)-Gln-Glu(OcHex)-Leu-Gly-Asn-Leu-Gln-Thr(Bzl)-Pro-Gln-Thr(Bzl)-Asp(OcHex)-Val-Gly-Ala-Gly-Thr(Bzl)-Pro—NH$_2$ Using Boc-Gln-Glu(OcHex)-Leu-Gly-Asn-Leu-Gln-Thr(Bzl)-Pro-Gln-Thr(Bzl)-Asp(OcHex)-Val-Gly-Ala-Gly-Thr(Bzl)-Pro—NH$_2$ (350 mg) and Boc-Lys(Z)-Leu-Ser(Bzl)—OH (109 mg), the same procedure as in Reference Example 70 was repeated to obtain 360 mg (yield: 83.5%) of the above objective compound having a melting point of 249°-256° C.

REFERENCE EXAMPLE 258

Preparation of
Boc-Leu-Gln-Thr(Bzl)-Pro-Thr(Bzl)-Asp(OcHex)-Val-Gly-Ala-Gly-Thr(Bzl)-Pro—NH$_2$ Using Boc-Gln-Thr(Bzl)-Pro-Thr(Bzl)-Asp(OcHex)-Val-Gly-Ala-Gly-Thr(Bzl)-Pro—NH$_2$ (1.61 g) and Boc-Leu-OSu (532 mg), the same procedure as in Reference Example 85 was repeated to obtain 1.59 g (yield: 91.6%) of the above objective compound having a melting point of 157°-164° C.

REFERENCE EXAMPLE 259

Preparation of
Boc-Leu-His-Leu-Gln-Thr(Bzl)-Pro-Thr(Bzl)-Asp(OcHex)-Val-Gly-Ala-Gly-Thr(Bzl)-Pro—NH$_2$ Using Boc-Leu-Gln-Thr(Bzl)-Pro-Thr(Bzl)-Asp(OcHex)-Val-Gly-Ala-Gly-Thr(Bzl)-Pro—NH$_2$ (1.54 g), Boc-Leu-His—OH (531 mg) and, in place of HOBT, HOSu (166 mg), the same procedure as in Reference Example 70 was repeated to obtain 1.64 g (yield: 91.9%) of the above objective compound having a melting point of 156°-164° C.

REFERENCE EXAMPLE 260

Preparation of
Boc-Glu(OcHex)-Leu-His-Leu-Gln-Thr(Bzl)-Pro-Thr(Bzl)-Asp(OcHex)-Val-Gly-Ala-Gly-Thr(Bzl)-Pro—NH$_2$ Using Boc-Leu-His-Leu-Gln-Thr(Bzl)-Pro-Thr(Bzl)-Asp(OcHex)-Val-Gly-Ala-Gly-Thr(Bzl)-Pro—NH$_2$ (1.59 g) and Boc-Glu(OcHex)—OH (424 mg), the same procedure as in Reference Example 70 was repeated to obtain 1.69 g (yield: 95.0%) of the above objective compound having a melting point of 167°–172° C.

REFERENCE EXAMPLE 261

Preparation of
Boc-Gln-Glu(OcHex)-Leu-His-Leu-Gln-Thr(Bzl)-Pro-Thr(Bzl)-Asp(OcHex)-Val-Gly-Ala-Gly-Thr(Bzl)-Pro—NH$_2$ Using Boc-Glu(OcHex)-Leu-His-Leu-Gln-Thr(Bzl)-Pro-Thr(Bzl)-Asp(OcHex)-Val-Gly-Ala-Gly-Thr(Bzl)-Pro-NH$_2$ (1.64 g) and Boc-Gln-ONp (435 mg), the same procedure as in Reference Example 85 was repeated to obtain 1.57 g (yield: 90.5%) of the above objective compound having a melting point of 217°–224° C. (decomposed).

REFERENCE EXAMPLE 262

Preparation of
Boc-Leu-Ser(Bzl)-Gln-Glu(OcHex)-Leu-His-Leu-Gln-Thr(Bzl)-Pro-Thr(Bzl)-Asp(OcHex)-Val-Gly-Ala-Gly-Thr(Bzl)-Pro—NH$_2$ Using Boc-Gln-Glu(OcHex)-Leu-His-Leu-Gln-Thr(Bzl)-Pro-Thr(Bzl)-Asp(OcHex)-Val-Gly-Ala-Gly-Thr(Bzl)-Pro—NH$_2$ (500 mg) and Boc-Leu-Ser(Bzl)—OH (141 mg), the same procedure as in Reference Example 70 was repeated to obtain 520 mg (yield: 90.9%) of the above objective compound having a melting point of 227°–235° C. (decomposed).

REFERENCE EXAMPLE 263

Preparation of
Boc-Lys(Z)-Leu-Ser(Bzl)-Gln-Glu(OcHex)-Leu-His-Leu-Gln-Thr(Bzl)-Pro-Thr(Bzl)-Asp(OcHex)-Val-Gly-Ala-Gly-Thr(Bzl)-Pro—NH$_2$ Using Boc-Gln-Glu(OcHex)-Leu-His-Leu-Gln-Thr(Bzl)-Pro-Thr(Bzl)-Asp(OcHex)-Val-Gly-Ala-Gly-Thr(Bzl)-Pro—NH$_2$ (500 mg) and Boc-Lys(Z)-Leu-Ser(Bzl)—OH (231 mg), the same procedure as in Reference Example 70 was repeated to obtain 600 mg (yield: 94.9%) of the above objective compound having a melting point of 236°–241° C. (decomposed).

REFERENCE EXAMPLE 264

Preparation of
Boc-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Gln-Thr(Bzl)-Pro-Arg(Tos)-Thr(Bzl)-Asp(OcHex)-Val-Gly-Ala-Gly-Thr(Bzl)-Pro—NH$_2$ (1.61 g) and Boc-Lys(Cl-Z)—OH (554 mg), the same procedure as in Reference Example 70 was repeated to obtain 1.74 g (yield: 93.0%) of the above objective compound having a melting point of 181°–187° C.

REFERENCE EXAMPLE 265

Preparation of Boc-Leu-His-Lys(Cl Z)-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH$_2$ (1.69 g), Boc-Leu-His—OH (442 mg) and, in place of HOBT, HOSu (138 mg), the same procedure as in Reference Example 70 was repeated to obtain 1.92 g (yield: 102.0%) of the above objective compound.

Melting point: 174°–177° C.

Amino acid analysis:

| | |
|---|---|
| Asp: 1.00 (1) | Leu: 0.96 (1) |
| Thr: 2.90 (3) | Lys: 0.97 (1) |
| Glu: 1.08 (1) | His: 0.92 (1) |
| Gly: 2.05 (2) | Arg: 0.93 (1) |
| Ala: 1.03 (1) | Pro: 2.05 (2) |
| Val: 1.10 (1) | |

REFERENCE EXAMPLE 266

Preparation of
Boc-Glu(OcHex)-Leu-His-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Leu-His-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH$_2$ (1.87 g) and Boc-Glu(OcHex)—OH (394 mg), the same procedure as in Reference Example 70 was repeated to obtain 1.89 g (yield: 92.2%) of the above objective compound having a melting point of 178°–181° C.

REFERENCE EXAMPLE 267

Preparation of
Boc-Gln-Glu(OcHex)-Leu-His-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Glu(OcHex)-Leu-His-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH$_2$ (1.84 g) and Boc-Gln-ONp (397 mg), the same procedure as in Reference Example 85 was repeated to obtain 1.96 g (yield: 101.2%) of the above objective compound.

Melting point: 213°–217° C.

Amino acid analysis:

| | |
|---|---|
| Asp: 1.03 (1) | Leu: 0.99 (1) |
| Thr: 2.97 (3) | Lys: 0.99 (1) |
| Glu: 2.95 (3) | His: 0.93 (1) |
| Gly: 2.02 (2) | Arg: 0.99 (1) |
| Ala: 1.02 (1) | Pro: 2.09 (2) |
| Val: 1.02 (1) | |

REFERENCE EXAMPLE 268

Preparation of
Boc-Lys(Z)-Leu-Ser(Bzl)-Gln-Glu(OcHex)-Leu-His-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH$_2$ Using Boc-Gln-Glu(OcHex)-Leu-His-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH$_2$ (500 mg) and Boc-Lys(Z)-Leu-Ser(Bzl)—OH (192 mg), the same procedure as in Reference Example 70 was repeated to obtain 580 mg (yield: 94.1%) of the above objective compound having a melting point of 240°–245° C. (decomposed).

REFERENCE EXAMPLE 269

Preparation of
Boc-Gly-Leu-Ser(Bzl)-Gln-Glu(OcHex)-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂

Using Boc-Gln-Glu(OcHex)-Leu-His-Gly-Leu-l Gln-Thr(Bzl)-Pro-Arg(Tos)-Thr(Bzl)-Asp(OcHex)-Val-Gly-Ala-Gly-Thr(Bzl)-Pro—NH₂ (500 mg) and Boc-Gly-Leu-Ser(Bzl)—OH (140 mg), the same procedure as in Reference Example 70 was repeated to obtain 570 mg (yield: 97.9%) of the above objective compound having a melting point of 179°–185° C.

REFERENCE EXAMPLE 270

Preparation of
Boc-Lys(Cl-Z)-Gln-Thr(Bzl)-Pro-Gln-Thr(Bzl)-Asp(OBzl)-Val-Gly-Ala-Gly-Thr(Bzl)-Pro—NH₂

Using Boc-Gln-Thr(Bzl)-Pro-Gln-Thr(Bzl)-Asp(OBzl)-Val-Gly-Ala-Gly-Thr(Bzl)-Pro—NH₂ (1.01 g) and Boc-Lys(Cl-Z)—OSu (475 mg), the same procedure as in Reference Example 85 was repeated to obtain 1.14 g (yield: 95.8%) of the above objective compound having a melting point of 169°–172° C.

REFERENCE EXAMPLE 271

Preparation of
Boc-Leu-His-Lys(Cl-Z)-Gln-Thr(Bzl)-Pro-Gln-Thr(Bzl)-Asp(OBzl)-Val-Gly-Ala-Gly Thr(Bzl)-Pro—NH₂

Using Box-Lys(Cl-Z)-Gln-Thr(Bzl)-Pro-Gln-Thr(Bzl)-Asp(OBzl)-Val-Gly-Ala-Gly-Thr(Bzl)-Pro—NH₂ (1.11 g), Boc-Leu-His—OH (324 mg) and, in place of HOBT, HOSu (101 mg), the same procedure as in Reference Example 70 was repeated to obtain 1.14 g (yield: 89.1%) of the above objective compound having a melting point of 199°–205° C. (decomposed).

REFERENCE EXAMPLE 272

Preparation of
Boc-Glu(OcHex)-Leu-His-Lys(Cl-Z)-Gln-Thr(Bzl)-Pro-Gln-Thr(Bzl)-Asp(OBzl)-Val-Gly-Ala-Gly-Thr(Bzl)-Pro—NH₂

Using Boc-Leu-His-Lys(Cl-Z)-Gln-Thr(Bzl)-Pro-Gln-Thr(Bzl)-Asp(OBzl)-Val-Gly-Ala-Gly-Thr(Bzl)-Pro—NH₂ (1.11 g) and Boc-Glu(OcHex)—OSu (326 mg), the same procedure as in Reference Example 85 was repeated to obtain 1.11 g (yield: 91.0%) of the above objective compound having a melting point of 205°–211° C. (decomposed).

REFERENCE EXAMPLE 273

Preparation of
Boc-Gln-Glu(OcHex)-Leu-His-Lys(cl-Z)-Gln-Thr(Bzl)-Pro-Gln-Thr(Bzl)-Asp(OBzl)-Val Gly-Ala-Gly-Thr(Bzl)-Pro—NH₂

Using Boc-Glu(OcHex)-Leu-His-Lys(Cl-Z)-Gln-Thr(Bzl)-Pro-Gln-Thr(Bzl)-Asp(OBzl)-Val-Gly-Ala-Gly-Thr(Bzl)-Pro—NH₂ (1.07 g) and Boc-Gin—ONp (247 mg), the same procedure as in Reference Example 85 was repeated to obtain 1.03 g (yield: 90.9%) of the above objective compound having a melting point of 218°–221° C. (decomposed).

REFERENCE EXAMPLE 274

Preparation of
Boc-Lys(Z)-Leu-Ser(Bzl)-Gln-Glu(OcHex)-Leu-His-Lys(Cl-Z)-Gln-Thr(Bzl)-Pro-Gln-Thr(Bzl)-Asp(OBzl)-Val-Gly Ala-Gly-Thr(Bzl)-Pro—NH₂

Using Boc-Gln-Glu(OcHex)-Leu-His-Lys(Cl-Z)-Gln-Thr(Bzl)-Pro-Gln-Thr(Bzl)-Asp(OBzl)-Val-Gly-Ala-Gly-Thr(Bzl) Pro—NH₂ (600 mg) and Boc-Lys(Z)-Leu-Ser(Bzl)—OH (240 mg), the same procedure as in Reference Example 70 was repeated to obtain 646 mg (yield: 88.3%) of the above objective compound having a melting point of 230°–236° C. (decomposed).

REFERENCE EXAMPLE 275

Preparation of
Boc-Gly-Leu-Gln-Thr(Bzl)-Pro-Gly-Thr(Bzl)-Asp(OcHex)-Val-Gly-Ala-Gly-Thr(Bzl)-Pro—NH₂

Using Boc-Gln-Thr(Bzl)-Pro-Gly-Thr(Bzl)-Asp(OcHex)-Val-Gly-Ala-Gly-Thr(Bzl)-Pro—NH₂ (500 mg) and Boc-Gly-Leu OH (110 mg), the same procedure as in Reference Example 70 was repeated to obtain 450 mg (yield: 81.2%) of the above objective compound having a melting point of 184°–186° C.

REFERENCE EXAMPLE 276

Preparation of
Boc-Leu-His-Gly-Leu-Gln-Thr(Bzl)-Pro-Gly Thr(Bzl)-Asp(OcHex)-Val-Gly-Ala-Gly-Thr(Bzl)-Pro—NH₂

Using Boc-Gly-Leu-Gln-Thr(Bzl)-Pro-Gly-Thr(Bzl)-Asp(OcHex)-Val-Gly-Ala-Gly-Thr(Bzl)-Pro—NH₂ (400 mg) and Boc-Leu-His—OH (102 mg), the same procedure as in Reference Example 70 was repeated to obtain 360 mg (yield: 78.8%) of the above objective compound having a melting point of 172°–180° C.

REFERENCE EXAMPLE 277

Preparation of
Boc-Glu(OBzl)-Leu-His-Gly-Leu-Gln-Thr(Bzl)-Pro-Gly-Thr(Bzl)-Asp(OcHex)-Val-Gly-Ala-Gly-Thr(Bzl)-Pro—NH₂

Using Boc-Leu-His-Gly-Leu-Gln-Thr(Bzl)-Pro-Gly-Thr(Bzl)-Asp(OcHex)-Val-Gly-Ala-Gly-Thr(Bzl)-Pro—NH₂ (320 mg) and Boc-Glu(OBzl)—OH (66 mg), the same procedure as in Reference Example 70 was repeated to obtain 280 mg (yield: 78.9%) of the above objective compound having a melting point of 205°–210° C.

REFERENCE EXAMPLE 278

Preparation of
Boc-Gln-Glu(OBzl)-Leu-His-Gly-Leu-Gln-Thr(Bzl)-Pro-Gly-Thr(Bzl)-Asp(OcHex)-Val-Gly-Ala-Gly-Thr(Bzl)-Pro—NH₂

Using Boc-Glu(OBzl)-Leu-His-Gly-Leu-Gln-Thr(Bzl)-Pro-Gly-Thr(Bzl)-Asp(OcHex)-Val-Gly-Ala-Gly-ThY(Bzl)-Pro—NH₂ (250 mg) and Boc-Gln—ONp (50 mg), the same procedure as in Reference Example 85 was repeated to obtain 200 mg (yield: 75.8%) of the above objective compound.

Melting point: 220°–231° C.
Amino acid analysis:

| | |
|---|---|
| Asp: 1.03 (1) | Val: 1.01 (1) |
| Thr: 2.98 (3) | Leu: 2.05 (2) |
| Glu: 3.00 (3) | His: 0.92 (1) |
| Gly: 3.97 (4) | Pro: 2.02 (2) |
| Ala: 1.02 (1) | |

REFERENCE EXAMPLE 279

Preparation of
Boc-Gly-Leu-Ser(Bzl)-Gln-Glu(OBzl)-Leu-His-Gly-Leu-Gln-Thr(Bzl)-Pro-Gly-Thr(Bzl)-Asp(OcHex)-Val-Gly-Ala-Gly-Thr(Bzl)-Pro—NH₂

Using Boc-Gln-Glu(OBzl)-Leu-His-Gly-Leu-Gln-Thr(Bzl)-Pro-Gly-Thr(Bzl)-Asp(OcHex)-Val-Gly-Ala-Gly-Thr(Bzl)—OH (41 mg) and Boc-Gly-Leu-Ser(Bzl)-Pro—NH₂ (170 mg), the same procedure as in Reference Example 70 was repeated to obtain 150 mg (yield: 78.9%) of the above objective compound having a melting point of 189°–193° C.

REFERENCE EXAMPLE 280

Preparation of ⌐Acp—Asn—Leu—Ser(Bzl)—Thr(Bzl)—
¬Asp—Gly—Leu—Gly—OH

Using Boc-Gly-Leu-Gly—OH (618 mg) and

⌐Acp—Asn—Leu—Ser(Bzl)—Thr(Bzl)—Asp—N₂H₃, the same procedure as in Reference Example 39 was repeated to obtain 852 mg (yield: 90.6%) of the above objective compound.
Melting point: 208°–226° C. (decomposed).
Amino acid analysis:

| | |
|---|---|
| Asp: 2.05 (2) | Gly: 2.44 (2) |
| Thr: 1.03 (1) | Leu: 2.37 (2) |
| Ser: 0.96 (1) | Acp: 0.97 (1) |

REFERENCE EXAMPLE 281

Preparation of
Boc-Ala-Leu-Ser(Bzl)-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂

Using Boc-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (500 mg) and Boc-Ala-Leu-Ser(Bzl)—OH (142 mg), the same procedure as in Reference Example 70 was repeated to obtain 550 mg (yield: 96.1%) of the above objective compound having a melting point of 253°–257° C. (decomposed)

REFERENCE EXAMPLE 282

Preparation of
Boc-Lys(COCH₃)-Leu-Ser(Bzl)-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂

Using Boc-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (449 mg) and Boc-Lys(COCH₃)-Leu-Ser(Bzl)—OH (170 mg), the same procedure as in Reference Example 70 was repeated to obtain 532 mg (yield: 88.6%) of the above objective compound.
Melting point: 228°–242° C. (decomposed).
Amino acid analysis:
Asp: 1.02 (1)
Thr: 2.93 (3)
Ser: 0.72 (1)
Glu: 4.05 (4)
Gly: 2.96 (3)
Ala: 0.99 (1)
Val: 1.00 (1)
Leu: 3.01 (3)
Lys: 2.04 (2)
Pro: 1.99 (2).

REFERENCE EXAMPLE 283

Preparation of
Boc-Asn-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂

By using 500 mg of Boc-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ and 186 mg of Boc-Asn-Lys(Cl-Z)-Leu—OH and the same procedure as in Reference Example 70 was repeated to obtain 590 mg (yield: 94.1%) of the above-mentioned objective compound. Melting point: 168°–170° C.

REFERENCE EXAMPLE 284

Preparation of
Boc-Gln-Glu(OcHex)-Leu-Asn-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂

By using 540 mg of Boc-Asn-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ and 142 mg of Boc-Gln-Glu(OcHex)-Leu—OH and the same procedure as in Reference Example 70 was repeated to obtain 610 mg (yield: 96.4%) of the above-mentioned objective compound.
Melting point: 227°–230° C.

REFERENCE EXAMPLE 285

Preparation of
Boc-Lys(Z)-Leu-Ser(Bzl)-Gln-Glu(OcHex)-Leu-Asn-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl) Pro—NH₂

By using 550 mg of Boc-Gln-Glu(OcHex)-Leu-Asn-Lys(Cl-Z)-Leu-Gln-Thr(Bzl)-Tyr(Bzl)-Pro-Arg(Tos)-Thr(Bzl)-Asp(OBzl)-Val-Gly-ALa-Gly-Thr(Bzl)-Pro—NH₂ and 146 mg of -Boc-Lys(Z)-Leu-Ser(Bzl)—OH, and the same procedure as in Reference Example 70 was repeated to obtain 620 mg (yield: 95.3%) of the above-mentioned objective compound.
Melting point: 240°-245° C. (decomposed)

REFERENCE EXAMPLE 286

Preparation of Boc-Gly-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ By using 500 mg of Boc-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ and 170 mg of Boc-Gly-Lys(Cl-Z)-Leu—OH, and the same procedure as in Reference Example 70 was repeated to obtain 580 mg (yield: 94.6%) of the above-mentioned objective compound.
Melting point: 170°-173° C.

REFERENCE EXAMPLE 287

Preparation of Boc-Gln-Glu(OcHex)-Leu-Gly-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ By using 530 mg of Boc-Gly-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ and 143 mg of Boc-Gln-Glu(OcHex)-Leu—OH, and the same procedure as in Reference Example 70 was repeated to obtain 610 mg (yield: 97.8%) of the above-mentioned objective compound.
Melting point: 194°-197° C.

REFERENCE EXAMPLE 288

Preparation of Boc-Lys(Z)-Leu-Ser(Bzl)-Gln-Glu(OcHex)-Leu-Gly-Lys(Cl-Z)-Leu-Gly-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ and 148 mg of Boc-Lys(Z)-Leu-Ser(Bzl)—OH, and the same procedure as in Reference Example 70 was repeated to obtain 620 mg (yield: 95.2%) of the above-mentioned objective compound.

Melting point: 213°-222° C.

REFERENCE EXAMPLE 289

Preparation of Boc-Gln-Glu(OcHex)-Leu-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ By using 510 mg of Boc-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ and 141 mg of Boc-Gln-Glu(OcHex)-Leu—OH, and the same procedure as in Reference Example 70 was repeated to obtain 590 mg (yield: 97.8%) of the above-mentioned objective compound.
Melting point: 215°-224° C.

REFERENCE EXAMPLE 290

Preparation of Boc-Lys(Z)-Leu-Ser(Bzl)-Gln-Glu(OcHex)-Leu-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Ala-Gly-Thr(Bzl)-Pro—NH$_2$ By using 540 mg of Boc-Gln-Glu(OcHex)-Leu-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ and 148 mg of Boc-Lys(Z)-Leu-Ser(Bzl)—OH, and the same procedure as in Reference Example 70 was repeated to obtain 620 mg (yield: 96.8%) of the above-mentioned objective compound.
Melting point: 235°-240° C. (decomposed).

REFERENCE EXAMPLE 291

Preparation of Boc-Asp(OcHex)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ By using 300 mg of Boc-Lys(Cl-Z)-Leu-Gln-Thr(Bzl)-Pro-Arg(Tos)-Thr(Bzl)-Asp(OcHex)-Val-Gln-Ala-Gly-Thr(Bzl)-Pro—NH$_2$ and 51 mg of Boc-Asp(OcHex)—OH, the same procedure as in Reference Example 70 was repeated to obtain 320 mg (yield: 98.3%) of the above-mentioned objective compound.
Melting point: 180°-183° C.

REFERENCE REXAMPLE 292

Preparation of Boc-Gln-Glu(OcHex)-Leu-Asp(OcHex)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ By using 290 mg of Boc-Asp(OcHex)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 82 mg of Boc-Gln-Glu(OcHex)-Leu—OH, and the same procedure as in Reference Example 70 was repeated to obtain 320 mg (yield: 93.1%) of the above-mentioned objective compound.
Melting point: 242°-248° C.

REFERENCE EXAMPLE 293

Preparation of Boc-Lys(Z)-Leu-Ser(Bzl)-Gln-Glu(OcHex)-Leu-Asp(OcHex)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ By using 290 mg of Boc-Gln-Glu(OcHex)-Leu-Asp(OcHex)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 81 mg of Boc-Lys(Z)-Leu-Ser(Bzl)—OH, and the same procedure as in Reference Example 70 was repeated to obtain 310 mg (yield: 89.8%) of the above-mentioned objective compound.
Melting point: 247°-249° C. (decomposed).

REFERENCE EXAMPLE 294

Preparation of Boc-Gln-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ By using 300 mg of Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 60 mg of Boc-Gln—ONp, and the same procedure as in Reference Example 85 was repeated to obtain 310 mg (yield: 98.0%) of the above-mentioned objective compound.
Melting point: 175°-179° C.

REFERENCE EXAMPLE 295

Preparation of
Boc-Gln-Glu(OcHex)-Leu-Gln-Lys(Cl-Z)-Leu-Gln-
Thr(Bzl)-Pro-Arg(Tos)-Thr(Bz)-Asp(OcHex)-Val-
Gly-Ala-Gly-Thr(Bzl)-Pro—NH$_2$ By using 280 mg of Boc-Gln-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 81 mg of Boc-Gln-Glu(OcHex)L-Leu—OH, and the same procedure as in Reference Example 70 was repeated to obtain 310 mg (yield: 93.2%) of the above-mentioned objective compound.

Melting point: 232°–235° C.

REFERENCE EXAMPLE 296

Preparation of
Boc-Lys(Z)-Leu-Ser(Bzl)-Gln-Glu(OcHex)-Leu-Gln-
Lys(Cl-Z)-Leu-Gln-Thr(Bzl)-Pro-Arg(Tos)-Thr(Bzl)-
Asp(OcHex)-Val-Gly-Ala-Gly-Thr(Bzl)-Pro—NH$_2$ By using 280 mg of Boc-Gln-Glu(OcHex)-Leu-Gln-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 80 mg of Boc-Lys(Z)-Leu-Ser(Bzl)—OH, and the same procedure as in Reference Example 70 was repeated to obtain 320 mg (yield: 95.6%) of the above-mentioned objective compound.

Melting point: 243°–250° C. (decomposed).

REFERENCE EXAMPLE 297

Preparation of
Boc-Leu-Lys(Cl-Z)-Leu-Gln-Thr(Bzl)-Pro-Arg(Tos)-
Thr(Bzl)-Asp(OcHex)-Val-Gly-Ala-Gly-Thr(Bzl)-
Pro—NH$_2$ By using 300 mg of Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 53 mg of Boc-Leu—OSu, and the same procedure as in Reference Example 85 was repeated to obtain 300 mg (yield: 95.5%) of the above-mentioned objective compound.

Melting point: 180°–183° C.

REFERENCE EXAMPLE 298

Preparation of
Boc-Gln-Glu(OcHex)-Leu-Leu-Lys(Cl-Z)-Leu-Gln-
Thr(Bzl)-Pro-Arg(Tos)-Thr(Bzl)-Asp(OcHex)-Val-
Gly-Ala-Gly-Thr(Bzl)-Pro—NH$_2$ By using 270 mg of Boc-Leu-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 79 mg of Boc-Gln-Glu(OcHex)-Leu—OH, and the same procedure as in Reference Example 70 was repeated to obtain 310 mg (yield: 96.1%) of the above-mentioned objective compound.

Melting point: 250°–254° C. (decomposed).

REFERENCE EXAMPLE 299

Preparation of Boc-Lys(Z)-Leu-Ser(Bzl)-Gln-Glu(OcHex)-Leu-Leu-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ By using 280 mg of Boc-Gln-Glu(OcHex)-Leu-Leu-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 81 mg of Boc-Lys(Z)-Leu-Ser(Bzl)—OH, and the same procedure as in Reference Example 70 was repeated to obtain 310 mg (yield: 92.1%) of the above-mentioned objective compound.

Melting point: 253°–256° C. (decomposed)

REFERENCE EXAMPLE 300

Preparation of
Boc-Phe-Lys(Cl-Z)-Leu-Gln-Thr(Bzl)-Pro-Arg(Tos)-
Thr(Bzl)-Asp(OcHex)-Val-Gly-Ala-Gly-Thr(Bzl)-
Pro—NH$_2$ By using 300 mg of Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 43 mg of Boc-Phe—OH, and the same procedure as in Reference Example 70 was repeated to obtain 310 mg (yield: 97.2%) of the above-mentioned objective compound.

Melting point: 177°–181° C.

REFERENCE EXAMPLE 301

Preparation of
Boc-Gln-Glu(OcHex)-Leu-Phe-Lys(Cl-Z)-Leu-Gln-
Thr(Bzl)-Pro-Arg(Tos)-Thr(Bzl)-Asp(OcHex)-Val-
Gly-Ala-Gly-Thr(Bzl)-Pro—NH$_2$ By using 280 mg of Boc-Phe-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 81 mg of Boc-Gln-Glu(OcHex)-Leu—OH, and the same procedure as in Reference Example 70 was repeated to obtain 310 mg (yield: 92.6%) of the above-mentioned objective compound.

Melting point: 246°–250° C. (decomposed).

REFERENCE EXAMPLE 302

Preparation of
Boc-Lys(Z)-Leu-Ser(Bzl)-Gln-Glu(OcHex)-Leu-Phe-
Lys(Cl-Z)-Leu-Gln-Thr(Bzl)-Pro-Arg(Tos)-Thr(Bzl)-
Asp(OcHex)-Val-Gly-Ala-Gly-Thr(Bzl)-Pro—NH$_2$ By using 280 mg of Boc-Gln-Glu(OcHex)-Leu-Phe-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 80 mg of Boc-Lys(Z)-Leu-Ser(Bzl)—OH, and the same procedure as in Reference Example 70 was repeated to obtain 330 mg (yield: 99.0%) of the above-mentioned objective compound.

Melting point: 251°–254° C. (decomposed).

REFERENCE EXAMPLE 303

Preparation of
Boc-Ala-Lys(Cl-Z)-Leu-Gln-Thr(Bzl)-Pro-Arg(Tos)-
Thr(Bzl)-Asp(OcHex)-Val-Gly-Ala-Gly-Thr(Bzl)-
Pro—NH$_2$ By using 300 mg of Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 46 mg of Boc-Ala—OSu, and the same procedure as in Reference Example 85 was repeated to obtain 300 mg (yield: 97.2%) of the above-mentioned objective compound.

Melting point: 178°–182° C.

REFERENCE EXAMPLE 304

Preparation of
Boc-Gln-Glu(OcHex)-Leu-Ala-Lys(Cl-Z)-Leu-Gln-
Thr(Bzl)-Pro-Arg(Tos)-Thr(Bzl)-Asp(OcHex)-Val-
Gly-Ala-Gly-Thr(Bzl)-Pro—NH$_2$ By using 270 mg of Boc-Ala-Lys(Cl-Z)-Leu-Gln-Thr(Bzl)-Pro-Arg(Tos)-Thr(Bzl)-Asp(OcHex)-Val- Gly-Ala-Gly-Thr(Bzl)-Pro—NH$_2$ and 81 mg of Boc-Gln-Glu(OcHex)-Leu—OH, and the same procedure as in Reference Example 70 was repeated to obtain 310 mg (yield: 95.9%) of the above-mentioned compound.

Melting point: 250°–253° C. (decomposed).

REFERENCE EXAMPLE 305

Preparation of
Boc-Lys(Z)-Leu-Ser(Bzl)-Gln-Glu(OcHex)-Leu-Ala-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ By using 280 mg of Boc-Gln-Glu(OcHex)-Leu-Ala-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 82 mg of Boc-Lys(Z)-Leu-Ser(Bzl)—OH, and the same procedure as in Reference Example 70 was repeated to obtain 330 mg (yield: 98.3%) of the above-mentioned objective compound.

Melting point: 251°–253° C. (decomposed).

REFERENCE EXAMPLE 306

Preparation of
Boc-Gln-Glu(OcHex)-Leu-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ By using 300 mg of Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 92 mg of Boc-Gln-Glu(OcHex)-Leu—OH, and the same procedure as in Reference Example 70 was repeated to obtain 360 mg (yield: 100.0%) of the above-mentioned objective compound.

Melting point: 227°–235° C.

REFERENCE EXAMPLE 307

Preparation of
Boc-Lys(Z)-Leu-Ser(Bzl)-Gln-Glu(OcHex)-Leu-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ By using 330 mg of Boc-Gln-Glu(OcHex)-Leu-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ and 100 mg of Boc-Lys(Z)-Leu-Ser(Bzl)—OH, and the same procedure as in Reference Example 70 was repeated to obtain 360 mg (yield: 90.2%) of the above-mentioned objective compound.

Melting point: 246°–250° C. (decomposed).

REFERENCE EXAMPLE 308

Preparation of
Boc-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 1.00 g of Boc-Gln-Thr(Bzl)-Asp(OcHex)-Val-Gly-Ala-Gly-Thr(Bzl)-Pro—NH$_2$ and 726 mg of Boc-Thr(Bzl)-Tyr(Cl$_2$-Bzl)-Pro—OH, and the same procedure as in Reference Example 70 was repeated to obtain 1.45 g (yield: 96.2%) of the above-mentioned objective compound.

Melting point: 193°–196° C.

REFERENCE EXAMPLE 309

Preparation of
Boc-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 1.40 g of Boc-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 339 mg of Boc-Gln—ONp, and the same procedure as in Reference Example 85 was repeated to obtain 1.36 g (yield: 90.8%) of the above-mentioned objective compound.

Melting point: 180°–183° C.

REFERENCE EXAMPLE 310

Preparation of
Boc-Asn-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 300 mg of Boc-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 119 mg of Boc-Asn-Lys(Cl-Z)-Leu—OH, and the same procedure as in Reference Example 70 was repeated to obtain 330 mg (yield: 86.8%) of the above-mentioned objective compound.

Melting point: 168°–172° C.

REFERENCE EXAMPLE 311

Preparation of
Boc-Gln-Glu(OcHex)-Leu-Asn-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 300 mg of Boc-Asn-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 84 mg of Boc-Gln-Glu(OcHex)-Leu—OH, and the same procedure as in Reference Example 70 was repeated to obtain 320 mg (yield: 89.8%) of the above-mentioned objective compound.

Melting point: 234°–236° C.

REFERENCE EXAMPLE 312

Preparation of
Boc-Lys(Z)-Leu-Ser(Bzl)-Gln-Glu(OcHex)-Leu-Asn-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 290 mg of Boc-Gln-Glu(OcHex)-Leu-Asn-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 80 mg of -Boc-Lys(Z)-Leu-Ser(Bzl)—OH, and the same procedure as in Reference Example 70 was repeated to obtain 330 mg (yield: 95.9%) of the above-mentioned objective compound.

Melting point: 241°–245° C. (decomposed).

REFERENCE EXAMPLE 313

Preparation of
Boc-Gly-Lys(Cl-Z)-Leu-Gln-Thr(Bzl)-Tyr(Cl-Bzl)-Pro-Gln-Thr(Bzl)-Asp(OcHex)-Val-Gly-Ala-Gly-Thr(Bzl)-Pro—NH$_2$ By using 300 mg of Boc-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 108 mg of Boc-Gly-Lys(Cl-Z)-Leu—OH, and the same procedure as in Reference Example 70 was repeated to obtain 340 mg (yield: 91.5%) of the above-mentioned objective compound.

Melting point: 170°–174° C.

REFERENCE EXAMPLE 314

Preparation of
Boc-Gln-Glu(OcHex)-Leu-Gly-Lys(Cl-Z)-Leu-Gln-Thr(Bzl)-Tyr(Cl-Bzl)-Pro-Gln-Thr(Bzl)-Asp(OcHex)-Val-Gly-Ala-Gly-Thr(Bzl)-Pro—NH$_2$ By using 310 mg of Boc-Gly-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 88 mg of Boc-Gln-Glu(OcHex)-Leu—OH, and the same procedure as in Reference Example 70 was repeated to obtain 330 mg (yield: 89.3%) of the above-mentioned objective compound.
Melting point: 198°–202° C.

REFERENCE EXAMPLE 315

Preparation of
Boc-Lys(Z)-Leu-Ser(Bzl)-Gln-Glu(OcHex)-Leu-Gly-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 300 mg of Boc-Gln-Glu(OcHex)-Leu-Gly-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 85 mg of Boc-Lys(Z)-Leu-Ser(Bzl)—OH, and the same procedure as in Reference Example 70 was repeated to obtain 350 mg (yield: 97.5%) of the above-mentioned objective compound.
Melting point: 216°–222° C.

REFERENCE EXAMPLE 316

Preparation of
Boc-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 600 mg of Boc-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 195 mg of Boc-Lys(Cl-Z)-Leu—OH, and the same procedure as in Reference Example 70 was repeated to obtain 640 mg (yield: 88.2%) of the above-mentioned objective compound.
Melting point: 170°–175° C.

REFERENCE EXAMPLE 317

Preparation of
Boc-Gln-Glu(OcHex)-Leu-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 300 mg of Boc-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 87 mg of Boc-Gln-Glu(OcHex)-Leu—OH, and the same procedure as in Reference Example 70 was repeated to obtain 340 mg (yield: 95.4%) of the above-mentioned objective compound.
Melting point: 231°–235° C. (decomposed).

REFERENCE EXAMPLE 318

Preparation of Boc-Lys(Z)-Leu-Ser(Bzl)-Gln-Glu(OcHex)-Leu-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 310 mg of Boc-Gln-Glu(OcHex)-Leu-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 89 mg of Boc-Lys(Z)-Leu-Ser(Bzl)—OH, and the same procedure as in Reference Example 70 was repeated to obtain 340 mg (yield: 92.0%) of the above-mentioned objective compound.
Melting point: 242°–246° C. (decomposed).

REFERENCE EXAMPLE 319

Preparation of
Boc-His(Tos)-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 300 mg of Boc-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 6.2 mg of Boc-His(Tos)—OH as well as 18 mg of HOSu, in place of HOBT, and the same procedure as in Reference Example 70 was repeated to obtain 300 mg (yield: 89.3%) of the above-mentioned objective compound.
Melting point: 171°–175° C.

REFERENCE EXAMPLE 320

Preparation of
Boc-Gln-Glu(OcHex)-Leu-His(Tos)-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 270 mg of Boc-His(Tos)-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 70 mg of Boc-Gln-Glu(OcHex)-Leu—OH, and the same procedure as in Reference Example 70 was repeated to obtain 280 mg (yield: 88.6%) of the above-mentioned objective compound.
Melting point: 174°–178° C.

REFERENCE EXAMPLE 321

Preparation of
Boc-Lys(Z)-Leu-Ser(Bzl)-Gln-Glu(OcHex)-Leu-His(Tos)-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ By using 250 mg of Boc-Gln-Glu(OcHex)-Leu-His(Tos)-Lys(Cl-Z)-Leu-Gln-Thr(Bzl)-Tyr(Cl$_2$-Bzl)-Pro-Gln-Thr(Bzl)-Asp(OcHex)-Val-Gly-Ala-Gly-Thr(Bzl)-Pro—NH$_2$ and 65 mg of Boc-Lys(Z)-Leu-Ser(Bzl)—OH, and the same procedure as in Reference Example 70 was repeated to obtain 270 mg (yield: 91.3%) of the above-mentioned compound.
Melting point 224°–230° C. (decomposed).

REFERENCE EXAMPLE 322

Preparation of
Boc-Leu-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 300 mg of Boc-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 45 mg of Boc-Leu—OH.-H$_2$O, and the same procedure as in Reference 70 was repeated to obtain 256 mg (yield: 80.8%) of the above-mentioned objective compound.
Melting point: 218°–221° C.

REFERENCE EXAMPLE 323

Preparation of
Boc-Gln-Glu(OcHex)-Leu-Leu-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 240 mg of Boc-Leu-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 77 mg of Boc-Gln-Glu(OcHex)-Leu—OH, and the same procedure as in Reference Example 70 was repeated to obtain 290 mg (yield: 99.8%) of the above-mentioned objective compound.
Melting point: 251°–255° C.

REFERENCE EXAMPLE 324

Preparation of
Boc-Lys(Z)-Leu-Ser(Bzl)-Gln-Glu(OcHex)-Leu-Leu-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 277 mg of Boc-Gln-Glu(OcHex)-Leu-Leu-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 86 mg of Boc-Lys(Z)-Leu-Ser(Bzl)—OH, and the same procedure as in Reference Example 70 was repeated to obtain 309 mg (yield: 92.0%) of the above-mentioned objective compound.
Melting point: 255°–259° C.

REFERENCE EXAMPLE 325

Preparation of
Boc-Asp(OcHex)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 300 mg of Boc-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 56 mg of Boc-Asp(OcHex)—OH, and the same procedure as in Reference Example 70 was repeated to obtain 236 mg (yield: 71.7%) of the above-mentioned compound.
Melting point: 210°–213° C.

REFERENCE EXAMPLE 326

Preparation of
Boc-Gln-Glu(OcHex)-Leu-Asp(OcHex)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 220 mg of Boc-Asp(OcHex)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 70 mg of Boc-Gln-Glu(OcHex)-Leu—OH, and the same procedure as in Reference Example 70 was repeated to obtain 259 mg (yield: 97.9%) of the above-mentioned objective compound.
Melting point: 240°–245° C.

REFERENCE EXAMPLE 327

Preparation of
Boc-Lys(Z)-Leu-Ser(Bzl)-Gln-Glu(OcHex)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 250 mg of Boc-Gln-Glu(OcHex)-Leu-Asp(OcHex)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 75 mg of Boc-Lys(Z)-Leu-Ser(Bzl)—OH, and the same procedure as in Reference Example 70 was repeated to obtain 270 mg (yield: 89.6%) of the above-mentioned objective compound.

REFERENCE EXAMPLE 328

Preparation of
Boc-Tyr(Cl$_2$-Bzl)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 440 mg of Boc-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 114 mg of Boc-Tyr(Cl$_2$-Bzl)—OH, and the same procedure as in Reference Example 70 was repeated to obtain 452 mg (yield: 88.9%) of the above-mentioned compound. Melting point: 209°–219° C.
Amino acid analysis data:

| Asp: 1.02 (1) | Val: 1.02 (1) |
|---|---|
| Thr: 2.93 (3) | Leu: 1.00 (1) |
| Glu: 2.07 (2) | Tyr: 0.94 (1) |
| Gly: 2.03 (2) | Lys: 0.97 (1) |
| Ala: 1.02 (1) | Pro: 2.01 (2) |

REFERENCE EXAMPLE 329

Preparation of
Boc-Gln-Glu(OcHex)-Leu-Tyr(Cl$_2$-Bzl)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 420 mg of Boc-Tyr(Cl$_2$-Bzl)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 122 mg of Boc-Gln-Glu(OcHex)-Leu—OH, and the same procedure as in Reference Example 70 was repeated to obtain 470 mg (yield: 94.1%) of the above-mentioned objective compound,
Melting point: 240°–255° C. (decomposed).
Amino acid analysis data:

| Asp: 1.02 (1) | Val: 1.01 (1) |
|---|---|
| Thr: 2.93 (3) | Leu: 2.00 (2) |
| Glu: 4.11 (4) | Tyr: 0.93 (1) |
| Gly: 2.20 (2) | Lys: 0.97 (1) |
| Ala: 1.01 (1) | Pro: 2.00 (2) |

REFERENCE EXAMPLE 330

Preparation of
Boc-Lys(Z)-Leu-Ser(Bzl)-Gln-Glu(OcHex)-Leu-Tyr(Cl$_2$-Bzl)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ By using 430 mg of Boc-Gln-Glu(OcHex)-Leu-Tyr(Cl$_2$-Bzl)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ and 205 mg of Boc-Lys(Z)-Leu-Ser(Bzl)—OH, and the same procedure as in Reference Example 70 was repeated to obtain 470 mg (yield: 91.4%) of the above-mentioned compound.
Melting point 249°–257° C. (decomposed).

REFERENCE EXAMPLE 331

Preparation of
Boc-Asn-Thr(Bzl)-Asp(OcHex)-Val-Gly-Ala-Gly-Thr(Bzl)-Pro—NH₂

By using 1.00 g of Boc-Thr(Bzl)-Asp(OcHex)-Val-Gly-Ala-Gly-Thr(Bzl)-Pro—NH₂ and 394 mg of Boc-Asn—ONp, and the same procedure as in Reference Example 85 was repeated to obtain 1.02 g (yield: 92.0%) of the above-mentioned objective compound.
Melting point: 221°–224° C.

REFERENCE EXAMPLE 332

Preparation of
Boc-Thr(Bzl)-Pro-Asn-Thr(Bzl)-Asp(OcHex)-Val-Gly-Ala-Gly-Thr(Bzl)-Pro—NH₂

By using 970 mg of Boc-Asn-Thr(Bzl)-Asp(OcHex)-Val-Gly-Ala-Gly-Thr(Bzl)-Pro—NH₂ and 395 mg of Boc-Thr(Bzl)-Pro—OH, and the same procedure as in Reference Example 70 was repeated to obtain 1.05 g (yield: 87.5%) of the above-mentioned objective compound.
Melting point: 181°–184° C.

REFERENCE EXAMPLE 333

Preparation of
Boc-Gln-Thr(Bzl)-Pro-Asn-Thr(Bzl)-Asp(OcHex)-Val-Gly-Ala-Gly-Thr(Bzl)-Pro—NH₂

By using 1.00 g of Boc-Thr(Bzl)-Pro-Asn-Thr(Bzl)-Asp(OcHex)-Val-Gly-Ala-Gly-Thr(Bzl)-Pro—NH₂ and 300 mg of Boc-Gln—ONp, and the same procedure as in reference Example 85 was repeated to obtain 900 mg (yield: 82.3%) of the above-mentioned objective compound.
Melting point: 167°–170° C.

REFERENCE EXAMPLE 334

Preparation of
Boc-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂

By using 550 mg of Boc-Gln-Thr(Bzl)-Pro-Asn-Thr(Bzl)-Asp(OcHex)-Val-Gly-Ala-Gly-Thr(Bzl)-Pro—NH₂ and 215 mg of Boc-Lys(Cl-Z)-Leu—OH, and the same procedure as in Reference Example 70 was repeated to obtain 600 mg (yield: 87.4%) of the above-mentioned objective compound.
Melting point: 193°–198° C.

REFERENCE EXAMPLE 335

Preparation of
Boc-Gln-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂

By using 280 mg of Boc-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂ and 62 mg of Boc-Gln—ONp, and the same procedure as in Reference Example 85 was repeated to obtain 250 mg (yield: 83.2%) of the above-mentioned objective compound.
Melting point: 207°–212° C.

REFERENCE EXAMPLE 336

Preparation of
Boc-Gln-Glu(OcHex)-Leu-Gln-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂

By using 220 mg of Boc-Gln-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂ and 68 mg of Boc-Gln-Glu(OcHex)-Leu—OH, and the same procedure as in Reference Example 70 was repeated to obtain 210 mg (yield: 80.8%) of the above-mentioned objective compound.
Melting point: 215°–227° C.
Amino acid analysis data:

| Asp: 2.01 (2), | Val: 1.02 (1), | Thr: 2.87 (3), |
| Leu: 2.00 (2), | Glu: 4.01 (4), | Lys: 0.99 (1), |
| Gly: 2.01 (2), | Pro: 2.10 (2), | Ala: 1.00 (1). |

REFERENCE EXAMPLE 337

Preparation of
Boc-Lys(Z)-Leu-Ser(Bzl)-Gln-Glu(OcHex)-Leu-Gln-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂

By using 190 mg of Boc-Gln-Glu(OcHex)-Leu-Gln-Lys-(Cl-Z)-Leu-Gln-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂ and 66 mg of Boc-Lys(Z)-Leu-Ser(Bzl)—OH, and the same procedure as in Reference Example 70 was repeated to obtain 193 mg (yield: 87.5%) of the above-mentioned objective compound.
Melting point: 235°–244°. (decomposed).

REFERENCE EXAMPLE 338

Preparation of
Boc-His(Tos)-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂

By using 280 mg of Boc-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂ and 75 mg of Boc-His(Tos)—OH as well as 22 mg of HOSu, in place of HOBT, and the same procedure as in Reference Example 70 was repeated to obtain 270 mg (yield: 83.5%) of the above-mentioned objective compound.
Melting point: 198°–205° C.

REFERENCE EXAMPLE 339

Preparation of
Boc-Gln-Glu(OcHex)-Leu-His(Tos)-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂

By using 240 mg of Boc-His(Tos)-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂ and 91 mg of Boc-Gln-Glu(OcHex)-Leu—OH as well as 22 mg of HOSu in place of HOBT, and the same procedure as in Reference Example 70 was repeated to obtain 240 mg (yield: 86.9%) of the above-mentioned objective compound.
Melting point: 188°–202° C.
Amino acid analysis data:

| Asp: 2.03 (2), | Val: 1.02 (1), | Thr: 2.89 (3), |

-continued

Leu: 1.99 (2),  Glu: 2.97 (3),  Lys: 0.99 (1),
Gly: 2.02 (2),  His: 0.96 (1),  Ala: 1.03 (1),
Pro: 2.10 (2).

REFERENCE EXAMPLE 340

Preparation of
Boc-Lys(Z)-Leu-Ser(Bzl)-Gln-Glu(OcHex)-Leu-His(-Tos)-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH$_2$ By using 210 mg of Boc-Gln-Glu(OcHex)-Leu-His(-Tos)-Lys(Cl-z)-Leu-Gln-Thr(Bzl)-Pro-Asn-Thr(Bzl)-Asp(OcHex)-Val-Gly-Ala-Gly-Thr(Bzl)-Pro—NH$_2$ and 71 mg of Boc-Lys(Z)-Leu-Ser(Bzl)—OH as well as 14 mg of HOSu in place of HOBT, and the same procedure as in Reference Example 70 was repeated to obtain 160 mg (yield: 63.5%) of the above-mentioned objective compound.

Melting point: 190°–200° C.
Amino acid analysis data:

Asp: 2.05 (2),  Val: 1.03 (1),  Thr: 2.90 (3),
Leu: 2.69 (3),  Ser: 0.54 (1),  Lys: 1.68 (2),
Glu: 2.92 (3),  His: 0.94 (1),  Gly: 2.03 (2),
Pro: 2.08 (2),  Ala: 1.04 (1).

REFERENCE EXAMPLE 341

Preparation of
Boc-Gly-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH$_2$ By using 300 mg of Boc-Gln-Thr(Bzl)-Pro-Asn-Thr(Bzl)-Asp(OcHex)-Val-Gly-Ala-Gly-Thr(Bzl)-Pro—NH$_2$ and 133 mg of Boc-Gly-Lys(Cl-Z)-Leu—OH, and the same procedure as in Reference Example 70 was repeated to obtain 338 mg (yield: 85.7%) of the above-mentioned objective compound.

Melting point: 201°–205° C.

REFERENCE EXAMPLE 342

Preparation of
Boc-Gln-Glu(OcHex)-Leu-Gly-Lys(Cl-Z)-Leu-Gln-Thr(Bzl)-Pro-Asn-Thr(Bzl)-Asp(OcHex)-Val-Gly-Ala-Thr(Bzl)-Pro—NH$_2$ By using 290 mg of Boc-Gly-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH$_2$ and 96 mg of Boc-Gln-Glu(OcHex)-Leu—OH, and the same procedure as in Reference Example 70 was repeated to obtain 310 mg (yield: 87.6%) of the above-mentioned objective compound.

Melting point: 224°–228° C.

REFERENCE EXAMPLE 343

Preparation of
Boc-Lys(Z)-Leu-Ser(Bzl)-Gln-Glu(OcHex)-Leu-Gly-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH$_2$ By using 280 mg of Boc-Gln-Glu(OcHex)-Leu-Gly-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH$_2$ and 89 mg of Boc-Lys(Z)-Leu-Ser(Bzl)—OH, and the same procedure as in Reference Example 70 was repeated to obtain 297 mg (yield: 87.6%) of the above-mentioned objective compound.

Melting point: 222°–235° C.
Amino acid analysis data:

Asp: 2.01 (2),  Ala: 1.02 (1),  Thr: 2.90 (3),
Val: 1.01 (1),  Ser: 0.81 (1),  Leu: 2.98 (3),
Glu: 3.07 (3),  Lys: 1.93 (2),  Gly: 2.98 (3),
Pro: 2.11 (2).

EXAMPLE 1

Preparation of ⌐Gly—Ser—Asn—Leu—Ser—Thr—Glu—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH$_2$ 700 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$3H$_2$O [reference is made to Japanese Patent Application Kokai (Laid—Open) No. 112099/1986] was dissolved in 4 ml of TFA. The solution was stirred for 40 minutes at room temperature. The reaction mixture was concentrated under reduced pressure. The residue was mixed with diethyl ether. The resulting precipitate was collected by filtration and dried over sodium hydroxide under reduced pressure.

The product was dissolved in 10 ml of DMF. The solution was adjusted to pH 6–7 with triethylamine with ice-cooling. Thereto were added 285 mg of ⌐Gly—Ser(Bzl)—
Asn—Leu—Ser(Bzl)—Thr(Bzl)—Glu—Val—Leu—Gly—OH, 32 mg of HOBT and 0.043 ml of WSC. The mixture was adjusted to pH 6–7 with 4N hydrochloric acid/dioxane and then stirred for 1 hour under ice-cooling and for 3 days at room temperature. The reaction mixture was concentrated under reduced pressure. The residue was mixed with 30 ml of water. The resulting precipitate was collected by filtration, water-washed and re-precipitated from methanolethyl acetate to obtain 850 mg of a crude protected peptide product.

210 mg of the crude protected peptide product was dissolved in a mixture of 10 ml of hydrogen fluoride and 1 ml of anisole. The solution was stirred for 60 minutes at 0° C. After the completion of the reaction, hydrogen fluoride was removed by distillation under reduced pressure. The residue was washed with diethyl ether and then dissolved in 1M acetic acid. The solution was freeze-dried to obtain 141 mg of a powder.

20 mg of the powder was dissolved in a 0.1% aqueous trifluoroacetic acid solution and subjected to high performance liquid chromatography under the following conditions to obtain 2.6 mg of an active powder.

| | |
|---|---|
| Column: | ODS-120T (21.5 mm × 30 cm, a product of TOYO SODA MFG. CO., LTD.) |
| Eluting method: | Linear concentration gradient (180 minutes) |
| Eluent: | 0.1% aqueous TFA solution/acetonitrile (100:0) (solution A)→(30:70) (solution B) |
| Flow rate: | 2 ml/min |
| Detection: | UV 280 nm |

Part of the active powder obtained above was subjected again to high performance liquid chromatography using an ODS-120T column (4.6 mm × 15 cm) in a manner similar to the above to determine the purity of the powder. The powder was also subjected to amino acid analysis.

Amino acid analysis:

| | |
|---|---|
| Asp: 2.02 (2) | Leu: 4.97 (5) |
| Thr: 3.88 (4) | Tyr: 0.81 (1) |
| Ser: 2.86 (3) | Lys: 2.04 (2) |
| Glu: 4.11 (4) | His: 0.99 (1) |
| Gly: 4.01 (4) | Arg: 0.97 (1) |
| Ala: 1.00 (1) | Pro: 1.89 (2) |

EXAMPLE 2

Preparation of ⌐Ser—Asn—Leu—Ser—Thr-4-CPA—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

400 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂.3H₂O [reference is made to Japanese Patent Application Kokai (Laid—Open) No. 112099/1986] was dissolved in 5 ml of TFA. The solution was stirred for 40 minutes at room temperature. The reaction mixture was concentrated under reduced pressure. The residue was mixed with diethyl ether. The resulting precipitate was collected by filtration and dried over sodium hydroxide under reduced pressure.

The above product was dissolved in 10 ml of DMF. The solution was adjusted to pH 6-7 with triethylamine with ice-cooling. Thereto were added 202 mg of ⌐Ser(Bzl)—Asn—Leu—Ser(Bzl)—Thr(Bzl)-4-CPA—Val—Leu—Gly—OH, 23 mg of HOBT and 0.030 ml of WSC. The mixture was adjusted to pH 6-7 with 4N hydrochloric acid/dioxane and then stirred for 1 hour under ice-cooling and for 3 days at room temperature. The reaction mixture was concentrated under reduced pressure. The residue was mixed with 30 ml of water. The resulting precipitate was collected by filtration, water-washed and reprecipitated from methanol-ethyl acetate to obtain 470 mg of a crude protected peptide product.

200 mg of the crude protected peptide product was dissolved in a mixture of 10 ml of hydrogen fluoride and 1 ml of anisole. The solution was stirred for 60 minutes at 0° C. After the completion of the reaction, hydrogen fluoride was removed by distillation under reduced pressure. The residue was washed with diethyl ether and then dissolved in 1M acetic acid. The solution was freeze-dried to obtain 149 mg of a powder.

20 mg of the powder was dissolved in a 0.1% aqueous trifluoroacetic acid solution and subjected to high performance liquid chromatography under the following conditions to obtain 2.5 mg of an active powder.

| | |
|---|---|
| Column: | ODS-120T (21.5 mm ID × 30 cm) |
| Eluting method: | Linear concentration gradient (180 minutes) |
| Eluent: | 0.1% aqueous TFA solution/90% acetonitrile (100:0) (solution A)→(30:70) (solution B) |
| Flow rate: | 2 ml/min |
| Detection: | UV280 nm |

Part of the active powder obtained above was again subjected to high performance liquid chromatography using an ODS-120T column (4.6 mm ID × 15 cm) in a manner similar to the above to determine the purity of the powder. The powder was also subjected to amino acid analysis.

| | |
|---|---|
| Asp: 2.03 (2) | Leu: 4.98 (5) |
| Thr: 3.91 (4) | Tyr: 0.84 (1) |
| Ser: 2.89 (3) | 4-CPA: 1.15 (1) |
| Glu: 3.03 (3) | Lys: 2.02 (2) |
| Gly: 3.00 (3) | His: 0.97 (1) |
| Ala: 1.00 (1) | Arg: 0.98 (1) |
| Val: 1.91 (2) | Pro: 2.13 (2) |

EXAMPLE 3

Preparation of ⌐β-Ala—Ser—Asn—Leu—Ser—Thr—Asp—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

400 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂.3H₂O [reference is made to Japanese Patent Application Kokai (Laid—Open) No. 112099/1986] was dissolved in 5 ml of TFA. The solution was stirred for 40 minutes at room temperature. The reaction mixture was concentrated under reduced pressure. The residue was mixed with diethyl ether. The resulting precipitate was collected by filtration and dried over sodium hydroxide under reduced pressure.

The above product was dissolved in 10 ml of DMF. The solution was adjusted to pH 6–7 with triethylamine with ice-cooling. Thereto were added 203 mg of

```
┌─────────────────────────────────────────────┐
└─β-Ala—Ser(Bzl)—Asn—Leu—Ser(Bzl)—Thr(Bzl)—Asp—Val—
Leu—Gly—OH,
```

23 mg of HOBT and 0.060 ml of WSC. The mixture was adjusted to pH 6–7 with 4N hydrochloric acid/dioxane and then stirred for 1 hour under ice-cooling and for 18 hours at room temperature. Thereto was added 0.030 ml of WSC with ice-cooling. The mixture was stirred for 18 hours at room temperature. The reaction mixture was concentrated under reduced pressure. The residue was mixed with 30 ml of water. The resulting precipitate was collected by filtration and reprecipitated from methanol-ethyl acetate to obtain 500 mg of a crude protected peptide product.

204 mg of this crude protected peptide product was dissolved in a mixture of 10 ml of hydrogen fluoride and 1 ml of anisole. The solution was stirred for 60 minutes at 0° C. Hydrogen fluoride was removed by distillation under reduced pressure. The residue was washed with diethyl ether and then dissolved in 1M acetic acid. The solution was freeze-dried to obtain 146 mg of a powder.

20 mg of the powder was dissolved in a 1% aqueous trifluoroacetic acid solution and subjected to high performance liquid chromatography under the following conditions to obtain 2.1 mg of an active powder.

| | |
|---|---|
| Column: | ODS-120T (21.5 mm × 30 cm) |
| Eluting method: | Linear concentration gradient (180 minutes) |
| Elutant: | 0.1% aqueous TFA solution/90% acetonitrile (100:0) (solution A)→(30:70) (solution B) |
| Flow rate: | 2 ml/min |
| Detection: | UV 280 nm |

Part of the active powder obtained above was again subjected to high performance liquid chromatography using an ODS-120T column (4.6 mm×15 cm) in a manner similar to the above to determine the purity of the powder. The powder was also subjected to amino acid analysis.

| | |
|---|---|
| Asp: 3.01 (3) | Leu: 4.99 (5) |
| Thr: 3.93 (4). | Tyr: 0.85 (1) |
| Ser: 2.96 (3) | β-Ala: 0.90 (1) |
| Glu: 3.06 (3) | Lys: 2.04 (2) |
| Gly: 3.07 (3) | His: 0.94 (1) |
| Ala: 1.02 (1) | Arg: 0.98 (1) |
| Val: 1.95 (2) | Pro: 1.96 (2) |

EXAMPLE 4

Preparation of

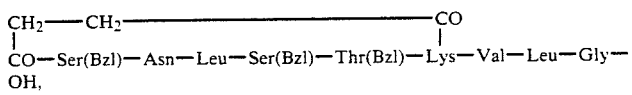

```
       ┌─COCH2CH2CO—Ser—Asn—Leu—Ser—
       │                                               ┐
Thr—Lys—Val—Leu—Gly—Lys—Leu—Ser—Gln—Glu—Leu—His—Lys—
Leu—Gln—Thr—Tyr—Pro—Arg—Thr—Asp—Val—Gly—Ala—Gly—Thr—
Pro—NH2
```

400 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH2 .3H2O [reference is made to Japanese Patent Application Kokai (Laid—Open) No. 112099/1986] was dissolved in 4 ml of TFA. The solution was stirred for 40 minutes at room temperature. The reaction mixture was concentrated under reduced pressure. The residue was mixed with diethyl ether. The resulting precipitate was collected by filtration and dried over sodium hydroxide under reduced pressure.

The above product was dissolved in 10 ml of DMF. The solution was adjusted to pH 6–7 with triethylamine with ice-cooling. Thereto were added 210 mg of

```
CH2————CH2——————————————CO
 │                                                       │
CO—Ser(Bzl)—Asn—Leu—Ser(Bzl)—Thr(Bzl)—Lys—Val—Leu—Gly—
OH,
```

23 mg of HOBT and 0.060 ml of WSC. The mixture was adjusted to pH 6–7 with 4N hydrochloric acid/dioxane and then stirred for 1 hour under ice-cooling and for 2 days at room temperature. The reaction mixture was concentrated under reduced pressure. The residue was mixed with 30 ml of water. The resulting precipitate was collected by filtration, water-washed and precipitated from methanol-ethyl acetate to obtain 530 mg of a crude protected peptide product. 206 mg of the crude protected peptide product was dissolved in a mixture of 10 ml of hydrogen fluoride and 1 ml of anisole. The solution was stirred for 60 minutes at 0° C. After the completion of the reaction, hydrogen fluoride was removed by distillation under reduced pressure. The residue was washed with diethyl ether and dissolved in 1M acetic acid. The solution was freeze-dried to obtain 146 mg of a powder.

20 mg of the powder was dissolved in a 0.1% aqueous trifluoroacetic acid solution and subjected to high performance liquid chromatography under the following conditions to obtain 2.1 mg of an active powder.

| | |
|---|---|
| Column: | ODS-120T (21.5 mm x 30 cm) |
| Eluting method: | Linear concentration gradient (180 minutes) |
| Elutant: | 0.1% aqueous TFA solution/90% acetonitrile (100:0) (solution A)→(30:70) (solution B) |
| Flow rate: | 2 ml/min |

-continued

Detection: UV 280 nm

Part of the active powder obtained above was again subjected to high performance liquid chromatography using an ODS-120T column (4.6 mm × 15 cm) in a manner similar to the above to determine the purity of the powder. The powder was also subjected to amino acid analysis.

Amino acid analysis:

| | 24 hours | 48 hours |
|---|---|---|
| Asp: | 2.05 (2) | 2.05 (2) |
| Thr: | 3.93 (4) | 3.81 (4) |
| Ser: | 3.03 (3) | 2.80 (3) |
| Glu: | 3.06 (3) | 3.01 (3) |
| Gly: | 3.03 (3) | 3.00 (3) |
| Ala: | 1.00 (1) | 0.99 (1) |
| Val: | 1.90 (2) | 2.00 (2) |
| Leu: | 5.02 (5) | 5.02 (5) |
| Tyr: | 0.83 (1) | 0.85 (1) |
| Lys: | 2.81 (3) | 3.00 (3) |
| His: | 0.90 (1) | 0.92 (1) |
| Arg: | 0.97 (1) | 0.95 (1) |
| Pro: | 1.90 (2) | 2.17 (2) |

Thus, the polypeptide of the present invention was identified.

EXAMPLE 5

Preparation of ⌐Gly—Ser—Asn—Leu—Ser—Thr—Asp—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using 306 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂.3H₂O [reference is made to Japanese Patent Application Kokai (Laid—Open) No. 112099/1986] and 123 mg of ⌐Gly—Ser(Bzl)—Asn—Leu—Ser(Bzl)—Thr(Bzl)—Asp—Val—Leu—Gly—OH, the same procedure as in Example 1 was repeated to obtain 384 mg of a crude protected peptide product.

200 mg of the crude protected peptide product was treated with hydrogen fluoride and anisole in the same manner as in Example 1 to obtain 113 mg of a powder.

20 mg of the powder was purified and determined for purity by high performance liquid chromatography under the same conditions as in Example 1 to obtain 2.0 mg of an active powder (the above objective compound). Amino acid analysis:

| | |
|---|---|
| Asp: 3.00 (3) | Leu: 4.90 (5) |
| Thr: 3.86 (4) | Tyr: 0.88 (1) |
| Ser: 2.87 (3) | Lys: 2.06 (2) |
| Glu: 3.02 (3) | His: 0.96 (1) |
| Gly: 3.96 (4) | Arg: 0.99 (1) |
| Ala: 1.00 (1) | Pro: 1.93 (2) |
| Val: 2.12 (2) | |

EXAMPLE 6

Preparation of ⌐Acp—Asn—Leu—Ser—Thr—Asp—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using 200 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂.3H₂O [reference is made to Japanese Patent Application Kokai (Laid—Open) No. 112099/1986] and 72 mg of ⌐Acp—Asn—Leu—Ser(Bzl)—Thr(Bzl)—Asp—Val—Leu—Gly—OH, the same procedure as in Example 1 was repeated to obtain 265 mg of a crude protected peptide product.

100 mg of the crude protected peptide product was treated with hydrogen fluoride and anisole in the same manner as in Example 1 to obtain 68 mg of a powder.

20 mg of the powder was purified and determined for purity by high performance liquid chromatography under the same conditions as in Example 1 to obtain 1.3 mg of an active powder (the above objective compound).

Amino acid analysis:

| | |
|---|---|
| Asp: 2.73 (3) | Leu: 4.90 (5) |
| Thr: 3.94 (4) | Tyr: 0.90 (1) |
| Ser: 1.94 (2) | Lys: 2.08 (2) |
| Glu: 3.09 (3) | His: 0.98 (1) |
| Gly: 3.02 (3) | Arg: 1.00 (1) |
| Ala: 1.02 (1) | Pro: 1.95 (2) |
| Val: 1.95 (2) | Acp: 0.77 (1) |

EXAMPLE 7

Preparation of ⌐Abu—Ser—Asn—Leu—Ser—Thr—Asp—
Val—Leu—Gly—Lys—Leu—Ser—Gln—Glu—Leu—His—Lys—Leu—Gln—Thr—
Tyr—Pro—Arg—Thr—Asp—Val—Gly—Ala—Gly—Thr—Pro—NH$_2$ Using 200 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$.3H$_2$O [reference is made to Japanese Patent Application Kokai (Laid—Open) No. 112099/1986] and 82 mg of ⌐Abu—Ser(Bzl)—Asn—Leu—Ser(Bzl)—Thr(Bzl)—Asp—
Val—Leu—Gly—OH, the same procedure as in Example 1 was repeated to obtain 268 mg of a crude protected peptide product.

100 mg of the crude protected peptide product was treated with hydrogen fluoride and anisole in the same manner as in Example 1 to obtain 60 mg of a powder.

20 mg of the powder was purified and determined for purity by high performance liquid chromatography under the same conditions as in Example 1 to obtain 0.98 mg of an active powder (the above objective compound).

Amino acid analysis:

| | |
|---|---|
| Asp: 2.81 (3) | Leu: 5.02 (5) |
| Thr: 3.83 (4) | Tyr: 0.84 (1) |
| Ser: 2.84 (3) | Lys: 2.00 (2) |
| Glu: 3.04 (3) | His: 0.92 (1) |
| Gly: 2.92 (3) | Arg: 0.94 (1) |
| Ala: 0.99 (1) | Pro: 1.82 (2) |
| Val: 2.19 (2) | Abu: 0.97 (1) |

EXAMPLE 8

Preparation of ⌐Ser—Asn—Leu—Ser—Thr—Cpc—Val—
Leu—Gly—Lys—Leu—Ser—Gln—Glu—Leu—His—Lys—Leu—Gln—Thr—
Tyr—Pro—Arg—Thr—Asp—Val—Gly—Ala—Gly—Thr—Pro—NH$_2$ Using 200 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$.3H$_2$O [reference is made to Japanese Patent Application Kokai (Laid—Open) No. 112099/1986] and 81 mg of ⌐Ser(Bzl)—Asn—Leu—Ser(Bzl)—Thr(Bzl)—Cpc—Val—
Leu—Gly—OH, the same procedure as in Example 1 was repeated to obtain 207 mg of a crude protected peptide product.

100 mg of this crude protected peptide product was treated with hydrogen fluoride and anisole in the same manner as in Example 1 to obtain 68 mg of a powder.

20 mg of the powder was purified and determined for purity by high performance liquid chromatography under the same conditions as in Example 1 to obtain 3.2 mg of an active powder (the above objective compound).

Amino acid analysis:

| | |
|---|---|
| Asp: 2.00 (2) | Leu: 5.00 (5) |
| Thr: 3.79 (4) | Tyr: 0.84 (1) |
| Ser: 2.84 (3) | Lys: 2.00 (2) |
| Glu: 3.03 (3) | His: 0.93 (1) |
| Gly: 2.99 (3) | Arg: 0.94 (1) |
| Ala: 1.05 (1) | Pro: 2.00 (2) |
| Val: 1.91 (2) | Cpc: 1.01 (1) |

EXAMPLE 9

Preparation of ⌐COCH$_2$CH$_2$CO—Asn—Leu—Ser—Thr—Lys—
Val—Leu—Gly—Lys—Leu—Ser—Gln—Glu—Leu—His—Lys—Leu—Gln—Thr—
Tyr—Pro—Arg—Thr—Asp—Val—Gly—Ala—Gly—Thr—Pro—NH$_2$ Using 300 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$.3H$_2$O [reference is made to Japanese Patent Application Kokai (Laid—Open) No. 112099/1986] and 136 mg of ⌐COCH$_2$CH$_2$CO—Asn—Leu—Ser(Bzl)—Thr(Bzl)—Lys—
Val—Leu—Gly—OH, the same procedure as in Example 1 was repeated to obtain 340 mg of a crude protected peptide product.

150 mg of this crude protected peptide product was treated with hydrogen fluoride and anisole in the same manner as in Example 1 to obtain 116 mg of a powder.

20 mg of the powder was purified and determined for purity by high performance liquid chromatography under the same conditions as in Example 1 to obtain 3.7 mg of an active powder (the above objective compound).

Amino acid analysis:

| | |
|---|---|
| Asp: 1.98 (2) | Leu: 5.00 (5) |
| Thr: 3.80 (4) | Tyr: 0.82 (1) |
| Ser: 1.86 (2) | Lys: 2.77 (3) |
| Glu: 3.00 (3) | His: 0.92 (1) |
| Gly: 2.97 (3) | Arg: 0.95 (1) |

-continued

| | |
|---|---|
| Ala: 1.01 (1) | Pro: 1.90 (2) |
| Val: 1.87 (2) | |

EXAMPLE 10

Preparation of ⌐Gly—Ser—Asn—Leu—Ser—Thr—Glu—Val—Leu—Gly—Lys(Bzl)—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using Boc-Lys(Bz)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ (300 mg) and ⌐Gly—Ser(Bzl)—Asn—Leu—Ser(Bzl)—Thr(Bzl)—Glu—Val—Leu—Gly—OH (153 mg).

the same procedure as in Example 1 was repeated to obtain 400 mg of a crude protected peptide product.

150 mg of this crude protected peptide product was treated with hydrogen fluoride and anisole in the same manner as in Example 1 to obtain 116 mg of a powder.

20 mg of the powder was purified and determined for purity by high performance liquid chromatography under the same conditions as in Example 1 to obtain 2.1 mg of an active powder (the above objective compound).

Amino acid analysis:

| | |
|---|---|
| Asp: 1.99 (2) | Leu: 5.00 (5) |
| Thr: 3.84 (4) | Tyr: 0.86 (1) |
| Ser: 2.80 (3) | Lys: 1.95 (2) |
| Glu: 4.04 (4) | His: 0.95 (1) |
| Gly: 3.96 (4) | Arg: 0.96 (1) |
| Ala: 0.99 (1) | Pro: 1.89 (2) |
| Val: 1.94 (2) | |

EXAMPLE 11

Preparation of ⌐β-Ala—Ser—Asn—Leu—Ser—Thr—Glu—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using 200 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂.3H₂O [reference is made to Japanese Patent Application Kokai (laid—Open) No. 112099/1986] and 82 mg of ⌐β-Ala—Ser(Bzl)—Asn—Leu—Ser(Bzl)—Thr(Bzl)—Glu—Val—Leu—Gly—OH, the same procedure as in Reference Example 1 was repeated to obtain 280 mg of a crude protected peptide product.

100 mg of this crude protected peptide product was treated with hydrogen fluoride and anisole in the same manner as in Example 1 to obtain 74 mg of a powder.

20 mg of the powder was purified and determined for purity by high performance liquid chromatography under the same conditions as in Example 1 to obtain 2.53 mg of an active powder (the above objective compound).

Amino acid analysis:

| | |
|---|---|
| Asp: 2.05 (2) | Leu: 5.18 (5) |
| Thr: 3.87 (4) | Tyr: 0.75 (1) |
| Ser: 2.89 (3) | α-Ala: 1.08 (1) |
| Glu: 4.04 (4) | Lys: 2.01 (2) |
| Gly: 3.04 (3) | His: 0.89 (1) |
| Ala: 1.03 (1) | Arg: 0.95 (1) |
| Val: 2.07 (2) | Pro: 1.89 (2) |

EXAMPLE 12

Preparation of ⌐Acp—Asn—Leu—Ser—Thr—Glu—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using 200 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂.3H₂O [reference is made to Japanese Patent Application Kokai (Laid—Open) No. 112099/1986 and 73 mg of ⌐Acp—Asn—Leu—Ser(Bzl)—Thr(Bzl)—Glu—Val—Leu—Gly—OH, the same procedure as in Example 1 was repeated to obtain 238 mg of a crude protected peptide product.

100 mg of this crude protected peptide product was treated with hydrogen fluoride and anisole in the same manner as in Example 1 to obtain 66 mg of a powder.

20 mg of the powder was purified and determined for purity by high performance liquid chromatography under the same conditions as in Example 1 to obtain 2.71 mg of an active powder (the above objective compound).

Amino acid analysis:

| | |
|---|---|
| Asp: 2.04 (2) | Leu: 5.14 (5) |
| Thr: 3.86 (4) | Tyr: 0.83 (1) |
| Ser: 1.92 (2) | Lys: 2.03 (2) |
| Glu: 4.11 (4) | His: 0.93 (1) |
| Gly: 3.05 (3) | Arg: 0.96 (1) |
| Ala: 1.03 (1) | Pro: 1.89 (2) |
| Val: 2.00 (1) | Acp: 1.07 (1) |

EXAMPLE 13

Preparation of ⌐Gly—Ser—Asn—Leu—Ser—Thr—Glu—Val—Leu—Gly—Lys—Leu—Ser—Gln—Glu—Leu—His—Lys(Bz)—Leu—Gln—Thr—Tyr—Pro—Arg—Thr—Asp—Val—Gly—Ala—Gly—Thr—Pro—NH₂

Using 200 mg of Boc-Lys(Z)-Leu-Ser(Bzl)-Gln-Glu(OBzl)-Leu-His-Lys(Bz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ and 103 mg of ⌐Gly—Ser(Bzl)—Asn—Leu—Ser(Bzl)—
Thr(Bzl)—Glu—Val—Leu—Gly—OH, the same procedure as in Example 1 was repeated to obtain 260 mg of a crude protected peptide product.

150 mg of this crude protected peptide product was treated with hydrogen fluoride and anisole in the same manner as in Example 1 to obtain 114 mg of a powder.

50 mg of the powder was purified and determined for purity by high performance liquid chromatography under the same conditions as in Example 1 to obtain 7.16 mg of an active powder (the above objective compound).

Amino acid analysis:

| | |
|---|---|
| Asp: 2.09 (2) | Leu: 5.13 (5) |
| Thr: 3.97 (4) | Tyr: 0.78 (1) |
| Ser: 2.98 (3) | Lys: 1.97 (2) |
| Glu: 4.07 (4) | His: 0.92 (1) |
| Gly: 4.00 (4) | Arg: 0.97 (1) |
| Ala: 1.00 (1) | Pro: 1.89 (2) |
| Val: 2.01 (2) | |

EXAMPLE 14

Preparation of ⌐Gly—Ser—Asn—Leu—Ser—Thr—Glu—Val—Leu—Gly—Lys(Bz)—Leu—Ser—Gln—Glu—Leu—His—Lys(Bz)—Leu—Gln—Thr—Tyr—Pro—Arg—Thr—Asp—Val—Gly—Ala—Gly—Thr—Pro—NH₂

Using Boc-Lys(Bz)-Leu-Ser(Bzl)-Gln-Glu(OBzl)-Leu-His-Lys(Bz)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ (200 mg) and ⌐Gly—Ser(Bzl)—Asn—Leu—Ser(Bzl)—Thr(Bzl)—Glu—Val—Leu—Gly—OH (105 mg), the same procedure as in Example 1 was repeated to obtain 260 mg of a crude protected peptide product.

150 mg of this crude protected peptide product was treated with hydrogen fluoride and anisole in the same manner as in Example 1 to obtain 98 mg of a powder.

50 mg of the powder was purified and determined for purity by high performance liquid chromatography under the same conditions as in Example 1 to obtain 6.99 mg of an active powder (the above objective compound).

Amino acid analysis:

| | |
|---|---|
| Asp: 2.03 (2) | Leu: 5.11 (5) |
| Thr: 3.93 (4) | Tyr: 0.80 (1) |
| Ser: 2.94 (3) | Lys: 1.96 (2) |
| Glu: 4.13 (4) | His: 0.95 (1) |
| Gly: 4.04 (4) | Arg: 0.98 (1) |
| Ala: 1.07 (1) | Pro: 1.92 (2) |
| Val: 1.95 (2) | |

EXAMPLE 15

Preparation of ⌐CH₂CO—Ser—Asn—Leu—Ser—Thr—Tyr—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using 200 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ [reference is made to Japanese patent application Kokai (Laid-Open) No. 112099/1986] and 104 mg of

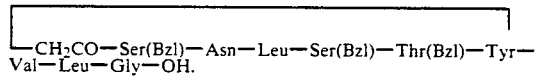
―CH₂CO—Ser(Bzl)—Asn—Leu—Ser(Bzl)—Thr(Bzl)—Tyr—Val—Leu—Gly—OH.

the same procedure as in Example 1 was repeated to obtain 270 mg of a crude protected peptide product.

150 mg of this crude protected peptide product was treated with hydrogen fluoride and anisole in the same manner as in Example 1 to obtain 118 mg of a powder.

50 mg of the powder was dissolved in a 0.1% aqueous trifluoroacetic acid solution and subjected to high performance liquid chromatography under the following conditions to obtain 4.75 mg of an active powder (the above objective compound).

| | |
|---|---|
| Column: | ODS-120T (21.5 mm × 30 cm, a product of TOYO SODA MFG. CO., LTD.) |
| Eluting method: | Linear concentration gradient (45 minutes) |
| Elutant: | 0.1% TFA solution: 90% acetonitrile/ 0.1% aqueous TFA solution 90:10 (solution A)→:30:70 (solution B) |
| Flow rate: | 15 ml/min |
| Detection: | UV 210 nm |

Part of the active powder obtained above was again subjected to high performance liquid chromatography using an ODS-120T column (4.6 mm × 15 cm) in a manner similar to the above to determine the purity of the powder. The powder was also subjected to amino acid analysis.

Amino acid analysis

| | |
|---|---|
| Asp: 2.04 (2) | Leu: 5.12 (5) |
| Thr: 3.90 (4) | Tyr: 0.79 (1) |
| Ser: 2.82 (3) | Lys: 2.05 (2) |
| Glu: 3.06 (3) | His: 0.96 (1) |
| Gly: 3.04 (3) | Arg: 0.98 (1) |
| Ala: 1.02 (1) | Pro: 2.02 (2) |

*Unable to measure because the peak of Val and the peak of Tyr(CH₂COOH) overlapped with each other.

EXAMPLE 16

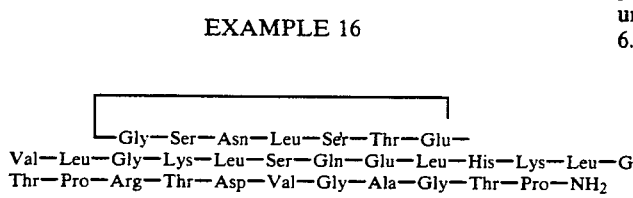
―Gly—Ser—Asn—Leu—Ser—Thr—Glu—Val—Leu—Gly—Lys—Leu—Ser—Gln—Glu—Leu—His—Lys—Leu—Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (200 mg) and

―Gly—Ser(Bzl)—Asn—Leu—Ser(Bzl)—

Thr(Bzl)—Glu—Val—Leu—Gly—OH (105 mg), the same procedure as in Example 1 was repeated to obtain 270 mg of a crude protected peptide product.

150 mg of this crude protected peptide product was treated with hydrogen fluoride and anisole in the same manner as in Example 1 to obtain 110 mg of a powder.

50 mg of the powder was purified and determined for purity by high performance liquid chromatography under the same conditions as in Example 15 to obtain 13.69 mg of an active powder (the above objective compound).

Amino acid analysis:

| | |
|---|---|
| Asp: 2.01 (2) | Val: 1.95 (2) |
| Thr: 3.82 (4) | Leu: 5.11 (5) |
| Ser: 2.84 (3) | Lys: 2.03 (2) |
| Glu: 4.16 (4) | His: 0.96 (1) |
| Gly: 4.12 (4) | Arg: 0.97 (1) |
| Ala: 1.00 (1) | Pro: 2.03 (2) |

EXAMPLE 17

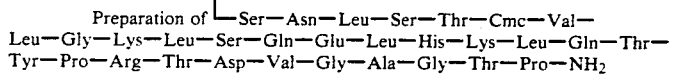
Preparation of ―Ser—Asn—Leu—Ser—Thr—Cmc—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using 100 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ [reference is made to Japanese patent application Kokai (Laid-Open) No. 112099/1986] and 78 mg of

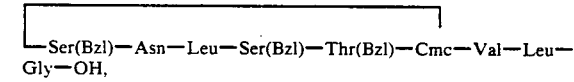
―Ser(Bzl)—Asn—Leu—Ser(Bzl)—Thr(Bzl)—Cmc—Val—Leu—Gly—OH, the same procedure as in Example 1 was repeated to obtain 134 mg of a crude protected peptide product.

134 mg of this crude protected peptide product was treated with hydrogen fluoride and anisole in the same manner as in Example 1 to obtain 88 mg of a powder.

50 mg of the powder was purified and determined for purity by high performance liquid chromatography under the same conditions as in Example 15 to obtain 6.16 mg of an active powder (the above objective compound).

Amino acid analysis:

| | |
|---|---|
| Asp: 2.05 (2) | Leu: 5.18 (5) |
| Thr: 3.91 (4) | Tyr: 0.85 (1) |
| Ser: 2.78 (3) | Lys: 2.06 (2) |
| Glu: 3.10 (3) | His: 0.98 (1) |
| Gly: 3.06 (3) | Arg: 1.00 (1) |

-continued

| Ala: 1.02 (1) | Pro: 1.84 (2) |
| Val: 2.02 (2) | Cmc: 1.02 (1) |

EXAMPLE 18

Preparation of ⌐Gly—Ser—Asn—Leu—Ser—Thr—Glu—
Val—Leu—Gly—Lys—Leu—Ser—Gln—Glu—Leu—His—Lys—Leu—Gln—
Thr—D—Tyr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His(Tos)-Lys(Cl-Z)-Leu-Gln-Thr(Bzl)-D-Tyr(Cl₂-Bzl)-Pro-Arg(Tos)-Thr(Bzl)-Asp(OcHex)-Val-Gly-Ala-Gly-Thr(Bzl)-Pro—NH₂ (300 mg) and ⌐Gly—Ser(Bzl)—Asn—Leu—
Ser(Bzl)—Thr(Bzl)—Glu—Val—Leu—Gly—OH (115 mg), the same procedure as in Example 1 was repeated to obtain 390 mg of a crude protected peptide product.

200 mg of this crude protected peptide product was treated with hydrogen fluoride and anisole in the same manner as in Example 1 to obtain 138 mg of a powder.

50 mg of the powder was purified and determined for purity by high performance liquid chromatography under the same conditions as in Example 15 to obtain 12.07 mg of an active powder (the above objective compound).

Amino acid analysis:

| Asp: 2.04 (2) | Leu: 5.14 (5) |
| Thr: 3.93 (4) | Tyr: 0.99 (1) |
| Ser: 2.84 (3) | Lys: 2.06 (2) |
| Glu: 4.09 (4) | His: 0.97 (1) |
| Gly: 3.96 (4) | Arg: 1.00 (1) |
| Ala: 1.00 (1) | Pro: 1.97 (2) |
| Val: 2.01 (2) | |

EXAMPLE 19

Preparation of ⌐Acp—Asn—Leu—Ser—Thr—Asp—Val—
Leu—Gly—Lys—Leu—Ser—Gln—Glu—Leu—His—Lys—Leu—Gln—Thr—
Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Acp—Asn—Leu—Ser(Bzl)—Thr(Bzl)—Asp—Val—

-continued
Leu—Gly—OH (71 mg).

the same procedure as in Example 1 was repeated to obtain 180 mg of a crude protected peptide product.

150 mg of this crude protected peptide product was treated with hydrogen fluoride and anisole in the same manner as in Example 1 to obtain 95 mg of a 50 mg of the powder was purified and determined for purity by high performance liquid chromatography under the same conditions as in Example 15 to obtain 13.5 mg of an active powder (the above objective compound).

Amino acid analysis:

| Asp: 2.71 (3) | Leu: 5.14 (5) |
| Thr: 3.91 (4) | Lys: 2.06 (2) |
| Ser: 1.87 (2) | His: 0.98 (1) |
| Glu: 3.15 (3) | Arg: 0.99 (1) |
| Gly: 3.12 (3) | Pro: 2.07 (2) |
| Ala: 1.04 (1) | Acp: 0.79 (1) |
| Val: 1.97 (2) | |

EXAMPLE 20

Preparation of ⌐Gly—Ser—Asn—Leu—Ser—Thr—Glu—
Val—Leu—Gly—Lys—Leu—Ser—Gln—Glu—Leu—His—Lys—Leu—Gln—
Thr—Leu—Pro—Arg—Thr—Asp—Val—Gly—Ala—Gly—Thr—Pro—NH₂

Using Boc-Lys(Z)-Leu-Ser(Bzl)-Gln-Glu(OBzl)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (100 mg) and ⌐Gly—Ser(Bzl)—Asn—Leu—Ser(Bzl)—Thr(Bzl)—
Glu—Val—Leu—Gly—OH (82 mg).

the same procedure as in Example 1 was repeated to obtain 144 mg of a crude protected peptide product.

144 mg of this crude protected peptide product was treated with hydrogen fluoride and anisole in the same manner as in Example 1 to obtain 100 mg of a powder.

50 mg of the powder was purified and determined for purity by high performance liquid chromatography under the same conditions as in Example 15 to obtain 9.3 mg of an active powder (the above objective compound).

Amino acid analysis:

| | |
|---|---|
| Asp: 1.99 (2) | Val: 2.08 (2) |
| Thr: 3.85 (4) | Leu: 6.06 (6) |
| Ser: 2.78 (3) | Lys: 2.03 (2) |
| Glu: 4.15 (4) | His: 0.97 (1) |
| Gly: 4.04 (4) | Arg: 0.99 (1) |
| Ala: 1.05 (1) | Pro: 2.00 (2) |

EXAMPLE 19

Preparation of ⌐β-Ala—Ser—Asn—Leu—Ser—Thr—
⌐
Asp—Val—Leu—Gly—Lys—Leu—Ser—Gln—Glu—Leu—His—Lys—Leu—
Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐β-Ala—Ser(Bzl)—Asn—Leu—Ser(Bzl)—Thr(Bzl)—
⌐
Asp—Val—Leu—Gly—OH (79 mg).

the same procedure as in Example 1 was repeated to obtain 220 mg of a crude protected peptide product.

150 mg of this crude protected peptide product was treated with hydrogen fluoride and anisole in the same as in Example 1 to obtain 104 mg of a powder.

50 mg of the powder was purified and determined for purity by high performance liquid chromatography under the same conditions as in Example 15 to obtain 11.9 mg of an active powder (the above objective compound).

Amino acid analysis:

| | |
|---|---|
| Asp: 3.00 (3) | Leu: 5.13 (5) |
| Thr: 3.88 (4) | β-Ala: 0.98 (1) |
| Ser: 2.88 (3) | Lys: 2.05 (2) |
| Glu: 3.08 (3) | His: 0.95 (1) |
| Gly: 3.06 (3) | Arg: 0.99 (1) |
| Ala: 1.06 (1) | Pro: 2.01 (2) |
| Val: 1.94 (2) | |

EXAMPLE 22

Preparation of ⌐Gly—Ser—Asn—Leu—Ser—Thr—Glu—
Val—Leu—Gly—Lys (COCH₃)—Leu—Ser—Gln—Glu—Leu—His—Lys—
Leu—Gln—Thr—Tyr—Pro—Arg—Thr—Asp—Val—Gly—Ala—Gly—Thr—
Pro—NH₂

Using Boc-Lys(COCH₃)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ (150 mg) and

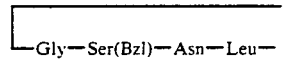

Ser(Bzl)—Thr(Bzl)—Glu—Val—Leu—Gly—OH (77 mg).

the same procedure as in Example 1 was repeated to obtain 180 mg of a crude protected peptide product.

100 mg of this crude protected peptide product was treated with hydrogen fluoride and anisole in the same manner as in Example 1 to obtain 73 mg of a powder.

50 mg of the powder was purified and determined for purity by high performance liquid chromatography under the same conditions as in Example 15 to obtain 6.6 mg of an active powder (the above objective compound).

Amino acid analysis:

| | |
|---|---|
| Asp: 2.00 (2) | Leu: 5.08 (5) |
| Thr: 3.84 (4) | Tyr: 0.88 (1) |
| Ser: 2.85 (3) | Lys: 2.05 (2) |
| Glu: 4.21 (4) | His: 0.95 (1) |
| Gly: 4.13 (4) | Arg: 0.97 (1) |
| Ala: 1.01 (1) | Pro: 1.95 (2) |
| Val: 1.97 (2) | |

EXAMPLE 23

Preparation of ⌐Gly—Ser—Asn—Leu—Ser—Thr—Glu—
Val—Leu—Gly—Lys (Cl—Bz)—Leu—Ser—Gln—Glu—Leu—His—Lys—Leu—
Gln—Thr—Tyr—Pro—Arg—Thr—Asp—Val—Gly—Ala—Gly—Thr—Pro—NH₂

Using Boc-Lys(Cl-BZ)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ (150 mg) and

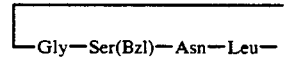

Ser(Bzl)—Thr(Bzl)—Glu—Val—Leu—Gly—OH (76 mg), the same procedure as in Example 1 was repeated to obtain 210 mg of a crude protected peptide product.

150 mg of this crude protected peptide product was treated with hydrogen fluoride and anisole in the same manner as in Example 1 to obtain 89 mg of a powder.

50 mg of the powder was purified and determined for purity by high performance liquid chromatography 9.5 mg of an active powder (the above objective compound).

Amino acid analysis:

| | |
|---|---|
| Asp: 1.99 (2) | Leu: 5.06 (5) |
| Thr: 3.82 (4) | Tyr: 0.87 (1) |
| Ser: 2.79 (3) | Lys: 2.01 (2) |
| Glu: 4.20 (4) | His: 0.98 (1) |
| Gly: 4.13 (4) | Arg: 0.99 (1) |
| Ala: 1.04 (1) | Pro: 2.00 (2) |
| Val: 1.98 (2) | |

EXAMPLE 24

Preparation of ⌐Abu—Asn—Leu—Ser—Thr—Cec—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using Boc-Lys(Z)-Leu-Ser(Bzl)-Gln-Glu(OBzl)-Leu-His-Lys(Cl-Z)-Leu-Gln-Thr(Bzl)-Leu-Pro-Arg(Tos)-Thr(Bzl)-Asp(OcHex)-Val-Gly-Ala-gly-Thr(Bzl)-Pro—NH₂ (150 mg) and ⌐Abu—Asn—Leu—Ser(Bzl)—Thr(Bzl)—Cec—Val—Leu—Gly—OH (69 mg), the same procedure as in Example 1 was repeated to obtain 180 mg of a crude protected peptide product.

150 mg of this crude protected peptide product was treated with hydrogen fluoride and anisole in the same manner as in Example 1 to obtain 109 mg of a powder.

50 mg of the powder was purified and determined for purity by high performance liquid chromatography under the same conditions as in Example 15 to obtain 6.9 mg of an active powder (the above objective compound).

Amino acid analysis:

| | |
|---|---|
| Asp: 2.04 (2) | Tyr: 0.86 (1) |
| Thr: 3.92 (4) | Lys: 2.04 (2) |
| Ser: 1.88 (2) | His: 0.95 (1) |
| Glu: 3.14 (3) | Arg: 0.99 (1) |
| Gly: 3.02 (3) | Pro: 1.98 (2) |
| Ala: 1.02 (1) | Abu: 1.22 (1) |
| Val: 1.95 (2) | Cec: 0.80 (1) |
| Leu: 5.07 (5) | |

EXAMPLE 21

Preparation of ⌐β-Ala—Asn—Leu—Ser—Thr—Cec—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ (150 mg) and ⌐β-Ala—Asn—Leu—Ser(Bzl)—Thr(Bzl)—Cec—Val—Leu—Gly—OH (68 mg), the same procedure as in Example 1 was repeated to obtain 190 mg of a crude protected peptide product.

150 mg of this crude protected peptide product was treated with hydrogen fluoride and anisole in the same manner as in Example 1 to obtain 105 mg of a powder.

50 mg of the powder was purified and determined for purity by high performance liquid chromatography under the same conditions as in Example 15 to obtain 7.3 mg of an active powder (the above objective compound).

Amino acid analysis:

| | |
|---|---|
| Asp: 2.09 (2) | Tyr: 0.87 (1) |
| Thr: 3.96 (4) | α-Ala: 1.04 (1) |
| Ser: 1.88 (2) | Lys: 2.03 (2) |
| Glu: 3.12 (3) | His: 0.92 (1) |
| Gly: 3.01 (3) | Arg: 1.00 (1) |
| Ala: 1.01 (1) | Pro: 1.97 (2) |
| Val: 1.92 (2) | Cec: 0.80 (1) |
| Leu: 5.04 (5) | |

EXAMPLE 22

Preparation of ⌐β-Ala—Ser—Asn—Leu—Ser—Thr—Asp—Gly—Leu—Gly—Lys—Leu—Ser—Gln—Glu—Leu—His—Lys—Leu—Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and

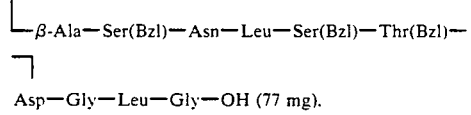

Asp—Gly—Leu—Gly—OH (77 mg).

the same procedure as in Example 1 was repeated to obtain 160 mg of a crude protected peptide product.

100 mg of this crude protected peptide product was treated with hydrogen fluoride and anisole in the same manner as in Example 1 to obtain 67 mg of a powder.

50 mg of the powder was purified and determined for purity by high performance liquid chromatography under the same conditions as in Example 15 to obtain 14.2 mg of an active powder (the above objective compound).

Amino acid analysis:

| | |
|---|---|
| Asp: 3.08 (3) | Leu: 5.25 (5) |
| Thr: 3.92 (4) | β-Ala: 1.01 (1) |
| Ser: 2.94 (2) | Lys: 2.02 (2) |
| Glu: 2.99 (3) | His: 0.93 (1) |
| Gly: 4.07 (4) | Arg: 0.97 (1) |
| Ala: 0.99 (1) | Pro: 1.86 (2) |
| Val: 0.96 (1) | |

EXAMPLE 27

Preparation of ⌐Gly—Ser—Asn—Leu—Ser—Thr—Glu—Val—Leu—Gly—Gly—Leu—Ser—Gln—Glu—Leu—His—Lys—Leu—Gln—Thr—Pro—Arg—Thr—Asp—Val—Gly—Ala—Gly—Thr—Pro—NH₂

Using Boc-Gly-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Gly—Ser(Bzl)—Asn—Leu—Ser(Bzl)—Thr(Bzl)—⌐

Glu—Val—Leu—Gly—OH (83 mg), the same procedure as in Example 1 was repeated to obtain 200 mg of a crude protected peptide product.

150 mg of this crude protected peptide produce was treated with hydrogen fluoride and anisole in the same manner as in Example 1 to obtain 104 mg of a powder.

50 mg of the powder was purified and determined for purity by high performance liquid chromatography under the same conditions as in Example 15 to obtain 17.1 mg of an active powder (the above objective compound).

Amino acid analysis:

| | |
|---|---|
| Asp: 2.02 (2) | Val: 1.94 (2) |
| Thr: 3.93 (4) | Leu: 5.17 (5) |
| Ser: 2.87 (3) | Lys: 1.01 (1) |
| Glu: 4.11 (4) | His: 0.95 (1) |
| Gly: 5.04 (5) | Arg: 1.02 (1) |
| Ala: 0.98 (1) | Pro: 1.96 (2) |

EXAMPLE 28

Preparation of ⌐Gly—Ser—Asn—Leu—Ser—Thr—Glu—Val—Leu—Gly—Lys—Leu—Ser—Gln—Glu—Leu—His—Gly—Leu—Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and

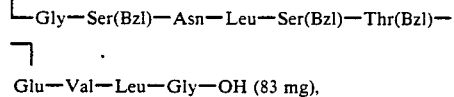

Leu—Gly—OH (88 mg).

the same procedure as in Example 1 was repeated to obtain 200 mg of a crude protected peptide product.

150 mg of this crude protected peptide product was treated with hydrogen fluoride and anisole in the same manner as in Example 1 to obtain 108 mg of a powder.

50 mg of the powder was purified and determined for purity by high performance liquid chromatography under the same conditions as in Example 15 to obtain 18.4 mg of an active powder (the above objective compound).

Amino acid analysis:

| | |
|---|---|
| Asp: 2.03 (2) | Val: 1.92 (2) |
| Thr: 3.91 (4) | Leu: 5.07 (5) |
| Ser: 2.89 (3) | Lys: 1.04 (1) |
| Glu: 4.15 (4) | His: 0.99 (1) |
| Gly: 5.00 (5) | Arg: 1.04 (1) |
| Ala: 1.02 (1) | Pro: 1.92 (2) |

EXAMPLE 29

Preparation of ⌐Gly—Ser—Asn—Leu—Ser—Thr—Glu—Val—Leu—Gly—Lys—Leu—Ser—Gln—Glu—Leu—His—Lys—Leu—Gln—Thr—Pro—Gly—Thr—Asp—Val—Gly—Ala—Gly—Thr—Pro—NH₂

Using Boc-Lys(Z)-Leu-Ser(Bzl)-Gln-Glu(OBzl)-Leu-His-Lys(Cl-Z)-Leu-Gln-Thr(Bzl)-Pro-Gly-Thr(Bzl)-Asp(OcHex)-Val-Gly-Ala-Gly-Thr(Bzl)-Pro—NH₂ (200 mg) and ⌐Gly—Ser(Bzl)—Asn—Leu—Ser(Bzl)—Thr(Bzl)—Glu—Val—
Leu—Gly—OH (95 mg).

the same procedure as in Example 1 was repeated to obtain 225 mg of a crude protected peptide product.

150 mg of this crude protected peptide product was treated with hydrogen fluoride and anisole in the same manner as in Example 1 to obtain 104 mg of a powder.

50 mg of the powder was purified and determined for purity by high performance liquid chromatography under the same conditions as in Example 15 to obtain 21.3 mg of an active powder (the above objective compound).

Amino acid analysis:

| | |
|---|---|
| Asp: 2.05 (2) | Val: 1.94 (2) |
| Thr: 3.91 (4) | Leu: 5.15 (5) |
| Ser: 2.79 (3) | Lys: 2.03 (2) |
| Glu: 4.08 (4) | His: 0.97 (1) |
| Gly: 5.07 (5) | Pro: 1.99 (2) |
| Ala: 1.01 (1) | |

EXAMPLE 30

Preparation of ⌐Gly—Ser—Asn—Leu—Ser—Thr—Glu—
Val—Leu—Gly—Lys—Leu—Ser—Gln—Glu—Leu—Asn—Lys—Leu—Gln—
Thr—Pro—Arg—Thr—Asp—Val—Gly—Ala—Gly—Thr—Pro—NH$_2$ Using Boc-Lys(Cl-Z)-Leu-Ser(Bzl)-Gln-Glu(O-cHex)-Leu-Asn-Lys(Cl-Z)-Leu-Ser(Bzl)-Gln-Arg(Tos)-Thr(Bzl)-Asp(OcHex)-Val-Gly-Ala-Gly-Thr(Bzl)-Pro—NH$_2$ (150 mg) and ⌐Gly—Ser(Bzl)—Asn—Leu—Ser(Bzl)—
Thr(Bzl)—Glu—Val—Leu—Gly—OH (83 mg), the same procedure as in Example 1 was repeated to obtain 200 mg of a crude protected peptide product.

150 mg of this crude protected peptide product was treated with hydrogen fluoride and anisole in the same manner as in Example 1 to obtain 106 mg of a powder.

50 mg of the powder was purified and determined for purity by high performance liquid chromatography under the same conditions as in Example 15 to obtain 10.9 mg of an active powder (the above objective compound).

Amino acid analysis:

| | |
|---|---|
| Asp: 3.00 (3) | Val: 1.93 (2) |
| Thr: 3.91 (4) | Leu: 5.14 (5) |
| Ser: 2.84 (3) | Lys: 2.06 (2) |
| Glu: 4.12 (4) | Arg: 1.02 (1) |
| Gly: 3.98 (4) | Pro: 1.99 (2) |
| Ala: 1.01 (1) | |

EXAMPLE 31

Preparation of ⌐Gly—Ser—Asn—Leu—Ser—Thr—Glu—
Val—Leu—Gly—Lys—Leu—Ser—Gln—Glu—Leu—Gly—Lys—Leu—Gln—
Thr—Pro—Arg—Thr—Asp—Val—Gly—Ala—Gly—Thr—Pro—NH$_2$ Using Boc-Lys(Cl-Z)-Leu-Ser(Bzl)-Gln-Glu(O-cHex)-Leu-Gly-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH$_2$ (150 mg) and ⌐Gly—Ser(Bzl)—Asn—Leu—Ser(Bzl)—
Thr(Bzl)—Glu—Val—Leu—Gly—OH (83 mg).

the same procedure as in Example 1 was repeated to obtain 200 mg of a crude protected peptide product.

150 mg of this crude protected peptide product was treated with hydrogen fluoride and anisole in the same manner as in Example 1 to obtain 108 mg of a powder.

50 mg of the powder was purified and determined for purity by high performance liquid chromatography under the same conditions as in Example 15 to obtain 12.6 mg of an active powder (the above objective compound).

Amino acid analysis:

| | |
|---|---|
| Asp: 2.01 (2) | Val: 1.93 (2) |
| Thr: 3.94 (4) | Leu: 5.08 (5) |
| Ser: 2.81 (3) | Lys: 2.04 (2) |
| Glu: 4.12 (4) | Arg: 1.02 (1) |
| Gly: 4.99 (5) | Pro: 2.05 (2) |
| Ala: 1.00 (1) | |

EXAMPLE 32

Preparation of ⌐β-Ala-β-Ala—Asn—Leu—Ser—Thr—
Asp—Val—Leu—Gly—Lys—Leu—Ser—Gln—Glu—Leu—His—Lys—Leu—
Gln—Thr—Tyr—Pro—Arg—Thr—Asp—Val—Gly—Ala—Gly—Thr—Pro—
NH$_2$ Using Boc-Lys(Z)-Leu-Ser(Bzl)-Gln-Glu(OBzl)-Leu-His-Lys(Cl-Z)-Leu-Gln-Thr(Bzl)-Thr(Bzl)-Pro-Arg(Tos)-Thr(Bzl)-Asp(OBzl)-Val-Gly-Ala-Gly-Thr(Bzl)Pro—NH₂ (150 mg) and ┌─────────────────────────────────────┐
└─β-Ala-β-Ala—Asn—Leu—Ser(Bzl)—
                                    ┐
Thr(Bzl)—Asp—Val—Leu—Gly—OH (69 mg).

the same procedure as in Example 1 was repeated to obtain 190 mg of a crude protected peptide product.

150 mg of this crude protected peptide product was treated with hydrogen fluoride and anisole in the same manner as in Example 1 to obtain 97 mg of a powder.

50 mg of the powder was purified and determined for purity by high performance liquid chromatography under the same conditions as in Example 15 to obtain 5.9 mg of an active powder (the above objective compound).

Amino acid analysis:

| | |
|---|---|
| Asp: 2.99 (3) | Leu: 5.07 (5) |
| Thr: 3.96 (4) | Tyr: 0.84 (1) |
| Ser: 1.92 (2) | β-Ala: 2.04 (2) |
| Glu: 3.09 (3) | Lys: 2.06 (2) |
| Gly: 3.05 (3) | His: 0.95 (1) |
| Ala: 1.01 (1) | Arg: 1.00 (1) |
| Val: 1.93 (2) | Pro: 1.94 (2) |

EXAMPLE 33

Preparation of ⌐Acp—Asn—Leu—Ser—Thr—Asp—Val—Leu—Gly—Lys—Leu—Ser—Gln—Glu—Leu—His—Lys—Leu—Gln—Thr—Pro—Gln—Thr—Asp—Val—Gly—Ala—Gly—Thr—Pro—NH₂

Using BocLys(Cl-Z)-Leu-Ser(Bzl)-Gln-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH₂ (150 mg) and ⌐Acp—Asn—Leu—Ser(Bzl)—Thr(Bzl) —Asp—Val—Leu—Gly—OH (77 mg), the same procedure as in Example 1 was repeated to obtain 180 mg of a crude protected peptide product.

150 mg of this crude protected peptide product was treated with hydrogen fluoride and anisole in the same manner as in Example 1 to obtain 105 mg of a powder.

50 mg of the powder was purified and determined for purity by high performance liquid chromatography under the same conditions as in Example 15 to obtain 17.8 mg of an active powder (the above objective compound).

Amino acid analysis:

| | |
|---|---|
| Asp: 2.74 (3) | Val: 1.97 (2) |
| Thr: 3.95 (4) | Leu: 5.24 (5) |
| Ser: 1.88 (2) | Lys: 2.09 (2) |
| Glu: 4.10 (4) | His: 0.98 (1) |
| Gly: 3.02 (3) | Pro: 2.04 (2) |
| Ala: 1.00 (1) | Acp: 0.86 (1) |

EXAMPLE 34

Preparation of ⌐Acp—Asn—Leu—Ser—Thr—Asp—Val—Leu—Gly—Lys—Leu—Ser—Gln—Glu—Leu—Asn—Lys—Leu—Gln—Thr—Pro—Gln—Thr—Asp—Val—Gly—Ala—Gly—Thr—Pro—NH₂

Using Boc-Lys(Z)-Leu-Ser(Bzl)-Gln-Glu(OcHex)-Leu-Asn-Lys(Cl-Z)-Leu-Gln-Thr(Bzl)-Pro-Gln-Thr(Bzl)-Asp(OcHex)-Val Gly-Ala-Gly-Thr(Bzl)-Pro—NH₂ (150 mg) and ⌐Acp—Asn—Leu—Ser(Bzl)—Thr(Bzl)—Asp—Val—Leu—Gly—OH (63 mg).

the same procedure as in Example 1 was repeated to obtain 170 mg of a crude protected peptide product.

150 mg of this crude protected peptide product was treated with hydrogen fluoride and anisole in the same manner as in Example 1 to obtain 110 mg of 50 mg of the powder was purified and determined for purity by high performance liquid chromatography under the same conditions as in Example 15 to obtain 10.4 mg of an active powder (the above objective compound).

Amino acid analysis:

| | |
|---|---|
| Asp: 3.73 (4) | Val: 1.93 (2) |
| Thr: 3.92 (4) | Leu: 5.21 (5) |
| Ser: 1.92 (2) | Lys: 2.08 (2) |
| Glu: 4.12 (4) | Pro: 2.05 (2) |
| Gly: 3.03 (3) | Acp: 0.70 (1) |
| Ala: 1.02 (1) | |

EXAMPLE 35

Preparation of ⌐Acp—Asn—Leu—Ser—Thr—Asp—Val—Leu—Gly—Lys—Leu—Ser—Gln—Glu—Leu—Gly—Lys—Leu—Gln—Thr—Pro—Gln—Thr—Asp—Val—Gly—Ala—Gly—Thr—Pro—NH₂

Using Boc-Lys(Z)-Leu-Ser(Bzl)-Gln-Glu(OcHex)-Leu-Gly-Lys(Cl-Z)-Leu-Gln-Thr(Bzl)-Pro-Gln- Thr(Bzl)-Asp(OcHex)-Val-Gly-Ala-Gly-Thr(Bzl)-Pro—NH₂ (150 mg) and

```
 ┌─────────────────────────────────────────┐
 └Acp—Asn—Leu—Ser(Bzl)—Thr(Bzl)—Asp—Val—Leu—Gly—
 OH (63 mg).
``` the same procedure as in Example 1 was repeated to obtain 170 mg of a crude protected peptide product.

150 mg of this crude protected peptide product was treated with hydrogen fluoride and anisole in the same manner as in Example 1 to obtain 80 mg of a powder.

50 mg of the powder was purified and determined for purity by high performance liquid chromatography under the same conditions as in Example 15 to obtain 4.7 mg of an active powder (the above objective compound).

Amino acid analysis:

| | |
|---|---|
| Asp: 2.78 (3) | Val: 1.95 (2) |
| Thr: 3.97 (4) | Leu: 5.20 (5) |
| Ser: 1.89 (2) | Lys: 2.08 (2) |
| Glu: 4.09 (4) | Pro: 1.97 (2) |
| Gly: 4.06 (4) | Acp: 0.77 (1) |
| Ala: 1.01 (1) | |

EXAMPLE 36

Preparation of ⌐Acp—Asn—Leu—Ser—Thr—Asp—Val—Leu—Gly—Lys—Leu—Ser—Gln—Glu—Leu—Asn—Lys—Leu—Gln—Thr—Pro—Arg—Thr—Asp—Val—Gly—Ala—Gly—Thr—Pro—NH₂

Using Boc-Lys(Cl-Z)-Leu-Ser(Bzl)-Gln-Glu(OcHex)-Leu-Asn-Lys(Cl-Z)-Leu-Gln-Thr(Bzl)-Pro-Arg(Tos)-Thr(Bzl)-Asp,(OcHex)-Val-Gly-Ala-Gly-Thr(Bzl)-Pro—NH₂ (150 mg) and

```
 ┌─────────────────────────────────────┐
 └Acp—Asn—Leu—Ser(Bzl)—Thr(Bzl)—Asp—
 Val—Leu—Gly—OH (62 mg),
``` the same procedure as in Example 1 was repeated to obtain 170 mg of a crude protected peptide product.

150 mg of this crude protected peptide product was treated with hydrogen fluoride and anisole in the same manner as in Example 1 to obtain 90 mg of a powder.

50 mg of the powder was purified and determined for purity by high performance liquid chromatography under the same conditions as in Example 15 to obtain 12.5 mg of an active powder (the above objective compound).

Amino acid analysis:

| | |
|---|---|
| Asp: 3.70 (4) | Val: 1.92 (2) |
| Thr: 3.94 (4) | Leu: 5.18 (5) |
| Ser: 1.93 (2) | Lys: 2.08 (2) |
| Glu: 3.11 (3) | Arg: 1.02 (1) |
| Gly: 3.07 (3) | Pro: 2.03 (2) |
| Ala: 1.02 (1) | Acp: 0.72 (1) |

EXAMPLE 37  Example 37

Preparation of ⌐Acp—Asn—Leu—Ser—Thr—Asp—Val—Leu—Gly—Lys—Leu—Ser—Gln—Glu—Leu—Gly—Lys—Leu—Gln—Thr—Pro—Arg—Thr—Asp—Val—Gly—Ala—Gly—Thr—Pro—NH₂

Using Boc-Lys(Cl-Z)-Leu-Ser(Bzl)-Gln-Glu(OcHex)-Leu-Gly-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and

```
 ┌─────────────────────────────────────────┐
 └Acp—Asn—Leu—Ser(Bzl)—Thr(Bzl)—Asp—Val—Leu—Gly—
 OH (63 mg),
``` the same procedure as in Example 1 was repeated to obtain 170 mg of a crude protected peptide product.

150 mg of this crude protected peptide product was treated with hydrogen fluoride and anisole in the same manner as in Example 1 to obtain 100 mg of a powder.

50 mg of the powder was purified and determined for purity by high performance liquid chromatography under the same conditions as in Example 15 to obtain 13.2 mg of an active powder (the above objective compound.)

Amino acid analysis:

| | |
|---|---|
| Asp: 2.87 (3) | Val: 2.04 (2) |
| Thr: 3.88 (4) | Leu: 5.23 (5) |
| Ser: 1.81 (2) | Lys: 2.06 (2) |
| Glu: 3.11 (3) | Arg: 1.00 (1) |
| Gly: 4.05 (4) | Pro: 2.03 (2) |
| Ala: 1.02 (1) | Acp: 0.92 (1) |

EXAMPLE 38

Preparation of ⌐Acp—Asn—Leu—Ser—Thr—Asp—Val—Leu—Gly—Lys—Leu—Ser—Gln—Glu—Leu—Gly—Lys—Leu—Gln—Thr—Pro—Arg—Thr—Asp—Val—Gly—Ala—Gly—Thr—Pro—NH₂

Using Boc-Lys(Cl-Z)-Leu-Ser(Bzl)-Gln-Glu(OcHex)-Leu-Gly-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Acp—Asn—Leu—Ser(Bzl)—Thr(Bzl)—Glu—Val—Leu—Gly—OH (60 mg).

the same procedure as in Example 1 was repeated to obtain 169 mg of a crude protected peptide product.

150 mg of this crude protected peptide product was treated with hydrogen fluoride and anisole in the same manner as in Example 1 to obtain 107 mg of a powder. 50 mg of the powder was purified and determined for purity by high performance liquid chromatography under the same conditions as in Example 15 to obtain 5.9 mg of an active powder (the above objective compound).

Amino acid analysis:

| Asp: 2.00 (2) | Val: 1.96 (2) |
|---|---|
| Thr: 3.88 (4) | Leu: 5.17 (5) |
| Ser: 1.83 (2) | Lys: 2.03 (2) |
| Glu: 4.08 (4) | Arg: 1.01 (1) |
| Gly: 3.96 (4) | Pro: 2.03 (2) |
| Ala: 1.02 (1) | Acp: 1.04 (1) |

EXAMPLE 39

Preparation of ⌐Gly—Ser—Asn—Leu—Ser—Thr—Glu—Val—Leu—Gly—Lys—Leu—Ser—Gln—Glu—Leu—Asn—Lys—Leu—Gln—Thr—Pro—Gln—Thr—Asp—Val—Gly—Ala—Gly—Thr—Pro—NH₂

Using Boc-Lys(Cl-Z)-Leu-Ser(Bzl)-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (150 mg) and ⌐Gly—Ser(Bzl)—Asn—Leu—Ser(Bzl)—Thr(Bzl)—Glu—Val—Leu—Gly—OH (69 mg), the same procedure as in Example 1 was repeated to obtain 190 mg of a crude protected peptide product.

150 mg of this crude protected peptide product was treated with hydrogen fluoride and anisole in the same manner as in Example 1 to obtain 117 mg of a powder. 50 mg of the powder was purified and determined for purity by high performance liquid chromatography under the same conditions as in Example 15 to obtain 21.2 mg of an active powder (the above objective compound).

Amino acid analysis:

| Asp: 3.01 (3) | Ala: 1.01 (1) |
|---|---|

| -continued | |
|---|---|
| Thr: 3.87 (4) | Val: 1.97 (2) |
| Ser: 2.77 (3) | Leu: 5.20 (5) |
| Glu: 5.14 (5) | Lys: 2.03 (2) |
| Gly: 3.98 (4) | Pro: 2.03 (2) |

EXAMPLE 40

Preparation of ⌐Gly—Ser—Asn—Leu—Ser—Thr—Glu—Ile—Leu—Gly—Lys—Leu—Ser—Gln—Glu—Leu—His—Lys—Leu—Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Gly—Ser(Bzl)—Asn—Leu—Ser(Bzl)—Thr(Bzl)—Glu—Ile—Leu—Gly—OH (64 mg), the same procedure as in Example 1 was repeated to obtain 179 mg of a crude protected peptide product.

150 mg of this crude protected peptide product was treated with hydrogen fluoride and anisole in the same manner as in Example 1 to obtain 90 mg of a powder. 50 mg of the powder was purified and determined for purity by high performance liquid chromatography under the same conditions as in Example 15 to obtain 9.3 mg of an active powder (the above objective compound Amino acid analysis:

| Asp: 2.07 (2) | Ile: 0.91 (1) |
|---|---|
| Thr: 3.95 (4) | Leu: 5.08 (5) |
| Ser: 2.88 (3) | Lys: 2.06 (2) |
| Glu: 4.09 (4) | His: 0.94 (1) |
| Gly: 4.01 (4) | Arg: 1.00 (1) |
| Ala: 1.00 (1) | Pro: 2.01 (2) |
| Val: 1.00 (1) | |

EXAMPLE 41

Preparation of ⌐Gly—Ser—Asn—Leu—Ser—Thr—Glu—Val—Leu—Gly—Lys—Leu—Ser—Gln—Glu—Leu—His—Lys—Leu—Gln—

-continued

Thr—Pro—Gln—Thr—Asp—Val—Gly—Ala—Gly—Thr—Pro—NH₂

Using Boc-Lys(Cl-Z)-Leu-Ser(Bzl)-Gln-Glu(O-cHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH₂ (150 mg) and ⌐–Gly—Ser(Bzl)—Asn—Leu—Ser(Bzl)—Thr(Bzl)—Glu—Val—Leu—Gly—OH (70 mg), the same procedure as in Example 1 was repeated to obtain 137 mg of a crude protected peptide product.

128 mg of this crude protected peptide product was treated with hydrogen fluoride and anisole in the same manner as in Example 1 to obtain 83 mg of a 33 mg of the powder was purified and determined for purity by high performance liquid chromatography under the same conditions as in Example 15 to obtain 7.2 mg of an active powder (the above objective compound).

Amino acid analysis:

| Asp: 2.03 (2) | Val: 2.00 (2) |
|---|---|
| Thr: 3.88 (4) | Leu: 5.22 (5) |
| Ser: 2.73 (3) | Lys: 2.04 (2) |
| Glu: 5.15 (5) | His: 0.97 (1) |
| Gly: 3.96 (4) | Pro: 2.03 (2) |
| Ala: 1.02 (1) | |

EXAMPLE 42

Preparation of ⌐–Gly—Ser—Asn—Leu—Ser—Thr—Glu—Val—Leu—Gly—Lys—Leu—Ser—Gln—Glu—Leu—Gly—Lys—Leu—Gln—Thr—Pro—Thr—Asp—Val—Gly—Ala—Gly—Thr—Pro—NH₂

Using Boc-Lys(Z)-Leu-Ser(Bzl)-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (150 mg) and ⌐–Gly—Ser(Bzl)—Asn—Leu—Ser(Bzl)—Thr(Bzl)—Glu—Val—Leu—Gly—OH (71 mg), the same procedure as in Example 1 was repeated to obtain 180 mg of a crude protected peptide product.

150 mg of this crude protected peptide product was treated with hydrogen fluoride and anisole in the same manner as in Example 1 to obtain 79 mg of a powder.

50 mg of the powder was purified and determined for purity by high performance liquid chromatography under the same conditions as in Example 15 to obtain 8.2 mg of an active powder (the above objective compound).

Amino acid analysis:

| Asp: 2.05 (2) | Ala: 1.02 (1) |
|---|---|
| Thr: 3.84 (4) | Val: 2.01 (2) |
| Ser: 2.77 (3) | Leu: 5.22 (5) |
| Glu: 5.08 (5) | Lys: 2.03 (2) |
| Gly: 4.95 (5) | Pro: 2.01 (2) |

EXAMPLE 43

Preparation of ⌐–Gly—Ser—Asn—Leu—Ser—Thr—Glu—Val—Leu—Gly—Lys—Leu—Ser—Gln—Glu(OEt)—Leu—His—Lys—Leu—Gln—Thr—Pro—Arg—Thr—Asp(OEt)—Val—Gly—Ala—Gly—Thr—Pro—NH₂

Using Boc-Lys(Cl-Z)-Leu-Ser(Bzl)-Gln-Glu(OEt)-Leu-His-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH₂ (150 mg) and ⌐–Gly—Ser(Bzl)—Asn—Leu—Ser(Bzl)—Thr(Bzl)—Glu—Val—Leu—Gly—OH (68 mg), the same procedure as in Example 1 was repeated to obtain 180 mg of a crude protected peptide product.

150 mg of this crude protected peptide product was treated with hydrogen fluoride and anisole in the same manner as in Example 1 to obtain 109 mg of a powder.

50 mg of the powder was purified and determined for purity by high performance liquid chromatography under the same conditions as in Example 15 to obtain 17.4 mg of an active powder (the above objective compound).

Amino acid analysis:

| Asp: 2.01 (2) | Val: 1.97 (2) |
|---|---|
| Thr: 3.91 (4) | Leu: 5.22 (5) |
| Ser: 2.75 (3) | Lys: 2.03 (2) |
| Glu: 4.15 (4) | His: 0.99 (1) |
| Gly: 3.92 (4) | Arg: 1.02 (1) |
| Ala: 1.01 (1) | Pro: 2.00 (2) |

EXAMPLE 44

Preparation of ⌐–Gly—Ser—Asn—Leu—Ser—Thr—Glu—

-continued

⌐Val—Leu—Gly—Lys—Leu—Ser—Gln—Glu—Leu—His—Lys—Leu—Gln—
Thr—Pro—Thr—Asp—Val—Gly—Ala—Gly—Thr—Pro—NH₂

Using Boc-Lys(Cl-Z)-Leu-Ser(Bzl)-Gln-Glu(O-cHex)-Leu-His(Tos)-Lys(Cl-Z)-Leu-Gln-Thr(Bzl)-Pro-Thr(Bzl)-Asp(OBzl)-Val-Gly-Ala-Gly-Thr(Bzl)-Pro—NH₂ (150 mg) and ⌐———————————————————⌐
└—Gly—Ser(Bzl)—Asn—Leu—Ser(Bzl)—Thr(Bzl)—Glu—
Val—Leu—Gly—OH (68 mg).

the same procedure as in Example 1 was repeated to obtain 170 mg of a crude protected peptide product.

150 mg of this crude protected peptide product was treated with hydrogen fluoride and anisole in the same manner as in Example 1 to obtain 80 mg of a powder.

50 mg of the powder was purified and determined for purity by high performance liquid chromatography under the same conditions as in Example 15 to obtain 32.4 mg of an active powder (the above objective compound).

Amino acid analysis:

| Asp: 2.01 (2) | Val: 1.98 (2) |
|---|---|
| Thr: 3.87 (4) | Leu: 5.18 (5) |
| Ser: 2.78 (3) | Lys: 2.05 (2) |
| Glu: 4.14 (4) | His: 0.98 (1) |
| Gly: 3.99 (4) | Pro: 2.02 (2) |
| Ala: 0.99 (1) | |

EXAMPLE 45

Preparation of ⌐—Gly—Ser—Asn—Leu—Ser—Thr—Glu—
Val—Leu—Gly—Lys—Leu—Ser—Gln—Glu—Leu—His—Lys—Leu—Gln—
Thr—Pro—Arg—Thr—Asp(OEt)—Val—Gly—Ala—Gly—Thr—Pro—NH₂

Using Boc-Lys(Cl-Z)-Leu-Ser(Bzl)-Gln-Glu(O-cHex)-Leu-His(Tos)-Lys(Cl-Z)-Leu-Gln-Thr(Bzl)-Pro-Arg(Tos)-Thr(Bzl)-Asp(OEt)-Val-Gly-Ala-Gly-Thr(Bzl)-Pro—NH₂ (150 mg) and ⌐———————————————
└— Gly — Ser(Bzl) — Asn — Leu —
———————————————⌐
Ser(Bzl)—Thr(Bzl)—Glu—Val—Leu—Gly—OH (63 mg), the same procedure as in Example 1 was repeated to obtain 170 mg of a crude protected peptide product.

150 mg of this crude protected peptide product was treated with hydrogen fluoride and anisole in the same manner as in Example 1 to obtain 109 mg of a powder.

50 mg of the powder was purified and determined for purity by high performance liquid chromatography under the same conditions as in Example 15 to obtain 27.4 mg of an active powder (the above objective compound).

Amino acid analysis:

| Asp: 2.02 (2) | Val: 1.98 (2) |
|---|---|
| Thr: 3.89 (4) | Leu: 5.19 (5) |
| Ser: 2.72 (3) | Lys: 2.04 (2) |
| Glu: 4.12 (4) | His: 0.99 (1) |
| Gly: 3.97 (4) | Arg: 1.01 (1) |
| Ala: 1.01 (1) | Pro: 2.07 (2) |

EXAMPLE 46

Preparation of ⌐—Gly—Ser—Asn—Leu—Ser—Thr—Glu—
Val—Leu—Gly—Lys—Leu—Ser—Gln—Glu—Leu—His—Lys—Gln—Thr—
Tyr—Pro—Arg—Thr—Asp—Val—Gly—Ala—Gly—Thr—Pro—NH₂

Using Boc-Lys(Cl-Z)-Leu-Ser(Bzl)-Gln-Glu(O-cHex)-Leu-His(Tos)-Lys(Cl-Z)-Gln-Thr(Bzl)-Tyr(Cl₂-Bzl)-Pro-Arg(Tos)-Thr(Bzl)-Asp(OBzl)-Val-Gly-Ala-Gly-Thr(Bzl)-Pro—NH₂ (150 mg) and ⌐————————
└—Gly—Ser(Bzl)—
————————————————⌐
Asn—Leu—Ser(Bzl)—Thr(Bzl)—Glu—Val—Leu—Gly—OH
(59 mg), the same procedure as in Example 1 was repeated to obtain 170 mg of a crude protected peptide product.

100 mg of this crude protected peptide product was treated with hydrogen fluoride and anisole in the same manner as in Example 1 to obtain 60 mg of a powder.

60 mg of the powder was purified and determined for purity by high performance liquid chromatography under the same conditions as in Example 15 to obtain 350 mg of an active powder (the above objective compound).

Amino acid analysis:

| Asp: 2.01 (2) | Leu: 4.03 (4) |
|---|---|
| Thr: 3.90 (4) | Tyr: 0.93 (1) |
| Ser: 2.73 (3) | Lys: 1.97 (2) |
| Glu: 4.09 (4) | His: 0.98 (1) |
| Gly: 4.05 (4) | Arg: 1.01 (1) |
| Ala: 1.00 (1) | Pro: 2.07 (2) |
| Val: 1.97 (2) | |

EXAMPLE 47

Preparation of ⌐Gly—Ser—Asn—Leu—Ser—Thr—Glu—
Val—Leu—Gly—Ala—Leu—Ser—Gln—Glu—Leu—Asn—Lys—Leu—Gln—
Thr—Pro—Gln—Thr—Asp—Val—Gly—Ala—Gly—Thr—Pro—NH₂

Using Boc-Ala-Leu-Ser(Bzl)-Gln-Glu(OcHex)-Leu-Asn-Lys(Cl-Z)-Leu-Gln-Thr(Bzl)-Pro-Fln-Thr(Bzl)-Asp(OcHex)-Val-Gly-Ala-Gl-Thr(Bzl)-Pro—NH₂ (150 mg)

└—Gly—Ser(Bzl)—Asn—Leu—Ser(Bzl)—Thr(Bzl)—Glu—Val—Leu—Gly—OH (75 mg).

the same procedure as in Example 1 was repeated to obtain 190 mg of a crude protected peptide product.

150 mg of this crude protected peptide product was treated with hydrogen fluoride and anisole in the same manner as in Example 1 to obtain 106 mg of a powder.

50 mg of the powder was purified and determined for purity by high performance liquid chromatography under the same conditions as in Example 15 to obtain 20.3 mg of an active powder (the above objective compound).

Amino acid analysis:

| Asp: 3.02 (3) | Ala: 1.98 (2) |
|---|---|
| Thr: 3.87 (4) | Val: 2.02 (2) |
| Ser: 2.72 (3) | Leu: 5.16 (5) |
| Glu: 5.12 (5) | Lys: 1.04 (1) |
| Gly: 4.07 (4) | Pro: 1.99 (2) |

EXAMPLE 48

Preparation of ⌐Gly—Ser—Asn—Leu—Ser—Thr—Glu—
Ile—Leu—Gly—Lys—Leu—Ser—Gln—Glu—Leu—His—Lys—Leu—Gln—
Thr—Pro—Gln—Thr—Asp—Val—Gly—Ala—Gly—Thr—Pro—NH₂

Using Boc-Lys(Cl-Z)-Leu-Ser(Bzl)-Gln-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro—NH₂ (150 mg) and └—Gly—Ser(Bzl)—Asn—Leu—Ser(Bzl)—Thr(Bzl)—Glu—Ile—Leu—Gly—OH (87 mg), the same procedure as in Example 1 was repeated to obtain 191 mg of a crude protected peptide product.

150 mg of this crude protected peptide product was treated with hydrogen fluoride and anisole in the same manner as in Example 1 to obtain 103 mg of a powder.

50 mg of the powder was purified and determined for purity by high performance liquid chromatography under the same conditions as in Example 15 to obtain 16.5 mg of an active powder (the above objective compound).

Amino acid analysis:

| Asp: 2.03 (2) | Val: 1.01 (1) |
|---|---|
| Thr: 3.83 (4) | Ile: 1.02 (1) |
| Ser: 2.62 (3) | Leu: 5.19 (5) |
| Glu: 5.13 (5) | Lys: 2.08 (2) |
| Gly: 4.12 (4) | His: 1.00 (1) |
| Ala: 0.97 (1) | Pro: 1.97 (2) |

EXAMPLE 49

Preparation of ⌐Acp—Asn—Leu—Ser—Thr—Glu—
Val—Leu—Gly—Lys—Leu—Ser—Gln—Glu—Leu—Asn—Lys—Leu—Gln—
Thr—Pro—Arg—Thr—Asp—Val—Gly—Ala—Gly—Thr—Pro—NH₂

Using Boc-Lys(Cl-Z)-Leu-Ser(Bzl)-Gln-Glu(OcHex)-Leu-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and └—Acp—Asn—Leu—Ser(Bzl)—Thr(Bzl)—Glu—Val—Leu—Gly—OH (60 mg), the same procedure as in Example 1 was repeated to obtain 147 mg of a crude protected peptide product.

145 mg of this crude protected peptide product was treated with hydrogen fluoride and anisole in the same manner as in Example 1 to obtain 91 mg of a powder.

50 mg of the powder was purified and determined for purity by high performance liquid chromatography under the same conditions as in Example 15 to obtain 13.1 mg of an active powder (the above objective compound).

Amino acid analysis:

| Asp: 3.04 (3) | Val: 2.03 (2) |
|---|---|
| Thr: 3.81 (4) | Leu: 5.20 (5) |
| Ser: 1.80 (2) | Lys: 2.07 (2) |
| Glu: 4.09 (4) | Pro: 1.98 (2) |
| Gly: 3.03 (3) | Acp: 1.05 (1) |
| Ala: 0.95 (1) | Arg: 0.98 (1) |

EXAMPLE 50

Preparation of ⌐Gly—Ser—Asn—Leu—Ser—Thr—Glu—
Val—Leu—Gly—Lys—Leu—Ser—Gln—Glu—Leu—Asn—Lys—Leu—Gln—
Thr—Leu—Pro—Gln—Thr—Asp—Val—Gly—Ala—Gly—Thr—Pro—NH₂

Using Boc-Lys(Cl-Z)-Leu-Ser(Bzl)-Gln-Glu(O-cHex)-Leu-Asn-Lys(Cl-Z)-Leu-Gln-Thr(Bzl)-Leu-Pro-Gln-Thr(Bzl)-Asp(OcHex)-Val-Gly-Ala-Gly-Thr(Bzl)-Pro—NH₂ (150 mg) and ⌐Gly—Ser(Bzl)—Asn—Leu—Ser(Bzl)—Thr(Bzl)—Glu—Val—Leu—Gly—OH (88 mg), the same procedure as in Example 1 was repeated to obtain 153 mg of a crude protected peptide product.

145 mg of this crude protected peptide product was treated with hydrogen fluoride and anisole in the same manner as in Example 1 to obtain 105 mg of a powder.

50 mg of the powder was purified and determined for purity by high performance liquid chromatography under the same conditions as in Example 15 to obtain 3.9 mg of an active powder (the above objective compound).

Amino acid analysis:

| | |
|---|---|
| Asp: 3.06 (3) | Ala: 1.05 (1) |
| Thr: 3.82 (4) | Val: 1.99 (2) |
| Ser: 2.73 (3) | Leu: 6.21 (6) |
| Glu: 5.06 (5) | Lys: 2.11 (2) |
| Gly: 4.00 (4) | Pro: 1.97 (2) |

EXAMPLE 51

Preparation of ⌐Gly—Ser—Asn—Leu—Ser—Thr—Glu—
Ile—Leu—Gly—Lys—Leu—Ser—Gln—Glu—Leu—Asn—Lys—Leu—Gln—
Thr—Pro—Arg—Thr—Asp—Val—Gly—Ala—Gly—Thr—Pro—NH₂

Using Boc-Lys(Cl-Z)-Leu-Ser(Bzl)-Gln-Glu(O-cHex)-Leu-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Gly—Ser(Bzl)—Asn—Leu—Ser(Bzl)—Thr(Bzl)—
Glu—Ile—Leu—Gly—OH (83 mg), the same procedure as in Example 1 was repeated to obtain 230 mg of a crude protected peptide product.

150 mg of this crude protected peptide product was treated with hydrogen fluoride and anisole in the same manner as in Example 1 to obtain 100 mg of a powder.

50 mg of the powder was purified and determined for purity by high performance liquid chromatography under the same conditions as in Example 15 to obtain 7.1 mg of an active powder (the above objective compound).

Amino acid analysis:

| | |
|---|---|
| Asp: 2.98 (3) | Val: 0.97 (1) |
| Thr: 3.78 (4) | Ile: 1.11 (1) |
| Ser: 2.70 (3) | Leu: 5.17 (5) |
| Glu: 4.06 (4) | Lys: 1.97 (2) |
| Gly: 4.15 (4) | Pro: 1.91 (2) |
| Ala: 0.93 (1) | Arg: 0.99 (1) |

EXAMPLE 52

Preparation of ⌐Gly—Ser—Asn—Leu—Ser—Thr—Glu—
Val—Leu—Gly—Lys(COCH₃)—Leu—Ser—Gln—Glu—Leu—Asn—Lys—
Leu—Gln—Thr—Pro—Gln—Thr—Asp—Val—Gly—Ala—Gly—Thr—Pro—NH₂

Using Boc-Lys(COCH₃)-Leu-Ser(Bzl)-Gln-Glu(O-cHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (340 mg) and ⌐Gly—Ser(Bzl)—Asn—Leu—Ser(Bzl)—Thr(Bzl)—Glu—Val—Leu—Gly—OH (164 mg), the same procedure as in Example 1 was repeated to obtain 440 mg of a crude protected peptide product.

200 mg of this crude protected peptide product was treated with hydrogen fluoride and anisole in the same manner as in Example 1 to obtain 160 mg of a powder.

160 mg of the powder was purified and determined for purity by high performance liquid chromatography under the same conditions as in Example 15 to obtain 51.2 mg of an active powder (the above objective compound).

Amino acid analysis:

| | |
|---|---|
| Asp: 3.00 (3) | Ala: 1.03 (1) |
| Thr: 3.82 (4) | Val: 2.05 (2) |
| Ser: 2.75 (3) | Leu: 5.14 (5) |
| Glu: 5.10 (5) | Lys: 2.04 (2) |
| Gly: 4.03 (4) | Pro: 2.05 (2) |

EXAMPLE 53

Preparation of ⌐—Gly—Ser—Asn—Leu—Ser—Thr—Glu—
Val—Leu—Gly—Ala—Leu—Ser—Gln—Glu—Leu—Asn—Asn—Leu—Gln—
Thr—Pro—Gln—Thr—Asp—Val—Gly—Ala—Gly—Thr—Pro—NH₂

Using Boc-Ala-Leu-Ser(Bzl)-Gln-Glu(OcHex)-Leu-Asn-Asn-Leu-Gln-Thr(Bzl)-Pro-Gln-Thr(Bzl)-Asp(OcHex)-Val-Gly-Ala-Gly-Thr(Bzl)-Pro—NH₂ (300 mg) and ⌐—Gly—Ser(Bzl)—Asn—Leu—Ser(Bzl)—Thr(Bzl)—Glu—Val—Leu—Gly—OH (160 mg), the same procedure as in Example 1 was repeated to obtain 400 mg of a crude protected peptide product.

200 mg of this crude protected peptide product was treated with hydrogen fluoride and anisole in the same manner as in Example 1 to obtain 163 mg of a powder.

50 mg of the powder was purified and determined for purity by high performance liquid chromatography under the same conditions as in Example 15 to obtain 14.1 mg of an active powder (the above objective compound).

Amino acid analysis:

| | |
|---|---|
| Asp: 3.93 (4) | Ala: 2.07 (2) |
| Thr: 3.82 (4) | Val: 2.02 (2) |
| Ser: 2.66 (3) | Leu: 5.09 (5) |
| Glu: 5.07 (5) | Pro: 2.03 (2) |
| Gly: 3.97 (4) | |

EXAMPLE 54

Preparation of ⌐—Gly—Ser—Asn—Leu—Ser—Thr—Glu—
Val—Leu—Gly—Lys—Leu—Ser—Gln—Glu—Leu—Gly—Asn—Leu—Gln—
Thr—Pro—Gln—Thr—Asp—Val—Gly—Ala—Gly—Thr—Pro—NH₂

Using Boc-Lys(Z)-Leu-Ser(Bzl)-Gln-Glu(OcHex)-Leu-Gly-Asn-Leu-Gln-Thr(Bzl)-Pro-Gln-Thr(Bzl)-Asp(OcHex)-Val-Gly-Ala-Gly-Thr(Bzl)-Pr-o-NH₂ (210 mg) and ⌐—Gly—
Ser(Bzl)—Asn—Leu—Ser(Bzl)—Thr(Bzl)—Glu—Val—Leu—Gly—OH (106 mg), the same procedure as in Example 1 was repeated to obtain 260 mg of a crude protected peptide 260 mg of this crude protected peptide product was treated with hydrogen fluoride and anisole in the same manner as in Example 1 to obtain 189 mg of a powder.

50 mg of the powder was purified and determined for purity by high performance liquid chromatography under the same conditions as in Example 15 to obtain 26.5 mg of an active powder (the above objective compound).

Amino acid analysis:

| | |
|---|---|
| Asp: 2.95 (3) | Ala: 1.07 (1) |
| Thr: 3.84 (4) | Val: 2.02 (2) |
| Ser: 2.68 (3) | Leu: 5.08 (5) |
| Glu: 5.07 (5) | Lys: 1.00 (1) |
| Gly: 4.91 (5) | Pro: 2.03 (2) |

EXAMPLE 55

Preparation of ⌐—Acp—Asn—Leu—Ser—Thr—Asp—Val—
Leu—Gly—Lys—Leu—Ser—Gln—Glu—Leu—His—Lys—Gln—Thr—
Tyr—Pro—Arg—Thr—Asp—Val—Gly—Ala—Gly—Thr—Pro—NH₂

Using Boc-Lys(Cl-Z)-Leu-Ser(Bzl)-Gln-Glu(OcHex)-Leu-His(Tos)-Lys(Cl-Z)-Gln-Thr(Bzl)-Tyr(Cl₂-Bzl)-Pro-Arg(Tos)-Thr(Bzl)-Asp(OBzl)-Val-Gly-Ala-Gly-Thr(Bzl)-Pro—NH₂ (95 mg) and ⌐—Acp—Asn—Leu—
Ser(Bzl)—Thr(Bzl)—Asp—Val—Leu—Gly—OH (33 mg).

the same procedure as in Example 1 was repeated to obtain 110 mg of a crude protected peptide product.

104 mg of this crude protected peptide product was treated with hydrogen fluoride and anisole in the same manner as in Example 1 to obtain 66 mg of a powder.

66 mg of the powder was purified and determined for purity by high performance liquid chromatography under the same conditions as in Example 15 to obtain 22.4 mg of an active powder (the above objective compound).

Amino acid analysis:

| | |
|---|---|
| Asp: 2.80 (3) | Leu: 4.11 (4) |
| Thr: 3.88 (4) | Tyr: 0.94 (1) |
| Ser: 1.92 (2) | Lys: 1.98 (2) |
| Glu: 3.02 (3) | His: 0.99 (1) |

| | |
|---|---|
| Gly: 3.09 (3) | Arg: 0.98 (1) |
| Ala: 0.97 (1) | Pro: 2.11 (2) |
| Val: 2.01 (2) | Acp: 0.90 (1) |

EXAMPLE 56

Preparation of Gly—Ser—Asn—Leu—Ser—Thr—Glu—Gly—Leu—Gly—Lys—Leu—Ser—Gln—Glu—Leu—His—Lys—Leu—Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and

Thr(Bzl)—Glu—Gly—Leu—Gly—OH (77 mg), the same procedure as in Example 1 was repeated to obtain 180 mg of a crude protected peptide product.

100 mg of this crude protected peptide product was treated with hydrogen fluoride and anisole in the same manner as in Example 1 to obtain 66 mg of a powder.

50 mg of the powder was purified and determined for purity by high performance liquid chromatography under the same conditions as in Example 15 to obtain 13.3 mg of an active powder (the above objective compound).

Amino acid analysis:

| | |
|---|---|
| Asp: 2.04 (2) | Val: 0.97 (1) |
| Thr: 3.92 (4) | Leu: 5.18 (5) |
| Ser: 2.84 (3) | Lys: 2.01 (2) |
| Glu: 4.06 (4) | His: 0.94 (1) |
| Gly: 5.08 (5) | Arg: 0.98 (1) |
| Ala: 0.99 (1) | Pro: 1.96 (2) |

EXAMPLE 57

Preparation of Gly—Ser—Asn—Leu—Ser—Thr—Glu—Gly—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂

Using Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ (200 mg) and

Thr(Bzl)—Glu—Gly—Leu—Gly—OH (100 mg).

the same procedure as in Example 1 was repeated to obtain 223 mg of a crude protected peptide product.

162 mg of this crude protected peptide product was treated with hydrogen fluoride and anisole in the same manner as in Example 1 to obtain 102 mg of a powder.

50 mg of the powder was purified and determined for purity by high performance liquid chromatography under the same conditions as in Example 15 to obtain 8.9 mg of an active powder (the above objective compound).

Amino acid analysis:

| | |
|---|---|
| Asp: 2.02 (2) | Leu: 5.06 (5) |
| Thr: 3.95 (4) | Tyr: 0.85 (1) |
| Ser: 2.76 (3) | Lys: 2.03 (2) |
| Glu: 4.10 (4) | His: 0.96 (1) |
| Gly: 4.96 (5) | Arg: 1.02 (1) |
| Ala: 1.03 (1) | Pro: 2.08 (2) |
| Val: 1.03 (1) | |

EXAMPLE 58

Preparation of Gly—Ser—Asn—Leu—Ser—Thr—Glu—Val—Leu—Gly—Leu—Ser—Gln—Glu—Leu—His—Leu—Gln—Thr—Pro—Thr—Asp—Val—Gly—Ala—Gly—Thr—Pro—NH₂

Using Boc-Leu-Ser(Bzl)-Gln-Glu(OcHex)-Leu-His-Leu-Gln-Thr(Bzl)-Pro-Thr(Bzl)-Asp(OcHex)-Val-Gly-Ala-Gly-Thr(Bzl)-Pro—NH₂ (150 mg) and

Asn—Leu—Ser(Bzl)—Thr(Bzl)—Glu—Val—Leu—Gly—OH (111 mg), the same procedure as in Example 1 was repeated to obtain 210 mg of a crude protected peptide product.

150 mg of this crude protected peptide product was treated with hydrogen fluoride and anisole in the same manner as in Example 1 to obtain 107 mg of a powder.

50 mg of the powder was purified and determined for purity by high performance liquid chromatography under the same conditions as in Example 15 to obtain 15.2 mg of an active powder (the above objective compound).

Amino acid analysis:

| | |
|---|---|
| Asp: 2.03 (2) | Ala: 1.02 (1) |
| Thr: 3.96 (4) | Val: 1.94 (2) |
| Ser: 2.84 (3) | Leu: 5.15 (5) |
| Glu: 4.12 (4) | His: 0.99 (1) |
| Gly: 4.00 (4) | Pro: 1.96 (2) |

EXAMPLE 59

Preparation of ⌐Gly—Ser—Asn—Leu—Ser—Thr—Glu—Val—Leu—Gly—Lys—Leu—Ser—Gln—Glu—Leu—His—Leu—Gln—Thr—Pro—Thr—Asp—Val—Gly—Ala—Gly—Thr—Pro—NH₂

Using Boc-Lys(Z)-Leu-Ser(Bzl)-Gln-Glu(OcHex)-Leu-His-Leu-Gln-Thr(Bzl)-Pro-Thr(Bzl)-Asp(OcHex)-Val-Gly-Ala-Gly-Thr(Bzl)-Pro—NH₂ (150 mg) and ⌐Gly—Ser(Bzl)—
Asn—Leu—Ser(Bzl)—Thr(Bzl)—Glu—Val—Leu—Gly—OH (101 mg).

the same procedure as in Example 1 was repeated to obtain 200 mg of a crude protected peptide product.

150 mg of this crude protected peptide product was treated with hydrogen fluoride and anisole in the same manner as in Example 1 to obtain 102 mg of a powder.

50 mg of the powder was purified and determined for purity by high performance liquid chromatography under the same conditions as in Example 15 to obtain 17.4 mg of an active powder (the above objective compound).

Amino acid analysis:

| | |
|---|---|
| Asp: 2.03 (2) | Val: 1.95 (2) |
| Thr: 3.91 (4) | Leu: 5.15 (5) |
| Ser: 2.85 (3) | Lys: 1.03 (1) |
| Glu: 4.08 (4) | His: 0.96 (1) |
| Gly: 4.04 (4) | Pro: 2.00 (2) |
| Ala: 1.00 (1) | |

EXAMPLE 60

Preparation of ⌐Gly—Ser—Asn—Leu—Ser—Thr—Glu—Val—Leu—Gly—Lys—Leu—Ser—Gln—Glu—Leu—His—Lys—Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Gly—Ser(Bzl)—Asn—Leu—Ser(Bzl)—Thr(Bzl)—Glu—Val—Leu—Gly—OH (85 mg), the same procedure as in Example 1 was repeated to obtain 190 mg of a crude protected peptide product.

150 mg of this crude protected peptide product was treated with hydrogen fluoride and anisole in the same manner as in Example 1 to obtain 98 mg of a powder.

50 mg of the powder was purified and determined for purity by high performance liquid chromatography under the same conditions as in Example 15 to obtain 14.4 mg of an active powder (the above objective compound).

Amino acid analysis:

| | | |
|---|---|---|
| Asp: 2.01 (2) | Gly: 4.00 (4) | Lys: 2.07 (2) |
| Thr: 3.91 (4) | Ala: 0.99 (2) | His: 0.97 (1) |
| Ser: 2.85 (3) | Val: 1.92 (2) | Arg: 1.03 (1) |
| Glu: 4.12 (4) | Leu: 4.13 (4) | Pro: 2.01 (2) |

EXAMPLE 61

Preparation of ⌐Gly—Ser—Asn—Leu—Ser—Thr—Glu—Val—Leu—Gly—Gly—Leu—Ser—Gln—Glu—Leu—His—Gly—Leu—Gln—Thr—Pro—Arg—Thr—Asp—Val—Gly—Ala—Gly—Thr—Pro—NH₂

Using Boc-Gly-Leu-Ser(Bzl)-Gln-Glu(OcHex)-Leu-His-Gly-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Gly—Ser(Bzl)—
Asn—Leu—Ser(Bzl)—Thr(Bzl)—Glu—Val—Leu—Gly—OH (96 mg), the same procedure as in Example 1 was repeated to obtain 190 mg of a crude protected peptide product.

150 mg of this crude protected peptide product was treated with hydrogen fluoride and anisole in the same manner as in Example 1 to obtain 108 mg of a powder.

50 mg of the powder was purified and determined for purity by high performance liquid chromatography under the same conditions as in Example 15 to obtain 17.6 mg of an active powder (the above objective compound).

Amino acid analysis:

| | | |
|---|---|---|
| Asp: 2.00 (2) | Gly: 6.17 (6) | His: 0.94 (1) |
| Thr: 3.86 (4) | Ala: 0.98 (1) | Arg: 0.99 (1) |
| Ser: 2.85 (3) | Val: 1.88 (2) | Pro: 1.98 (2) |
| Glu: 4.02 (4) | Leu: 5.34 (5) | |

EXAMPLE 62

Preparation of ⌐Acp—Asn—Leu—Ser—Thr—Asp—Val—Leu—Gly—Lys—Leu—Ser—Gln—Glu—Leu—His—Lys—Gln—Thr—Pro—Gln—Thr—Asp—Val—Gly—Ala—Gly—Thr—Pro—NH₂

Using Boc-Lys(Z)-Leu-Ser(Bzl)-Gln-Glu(OcHex)-Leu-His-Lys(Cl-Z)-Gln-Thr(Bzl)-Pro-Gln-Thr(Bzl)-Asp(OBzl)-Val-Gly-Ala-Gly-Thr(Bzl)-Pro—NH₂ (150 mg) and ⌐Acp—Asn—Leu—Ser(Bzl)—Thr(Bzl)—Asp—Val—Leu—Gly—OH (80 mg).

the same procedure as in Example 1 was repeated to obtain 190 mg of a protected peptide product.

150 mg of this crude protected peptide product was treated with hydrogen fluoride and anisole in the same manner as in Example 1 to obtain 114 mg of a powder.

50 mg of the powder was purified and determined for purity by high performance liquid chromatography under the same conditions as in Example 15 to obtain 15.6 mg of an active powder (the above objective compound).

Amino acid analysis:

| | |
|---|---|
| Asp: 2.75 (3) | Val: 1.96 (2) |
| Thr: 3.97 (4) | Leu: 4.22 (4) |
| Ser: 1.94 (2) | Lys: 2.06 (2) |
| Glu: 4.11 (4) | His: 0.98 (1) |
| Gly: 3.02 (3) | Pro: 1.98 (2) |
| Ala: 1.00 (1) | Acp: 0.83 (1) |

EXAMPLE 63

Preparation of ⌐Gly—Ser—Asn—Leu—Ser—Thr—Glu—Val—Leu—Gly—Gly—Leu—Ser—Gln—Glu—Leu—His—Gly—Leu—Gln—Thr—Pro—Gly—Thr—Asp—Val—Gly—Ala—Gly—Thr—Pro—NH₂

Using Boc-Gly-Leu-Ser(Bzl)-Gln-Glu(OBzl)-Leu-His-Gly-Leu-Gln-Thr(Bzl)-Pro-Gly-Thr(Bzl)-Asp(O-cHex)-Val-Gly-Ala-Gly-Thr(Bzl)-Pro—NH₂ (120 mg) and ⌐Gly—Ser(Bzl)—Asn—Leu—Ser(Bzl)—Thr(Bzl)—Glu—Val—Leu—Gly—OH (66 mg).

the same procedure as in Example 1 was repeated to obtain 186 mg of a crude protected peptide product.

100 mg of this crude protected peptide product was treated with hydrogen fluoride and anisole in the same manner as in Example 1 to obtain 76 mg of a powder.

50 mg of the powder was purified and determined for purity by high performance liquid chromatography under the same conditions as in Example 15 to obtain 19.6 mg of an active powder (the above objective compound).

Amino acid analysis:

| | |
|---|---|
| Asp: 2.03 (2) | Ala: 0.99 (1) |
| Thr: 3.91 (4) | Val: 1.99 (2) |
| Ser: 2.83 (3) | Leu: 5.25 (5) |
| Glu: 4.08 (4) | His: 0.95 (1) |
| Gly: 7.00 (7) | Pro: 1.98 (2) |

EXAMPLE 64

Preparation of ⌐Acp—Asn—Leu—Ser—Thr—Asp—Gly—Leu—Gly—Lys—Leu—Ser—Gln—Glu—Leu—His—Lys—Leu—Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His(Tos)-Lys Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Acp—Asn—Leu—Ser(Bzl)—Thr(Bzl)—Asp—Gly—Leu—Gly—OH (68 mg), the same procedure as in Example 1 was repeated to obtain 140 mg of a crude protected peptide product.

100 mg of this crude protected peptide product was treated with hydrogen fluoride and anisole in the same manner as in Example 1 to obtain 72 mg of a powder.

50 mg of the powder was purified and determined for purity by high performance liquid chromatography under the same conditions as in Example 15 to obtain 6.3 mg of an active powder (the above objective compound).

Amino acid analysis:

| | |
|---|---|
| Asp: 2.80 (3) | Leu: 5.30 (5) |
| Thr: 3.93 (4) | Lys: 2.01 (2) |
| Ser: 1.89 (2) | His: 0.93 (1) |
| Glu: 3.06 (3) | Arg: 1.00 (1) |
| Gly: 4.13 (4) | Pro: 1.95 (2) |
| Ala: 0.99 (1) | Acp: 0.88 (1) |
| Val: 1.01 (1) | |

EXAMPLE 65

Preparation of ⌐Acp—Asn—Leu—Ser—Thr—Asp—Val—Leu—Gly—Lys—Leu—Ser—Gln—Glu—Leu—His—Lys—Gln—Thr—Pro—Arg—Thr—Asp—Val—Gly—Ala—Gly—Thr—Pro—NH₂

Using Boc-Lys(Z)-Leu-Ser(Bzl)-Gln-Glu(OcHex)-Leu-His-Lys(Cl-Z)-Gln-Thr(Bzl)-Pro-Arg(Tos)-Thr(Bzl)-Asp(OcHex)-Val-Gly-Ala-Gly-Thr(Bzl)-Pro—NH₂ (150 mg) and ⌐Acp—Asn—Leu—Ser(Bzl)—Thr(Bzl)—Asp—Val—Leu—Gly—OH (60 mg).

the same procedure as in Example 1 was repeated to obtain 170 mg of a crude protected peptide product.

150 mg of this crude protected peptide product was treated with hydrogen fluoride and anisole in the same manner as in Example 1 to obtain 106 mg of a powder.

50 mg of the powder was purified and determined for purity by high performance liquid chromatography under the same conditions as in Example 15 to obtain 14.8 mg of an active powder (the above objective compound).

Amino acid analysis:

| | |
|---|---|
| Asp: 2.79 (3) | Leu: 4.24 (4) |
| Thr: 3.97 (4) | Lys: 2.05 (2) |
| Ser: 1.96 (2) | His: 0.97 (1) |
| Glu: 3.06 (3) | Arg: 1.01 (1) |
| Gly: 3.04 (3) | Pro: 1.96 (2) |
| Ala: 0.98 (1) | Acp: 0.79 (1) |
| Val: 1.96 (2) | |

EXAMPLE 66

Preparation of ⌐Acp—Asn—Leu—Ser—Thr—Asp—Val—Leu—Gly—Ala—Leu—Ser—Gln—Glu—Leu—Asn—Lys—Leu—Gln—Thr—Pro—Gln—Thr—Asp—Val—Gly—Ala—Gly—Thr—Pro—NH₂

Using Boc-Ala-Leu-Ser(Bzl)-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (150 mg) and ⌐Acp—Asn—Leu—Ser(Bzl)—Thr(Bzl)—Asp—Val—Leu—Gly—OH (67 mg), the same procedure as in Example 1 was repeated to obtain 190 mg of a crude protected peptide 150 mg of this crude protected peptide product was treated with hydrogen fluoride and anisole in the same manner as in Example 1 to obtain 100 mg of 50 mg of the powder was purified and determined for purity by high performance liquid chromatography under the same conditions as in Example 15 to obtain 15.3 mg of an active powder (the above objective compound).

Amino acid analysis:

| | |
|---|---|
| Asp: 3.82 (4) | Val: 2.00 (2) |
| Thr: 3.90 (4) | Leu: 5.24 (5) |
| Ser: 1.88 (2) | Lys: 1.07 (1) |
| Glu: 4.17 (4) | Pro: 2.03 (2) |
| Gly: 3.07 (3) | Acp: 0.81 (1) |
| Ala: 2.02 (2) | |

EXAMPLE 67

Preparation of ⌐Acp—Asn—Leu—Ser—Thr—Asp—Val—Leu—Gly—Ala—Leu—Ser—Gln—Glu—Leu—Gly—Lys—Leu—Gln—Thr—Pro—Gln—Thr—Asp—Val—Gly—Ala—Gly—Thr—Pro—NH₂

Using Boc-Ala-Leu-Ser(Bzl)-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ (150 mg) and ⌐Acp—Asn—Leu—Ser(Bzl)—Thr(Bzl)—Asp—Val—Leu—Gly—OH (68 mg), the same procedure as in Example 1 was repeated to obtain 190 mg of a crude protected peptide product.

150 mg of this crude protected peptide product was treated with hydrogen fluoride and anisole in the same manner as in Example 1 to obtain 74 mg of a powder.

50 mg of the powder was purified and determined for purity by high performance liquid chromatography under the same conditions as in Example 15 to obtain 16.9 mg of an active powder (the above objective compound).

Amino acid analysis:

| Asp: 2.79 (3) | Val: 2.02 (2) |
|---|---|
| Thr: 3.93 (4) | Leu: 5.21 (5) |
| Ser: 1.86 (2) | Lys: 1.05 (1) |
| Glu: 4.18 (4) | Pro: 2.03 (2) |
| Gly: 4.06 (4) | Acp: 0.85 (1) |
| Ala: 2.04 (2) | |

EXAMPLE 68

Preparation of ⌐Gly—Ser—Asn—Leu—Ser—Thr—Glu—Val—Leu—Gly—Ala—Leu—Ser—Gln—Glu—Leu—Gly—Lys—Leu—Gln—Thr—Pro—Gln—Thr—Asp—Val—Gly—Ala—Gly—Thr—Pro—NH$_2$ Using Boc-Ala-Leu-Ser(Bzl)-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ (150 mg) and ⌐Gly—Ser(Bzl)—Asn—Leu—Ser(Bzl)—Thr(Bzl)—Glu—Val—Leu—Gly—OH (77 mg), the same procedure as in Example 1 was repeated to obtain 200 mg of a crude protected peptide product.

150 mg of this crude protected peptide product was treated with hydrogen fluoride and anisole in the same manner as in Example 1 to obtain 99 mg of a powder.

50 mg of the powder was purified and determined for purity by high performance liquid chromatography under the same conditions as in Example 15 to obtain 22.4 mg of an active powder (the above objective compound).

Amino acid analysis:

| Asp: 2.02 (2) | Ala: 1.98 (2) |
|---|---|
| Thr: 3.88 (4) | Val: 2.02 (2) |
| Ser: 2.74 (3) | Leu: 5.19 (5) |
| Glu: 5.14 (5) | Lys: 1.03 (1) |
| Gly: 5.06 (5) | Pro: 1.95 (2) |

EXAMPLE 69

Preparation of ⌐Gly—Ser—Asn—Leu—Ser—Thr—Glu—Val—Leu—Gly—Lys(COCH$_3$)—Leu—Ser—Gln—Glu—Leu—Gly—Lys—Leu—Gln—Thr—Pro—Gln—Thr—Asp—Val—Gly—Ala—Gly—Thr—Pro—NH$_2$ Using Boc-Lys(COCH$_3$)-Leu-Ser(Bzl)-Gln-Glu(OcHex)-Leu-Gly-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH$_2$ (150 mg) and ⌐Gly—Ser(Bzl)—Asn—Leu—Ser(Bzl)—Thr(Bzl)—Glu—Val—Leu—Gly—OH (92 mg).

the same procedure as in Example 1 was repeated to obtain 172 mg of a crude protected peptide product.

150 mg of this crude protected peptide product was treated with hydrogen fluoride and anisole in the same manner as in Example 1 to obtain 110 mg of a powder.

50 mg of the powder was purified and determined for purity by high performance liquid chromatography under the same conditions as in Example 15 to obtain 16.4 mg of an active powder (the above objective compound).

Amino acid analysis:

| Asp: 2.02 (2) | Ala: 0.98 (1) |
|---|---|
| Thr: 3.88 (4) | Val: 2.03 (2) |
| Ser: 2.76 (3) | Leu: 5.14 (5) |
| Glu: 5.10 (5) | Lys: 2.05 (2) |
| Gly: 5.05 (5) | Pro: 1.97 (2) |

EXAMPLE 70

Preparation of ⌐Gly—Ser—Asn—Leu—Ser—Thr—Glu—Val—Leu—Gly—Lys—Leu—Ser—Gln—Glu—Leu—Asn—Lys—Leu—Gln—Thr—Tyr—Pro—Arg—Thr—Asp—Val—Gly—Ala—Gly—Thr—Pro—NH$_2$ By using 150 mg of Boc-Lys(Z)-Leu-Ser(Bzl)-Gln-Glu(OcHex)-Leu-Asn-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$ and 62 mg of ⌐Gly—Ser(Bzl)—Asn—Leu—Ser(Bzl)—Thr(Bzl)—Glu—Val—Leu—Gly—OH, and the same procedure as in Example 1 was repeated to obtain 180 mg of a crude product of protected peptide.

Then 160 mg of the crude product of protected peptide was treated with hydrogen fluoride and anisole by procedures similar to those employed in Example 1 to obtain 123 mg of powdery product.

50 Milligrams of said powdery product was purified and determined for purity by means of a high performance liquid chromatography under conditions similar to those employed in Example 15 to obtain 9.2 mg of active powdery product of the above-mentioned objective compound.

Amino acid analysis data:

| | |
|---|---|
| Asp: 2.97 (3) | Val: 1.95 (2) |
| Thr: 3.74 (4) | Leu: 5.05 (5) |
| Ser: 2.72 (3) | Tyr: 0.95 (1) |
| Glu: 4.06 (4) | Lys: 2.03 (2) |
| Gly: 4.08 (4) | Arg: 1.01 (1) |
| Ala: 1.08 (1) | Pro: 2.08 (2) |

EXAMPLE 71

Preparation of ⌐Gly—Ser—Asn—Leu—Ser—Thr—Glu—Val—Leu—Gly—Lys—Leu—Ser—Gln—Glu—Leu—Gly—Lys—Leu—Gln—Thr—Tyr—Pro—Arg—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Gly-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ and 62 mg of ⌐Gly—Ser(Bzl)—Asn—Leu—Ser(Bzl)—
⌐
Thr(Bzl)—Glu—Val—Leu—Gly—OH, and the same procedure as in Example 1 was repeated to obtain 190 mg of a crude product of protected peptide.

Then, 150 mg of the crude product of protected peptide was treated with hydrogen fluoride and anisole by procedures similar to those employed in Example 1 to obtain 111 mg of powdery product.

50 Milligrams of said powdery product was purified and determined for purity by means of a high performance liquid chromatography under conditions similar to those employed in Example 15 to obtain 13.2 mg of

| | |
|---|---|
| Asp: 1.99 (2) | Val: 1.98 (2) |
| Thr: 3.75 (4) | Leu: 5.03 (5) |
| Ser: 2.70 (3) | Tyr: 0.93 (1) |
| Glu: 4.05 (4) | Lys: 2.01 (2) |
| Gly: 5.13 (5) | Arg: 1.02 (1) |
| Ala: 1.04 (1) | Pro: 2.06 (2) |

EXAMPLE 72

Preparation of ⌐Gly—Ser—Asn—Leu—Ser—Thr—Glu—Val—Leu—Gly—Lys—Leu—Ser—Gln—Glu—Leu—Lys—Leu—Gln—Thr—Tyr—Pro—Arg—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH₂ and 63 mg of ⌐Gly—Ser(Bzl)—Asn—Leu—Ser(Bzl)—
⌐
Thr(Bzl)—Glu—Val—Leu—Gly—OH.

and the same procedure as in Example 1 was repeated to obtian 190 mg of a crude product of protected peptide.

Then, 150 mg of the crude product of protected peptide was treated with hydrogen fluoride and anisole by procedures similar to those employed in Example 1 to obtain 104 mg of powdery product.

50 Milligrams of said powdery product was purified and determined for purity by means of a high performance liquid chromatography under conditions similar to those employed in Example 15 to obtian 12.9 mg of active powdery product of the above-mentioned objective compound.

Amino acid analysis data:

| | |
|---|---|
| Asp: 1.99 (2) | Val: 1.98 (2) |
| Thr: 3.75 (4) | Leu: 5.06 (5) |
| Ser: 2.67 (3) | Tyr: 0.91 (1) |
| Glu: 4.07 (4) | Lys: 2.02 (2) |
| Gly: 4.06 (4) | Arg: 1.03 (1) |
| Ala: 1.04 (1) | Pro: 2.09 (2) |

EXAMPLE 73

Preparation of ⌐Acp—Asn—Leu—Ser—Thr—Asp—Val—Leu—Gly—Lys—Leu—Ser—Gln—Glu—Leu—Asp—Lys—Leu—Gln—Thr—Pro—Arg—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Asp(OcHex)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ and 58 mg of

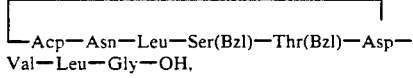
Acp—Asn—Leu—Ser(Bzl)—Thr(Bzl)—Asp—Val—Leu—Gly—OH, and the same procedure as in Example 1 was repeated to obtain 190 mg of a crude product of protected peptide.

Then, 150 mg of the crude product of protected peptide was treated with hydrogen fluoride and anisole by procedures similar to those employed in Example 1 to obtain 90 mg of powdery product.

50 Milligrams of said powdery product was purified and determined for purity by means of a high performance liquid chromatography under conditions similar to those employed in Example 15 to obtain 17.5 mg of active powdery product of the above-mentioned objective compound.

Amino acid analysis data:

| Asp: 3.75 (4) | Val: 1.97 (1) |
| Thr: 3.85 (4) | Leu: 5.05 (5) |
| Ser: 1.88 (2) | Lys: 1.97 (2) |
| Glu: 3.06 (3) | Arg: 1.01 (1) |
| Gly: 2.99 (3) | Pro: 2.10 (2) |
| Ala: 1.00 (1) | Acp: 0.79 (1) |

EXAMPLE 74

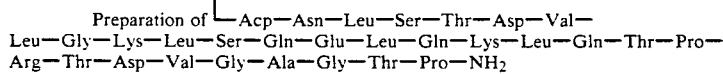
Preparation of Acp—Asn—Leu—Ser—Thr—Asp—Val—Leu—Gly—Lys—Leu—Ser—Gln—Glu—Leu—Gln—Lys—Leu—Gln—Thr—Pro—Arg—Thr—Asp—Val—Gly—Ala—Gly—Thr—Pro—NH₂

BY using 150 mg of Boc-Lys(Z)-Leu-Ser(Bzl)-Gln-Glu(OcHex)-Leu-Gln-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ and 59 mg of

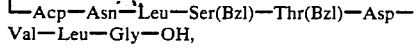
Acp—Asn—Leu—Ser(Bzl)—Thr(Bzl)—Asp—Val—Leu—Gly—OH, and the same procedure as in Example 1 was repeated to obtain 190 mg of a crude product of protected Then, 150 mg of the crude product of protected peptide was treated with hydrogen fluoride and anisole by procedures similar to those employed in Example 1 to obtain 103 mg of powdery product.

50 Milligrams of said powdery product was purified and determined for purity by means of a high performance liquid chromatography under conditions similar to those employed in Example 15 to obtain 21.7 mg of active powdery product of the above-mentioned objective compound.

Amino acid analysis data:

| Asp: 2.80 (3) | Val: 2.01 (2) |
| Thr: 3.83 (4) | Leu: 5.07 (5) |
| Ser: 1.80 (2) | Lys: 1.96 (2) |
| Glu: 4.07 (4) | Arg: 1.01 (1) |
| Gly: 2.98 (3) | Pro: 2.09 (2) |
| Ala: 0.98 (1) | Acp: 0.85 (1) |

EXAMPLE 75

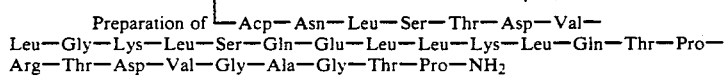
Preparation of Acp—Asn—Leu—Ser—Thr—Asp—Val—Leu—Gly—Lys—Leu—Ser—Gln—Glu—Leu—Leu—Lys—Leu—Gln—Thr—Pro—Arg—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Leu-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ and 59 mg of

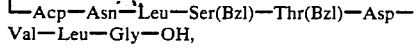
Acp—Asn—Leu—Ser(Bzl)—Thr(Bzl)—Asp—Val—Leu—Gly—OH, and the same procedure as in Example 1 was repeated to obtian 180 mg of a crude product of protected peptide.

Then, 150 mg of the crude product of protected peptide was treated with hydrogen fluoride and anisole by procedures similar to those employed in Example 1 to obtain 108 mg of powdery product.

50 Milligrams of said powdery product was purified and determined for purity by means of a high performance liquid chromatography under conditions similar to those employed in Example 15 to obtain 19.4 mg of the above-mentioned objective compound.

Amino acid analysis data:

| Asp: 2.77 (3) | Val: 2.02 (2) |
| Thr: 3.83 (4) | Leu: 6.10 (6) |
| Ser: 1.81 (2) | Lys: 1.98 (2) |
| Glu: 3.04 (3) | Arg: 1.00 (1) |
| Gly: 3.03 (3) | Pro: 2.01 (2) |
| Ala: 1.00 (1) | Acp: 0.82 (1) |

EXAMPLE 76

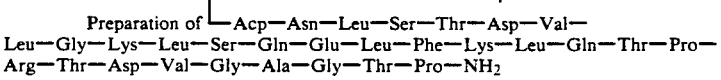
Preparation of Acp—Asn—Leu—Ser—Thr—Asp—Val—Leu—Gly—Lys—Leu—Ser—Gln—Glu—Leu—Phe—Lys—Leu—Gln—Thr—Pro—Arg—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Phe-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ and 59 mg of

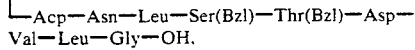

the same procedure as in Example 1 was repeated to obtain 180 mg of a crude product of protected peptide.

Then, 150 mg of the crude product of protected peptide was treated with hydrogen fluoride and anisole by procedures similar to those employed in Example 1 to obtian 64 mg of powdery product.

50 Milligrams of said powdery product was purified and determined for purity by means of a high performance liquid chromatography under conditions similar to those employed in Example 15 to obtain 11.6 mg of active powdery product of the above-mentioned objective compound.

Amino acid analysis data:

| | |
|---|---|
| Asp: 2.77 (3) | Val: 1.98 (2) |
| Thr: 3.86 (4) | Leu: 5.09 (5) |
| Ser: 1.85 (2) | Phe: 0.98 (1) |
| Glu: 3.04 (3) | Lys: 1.99 (2) |
| Gly: 3.05 (3) | Arg: 0.99 (1) |
| Ala: 0.99 (1) | Pro: 2.03 (2) |
| Acp: 0.80 (1) | |

EXAMPLE 77

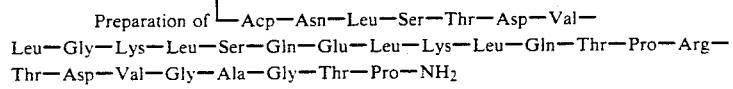

Preparation of Acp—Asn—Leu—Ser—Thr—Asp—Val—Leu—Gly—Lys—Leu—Ser—Gln—Glu—Leu—Ala—Lys—Leu—Gln—Thr—Pro—Arg—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Ala-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro—NH₂ and 60 mg of

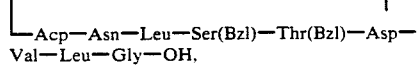

and the same precedure as in Example 1 was repeated to obtain 190 mg of a crude product of protected peptide.

Then, 150 mg of the crude product of protected peptide was treated with hydrogen fluoride and anisole by procedures similar to those employed in Example 1 to obtain 108 mg of powdery product.

50 Milligrams of said powdery product was purified and determined for purity by means of a high performance liquid chromatography under conditions similar to those employed in Exmaple 15 to obtain 10.7 mg of active powdery product of the above-mentioned objective compound.

Amino acid analysis data:

| | |
|---|---|
| Asp: 2.79 (3) | Val: 1.99 (2) |
| Thr: 3.86 (4) | Leu: 5.11 (5) |
| Ser: 1.82 (2) | Lys: 1.98 (2) |
| Glu: 3.05 (3) | Arg: 1.00 (1) |
| Gly: 3.01 (3) | Pro: 1.97 (2) |
| Ala: 2.22 (2) | Acp: 0.81 (1) |

EXAMPLE 78

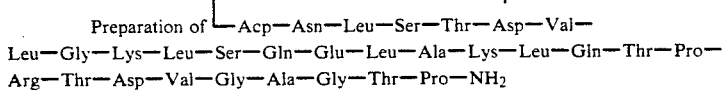

Preparation of Acp—Asn—Leu—Ser—Thr—Asp—Val—Leu—Gly—Lys—Leu—Ser—Gln—Glu—Leu—Lys—Leu—Gln—Thr—Pro—Arg—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Lys(Cl-Z)-Leu-Gln-Thr Bzl)-Pro-Arg(Tos)-Thr(Bzl)-Asp(OcHex)-Val-Gly-Ala-Gly-Thr(Bzl)-Pro—NH₂ and 62 mg of Acp—Asn—Leu—Ser(Bzl)—Thr(Bzl)—Asp—Val—Leu—Gly—OH, and the same procedure as in Example 1 was repeated to obtain 180 mg of a crude product of protected peptide.

Then, 150 mg of the crude product of protected peptide was treated with hydrogen fluoride and anisole by procedures similar to those employed in Example 1 to obtain 108 mg of powdery product.

50 Milligrams of said powdery product was purified and determined for purity by means of a high performance liquid chromatography under conditions similar to those employed in Example 15 to obtain 21.6 mg of active powdery product of the above-mentioned objective compound.

Amino acid analysis data:

| | |
|---|---|
| Asp: 2.77 (3) | Val: 1.97 (2) |
| Thr: 3.89 (4) | Leu: 5.09 (5) |
| Ser: 1.86 (2) | Lys: 2.00 (2) |
| Glu: 3.09 (3) | Arg: 1.02 (1) |
| Gly: 3.00 (3) | Pro: 2.09 (2) |
| Ala: 0.99 (1) | Acp: 0.78 (1) |

EXAMPLE 79

Preparation of ⌐Acp—Asn—Leu—Ser—Thr—Asp—Val—
Leu—Gly—Lys—Leu—Ser—Gln—Glu—Leu—Asn—Lys—Leu—Gln—Thr—Tyr—
Pro—Gln—Thr—Asp—Val—Gly—Ala—Gly—Thr—Pro—NH$_2$ By using 150 mg of Boc-Lys(Z)-Leu-Ser(Bzl)-Gln-Glu(OcHex)-Leu-Asn-Lys(Cl-Z)-Leu-Gln-Thr(Bzl)-Tyr(Cl$_2$Bzl)-Pro-Gln-Thr(Bzl)-Asp(OcHex)-Val-Gly-Ala-Gly-Thr(Bzl)-Pro—NH$_2$ and 56 mg of ⌐Acp—Asn—Leu—Ser(Bzl)—
Thr(Bzl)—Asp—Val—Leu—Gly—OH, and the same procedure as in Example 1 was repeated to obtain 180 mg of a crude product of protected peptide.

Then, 150 mg of the crude product of protected peptide was treated with hydrogen fluoride and anisole by procedures similar to those employed in Example 1 to obtain 86 mg of powdery product.

50 Milligrams of said powdery product was purified and determined for purity by means of a high performance liquid chromatography under conditions similar to those employed in Example 15 to obtain 14.4 mg of active powdery product of the above-mentioned objective compound.

Amino acid analysis data:

| | |
|---|---|
| Asp: 3.80 (4) | Val: 2.01 (2) |
| Thr: 3.86 (4) | Leu: 5.08 (5) |
| Ser: 1.79 (2) | Tyr: 0.97 (1) |
| Glu: 4.08 (4) | Lys: 1.99 (2) |
| Gly: 3.04 (3) | Pro: 1.96 (2) |
| Ala: 1.00 (1) | Acp: 0.81 (1) |

EXAMPLE 80

Preparation of ⌐Acp—Asn—Leu—Ser—Thr—Asp—Val—
Leu—Gly—Lys—Leu—Ser—Gln—Glu—Leu—Gly—Lys—Leu—Gln—Thr—Tyr—
Pro—Gln—Thr—Asp—Val—Gly—Ala—Gly—Thr—Pro—NH$_2$ By using 150 mg of Boc-Lys(Z)-Leu-Ser(Bzl)-Gln-Glu(OcHex)-Leu-Gly-Lys(Cl-Z)-Leu-Gln-Thr(Bzl)-Tyr(Cl$_2$Bzl)-Pro-Gln-Thr(Bzl)-Asp(OcHex)-Val-Gly-Ala-Gly-Thr(Bzl)-Pro—NH$_2$ and 58 mg of ⌐Acp—Asn—Leu—Ser(Bzl)—
Thr(Bzl)—Asp—Val—Leu—Gly—OH, and the same procedure as in Example 1 was repeated to obtain 200 mg of a crude product of protected peptide.

Then, 170 mg of the crude product of protected peptide was treated with hydrogen fluoride and anisole by procedure similar to those employed in Example 1 to obtain 105 mg of powdery product.

50 Milligrams of said powdery product was purified and determined for purity by means of a high performance liquid chromatography under conditions similar to those employed in Exmaple 15 to obtain 10.7 mg of active powdery product of the above-mentioned objective compound.

Amino acid analysis data:

| | |
|---|---|
| Asp: 2.93 (3) | Val: 2.02 (2) |
| Thr: 3.82 (4) | Leu: 5.09 (5) |
| Ser: 1.73 (2) | Tyr: 1.01 (1) |
| Glu: 4.08 (4) | Lys: 1.98 (2) |
| Gly: 4.02 (4) | Pro: 2.05 (2) |
| Ala: 1.00 (1) | Acp: 0.92 (1) |

EXAMPLE 81

Preparation of ⌐Acp—Asn—Leu—Ser—Thr—Asp—Val—
Leu—Gly—Lys—Leu—Ser—Gln—Glu—Leu—Lys—Leu—Gln—Thr—Tyr—Pro—
Gln—Thr—Asp—Val—Gly—Ala—Gly—Thr—Pro—NH$_2$ By using 150 mg of Boc-Lys(Z)-Leu-Ser(Bzl)-Gln-Glu(OcHex)-Leu-Lys(Cl-Z)-Leu-Gln-Thr(Bzl)-Tyr(Cl$_2$Bzl)-Pro-Gln-Thr(Bzl)-Asp(OcHex)-Val-Gly-Ala-Gly-Thr(Bzl)-Pro—NH$_2$ and 59 mg of ⌐Acp—Asn—Leu—Ser(Bzl)—
Thr(Bzl)—Asp—Val—Leu—Gly—OH, and the same procedure as in Example 1 was repeated to obtain 190 mg of a crude product of protected peptide.

Then, 150 mg of the crude product of protected peptide was treated with hydrogen fluoride and anisole by procedures similar to those employed in Example 1 to obtain 101 mg of powdery product.

50 Milligrams of said powdery product was purified and determined for purity by means of a high performance liquid chromatography under conditions similar to those employed in Example 15 to obtain 11.6 mg of active powdery product of the above-mentioned objective compound.

Amino acid analysis data:

| | |
|---|---|
| Asp: 2.90 (3) | Val: 2.04 (2) |

-continued

| | |
|---|---|
| Thr: 3.81 (4) | Leu: 5.14 (5) |
| Ser: 1.75 (2) | Tyr: 1.00 (1) |
| Glu: 4.07 (4) | Lys: 1.99 (2) |
| Gly: 3.04 (3) | Pro: 2.03 (2) |
| Ala: 0.99 (1) | Acp: 0.91 (1) |

EXAMPLE 82

Preparation of ⌐Acp—Asn—Leu—Ser—Thr—Asp—Val—Leu—Gly⌐—Lys—Leu—Ser—Gln—Glu—Leu—His—Lys—Leu—Gln—Thr—Tyr—Pro—Gln—Thr—Asp—Val—Gly—Ala—Gly—Thr—Pro—NH₂

By using 150 mg of Boc-Lys(Z)-Leu-Ser(Bzl)-Gln-Glu(OcHex)-Leu-His(Tos)-Lys(Cl-Z)-Leu-Gln-Thr(Bzl)-Tyr(Cl₂Bzl)-Pro-Gln-Thr(Bzl)-Asp(OcHex)-Val-Gly-Ala-Gly-Thr(Bzl)-Pro—NH₂ and 54 mg of ⌐Acp—Asn—Leu—Ser(Bzl)—Thr(Bzl)—Asp—Val—Leu—Gly⌐—OH, and the same procedure as in Example 1 was repeated to obtain 180 mg of a crude product of protected peptide.

Then, 150 mg of the crude product of protected peptide was treated with hydrogen fluoride and anisole by procedures similar to those employed in Example 1 to obtain 110 mg of powdery product.

50 Milligrams of said powdery product was purified and determined for purity by means of a high performance liquid chromatography under conditions similar to those employed in Example 15 to obtain 12.0 mg of active powdery product of the above-mentioned objective compound.

Amino acid analysis data:

| | |
|---|---|
| Asp: 2.93 (3) | Val: 2.10 (2) |
| Thr: 3.80 (4) | Leu: 5.10 (5) |
| Ser: 1.72 (2) | Tyr: 1.00 (1) |
| Glu: 4.00 (4) | Lys: 1.93 (2) |
| Gly: 3.12 (3) | His: 0.92 (1) |
| Ala: 1.01 (1) | Pro: 2.02 (2) |
| | Acp: 0.86 (1) |

EXAMPLE 83

Preparation of ⌐Acp—Asn—Leu—Ser—Thr—Asp—Val—Leu—Gly⌐—Lys—Leu—Ser—Gln—Glu—Leu—Leu—Lys—Leu—Gln—Thr—Pro—Gln—Thr—Asp—Val—Gly—Ala—Gly—Thr—Pro—NH₂

By using 100 mg of Boc-Lys(Z)-Leu-Ser(Bzl)-Gln-Glu(OcHex)-Leu-Leu-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ and 52 mg of ⌐Acp—Asn—Leu—Ser(Bzl)—Thr(Bzl)—Asp—Val—Leu—Gly⌐—OH.

and the same procedure as in Example 1 was repeated to obtain 127 mg of a crude product of protected peptide.

Then, 110 mg of the crude product of protected peptide was treated with hydrogen fluoride and anisole by procedures similar to those employed in Example 1 to obtain 85 mg of powdery product.

50 Milligrams of said powdery product was purified and determined for purity by means of a high performance liquid chromatography under conditions similar to those employed in Example 15 to obtain 14.0mg of active powdery product of the above-mentioned objective compound.

Amino acid analysis data:

| | |
|---|---|
| Asp: 2.78 (3) | Val: 1.96 (2) |
| Thr: 3.92 (4) | Leu: 6.15 (6) |
| Ser: 1.87 (2) | Lys: 2.02 (2) |
| Glu: 4.09 (4) | Pro: 1.98 (2) |
| Gly: 3.03 (3) | Acp: 0.85 (1) |
| Ala: 1.00 (1) | |

EXAMPLE 84

Preparation of ⌐Acp—Asn—Leu—Ser—Thr—Asp—Val—Leu—Gly⌐—Lys—Leu—Ser—Gln—Glu—Leu—Asp—Lys—Leu—Gln—Thr—Pro—Gln—Thr—Asp—Val—Gly—Ala—Gly—Thr—Pro—NH₂

By using 100 mg of Boc-Lys(Z)-Leu-Ser(Bzl)-Gln-Glu(OcHex)-Leu-Asp(Ochex)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ and 51 mg of ⌐Acp—Asn—Leu—Ser(Bzl)—Thr(Bzl)—Asp—Val—Leu—Gly⌐—OH, and the same procedure as in Example 1 was repeated to obtain 129 mg of a crude product of protected peptide.

Then, 110 mg of the crude product of protected peptide was treated with hydrogen fluoride and anisole by procedures similar to those employed in Example 1 to obtian 71 mg of powdery product.

50 Milligrams of said powdery product was purified and determined for purity by means of a high performance liquid chromatography under conditions similar to those employed in Example 15 to obtain 14.9 mg of active powdery product of the above-mentioned objective compound.

Amino acid analysis data:

| | |
|---|---|
| Asp: 3.75 (4) | Val: 1.93 (2) |
| Thr: 3.90 (4) | Leu: 5.07 (5) |
| Ser: 1.85 (2) | Lys: 2.01 (2) |
| Glu: 4.07 (4) | Pro: 2.03 (2) |
| Gly: 3.00 (3) | Acp: 0.85 (1) |
| Ala: 0.99 (1) | |

EXAMPLE 85

Preparation of ⌐Acp—Asn—Leu—Ser—Thr—Asp—Val—Leu—Gly—Lys—Leu—Ser—Gln—Glu—Leu—Tyr—Lys—Leu—Gln—Thr—Pro—Gln—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Tyr(Cl₂-Bzl)-Lys(Cl-Z)-Leu-Gln-Thr(Bzl)-Pro-Gln-Thr(Bzl)-Asp(OcHex)-Val-Gly-Ala-Gly-Thr(Bzl)-Pro—NH₂ and 64 mg of ⌐Acp—Asn—Leu—Ser(Bzl)—
Thr(Bzl)—Asp—Val—Leu—Gly—OH, and the same procedure as in Example 1 was repeated to obtain 174 mg of a crude product of protected peptide.

Then, 120 mg of the crude product of protected peptide was treated with hydrogen fluoride and anisole by procedures similar to those employed in Example 1 to obtain 83 mg of powdery product.

50 Milligrams of said powdery product was purified and determined for purity by means of a high performance liquid chromatography under conditions similar to those employed in Example 15 to obtain 10.1 mg of active powdery product of the above-mentioned objective compound.

Amino acid analysis data:

| | |
|---|---|
| Asp: 2.81 (3) | Val: 2.04 (2) |
| Thr: 3.87 (4) | Leu: 5.15 (5) |
| Ser: 1.88 (2) | Tyr: 0.94 (1) |
| Glu: 4.01 (4) | Lys: 1.99 (2) |
| Gly: 3.06 (3) | Pro: 1.96 (2) |
| Ala: 0.97 (1) | Acp: 0.84 (1) |

EXAMPLE 86

Preparation of ⌐Acp—Asn—Leu—Ser—Thr—Asp—Val—Leu—Gly—Lys—Leu—Ser—Gln—Glu—Leu—Gln—Lys—Leu—Gln—Thr—Pro—Asn—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Gln-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂ and 62 mg of ⌐Acp—Asn—Leu—Ser(Bzl)—Thr(Bzl)—Asp—Val—Leu—Gly—OH.

and the same procedure as in Example 1 was repeated to obtain 174 mg of protected peptide.

Then, 130 mg of the crude product of protected peptide was treated with hydrogen fluoride and anisole by procedures similar to those employed in Example 1 to obtain 96 mg of powdery product.

50 Milligrams of said powdery product was purified and determined for purity by means of a high performance liquid chromatography under conditions similar to those employed in Example 15 to obtain 13.1 mg of active powdery product of the above-mentioned objective compound.

Amino acid analysis data:

| | |
|---|---|
| Asp: 3.79 (4) | Val: 2.00 (2) |
| Thr: 3.89 (4) | Leu: 5.13 (5) |
| Ser: 1.83 (2) | Lys: 2.01 (2) |
| Glu: 4.07 (4) | Pro: 2.05 (2) |
| Gly: 3.06 (3) | Acp: 0.84 (1) |
| Ala: 1.00 (1) | |

EXAMPLE 87

Preparation of ⌐Acp—Asn—Leu—Ser—Thr—Asp—Val—Leu—Gly—Lys—Leu—Ser—Gln—Glu—Leu—His—Lys—Leu—Gln—Thr—Pro—Asn—Thr—Asp—Val—Gly—Ala—Gly—Thr—Pro—NH₂

By using 150 mg of Boc-Lys(Z)-Leu-Ser(Bzl)-Gln-Glu(OcHex)-Leu-His(Tos)-Lys(Cl-Z)-Leu-Gln-Thr(Bzl)-Pro-Asn-Thr(Bzl)-Asp(OcHex)-Val-Gly-Ala-Gly-Thr(Bzl)-Pro—NH₂ and 60 mg of ⌐Acp—Asn—Leu—Ser(Bzl)—Thr(Bzl)—Asp—Val—Leu—Gly—OH, and the same procedure as in Example 1 was repeated to obtain 153 mg of a crude product of protected peptide.

Then, 110 mg of the crude product of protected peptide was treated with hydrogen fluoride and anisole by procedures similar to those employed in Example 1 to obtain 79 mg of powdery product.

50 Milligrams of said powdery product was purified and determined for purity by means of a high performance liquid chromatography under conditions similar to those employed in Example 15 to obtain 10.8 mg of active powdery product of the above-mentioned objective compound.

Amino acid analysis data:

| Asp: 3.78 (4) | Val: 2.00 (2) |
|---|---|
| Thr: 3.87 (4) | Leu: 5.08 (5) |
| Ser: 1.79 (2) | Lys: 1.93 (2) |
| Glu: 3.05 (3) | His: 0.98 (1) |
| Gly: 3.05 (3) | Pro: 2.05 (2) |
| Ala: 0.99 (1) | Acp: 0.81 (1) |

EXAMPLE 88

Preparation of ⌐Acp—Asn—Leu—Ser—Thr—Asp—Val—Leu—Gly—Lys—Leu—Ser—Gln—Glu—Leu—Gly—Lys—Leu—Gln—Thr—Pro—Asn—Thr—Asp—Val—Gly—Ala—Gly—Thr—Pro—NH₂

By using 150 mg of Boc-Lys(Z)-Leu-Ser(Bzl)-Gln-Glu(OcHex)-Leu-Gly-Lys(Cl-Z)-Leu-Gln-Thr(Bzl)-Pro-Asn-Thr(Bzl)-Asp(OcHex)-Val-Gly-Ala-Thr(Bzl)-Pro—NH₂ and 64 mg of ⌐Acp—Asn—Leu—Ser(Bzl)—Thr(Bzl)—Asp—Val—Leu—Gly—OH.

and the same procedure as in Example 1 was repeated to obtain 175 mg of a crude product of protected peptide.

The 130 mg of the crude product of protected peptide was treated with hydrogen fluoride and anisole by procedures similar to those employed in Example 1 to obtain 80 mg of powdery product.

50 Milligrams of said powdery product was purified and determined for purity by means of a high performance liquid chromatography under conditions similar to those employed in Example 15 to obtain 15.2 mg of active powdery product of the above-mentioned objective compound.

Amino acid analysis data:

| Asp: 3.88 (4) | Val: 2.02 (2) |
|---|---|
| Thr: 3.82 (4) | Leu: 5.16 (5) |
| Ser: 1.77 (2) | Lys: 2.00 (2) |
| Glu: 3.05 (3) | Pro: 2.04 (2) |
| Gly: 4.04 (4) | Acp: 0.92 (1) |
| Ala: 0.99 (1) | |

REFERENCE PREPARATION EXAMPLE 1

Preparation of
Boc-Ser(Bzl)-Asn-Leu-Ser(Bzl)-Thr(Bzl)-Glu-OBzl 6.00 g of Boc-Ser(Bzl)-Thr(Bzl)-Glu-OBzl.H₂O was dissolved in 20 ml of TFA with ice-cooling. The solution was stirred for 30 minutes at room temperature. The reaction mixture was concentrated under reduced pressure. The residue was dried over sodium hydroxide under reduced pressure.

A solution of 4.75 g of Boc-Ser(Bzl)-Asn-Leu—N₂H₃ dissolved in 40 ml of DMF was stirred at −15° C. Thereto were added 4.42 ml of 4N hydrochloric acid/dioxane and then 1.20 ml of isoamyl nitrite to form an azide. 4.00 ml of triethylamine was added to effect neutralization.

The above TFA-treated product was dissolved in 40 ml of DMF. The solution was neutralized with triethylamine with ice-cooling. Thereto was added the above azide compound. The mixture was allowed to stand overnight at 4° C. The reaction mixture was concentrated under reduced pressure. The residue was mixed with water. The resulting precipitate was collected by filtration and recrystallized from methanol to obtain 7.40 g (yield: 80.5%) of the above objective compound having a melting point of 190–192° C.

REFERENCE PREPARATION EXAMPLE 2

Preparation of ⌐Ser(Bzl)—Asn—Leu—Ser(Bzl)—Thr(Bzl)—Glu—OBzl 2.39 g of Boc-Ser(Bzl)-Asn-Leu-Ser(Bzl)-Thr(Bzl)-Glu-OBzl was dissolved in 15 ml of dry pyridine. Thereto was added 2.50 g of TFA-ONp. The mixture was allowed to stand for 4 hours at 40° C. The reaction mixture was concentrated under reduced pressure. The residue was mixed with isoporpyl ether. The resulting precipitate was collected by filtration and dried. The product was dissolved in 10 ml of TFA with ice-cooling. The solution was stirred for 30 minutes at room temperature. The reaction mixture was concentrated under reduced pressure. The residue was mixed with ethyl acetate. The resulting precipitate was collected by filtration and dried over sodium hydroxide under reduced pressure. The above TFA-treated product was dissolved in 15 ml of DMF. The solution was dropped into 400 ml of dry pyridine in 2 hours with stirring at 50° C. The mixture was stirred for 5 hours at 50° C. The reaction mixture was concentrated under reduced pressure. The residue was dissolved in 100 ml of ethyl acetate. The solution was washed with three 50-ml portions of 1N hydrochloric acid and two 50-ml portions of water in this order. Ethyl acetate was removed by distillation under reduced pressure. The residue was mixed with methanol. The resulting insolubles were removed by filtration. The fitrate was mixed with ethyl acetate. The solution was concentrated under reduced pressure. The residue was mixed with isopropyl ether. The resulting precipitate was collected by filtration to obtain 1.34 g (yield: 62.7%) of the above objective compound having a melting point of 207–210° C.

REFERENCE PREPARATION EXAMPLE 3

Preparation of ⌐Ser(Bzl)—Asn—Leu—Ser(Bzl)—Thr(Bzl)—Glu—N₂H₃

1.22 g of

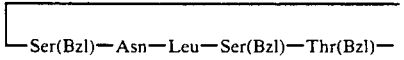
Glu—OBzl was dissolved in 30 ml of methanol. Thereto was added 1.00 ml of NH$_2$NH$_2$.H$_2$O. The mixture was allowed to stand for 2 days at room temperature. The reaction mixture was concentrated under reduced pressure. The residue was mixed with isopropyl ether. The resulting insolubles were collected by filtration and suspended in a mixture of methanol and ethyl acetate. The suspension was concentrated under reduced pressure. The residue was mixed with ethyl acetate. The resulting precipitate was collected by filtration to obtain 0.82 g (yield: 72.8%) of the above objective compound having a melting point of 169–176° C.

REFERENCE PREPARATION EXAMPLE 4

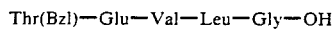
Preparation of Ser(Bzl)—Asn—Leu—Ser(Bzl)—Thr(Bzl)—Glu—Val—Leu—Gly—OH 1.00 g of Boc—Val—Leu—Gly—OH was dissolved in 5 ml of TFA with ice-cooling. The solution was stirred for 30 minutes at room temperature. The reaction mixture was concentrated under reduced pressure. The residue was dried over sodium hydroxide under reduced pressure.

0.80 g of

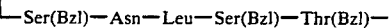
Glu—N$_2$H$_3$ was dissolved in 10 ml of DMF. To the solution were added 0.45 ml of 4N hydrochloric acid/dioxane and 0.17 ml of isoamyl nitrite in this order, with stirring at $-15°$ C., to form an azide. Then, triethylamine was added to effect neutralization.

The above TFA-treated product was dissolved in 30 ml of DMF. The solution was neutralized with triethylamine with ice-cooling. Thereto was added the above azide compound. The mixture was stirred overnight with ice-cooling. The reaction mixture was concentrated under reduced pressure. The residue was mixed with 0.5N hydrochloric acid. The resulting precipitate was collected by filtration and washed with water and hot methanol in this order to obtain 0.31 g (yield: 30.3%) of the above objective compound.

Melting point: 210° (softened) -244° C.

Amino acid analysis:

| | |
|---|---|
| Asp: 1.05 (1) | Gly: 1.02 (1) |
| Thr: 1.05 (1) | Val: 0.94 (1) |
| Ser: 1.90 (2) | Leu: 1.95 (2) |
| Glu: 1.08 (1) | |

REFERENCE PREPARATION EXAMPLE 5

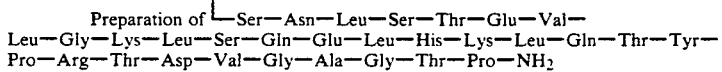
Preparation of Ser—Asn—Leu—Ser—Thr—Glu—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH$_2$ 400 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro—NH$_2$.3H$_2$O [reference is made to Japanese patent application Kokai (Laid-Open) No. 112099/1986] was dissolved in 5 ml of TFA. The solution was stirred for 40 minutes at room temperature. The reaction mixture was concentrated under reduced pressure. The residue was mixed with diethyl ether. The resulting precipitate was collected by filtration and dried over sodium hydroxide under reduced pressure.

The above product was dissolved in 10 ml of DMF. The solution was adjusted to pH 6–7 with triethylamine with ice-cooling. Thereto were added 193 mg of

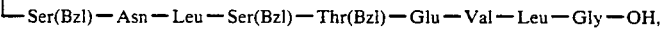
Ser(Bzl)—Asn—Leu—Ser(Bzl)—Thr(Bzl)—Glu—Val—Leu—Gly—OH, 23 mg of HOBT and 0.030 ml of WSC. The mixture was adjusted to pH 6–7 with 4N hydrochloric acid/dioxane and stirred for 1 hour under ice-cooling and for 18 hours at room temperature. The reaction mixture was concentrated under reduced pressure. The residue was mixed with 30 ml of water. The resulting precipitate was collected by filtration and reprecipitated from methanol-ethyl acetate to obtain 420 mg of a crude protected peptide product.

250 mg of this crude protected peptide product was dissolved in a mixture of 10 ml of hydrogen fluoride and 1 ml of anisole. The solution was stirred for 60 minutes at 0° C. Hydrogen fluoride was removed by distillation under reduced pressure. The residue was washed with diethyl ether and dissolved in 1M acetic acid. The solution was freeze-dried to obtain 147 mg of a powder.

20 mg of this powder was dissolved in a 0.1% aqueous trifluoroacetic acid solution and subjected to high performance liquid chromatography under the following conditions to obtain 1.8 mg of an active powder.

| | |
|---|---|
| Column: | ODS-120T (21.5 mm × 30 cm) |
| Eluting method: | Linear concentration gradient (180 minutes) |
| Elutant: | 0.1% aqueous TFA solution/90% acetonitrile (100:0) (solution A) → (30:70) (solution B) |
| Flow rate: | 2 ml/min |
| Detection: | UV 280 nm |

Part of the above active powder was again subjected to high performance liquid chromatography using an ODS-120T column (4.6 mm×15 cm) to determine the purity of the powder. The powder was also subjected to amino acid analysis.

Amino acid analysis:

Asp: 2.05 (2)
Thr: 3.90 (4)
Ser: 2.94 (3)
Glu: 4.08 (4)
Gly: 3.03 (3)
Ala: 1.00 (1)
Val: 1.96 (2)
Leu: 4.99 (5)
Tyr: 0.79 (1)
Lys: 2.01 (2)
His: 0.99 (1)
Arg: 0.97 (1)
Pro: 1.98 (2)

The polypeptide obtained in Reference Preparation Example 5 has excellent action for reducing calcium concentration in blood, gives low side effect, is stable also in a solution state, has high water solubility, and exhibits good absorbability, prolonged action, high pharmacological effect and low toxicity.

Biological Activity Test—I

A polypeptide derivative of the present invention was used as a test sample, and it was diluted to a suitable concentration by using a 1%-sodium acetate aqueous solution (in which 0.1% of bovine serum albumin is contained, and having pH 5.0), then thus obtained solution was administered intravenously in an amount of 0.2 ml/100 body weight to a Wister strain male rat (about 180 g of body weight). One hour after the administration, the rat was anesthetized with diethyl ether, and the blood was sampled from abdominal vein then the serum sample was obtained.

The concentration of calcium in said serum was determined by means of calorimetric procedure in accordance with OCPC method [BUNSEKI-KAGAKU-SHIMPO-SOHSETSU (Review of Progresses in Analytical Chemistry, Vol. 17, pp. 127–136, (1968) by Masayuki Saitoh; American Journal of Clinical Pathology. Vol. 45, pp. 290–296, (1966) by Connerty, H. V., and Briggs, A. R.; RINSHOH-BYOHRI (Clinical Pathology), Vol. 17, Supplemental Issue, pp. 85, (1969) by Etsuko Yoshida], by using a biochemical automatic analytical equipment (COBAS BIO, manufactured by Hoffmann-La Roche & Co., A. G.)

As the result, the concentration of calcium in the serums obtained from the rats in control group, to which the test sample of polypeptide derivative of the present invention was not administered, was 10.49 mg/kg (an average value calculated from the data obtained from 4 rats in one control group). On the other hand, the polypeptide derivative of the present invention prepared in Example 1 was used as a test sample and was administered intravenously to the rats in test group in the concentration of 6.25, 12.5 and 25 ng/kg, respectively, and determined the concentrations of calcium in the serums obtained from the said rats in test group were shown gradually decreased depend on the lowering of the dosages of the test sampls, thus they were determined as 8.91, 8.00 and 7.22 mg/dl (average values calculated from the data obtained from 4 rats in one test group), respectively. In addition to the above, other polypeptide derivatives of the present invention prepared in other Examples were used as test samples, and condusted tests by procedures similar to the above. The concentrations of calcium in the serums obtained from the test rats in test groups to which each of the test samples was administered in the concentrations of 6.25, 12.5 and 25 ng/kg, respectively were determined, the results are shown in Table 1 as follows.

As can be seen from the results shown in Table 1, it is clearly understood that any one of these polypeptide derivatives of the present invention possess excellent activity for lowering the concentration of calcium in the serum.

TABLE 1

| Example No. of polypeptide as test sample | Concentration of calcium in the serum (mg/dl) Dosage of test compound (ng/kg) | | | |
|---|---|---|---|---|
| | Test groups | | | Control group |
| | 6.25 | 12.5 | 25.0 | 0 |
| Example 1 | 8.91 | 8.00 | 7.22 | 10.49 |
| Example 3 | 9.02 | 8.40 | 7.55 | 9.51 |
| Example 5 | 8.99 | 8.19 | 7.59 | 9.51 |
| Example 6 | 8.67 | 8.29 | 7.85 | 10.05 |
| Example 7 | 9.49 | 8.17 | 7.67 | 10.27 |
| Example 8 | 8.55 | 7.93 | 7.87 | 9.66 |
| Example 10 | 9.40 | 8.86 | 8.15 | 9.94 |
| Example 11 | 9.16 | 8.47 | 7.79 | 10.06 |
| Example 12 | 9.18 | 8.57 | 7.76 | 10.06 |
| Example 13 | 9.35 | 8.94 | 8.19 | 9.69 |
| Example 15 | 9.10 | 8.47 | 7.78 | 9.83 |
| Example 16 | 9.00 | 8.07 | 7.20 | 9.60 |
| Example 18 | 8.52 | 8.04 | 7.74 | 9.85 |
| Example 19 | 8.98 | 8.11 | 7.78 | 9.77 |
| Example 20 | 9.05 | 8.30 | 7.90 | 9.77 |
| Example 21 | 9.13 | 8.31 | 7.64 | 9.90 |
| Example 22 | 9.08 | 8.34 | 7.76 | 10.15 |
| Example 30 | 8.42 | 7.77 | 7.09 | 10.49 |
| Example 31 | 8.78 | 8.00 | 7.26 | 10.49 |
| Example 33 | 9.28 | 8.22 | 7.44 | 10.29 |
| Example 36 | 8.58 | 7.98 | 7.35 | 10.01 |
| Example 37 | 8.44 | 7.82 | 7.43 | 10.01 |
| Example 38 | 8.63 | 8.15 | 7.50 | 10.20 |
| Example 39 | 8.98 | 7.97 | 7.58 | 10.20 |
| Example 40 | 8.89 | 8.25 | 7.70 | 9.92 |
| Example 41 | 8.43 | 8.13 | 7.20 | 9.90 |
| Example 46 | 8.47 | 7.67 | 7.35 | 9.90 |
| Example 47 | 8.65 | 8.42 | 7.45 | 9.90 |
| Example 48 | 8.75 | 7.83 | 7.33 | 9.91 |
| Example 50 | 8.94 | 8.26 | 7.42 | 9.88 |
| Example 51 | 8.61 | 7.74 | 7.11 | 9.91 |
| Example 52 | 8.42 | 7.54 | 6.85 | 9.91 |
| Example 55 | 9.30 | 8.53 | 7.45 | 9.78 |
| Example 70 | 8.54 | 7.85 | 7.49 | 9.92 |
| Example 71 | 8.40 | 8.20 | 7.47 | 9.92 |
| Example 74 | 8.81 | 7.65 | 7.16 | 9.85 |
| Example 75 | 9.00 | 8.14 | 7.39 | 9.85 |
| Example 77 | 8.55 | 7.77 | 7.22 | 9.85 |
| Example 85 | 8.31 | 7.77 | 6.93 | 9.50 |

Biological Activity Test—II

The activity for inhibiting the secretion of the gastric juice shown by the polypeptide derivatives according to the present invention were conducted as follows. Thus, Wister strain male rats (having average body weight of 180–230 g) were used as test animals. The test rat was abstained from food onvernight, and the pylorus portion was ligated under the condition of anesthetized with diethyl ether by a method according to that described in an article "Gasteroenterology", Vol. 5, pp. 43–61 (1945) by Shay, et al. Four hours after, the stomach of the rat was enucleated under the condition of anesthesia with diethyl ether and the gastric juice was sampled and the amount thereof was measured. The amount of the gastric juice was determined as the amount of supernatant obtained from centrifugation of the content of the stomach.

A polypeptide derivative prepared from each of Examples in the present invention was used as a test sample, and it was diluted with a 1%-sodium acetate aqueous solution (in which 0.1% of bovine serum is contained), and said solution was intravenously administered in the ratio of 0.625μg/2 ml/kg to the pylorus of the test rat (Test group). As to the control group, 1%-sodium acetate aqueous solution without containing the polypeptide derivative of the present invention was administered to the other test rats.

The results of the test are shown in Table 2 as follows.

As can be seen from the results shown in Table 2, it is clearly understood that any one of the polypeptide derivatives of the present invention possess excellent activity for inhibiting the secretion of the gastric juice.

TABLE 2

| Example No. of polypeptide as test sample | Amount of the secreted gastric juice (ml) | |
|---|---|---|
| | Test group | Control group |
| Example 1 | 0.88 | 2.90 |
| Example 16 | 0.60 | 2.90 |
| Example 20 | 0.48 | 2.90 |
| Example 30 | 0.58 | 3.19 |
| Example 33 | 1.41 | 3.19 |
| Example 37 | 0.95 | 3.19 |
| Example 39 | 1.18 | 3.19 |
| Example 46 | 0.73 | 3.19 |
| Example 52 | 1.88 | 3.19 |

What is claimed is:

1. A polypeptide derivative, an acid-addition salt thereof or a complex thereof represented by the general formula $(1-a^1)$,

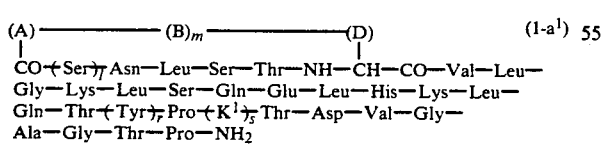

wherein
(A) is a lower alkylene group or a phenylene group;
(B) is a —NHCO— group;
(D) is a lower alkylene group;
($K^1$) is a glutamine residue, a glycine residue or an asparagine residue, respectively;
and each of l, m, r and s is 0 or 1, respectively; provided that, when l is 0, then A should not be a methylene group; and when m is 0, then A is a phenylene group; further the amino group in the side-chain of the lysine residue may be acylated.

2. A polypeptide derivative, an acid-addition salt thereof or a complex thereof represented by the general formula $(1-a^2)$,

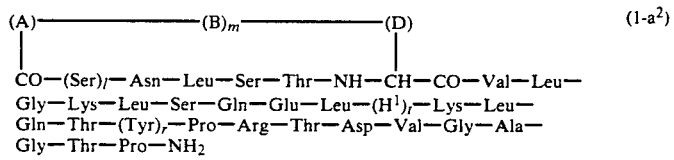

wherein
(A) is a lower alkylene group or a phenylene group;
(B) is a —NHCO— group;
(D) is a lower alkylene group;
($H^1$) is an asparagine residue, a glycine residue, an aspartic acid residue, a glutamine residue, a leucine residue, a phenylalanine residue or an alanine residue; and each of l, m, r and t is 0 or 1, respectively; provided that when l is 0, then A should not be a methylene group and when m is 0, then A is a phenylene group; further the amino group of the side-chain in the lysine may be acylated.

3. A polypeptide derivative, an acid-addition salt thereof or a complex thereof represented by the general formula $(1-a^3)$,

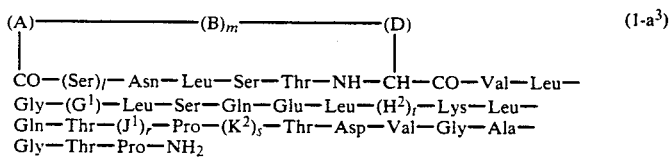

wherein
(A) is a lower alkylene group or a phenylene group;
(B) is a —NHCO— group;
(D) is a lower alkylene group;
($G^1$) is a lysine residue or an alanine residue;
($H^2$) is an asparagine residue, a glycine residue, a glutamine residue, a tyrosine residue, a leucine residue or an aspartic acid residue;
($J^1$) is a tyrosine residue or a leucine residue;
($K^2$) is a glutamine residue or an asparagine residue, respectively;
and each of l, m, r and t is 0 or 1, respectively; provided that when l is 0, than A should not be a methylene group and when m is 0, then A is a phenylene group; further the amino group of the side-chain in the lysine residue may be acylated.

4. A polypeptide derivative, an acid-addition salt thereof or a complex thereof, wherein the general formula is $(1-b)$, which is a combination of the general formulas $(1-b^1)$ and $(1-b^2)$,

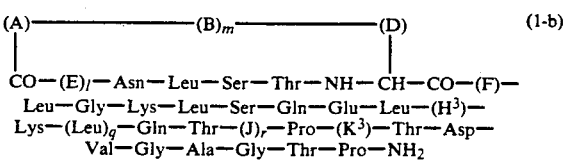

wherein
(A) is a lower alkylene group or a phenylene group;

(B) is a —NHCO— group;
(D) is a lower alkylene group;
(E) is a serine residue, a γ-aminobutyric acid residue or a β-alanine residue;
(F) is a valine residue, a glycine residue or an isoleucine residue;
($H^3$) is a histidine residue or an asparagine residue;
(J) is a tyrosine residue, a D-tyrosine residue or a leucine residue;
($K^3$) is an asparagine residue or a glutamine residue, respectively;

and each of l, m, q and r is 0 or 1, respectively; provided that when l is 0, then A should not be a methylene group and when m is 0, then A is a phenylene group; further the amino group of the side-chain in the lysine residue may be acylated, and the carboxyl groups on the side-chain in the asparatic acid residue and glutamic acid residue may be esterified; provided that excluding the case when ($H^3$) is a histidine residue and also ($K^3$) is an arginine residue, then (F) is an isoleucine residue.

5. A polypeptide derivative, an acid-addition salt thereof or a complex thereof represented by the general formula (1−c),

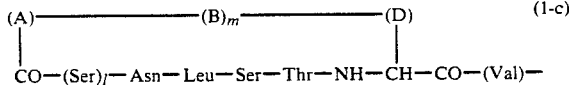

|
CO—(Ser)$_l$—Asn—Leu—Ser—Thr—NH—CH—CO—(Val)—

-continued

Leu—Gly—($G^2$)—Leu—Ser—Gln—Glu—Leu—His-
                                    —($I^1$)—
    Leu—Gln—Thr—(Tyr)$_r$—Pro—Arg—Thr—Asp—Val—
              Gly—Ala—Gly—Thr—Pro—NH$_2$ wherein
(A) is a lower alkylene group or a phenylene group;
(B) is a —NHCO— group;
(D) is a lower alkylene group;
($G^2$) is a lysine residue or a glycine residue;
($I^1$) is a lysine residue or a glycine residue, respectively;

and each of l, m, and r is 0 or 1; provided that when l is 0, then A should not be a methylene group and when m is 0, then A is a phenylene group; further the amino group of the side-chain in the lysine residue may be acylated; provided that excluding the case when both ($G^2$) and ($I^1$) are lysine residue at the same time.

6. A polypeptide derivative, an acid-addition salt thereof or a complex thereof according to claim 2, wherein the polypeptide derivative is (Example 33)

⌐Acp—Asn—Leu—Ser—Thr—Asp—Val—
Leu—Gly—Lys—Leu—Ser—Gln—Glu—Leu—His—Lys—Leu—Gln—Thr—Pro—Gln—
Thr—Asp—Val—Gly—Ala—Gly—Thr—Pro—NH$_2$ or (Example 41)

⌐Gly—Ser—Asn—Leu—Ser—Thr—Glu—Val—Leu—Gly—Lys—Leu—Ser—
Gln—Glu—Leu—His—Lys—Leu—Gln—Thr—Pro—Gln—Thr—Asp—Val—Gly—
Ala—Gly—Thr—Pro—NH$_2$.

7. A polypeptide derivative, an acid-addition salt thereof or a complex thereof according to claim 2, wherein the polypeptide derivative is (Example 37)

⌐Acp—Asn—Leu—Ser—Thr—Asp—Val—
Leu—Gly—Lys—Leu—Ser—Gln—Glu—Leu—Gly—Lys—Leu—Gln—Thr—Pro—Arg—
Thr—Asp—Val—Gly—Ala—Gly—Thr—Pro—NH$_2$.

8. A polypeptide derivative, an acid-addition salt thereof or a complex thereof according to claim 3, wherein the polypeptide derivative is selected from the group consisting of (Example 30)

⌐Gly—Ser—
Asn—Leu—Ser—Thr—Glu—Val—Leu—Gly—Lys—Leu—Ser—Gln—Glu—Leu—Asn—Lys—
Leu—Gln—Thr—Pro—Arg—Thr—Asp—Val—Gly—Ala—Gly—Thr—Pro—NH$_2$.

(Example 31)

⌐Gly—Ser—Asn—Leu—Ser—Thr—Glu—Val—Leu—Gly—Lys—Leu—Ser—
Gln—Glu—Leu—Gly—Lys—Leu—Gln—Thr—Pro—Arg—Thr—Asp—Val—Gly—Ala—
Gly—Thr—Pro—NH$_2$, (Example 36)

⌐Acp—Asn—Leu—Ser—Thr—Asp—Val—Leu—Gly—Lys—Leu—Ser—Gln—
Glu—Leu—Asn—Lys—Leu—Gln—Thr—Pro—Arg—Thr—Asp—Val—Gly—Ala—
Gly—Thr—Pro—NH$_2$, (Example 38)

┌─────────────────────────────────────────────────────┐
└─Acp—Asn—Leu—Ser—Thr—Glu—Val—Leu—Gly—Lys—Leu—Ser—Gln—
Glu—Leu—Gly—Lys—Leu—Gln—Thr—Pro—Arg—Thr—Asp—Val—Gly—Ala—Gly—
Thr—Pro—NH$_2$.

(Example 74)

┌─────────────────────────────────────────────────────┐
└─Acp—Asn—Leu—Ser—Thr—Asp—Val—Leu—Gly—Lys—Leu—Ser—Gln—
Glu—Leu—Gln—Lys—Leu—Gln—Thr—Pro—Arg—Thr—Asp—Val—Gly—Ala—Gly—
Thr—Pro—NH$_2$.

and (Example 77)

┌─────────────────────────────────────────────────────┐
└─Acp—Asn—Leu—Ser—Thr—Asp—Val—Leu—Gly—Lys—Leu—Ser—Gln—
Glu—Leu—Ala—Lys—Leu—Gln—Thr—Pro—Arg—Thr—Asp—Val—Gly—Ala—
Gly—Thr—Pro—NH$_2$.

9. A polypeptide derivative, an acid-addition salt thereof or a complex thereof according to claim 4, wherein the polypeptide derivative is selected from the group consisting of 10. The polypeptide derivative, an acid-addition salt thereof or a complex thereof according to claim 4, wherein the polypeptide derivative is (Example 46)

└─Gly—Ser—Asn—Leu—Ser—Thr—
┐
Glu—Val—Leu—Gly—Lys—Leu—Ser—Gln—Glu—Leu—His—Lys—Gln—Thr—
Tyr—Pro—Arg—Thr—Asp—Val—Gly—Ala—Gly—Thr—Pro—NH$_2$.

11. A polypeptide derivative, an acid-addition salt thereof or a complex thereof according to claim 4, wherein the polypeptide derivative is selected from the group consisting of (Example 39)

┌──────┐
└─Gly—Ser—
┌─────────────────────────────────────────────────────┐
Asn—Leu—Ser—Thr—Glu—Val—Leu—Gly—Lys—Leu—Ser—Gln—Glu—Leu—Asn—Lys—
Leu—Gln—Thr—Pro—Gln—Thr—Asp—Val—Gly—Ala—Gly—Thr—Pro—NH$_2$, (Example 47)

┌─────────────────────────────────────────────────────┐
└─Gly—Ser—Asn—Leu—Ser—Thr—Glu—Val—Leu—Gly—Ala—Leu—
Ser—Gln—Glu—Leu—Asn—Lys—Leu—Gln—Thr—Pro—Gln—Thr—Asp—Val—
Gly—Ala—Gly—Thr—Pro—NH$_2$.

(Example 50)

┌─────────────────────────────────────────────────────┐
└─Gly—Ser—Asn—Leu—Ser—Thr—Glu—Val—Leu—Gly—Lys—Leu—Ser—
Gln—Glu—Leu—Asn—Lys—Leu—Gln—Thr—Leu—Pro—Gln—Thr—Asp—Val—
Gly—Ala—Gly—Thr—Pro—NH$_2$, (Example 52)

┌─────────────────────────────────────────────────────┐
└─Gly—Ser—Asn—Leu—Ser—Thr—Glu—Val—Leu—Gly—Lys(COCH$_3$)—
Leu—Ser—Gln—Glu—Leu—Asn—Lys—Leu—Gln—Thr—Pro—Gln—Thr—Asp—
Val—Gly—Ala—Gly—Thr—Pro—NH$_2$, and (Example 85)

┌─────────────────────────────────────────────────────┐
└─Acp—Asn—Leu—Ser—Thr—Asp—Val—Leu—Gly—Lys—Leu—Ser—Gln—
Glu—Leu—Tyr—Lys—Leu—Gln—Thr—Pro—Gln—Thr—Asp—Val—Gly—Ala—
Gly—Thr—Pro—NH$_2$.

(Example 40)

┌──────┐
└─Gly—Ser—

```
┌─────────────────────────────────────────────────────────────┐
Asn—Leu—Ser—Thr—Glu—Ile—Leu—Gly—Lys—Leu—Ser—Gln—Glu—Leu—His—Lys—
Leu—Gln—Thr—Pro—Arg—Thr—Asp—Val—Gly—Ala—Gly—Thr—Pro—NH₂.
```
(Example 48)

```
     ┌─────────────────────────────────────────────────────────┐
└—Gly—Ser—Asn—Leu—Ser—Thr—Glu—Ile—Leu—Gly—Lys—Leu—Ser—
Gln—Glu—Leu—His—Lys—Leu—Gln—Thr—Pro—Gln—Thr—Asp—Val—Gly—
Ala—Gly—Thr—Pro—NH₂.
``` and (Example 51)

```
     ┌─────────────────────────────────────────────────────────┐
└—Gly—Ser—Asn—Leu—Ser—Thr—Glu—Ile—Leu—Gly—Lys—Leu—Ser—
Gln—Glu—Leu—Asn—Lys—Leu—Gln—Thr—Pro—Arg—Thr—Asp—Val—Gly—
Ala—Gly—Thr—Pro—NH₂.
```

12. The polypeptide derivative, an acid-addition salt thereof or a complex thereof according to claim 4, wherein the polypeptide derivative is selected from the group consisting of (Example 1)

```
    ┌─────────┐
└—Gly—Ser—
```
```
                                                              │
Asn—Leu—Ser—Thr—Glu—Val—Leu—Gly—Lys—Leu—Ser—Gln—Glu—Leu—His—Lys—
Leu—Gln—Thr—Tyr—Pro—Arg—Thr—Asp—Val—Gly—Ala—Gly—Thr—Pro—NH₂.
```

(Example 9)

```
     ┌──────────────────────────────────────────────────────┐
└—COCH₂CH₂CO—Asn—Leu—Ser—Thr—Lys—Val—Leu—Gly—Lys—Leu—
Ser—Gln—Glu—Leu—His—Lys—Leu—Gln—Thr—Tyr—Pro—Arg—Thr—Asp—
Val—Gly—Ala—Gly—Thr—Pro—NH₂.
```

(Example 16)

```
     ┌─────────────────────────────────────────────────────┐
└—Gly—Ser—Asn—Leu—Ser—Thr—Glu—Val—Leu—Gly—Lys—Leu—Ser—
Gln—Glu—Leu—His—Lys—Leu—Gln—Thr—Pro—Arg—Thr—Asp—Val—Gly—
Ala—Gly—Thr—Pro—NH₂.
```

(Example 18)

```
     ┌─────────────────────────────────────────────────────┐
└—Gly—Ser—Asn—Leu—Ser—Thr—Glu—Val—Leu—Gly—Lys—Leu—Ser—
Gln—Glu—Leu—His—Lys—Leu—Gln—Thr—D—Tyr—Pro—Arg—Thr—Asp—Val—
Gly—Ala—Gly—Thr—Pro—NH₂.
```

(Example 19)

```
     ┌─────────────────────────────────────────────────────┐
└—Acp—Asn—Leu—Ser—Thr—Asp—Val—Leu—Gly—Lys—Leu—Ser—Gln—
Glu—Leu—His—Lys—Leu—Gln—Thr—Pro—Arg—Thr—Asp—Val—Gly—Ala—
Gly—Thr—Pro—NH₂.
```

(Example 21)

```
     ┌─────────────────────────────────────────────────────┐
└—β-Ala—Ser—Asn—Leu—Ser—Thr—Asp—Val—Leu—Gly—Lys—Leu—
Ser—Gln—Glu—Leu—His—Lys—Leu—Gln—Thr—Pro—Arg—Thr—Asp—Val—
Gly—Ala—Gly—Thr—Pro—NH₂.
```

(Example 22)

```
     ┌─────────────────────────────────────────────────────┐
└—Gly—Ser—Asn—Leu—Ser—Thr—Glu—Val—Leu—Gly—Lys(COCH₃—
Leu—Ser—Gln—Glu—Leu—His—Lys—Leu—Gln—Thr—Pro—Arg—Thr—
Asp—Val—Gly—Ala—Gly—Thr—Pro—NH₂,
``` and (Example 23)

```
     ┌─────────────────────────────────────────────────────┐
└—Gly—Ser—Asn—Leu—Ser—Thr—Glu—Val—Leu—Gly—Lys(Cl—Bz)—
Leu—Ser—Gln—Glu—Leu—His—Lys—Leu—Gln—Thr—Tyr—Pro—Arg—Thr—
Asp—Val—Gly—Ala—Gly—Thr—Pro—NH₂.
```

13. A pharmaceutical composition for treatment of hypercalcemia, containing, as the active ingredient, a polypeptide derivative, an acid addition salt thereof or a complex thereof as claimed in any one of claims 1-12.

14. A pharmaceutical composition for treatment of hypercalcemia according to claim 13, wherein the polypeptide derivative, acid-addition salt or complex thereof represented by the general formula (1) is selected from the (Example 33)

```
┌─────────────────────────────────────────┐
└─Acp—Asn—Leu—Ser—Thr—Asp—Val—Leu—Gly—
Lys—Leu—Ser—Gln—Glu—Leu—His—Lys—Leu—Gln—Thr—Pro—Gln—Thr—
Asp—Val—Gly—Ala—Gly—Thr—Pro—NH₂,
```

(Example 37)

```
┌─────────────────────────────────────────┐
└─Acp—Asn—Leu—Ser—Thr—Asp—Val—Leu—Gly—Lys—Leu—Ser—Gln—Glu—
Leu—Gly—Lys—Leu—Gln—Thr—Pro—Arg—Thr—Asp—Val—Gly—Ala—Gly—
Thr—Pro—NH₂,
``` and (Example 46)

```
┌─────────────────────────────────────────┐
└─Gly—Ser—Asn—Leu—Ser—Thr—Glu—Val—Leu—Gly—Lys—Leu—Ser—Gln—
Glu—Leu—His—Lys—Gln—Thr—Tyr—Pro—Arg—Thr—Asp—Val—Gly—Ala—
Gly—Thr—Pro—NH₂.
```

15. A method for the treatment of hypercalcemia in warm-blooded animals comprising administering to said warm-blooded animal a serum plasma calcium-lowering effective amount of a polypeptide derivative, an acid additional salt thereof or a complex thereof as claimed in any one of claims 1–12.

16. A polypeptide derivative, an acid-addition salt thereof or a complex thereof as claimed in any one of claims 1–5, wherein (A) is a straight chain or branched chain lower alkylene group having 1 or 6 carbon atoms, or an o-phenylene, meta-phenylene or p-phenylene group.

17. A polypeptide derivative, an acid-addition salt thereof or a complex thereof as claimed in any one of claims 1–5, wherein said oxyphenylene group is an oxy-o-phenylene, oxy-meta-phenylene or oxy-p-phenylene group.

18. A polypeptide derivative, an acid-addition salt thereof or a complex thereof as claimed in any one of claims 1–5, wherein (D) is a straight chain or branched chain lower alkylene group having 1 to 6 carbon atoms.

19. A polypeptide derivative, an acid-addition salt thereof or a complex thereof as claimed in any one of claims 1–5, wherein the acyl group for acylating the amino group of the side-chain in the lysine residue is a lower alkanoyl group or a benzoyl group, wherein said benzoyl group is substituted with 1 to 3 substituents selected from the group consisting of a lower alkyl group, a lower alkoxy group and a halogen atom.

20. The polypeptide derivative, an acid-addition salt thereof or a complex thereof as claimed in claim 19, wherein the lower alkanoyl group is a straight chain or branched chain alkanoyl group having 1 to 6 carbon atoms.

21. The polypeptide derivative, an acid-addition salt thereof or a complex thereof as claimed in claim 19, wherein said substituent of the benzoyl group is a lower alkyl group selected from the group consisting of straight chain and branched chain alkyl groups having 1 to 6 carbon atoms.

22. The polypeptide derivative, an acid-addition salt thereof or a complex thereof as claimed in claim 19, wherein said substituent of the benzoyl group is a lower alkoxyl group selected from the group consisting of straight chain and branched chain alkoxyl groups having 1 to 6 carbon atoms.

23. A polypeptide derivative, an acid-addition salt thereof or a complex thereof as claimed in any one of claims 1–5, wherein the ester residue for esterifying the carboxyl group of the side chain in aspartic acid or glutamic acid is an alkyl group having 1 to 6 carbon atoms.

* * * * *

UNITED STATES PATENT AND TRADEMARK OFFICE
CERTIFICATE OF CORRECTION

PATENT NO. : 5,162,305

DATED : November 10, 1992

INVENTOR(S) : Setsuro Fujii et al.

It is certified that error appears in the above-identified patent and that said Letters Patent is hereby corrected as shown below:

Claim 2, column 172, line 19, change "(H1)" to --($H^1$)--;
Claim 3, column 172, line 51, change "than" to --then--;
Claim 4, column 173, line 17, change "asparatic" to --aspartic--;
Claim 6, column 174, line 20, change "claim 2" to --claim 1--;
Claim 8, column 174, line 47, change "claim 3" to --claim 2--;
Claim 9, column 175, line 20, change "claim 4" to --claim 3--;
Claim 10, column 176, line 19, change "The" to --A--;
Claim 12, column 177, line 57, change "Lys($COCH_3$" to --Lys($COCH_3$)--;
            line 58, before "Pro" insert --Tyr- --;
Claim 13, column 178, line 18, change "acid addition" to --acid-addition--;
Claim 14, column 179, line 3, after "the" insert --group consisting of--; and
Claim 16, column 179, line 31, before "6" change "or" to --to--.

Signed and Sealed this

Second Day of November, 1993

BRUCE LEHMAN

*Attest:*

*Attesting Officer*            *Commissioner of Patents and Trademarks*